(12) United States Patent
Barelle et al.

(10) Patent No.: US 10,202,438 B2
(45) Date of Patent: Feb. 12, 2019

(54) SYNTHETIC LIBRARY OF SPECIFIC BINDING MOLECULES

(71) Applicant: THE UNIVERSITY COURT OF THE UNIVERSITY OF ABERDEEN, Aberdeen (GB)

(72) Inventors: Caroline Jane Barelle, Aberdeen (GB); William James Jonathan Finlay, Dublin (IE); Alfredo Darman-In-Sheehan, Dublin (IE); Andrew Justin Radcliffe Porter, Aberdeen (GB)

(73) Assignee: THE UNIVERSITY COURT OF THE UNIVERSITY OF ABERDEEN, Aberdeen (GB)

( * ) Notice: Subject to any disclaimer, the term of this patent is extended or adjusted under 35 U.S.C. 154(b) by 382 days.

(21) Appl. No.: 14/786,074

(22) PCT Filed: Apr. 23, 2014

(86) PCT No.: PCT/EP2014/058251
§ 371 (c)(1),
(2) Date: Oct. 21, 2015

(87) PCT Pub. No.: WO2014/173959
PCT Pub. Date: Oct. 30, 2014

(65) Prior Publication Data
US 2016/0176951 A1    Jun. 23, 2016

Related U.S. Application Data

(60) Provisional application No. 61/815,043, filed on Apr. 23, 2013.

(51) Int. Cl.
*C07K 16/00* (2006.01)
*C07K 16/18* (2006.01)
(Continued)

(52) U.S. Cl.
CPC ........ *C07K 16/005* (2013.01); *A61K 49/0002* (2013.01); *C07K 16/18* (2013.01);
(Continued)

(58) Field of Classification Search
CPC .. C07K 16/005; C07K 16/40; C07K 16/2803; C07K 16/28; C07K 16/18;
(Continued)

(56) References Cited

U.S. PATENT DOCUMENTS 7,977,071 B2   7/2011   Nuttal et al.
9,475,870 B2   10/2016  Barelle et al.
(Continued)

FOREIGN PATENT DOCUMENTS

EP   2281837 A2   8/2002
EP   2202243 A2   6/2010
(Continued)

OTHER PUBLICATIONS

Alt, Margitta, et. al., FEBS Letters, vol. 454, pp. 90-94 (1999).
(Continued)

*Primary Examiner* — Jeremy C Flinders
(74) *Attorney, Agent, or Firm* — Arrigo, Lee, Guttman & Mouta-Bellum LLP

(57) ABSTRACT

The present invention provides methods for the production of a library of antigen specific antigen binding molecules having a peptide domain structure represented by the following formula (I): FW 1-CDR1-FW2-HV2-FW3a-HV4-FW3b-CDR3-FW4 comprising (1) isolating RNA from a member of a species in the Elasmobranchii subclass; (2) amplifying DNA sequences from RNA obtained; (3) selecting a DNA sequence from the database prepared; (4) amplifying DNA sequences encoding two or more contiguous peptide domains of FW1-CDR1-FW2-HV2-FW3a-HV4-FW3b-CDR3-FW4; (5) ligating together said amplified
(Continued)

DNA sequences to form DNA sequences encoding an antigen specific binding molecule; (6) cloning the amplified DNA obtained into a display vector; and (7) transforming a host with said display vector to produce a library of said antigen specific antigen binding molecules. The invention also provides methods for the production of an antigen specific antigen binding molecule as defined, pharmaceutical compositions comprising such molecules and uses thereof in medicine.

3 Claims, 28 Drawing Sheets

Specification includes a Sequence Listing.

(51) Int. Cl.
    *C07K 16/28*     (2006.01)
    *C07K 16/40*     (2006.01)
    *A61K 49/00*     (2006.01)
    *G01N 33/68*     (2006.01)
    *C12N 15/10*     (2006.01)
    *A61K 39/00*     (2006.01)

(52) U.S. Cl.
    CPC .......... *C07K 16/28* (2013.01); *C07K 16/2803* (2013.01); *C07K 16/2827* (2013.01); *C07K 16/40* (2013.01); *C12N 15/1037* (2013.01); *G01N 33/6872* (2013.01); *A61K 2039/505* (2013.01); *C07K 2317/14* (2013.01); *C07K 2317/20* (2013.01); *C07K 2317/24* (2013.01); *C07K 2317/565* (2013.01); *C07K 2317/567* (2013.01); *C07K 2317/569* (2013.01); *C07K 2317/73* (2013.01); *C07K 2317/76* (2013.01); *C07K 2317/92* (2013.01); *G01N 2333/70532* (2013.01)

(58) Field of Classification Search
    CPC ............ C07K 16/2827; C12N 15/1037; G01N 33/6872; A61K 49/0002
    See application file for complete search history.

(56) References Cited

U.S. PATENT DOCUMENTS

| | | |
|---|---|---|
| 2011/0129473 A1 | 6/2011 | Paniagua-Solis |
| 2016/0068600 A1 | 3/2016 | Barelle et al. |
| 2017/0096475 A1 | 4/2017 | Barelle et al. |

FOREIGN PATENT DOCUMENTS

| | | | | |
|---|---|---|---|---|
| EP | 2277913 A2 | 1/2011 | | |
| EP | 2277914 A2 | 1/2011 | | |
| JP | 2008-536490 A | 9/2008 | | |
| WO | 01/75091 A2 | 10/2001 | | |
| WO | 03/014161 A2 | 2/2003 | | |
| WO | 03/102157 | 12/2003 | | |
| WO | 2005/021719 A1 | 3/2005 | | |
| WO | 2005/042743 A2 | 5/2005 | | |
| WO | WO-2005118629 A1 * | 12/2005 | ........... | C07K 14/461 |
| WO | 2006/099747 A1 | 9/2006 | | |
| WO | 2006/102095 A2 | 9/2006 | | |
| WO | 2006122787 A2 | 11/2006 | | |
| WO | 2008028977 A2 | 9/2007 | | |
| WO | 2008043821 A1 | 4/2008 | | |
| WO | 2008096158 A2 | 8/2008 | | |
| WO | 2009/026638 A1 | 3/2009 | | |
| WO | 2010/040175 A2 | 4/2010 | | |
| WO | 2013/167883 A1 | 4/2012 | | |
| WO | 2012/073048 A2 | 6/2012 | | |
| WO | 2014/173975 A1 | 10/2014 | | |
| WO | 2005/118629 A1 | 12/2015 | | |

OTHER PUBLICATIONS

Coppieters, Ken, et al., Arthritis & Rheumatism, vol. 54, No. 6, pp. 1856-1866 (2006).
Dennis, Mark S., et. al., The Journal of Biological Chemistry, vol. 277, No. 38, pp. 35035-35043 (2002).
Henderson et al., "Structure of an IgNAR-AMA1 Complex: Targeting a Conserved Hydrophobic Cleft Broadens Malarial Strain Recognition," Structure, vol. 15, pp. 1452-1466, (2007).
The International Search Report and Written Opinion for International Application No. PCT/GB2013/051183.
Stanfield, R.L. et al., Sciene, vol. 305, pp. 1770-1773 (2004).
Greenberg, Andrew S., Nature, vol. 374, pp. 168-173 (1995).
Holt, Lucy J., et al., Protein Engineering, Design & Selection, vol. 21, No. 5, pp. 283-288 (2008).
Wuunder, Andreas, et. al., J Immunol., vol. 170, pp. 4793-4801 (2003).
Muller, Dafne, et. al., The Journal of Biological Chemistry, vol. 282, No. 17, pp. 12650-12660 (2007).
Muller, Mischa et al., mAbs, vol. 4, No. 6, pp. 673-685 (2012).
Nguyen, Allen, et al., Protein Engineering, Design & Selection. vol. 19, No. 7, pp. 291-297 (2006).
Wuunder, Andreas, et. al., Int. J. Cancer, vol. 76, pp. 884-890 (1998).
Pedley, R.B., et. al., Br. J. Cancer, vol. 70, pp. 1136-1131 (1994).
Smith, Bryan J., el. al., Bioconjugate Chem., vol. 12, pp. 750-756 (2001).
Stork, Roland, Protein Engineering, Design & Selection, vol. 20, No. 11, pp. 569-576 (2007).
Stork, Roland, The Journal of Biological Chemistry, vol. 283, No. 12,, pp. 7804-7812 (2008).
Atschul et al., J. Mol. Biol. (1990) 215, 403-410.
Bloom, L. and V. Calabro, Drug Discov Today, 2009. 14(19-20): p. 949-55.
Bostrom, J. and G. Fuh, Methods Mol Biol, 2009. 562: p. 17-35.
Bostrom, J., et al., Methods Mol Biol, 2009. 525: p. 353-76.
Chen, W., et al., J Mol Biol, 2008. 382(3): p. 779-89.
Crea et al., Proc. Nat'l. Acad. Sci. USA, (1978) 75: 5765-5769.
Damschroder, et al., Molecular Immunology, 44 (11), 3049-60 (2007).
Dall'Acqua W F, et al., Methods, 36 (1), 43-60. (2005).
Devereux, et al., Nucleic acids Research, 12, 387 (1984).
Diaz, M., et al., Immunogenetics, 2002. 54(7): p. 501-12.
Dimitrov, D.S., MAbs, 2009. 1(1): p. 26-8.
Dooley, H., et al., Proc Natl Acad Sci U S A, 2006. 103(6): p. 1846-51.
Dooley, H., M.F. Flajnik, and A.J. Porter, Mol Immunol, 2003. 40(1): p. 25-33.
Enshell-Seijffers et al, Nucleic Acids Res. (2001); 29(10).
Fennell, B.J., et al., J Mol Biol, 2010. 400(2): p. 155-70.
Gebauer, M. and A. Skerra, Curr Opin Chem Biol, 2009. 13(3): p. 245-55.
Holliger, P. and P.J. Hudson, Nat Biotechnol, 2005. 23(9): p. 1126-36.
Holt, L J, et al., Trends in Biotechnology, 21 (11), pp. 484-490. (2003).
Hufton et al, J Immunol Methods. (1999), 231, (1-2): 39-51.
Jirholt, P, et al., Protein Engineering, 14 (1), 67-74 (2001).
Jirholt, P, et L., Gene, 215 (2) 471-76 (1998).
Knappik et al.; J. Mol. Biol. (1999), 296, 57-86.
Kovalenko, O V., et al., J of Biological Chemistry, 288 (24), 17408-419 (2013).
Liu, J.L., et al., Mol Immunol, 2007. 44(7): p. 1775-8.
Liu, J.L., G.P. Anderson, and E.R. Goldman, BMC Biotechnol, 2007. 7: p. 78.
Natsume, A, et al., Cancer Research, 68(10), 3863-72 (2008).
Natsume, A, et al., Drug Design, Development and Therapy, 3, 7-16 (2009).
Nuttall, S.D., et al., Eur J Biochem, 2003. 270(17): p. 3543-54.
Nuttall, S.D., et al., FEBS Lett, 2002. 516(1-3): p. 80-6.
Nuttall, S.D., et al., Mol Immunol, 2001. 38(4): p. 313-26.
Nuttall, S.D., et al., Proteins, 1999. 36(2): p. 217-27.
Nuttall, S.D., et al., Proteins, 2004. 55(1): p. 187-97.

(56) References Cited

OTHER PUBLICATIONS

Pereboev et al J Virol. (2001); 75(15): 7107-13.
Rondot et al Nat Biotechnol. (2001); 19(1): 75-8.
Shao, C.Y., C.J. Secombes, and A.J. Porter, Mol Immunol, 2007. 44(4): p. 656-65.
Smith, L., et al., Developmental and Comparative Immunology, 36(4), 665-679 (2012).
Tasumi, S., et al., Proc Natl Acad Sci U S A, 2009. 106(31): p. 12891-6.
Virnekas, B., et al., Nucleic Acids Res, 1994. 22(25): p. 5600-7.
Weiss et al, Protein Sci (2000) 9 (4): 647-54.
Wesolowski, J., et al., Med Microbiol Immunol, 2009. 198(3): p. 157-74.
Wong et al, Gene, (1988) 68, pp. 193.

\* cited by examiner

| Target | Ka (1/Ms) | Kd (1/s) | KD (nM) |
|---|---|---|---|
| hDLL4 | 4.027X10$^5$ | 0.007518 | 18.67 |
| | 3.130X10$^5$ | 0.005543 | 17.71 |
| | 7.081X10$^5$ | 0.001762 | 2.49 |
| | 9.645X10$^4$ | 0.00557 | 57.75 |
| HSA | 1.771x10$^5$ | 0.001766 | 9.968 |
| | 5.991x10$^5$ | 0.001903 | 3.18 |
| hRAGE | 1.371X10$^5$ | 0.001959 | 14.29 |
| | 1.534X10$^5$ | 0.01155 | 75.29 |
| | 1.967X10$^5$ | 0.002146 | 10.91 |
| | 1.003X10$^4$ | 7.35X10$^4$ | 73.29 |
| | 1.706X10$^5$ | 0.009751 | 57.17 |

Fig. 5

|  | Medium | WT-2V | 9 | 10 | 13 | 24 | 38 | 43 | CONTROL |
|---|---|---|---|---|---|---|---|---|---|
| HEK293-Parental | 845 | 826 | 1153 | 977 | 902 | 779 | 955 | 911 | 1176 |
| HEK293-HuDLL4 | 698 | 708 | 19199 | 28790 | 6657 | 6059 | 3012 | 6530 | 36287 |
| HEK293-MuDLL4 | 797 | 787 | 38716 | 63272 | 17888 | 4772 | 4394 | 10318 | 50590 |

|  | Medium | WT-2V | 46 | 49 | 50 | 53 | 68 | 72 | CONTROL |
|---|---|---|---|---|---|---|---|---|---|
| HEK293-Parental | 745 | 754 | 1041 | 816 | 996 | 1022 | 915 | 1199 | 896 |
| HEK294-HuDLL4 | 527 | 539 | 11474 | 17905 | 11891 | 22185 | 15475 | 34231 | 29936 |
| HEK293-MuDLL4 | 545 | 596 | 25345 | 41899 | 29617 | 43070 | 37951 | 57041 | 65037 |

|  | Medium | WT-2V | 81 | 82 | 83 | E4 | 1-15 | 1-35 | 1-42 | CONTROL |
|---|---|---|---|---|---|---|---|---|---|---|
| HEK293-Parental | 754 | 762 | 1018 | 903 | 766 | 850 | 842 | 766 | 764 | 832 |
| HEK293-HuDLL4 | 632 | 654 | 11123 | 7058 | 4240 | 13463 | 34227 | 4636 | 5867 | 13180 |
| HEK293-MuDLL4 | 698 | 754 | 33970 | 23616 | 18712 | 12773 | 15516 | 12352 | 23839 | 36629 |

Fig. 6B

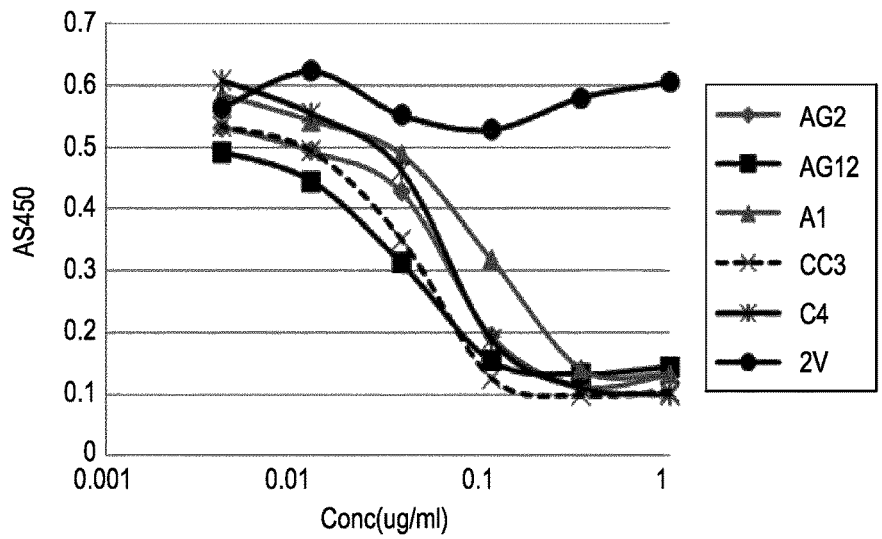
Fig. 7A
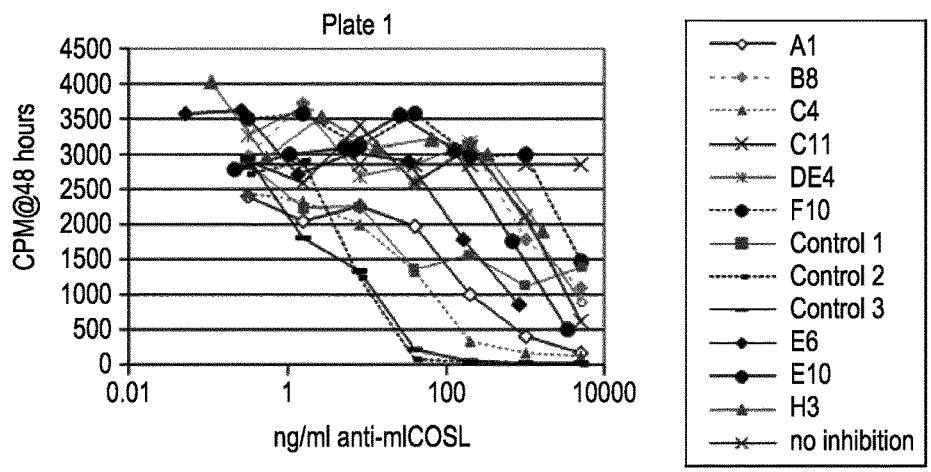
Fig. 7B
| Clone Name | Average hDLL4 neutralisation (%) |
|---|---|
| +ve control | 75 |
| 10 | 61 |
| 72(1) | 62 |
| 78 | 42 |
| 81 | 57 |
| 83 | 60 |
| A05 | 63 |
| E4 | 72 |
Fig. 7C

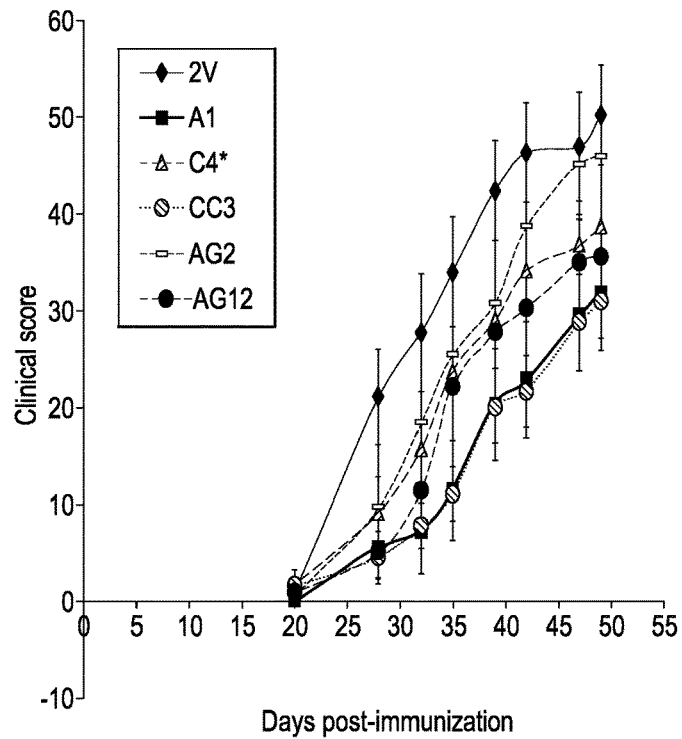
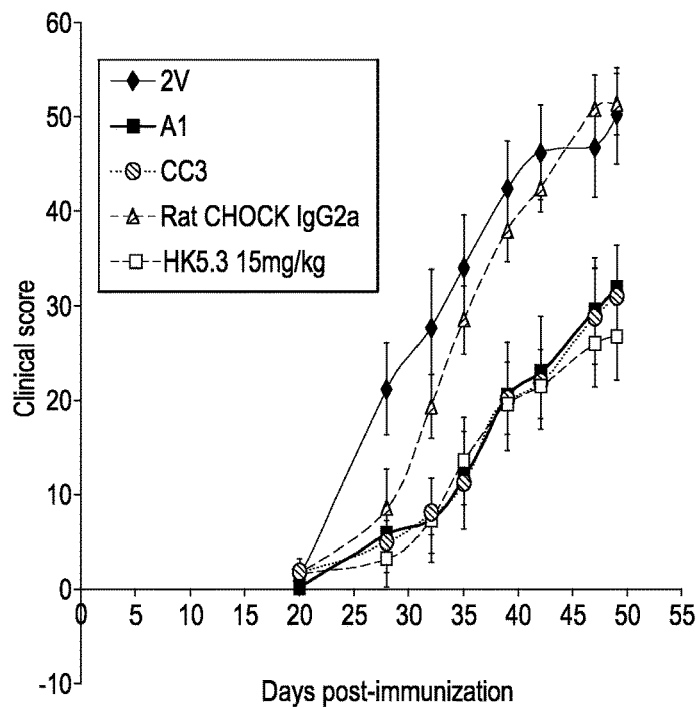
Fig. 8

2V, nucleotide [SEQ ID NO: 9]
ACAAGAGTAGACCAAACACCAAGAACGGCAACAGGAGAACAGGAGAATCCCTGACCATCAACTGGCTCCTAACTGATACCAGCTATGGTTTGTACAGCACATCC
TGGTTCCGGAAAAATCCGGGTACAACAGACTGGGAACGCATGTCGATTGGGCGGCCGATATGTCGAATCAGTCAACAAGGGAGCAAAGTCATTTCTCTGGAATC
AAGGACCTAACAGTTGCAGAGACTGCCACGTATTATTGCAAAGCTCAAAGCCTCGCAATCAGTACGCGCTCTTACTGTTATGACGGAGCTGGCACCGTGCTGACT
GTGAAC 2V, protein [SEQ ID NO: 10]
TRVDQTPRTATKETGESLTINCVLTDTSYGLYSTSWFRKNPGTTDWERMSIGGRYVESVNKGAKSFSLRIKDLTVADSATYYCKAQSLAISTRSYWYDGAGTVLT
VN 5V, nucleotide [SEQ ID NO: 11]
GCAAGTGTAAACCAAACACCAAGAACGGCAACAGGCCGAATCCCTGACCATCAACTGCGTTGTAACTGGTGCCAGCTATGCTTGGAGCAGCACATAC
TGGTACCGGAAAAATCCGGGTTCATCAAACCAGGAGCGGATATCGATTGAATGTGAATCAGTCAACAAGCGAACAATGTCATTTCTCTGGAATC
AAGGACCTAACAGTTGCAGAGACTGCCAGACGTCCAGAGCTTATCGAGAGCTTATCGATGGAGTCCATAGGGGTTACGATGTCTACGGAGCTGGCACCGTGCTG
ACTGTGAAC 5V, protein [SEQ ID NO: 12]
ASVNQTPRTATKETGESLTINCVVTGASYAWSSTYWYRKNPGSSNQERISISGRYVESVNKRTMSFSLRIKDLTVADSATYICRAYRMESIAGRGYDVYGAGTVL
TVN

Fig. 9

| Oligo Name | Sequence (5'→3') | (Encoded amino acids) |
|---|---|---|
| Rev_Over_1 | aacacaattaatggtcaggctttcacc | N/A |
| Rev_Over_2 | ataggttgcgctatctgcaacggtcag | N/A |
| | | |
| 2V-1-H1mut-F | ctgaccattaattgtgttctgaccgatacc(RRK)tat(GST)(TKG)(TWC)(KCC)accagctggtttcgtaaaaatccg | (K,R,D,E,N,S,G)(G,A)(W,L)(F,Y)(S,A) |
| 2V-1-H2mut-F | Ctgaccattaattgtgttctgaccgatacc(RRK)tat(KCT)(TKG)(TWC)(KCC)accagctggtttcgtaaaaatccg | (K,R,D,E,N,S,G)(A,S)(W,L)(F,Y)(S,A) |
| 2V-1-H3mut-F | Ctgaccattaattgtgttctgaccgatacc(RRK)tat(GST)(TKG)(KCT)(KCC)accagctggtttcgtaaaaatccg | (K,R,D,E,N,S,G)(G,A)(W,L)(A,S)(S,A) |
| 2V-1-Wmut-F | ctgaccattaattgtgttctgaccgataccTRMTRMTRMtggTRMTRMaccagctggtttcgtaaaaatccg | (All except C) |
| 2V-1-mut-F | ctgaccattaattgtgttctgaccgataccTRMTRMTRMTRMTRMaccagctggtttcgtaaaaatccg | (All except C) |
| 2V-3-8mut | gcaacctattactgtaaagcaTRMTRMTRMTRMTRMTRMtggtatgatggtgcaggcaccgttctg | (All except C) |
| 2V-3-10mut | gcaacctattactgtaaagcaTRMTRMTRMTRMTRMTRMTRMTRMtggtatgatggtgcaggcaccgttctg | (All except C) |
| 2V-3-12mut | gcaacctattactgtaaagcaTRMTRMTRMTRMTRMTRMTRMTRMTRMTRMtggtatgatggtgcaggcaccgttctg | (All except C) |
| 2V-3-14mut | gcaacctattactgtaaagcaTRMTRMTRMTRMTRMTRMTRMTRMTRMTRMTRMTRMtggtatgatggtgcaggcaccgttctg | (All except C) |
| 2V-3-16mut | gcaacctattactgtaaagcaTRMTRMTRMTRMTRMTRMTRMTRMTRMTRMTRMTRMTRMTRMtggtatgatggtgcaggcaccgttctg | (All except C) |
| | | |
| 5V-1-H1mut-F | Ctgaccattaattgtgttgttaccggtgca(RRK)tat(GST)(TKG)(TWC)(KCC)acctattggtatcgtaaaaatccg | (K,R,D,E,N,S,G)(G,A)(W,L)(F,Y)(S,A) |
| 5V-1-H2mut-F | Ctgaccattaattgtgttgttaccggtgca(RRK)tat(KCT)(TKG)(TWC)(KCC)acctattggtatcgtaaaaatccg | (K,R,D,E,N,S,G)(A,S)(W,L)(F,Y)(S,A) |
| 5V-1-H3mut-F | Ctgaccattaattgtgttgttaccggtgca(RRK)tat(GST)(TKG)(KCT)(KCC)acctattggtatcgtaaaaatccg | (K,R,D,E,N,S,G)(G,A)(W,L)(A,S)(S,A) |
| 5V-1-Wmut-F | ctgaccattaattgtgttgttaccggtgcaTRMTRMTRMtggTRMTRMacctattggtatcgtaaaaatccg | (All except C) |
| 5V-1-mut-F | ctgaccattaattgtgttgttaccggtgcaTRMTRMTRMTRMTRMacctattggtatcgtaaaaatccg | (All except C) |
| 5V-3-9mut | gcaacctatatctgtcgtgccTRMTRMTRMTRMTRMTRMTRMgatgtttatggtgcaggcaccgttctg | (All except C) |
| 5V-3-11mut | gcaacctatatctgtcgtgccTRMTRMTRMTRMTRMTRMTRMTRMTRMgatgtttatggtgcaggcaccgttctg | (All except C) |
| 5V-3-13mut | gcaacctatatctgtcgtgccTRMTRMTRMTRMTRMTRMTRMTRMTRMTRMTRMgatgtttatggtgcaggcaccgttctg | (All except C) |

Fig. 10(a)

| CDR1 position | 1 | 2 | 3 | 4 | 5 | 6 |
|---|---|---|---|---|---|---|
| Residue found in natural database (%) | Y (2)<br>T (3)<br>R(3)<br>I (4)<br>K(4)<br>N(18)<br>S(57) | C* (33)<br>Y (57) | P (6)<br>S (15)<br>A (23)<br>G (46) | W (13)<br>L (83) | H (5)<br>S (28)<br>Y (59) | N (3)<br>R (7)<br>G (14)<br>S (66) |
| Total % of natural database | 91 | 90 | 90 | 96 | 92 | 90 |
| Expected % of natural database coverage using CDR1-mutR | 100 | 57 | 100 | 100 | 100 | 100 |
| Expected % coverage using CDR1-mutR W | 100 | 57 | 100 | 13 | 100 | 100 |
| Expected % coverage using CDR1-H1, H2 & H3 | 86 (RRK codon used encodes KRDENSG) | 57 (Maintained TAT codon for Y) | 84 (GST or KCT codon used encodes G, A, or S) | 100 (TKG codon used encodes for W or L) | 88 (TWC or KCT codon used encodes for S, Y, F, or A) | 67 (KCC codon used encodes for S or A) |

Codon:           Encoded amino acids:
TRM           All except C
RRK           (KRDENSG)
GST           (G/A)
TKG           (W/L)
TWC           (F/Y)
KCC           (S/A)
KCT           (A/S)

Fig. 10(b)

```
2V2V2V: TRVDQTPRTATKETGESLTINCVLTDT------TSWFRKNPGTTDWERMSGRYVESVNKGAKSFSLRIKDLTVADSATYICKA------DGAGTVLTVN
2V2V5V: TRVDQTPRTATKETGESLTINCVLTDT------TSWFRKNPGTTDWERMSGRYVESVNKGAKSFSLRIKDLTVADSATYICRA------YGAGTVLTVN
2V5V2V: TRVDQTPRTATKETGESLTINCVTGA-------TYWYRKNPGSSNQERISSGRYVESVNKRTMSFSLRIKDLTVADSATYICKA------DGAGTVLTVN
2V5V5V: TRVDQTPRTATKETGESLTINCVTGA-------TYWYRKNPGSSNQERISSGRYVESVNKRTMSFSLRIKDLTVADSATYICRA------YGAGTVLTVN
5V5V5V: ASVNQTPRTATKETGESLTINCVTGA-------TYWYRKNPGSSNQERISSGRYVESVNKRTMSFSLRIKDLTVADSATYICRA------YGAGTVLTVN
5V5V2V: ASVNQTPRTATKETGESLTINCVTGA-------TYWYRKNPGSSNQERISSGRYVESVNKRTMSFSLRIKDLTVADSATYICKA------DGAGTVLTVN
5V2V5V: ASVNQTPRTATKETGESLTINCVLTDT------TSWFRKNPGTTDWERMSGRYVESVNKGAKSFSLRIKDLTVADSATYICRA------YGAGTVLTVN
5V2V2V: ASVNQTPRTATKETGESLTINCVLTDT------TSWFRKNPGTTDWERMSGRYVESVNKGAKSFSLRIKDLTVADSATYICKA------DGAGTVLTVN
```

Fig. 12

| | |
|---|---|
| DL1  | TRVDQTPRTATKETGESLTINCVLTDTRYALSATSWFRKNPGTTDWERMSIGGRYVESVNKGAKSFSLRIKDLTVADSATYICRADWTAFDVYGAGTVLTVN |
| DL2  | TRVDQTPRTATKETGESLTINCVLTDTNSVWYTTSWFRKNPGTTDWERMSIGGRYVESVNKGAKSFSLRIKDLTVADSATYICRAFPMWFWYEPDVYGAGTVLTVN |
| DL3  | ASVNQTPRTATKETGESLTINCVLTDTPSHEFFTSWFRKNPGTTDWERMSIGGRYVESVNKGAKSFSLRIKDLTVADSATYICRAAHKLSXGFDDVYGAGTVLTVN |
| DL4  | TRVDQTPRTATKETGESLTINCVLTDTTPQWWTTSWFRKNPGTTDWERMSIGGRYVESVNKGAKSFSLRIKDLTVADSATYICRAALWSWWPYDVYGAGTVLTVN |
| DL5  | ASVNQTPRTATKETGESLTINCVLTDTRYGWYSTSWFRKNPGTTDWERMSIGGRYVESVNKGAKSFSLRIKDLTVADSATYICRANGFQDSFADVYGAGTVLTVN |
| DL6  | ASVNQTPRTATKETGESLTINCVLTDTDYGWYSTSWFRKNPGTTDWERMSIGGRYVESVNKGAKSFSLRIKDLTVADSATYICRAANGLARSMADVYGAGTVLTVN |
| DL7  | ASVNQTPRTATKETGESLTINCVLTDTNYGHYSTSWFRKNPGTTDWERMSIGGRYVESVNKGAKSFSLRIKDLTVADSATYICRANGWARSYEDVYGAGTVLTVN |
| DL8  | TRVDQTPRTATKETGESLTINCVLTDTGYALFSTSWFRKNPGTTDWERMSIGGRYVESVNKGAKSFSLRIKDLTVADSATYICRAAWFPYWVQNMDVYGAGTVLTVN |
| DL9  | TRVDQTPRTATKETGESLTINCVLTDTGYALYSTSWFRKNPGTTDWERMSIGGRYVESVNKGAKSFSLRIKDLTVADSATYICRAAWIPYLVRDMRDVYGAGTVLTVN |
| DL10 | TRVDQTPRTATKETGESLTINCVLTDTRYALFATSWFRKNPGTTDWERMSIGGRYVESVNKGAKSFSLRIKDLTVADSATYICRAAWQPYNVDSIWDVYGAGTVLTVN |
| DL11 | TRVDQTPRTATKETGESLTINCVLTDTSYGLSATSWFRKNPGTTDWERMSIGGRYVESVNKGAKSFSLRIKDLTVADSATYICRAAWQPPNNDSIWDVYGAGTVLTVN |
| DL12 | TRVDQTPRTATKETGESLTINCVLTDTYALLSTSWFRKNPGTTDWERMSIGGRYVESVNKGAKSFSLRIKDLTVADSATYICRAAWPYSVDSMWDVYGAGTVLTVN |
| DL13 | TRVDQTPRTATKETGESLTINCVLTDTFPWLHTSWFRKNPGTTDWERMSIGGRYVESVNKGAKSFSLRIKDLTVADSATYICRAAWPNWVSNSWDVYGAGTVLTVN |
| DL14 | ASVNQTPRTATKETGESLTINCVLTDTDICYSWFSTSWFRKNPGTTDWERMSIGGRYVESVNKGAKSFSLRIKDLTVADSATYYCKAAKAWEVWAIKHWWDGAGTVLTVN |
| DL15 | TRVDQTPRTATKETGESLTINCVLTDTGYSWFSTSWFRKNPGTTDWERMSIGGRYVESVNKGAKSFSLRIKDLTVADSATYICRAWNWWADKMEDVYGAGTVLTVN |
| DL16 | ASVNQTPRTATKETGESLTINCVLTDTNGWYATSWFRKNPGTTDWERMSIGGRYVESVNKGAKSFSLRIKDLTVADSATYICRAIWWNEPDVYGAGTVLTVN |
| DL17 | ASVNQTPRTATKETGESLTINCVLTDTHYWATSWFRKNPGTTDWERMSIGGRYVESVNKGAKSFSLRIKDLTVADSATYICRAFHPQGGMSSQDVYGAGTVLTVN |
| DL18 | TRVDQTPRTATKETGESLTINCVLTDTNWSWHATSWFRKNPGTTDWERMSIGGRYVESVNKGAKSFSLRIKDLTVADSATYICRABNYWDSWFWAPDVYGAGTVLTVN |

Fig. 13

```
DL19  TRVDQTPRTATKETGESLTINCVLTDTGYSLFSTSWFRKNPGITDWERMSIGGRYVESVNKGAKSFSLRIKDLTVADSATYICRAEQVSWMSWWPWDVYGAGTVLTVN
DL20  ASVNQTPRTATKETGESLTINCVLTDTNYGWYSTSWFRKNPGITDWERMSIGGRYVESVNKGAKSFSLRIKDLTVADSATYYCKAESFVHIWTWYDGAGTVLTVN
DL21  TRVDQTPRTATKETGESLTINCVLTDTRYALFATSWFRKNPGITDWERMSIGGRYVESVNKGAKSFSLRIKDLTVADSATYICRAETWTWWPLMEDVYGAGTVLTVN
DL22  ASVNQTPRTATKETGESLTINCVLTDTGYAWYSTSWFRKNPGITDWERMSIGGRYVESVNKGAKSFSLRIKDLTVADSATYICRAVWQWWIPWKNDVYGAGTVLTVN
DL23  ASVNQTPRTATKETGESLTINCVLTDTNYSWFATSWFRKNPGITDWERMSIGGRYVESVNKGAKSFSLRIKDLTVADSATYICRAGHKYAIGYXDVYGAGTVLTVN
DL24  ASVNQTPRTATKETGESLTINCVLTDTNYSWFATSWFRKNPGITDWERMSIGGRYVESVNKGAKSFSLRIKDLTVADSATYICRAGHKYAXGCPDVYGAGTVLTVN
DL25  TRVDQTPRTATKETGESLTINCVLTDTGYSLFSTSWFRKNPGITDWERMSIGGRYVESVNKGAKSFSLRIKDLTVADSATYICRAGMFWAWWPWYQDMYGAGTVLTVN
DL26  TRVDQTPRTATKETGESLTINCVLTDTNVGLESTSWFRKNPGITDWERMSIGGRYVESVNKGAKSFSLRIKDLTVADSATYICRAGTWMFWPLLDVYGAGTVLTVN
DL27  ASVNQTPRTATKETGESLTINCVLTDTWWSWWDTSWFRKNPGITDWERMSIGGRYVESVNKGAKSFSLRIKDLTVADSATYICRAGVLPWSPWGYWDVYGAGTVLTVN
DL28  TRVDQTPRTATKETGESLTINCVLTDTWHPWWYTSWFRKNPGITDWERMSIGGRYVESVNKGAKSFSLRIKDLTVADSATYICRAGMWWSWPFYDVYGAGTVLTVN
DL29  ASVNQTPRTATKETGESLTINCVLTDTWMWWHQTSWFRKNPGITDWERMSIGGRYVESVNKGAKSFSLRIKDLTVADSATYICRAHSSINGWREDVYGAGTVLTVN
DL30  ASVNQTPRTATKETGESLTINCVLTDTNYALSATSWFRKNPGITDWERMSIGGRYVESVNKGAKSFSLRIKDLTVADSATYICRAISYVWWGYTDVYGAGTVLTVN
DL31  TRVDQTPRTATKETGESLTINCVLTDTDATWFHTSWFRKNPGITDWERMSIGGRYVESVNKGAKSFSLRIKDLTVADSATYICRAWPSAYINWADVYGAGTVLTVN
DL32  ASVNQTPRTATKETGESLTINCVLTDTWPYTSWFRKNPGITDWERMSIGGRYVESVNKGAKSFSLRIKDLTVADSATYICRAGTWNPWPWDVYGAGTVLTVN
DL33  ASVNQTPRTATKETGESLTINCVLTDTGYAWFATSWFRKNPGITDWERMSIGGRYVESVNKGAKSFSLRIKDLTVADSATYICRAMHPWWPFSHWWDVYGAGTVLTVN
DL34  ASVNQTPRTATKETGESLTINCVLTDTESPWWYTSWFRKNPGITDWERMSIGGRYVESVNKGAKSFSLRIKDLTVADSATYICRAMWMWWQVYDVYGAGTVLTVN
DL35  ASVNQTPRTATKETGESLTINCVLTDTGYGLSATSWFRKNPGITDWERMSIGGRYVESVNKGAKSFSLRIKDLTVADSATYICRAWFHWAWWQHDVYGAGTVLTVN
DL36  ASVNQTPRTATKETGESLTINCVLTDTRYSLYSTSWFRKNPGITDWERMSIGGRYVESVNKGAKSFSLRIKDLTVADSATYICRAPAGMATYADVYGAGTVLTVN
```

```
DL57  ASVNQTPRTATKETGESLTINCVLTDTCDVCPGTSWFRKNPGTTDWERMSIGGRYVESVNKGAKSFSLRIKDLTVADSATYICRAHRVRSTYEDYYGAGTVLTVN
DL58  ASVNQTPRTATKETGESLTINCVLTDTWYWWKTSWFRKNPGTTDWERMSIGGRYVESVNKGAKSFSLRIKDLTVADSATYICRALFPLQWMTDYYGAGTVLTVN
DL59  ASVNQTPRTATKETGESLTINCVLTDTSYALYATSWFRKNPGTTDWERMSIGGRYVESVNKGAKSFSLRIKDLTVADSATYICRALTWPFKWWAPDYYGAGTVLTVN
DL60  ASVNQTPRTATKETGESLTINCVLTDTSYAWFSTSWFRKNPGTTDWERMSIGGRYVESVNKGAKSFSLRIKDLTVADSATYICRALLWDWWPEDYYGAGTVLTVN
DL61  ASVNQTPRTATKETGESLTINCVLTDTEYGWATSWFRKNPGTTDWERMSIGGRYVESVNKGAKSFSLRIKDLTVADSATYICRASNGYQQAWQWDYYGAGTVLTVN
DL62  ASVNQTPRTATKETGESLTINCVLTDTWLPWQTSWFRKNPGTTDWERMSIGGRYVESVNKGAKSFSLRIKDLTVADSATYICRASSPWWGWGWDYYGAGTVLTVN
DL63  ASVNQTPRTATKETGESLTINCVLTDTGYAWFSTSWFRKNPGTTDWERMSIGGRYVESVNKGAKSFSLRIKDLTVADSATYICRASVPTTWWWYGNDYYGAGTVLTVN
DL64  TRVDQTPRTATKETGESLTINCVLTDTGYAWYATSWFRKNPGTTDWERMSIGGRYVESVNKGAKSFSLRIKDLTVADSATYICRASWWWTWPMDYYGAGTVLTVN
DL65  ASVNQTPRTATKETGESLTINCVLTDTSYALYATSWFRKNPGTTDWERMSIGGRYVESVNKGAKSFSLRIKDLTVADSATYICRASVYQWWVPVPADYYGAGTVLTVN
DL66  TRVDQTPRTATKETGESLTINCVLTDTYALSSTSWFRKNPGTTDWERMSIGGRYVESVNKGAKSFSLRIKDLTVADSATYICRASWPYWVETMDDYYGAGTVLTVN
DL67  TRVDQTPRTATKETGESLTINCVLTDTTHQWFTSWFRKNPGTTDWERMSIGGRYVESVNKGAKSFSLRIKDLTVADSATYICRASWYPWDWYQPDYYGAGTVLTVN
DL70  TRVDQTPRTATKETGESLTINCVLTDTWMPADTSWFRKNPGTTDWERMSIGGRYVESVNKGAKSFSLRIKDLTVADSATYICRAQWEAFSWWWKDYYGAGTVLTVN
DL71  TRVDQTPRTATKETGESLTINCVLTDTGYSWFATSWFRKNPGTTDWERMSIGGRYVESVNKGAKSFSLRIKDLTVADSATYICRAVWAWWPIDYYGAGTVLTVN
DL72  TRVDQTPRTATKETGESLTINCVLTDTSYALSSTSWFRKNPGTTDWERMSIGGRYVESVNKGAKSFSLRIKDLTVADSATYICRAWPYWVDFTMDYYGAGTVLTVN
DL73  ASVNQTPRTATKETGESLTINCVLTDTPASSHFTSWFRKNPGTTDWERMSIGGRYVESVNKGAKSFSLRIKDLTVADSATYICRAHPFSRVENIMDYYGAGTVLTVN
DL74  TRVDQTPRTATKETGESLTINCVLTDTPQQWFQTSWFRKNPGTTDWERMSIGGRYVESVNKGAKSFSLRIKDLTVADSATYICRANWYKWDDYYGAGTVLTVN
DL75  TRVDQTPRTATKETGESLTINCVLTDTSEFHHFTSWFRKNPGTTDWERMSIGGRYVESVNKGAKSFSLRIKDLTVADSATYICRAPMYRRNTWEEDYYGAGTVLTVN
DL76  TRVDQTPRTATKETGESLTINCVLTDTSEFHHFTSWFRKNPGTTDWERMSIGGRYVESVNKGAKSFSLRIKDLTVADSATYICRAPMYWRNTWEEDYYGAGTVLTVN
DL77  ASVNQTPRTATKETGESLTINCVLTDTVYSWFSTSWFRKNPGTTDWERMSIGGRYVESVNKGAKSFSLRIKDLTVADSATYCCKAPWFEQWWEIMYDGAGTVLTVN
```

Fig. 13
(continued)

| ID | Sequence |
|---|---|
| DL78 | TRVDQTPRTATKETGESLTINCVLTDTNYSLYATSWFRKNPGTTDWERMSIGGRYVESVNKGAKSFSLRIKDLTVADSATYICRAWFPYFISDMWDVYGAGTVLTVN |
| DL79 | TRVDQTPRTATKETGESLTINCVLTDTRYALASTSWFRKNPGTTDWERMSIGGRYVESVNKGAKSFSLRIKDLTVADSATYICRAWHPFTVTNMPDVYGAGTVLTVN |
| DL80 | TRVDQTPRTATKETGESLTINCVLTDTGYALFSTSWFRKNPGTTDWERMSIGGRYVESVNKGAKSFSLRIKDLTVADSATYICRAWIPWVFDMWDVYGAGTVLTVN |
| DL81 | TRVDQTPRTATKETGESLTINCVLTDTDYGLYATSWFRKNPGTTDWERMSIGGRYVESVNKGAKSFSLRIKDLTVADSATYICRAWKPYMVHLWDVYGAGTVLTVN |
| DL82 | TRVDQTPRTATKETGESLTINCVLTDTGYALASTSWFRKNPGTTDWERMSIGGRYVESVNKGAKSFSLRIKDLTVADSATYICRAWMPFNVRTPGDVYGAGTVLTVN |
| DL83 | TRVDQTPRTATKETGESLTINCVLTDTDYSLFSTSWFRKNPGTTDWERMSIGGRYVESVNKGAKSFSLRIKDLTVADSATYICRAWMPYTVDSSDVYGAGTVLTVN |
| DL84 | TRVDQTPRTATKETGESLTINCVLTDTKYALFSTSWFRKNPGTTDWERMSIGGRYVESVNKGAKSFSLRIKDLTVADSATYICRAWQPYEVVHMWDVYGAGTVLTVN |
| DL85 | TRVDQTPRTATKETGESLTINCVLTDTRYALFATSWFRKNPGTTDWERMSIGGRYVESVNKGAKSFSLRIKDLTVADSATYCKAVYAMPKWYDGAGTVLTVN |
| DL86 | TRVDQTPRTATKETGESLTINCVLTDTGYGLFSTSWFRKNPGTTDWERMSIGGRYVESVNKGAKSFSLRIKDLTVADSATYICRAWGWWWKPQDVYGAGTVLTVN |
| DL87 | ASVNQTPRTATKETGESLTINCVLTDTWMPWLFTSWFRKNPGTTDWERMSIGGRYVESVNKGAKSFSLRIKDLTVADSATYICRAWPYTAWYDVYGAGTVLTVN |
| DL88 | ASVNQTPRTATKETGESLTINCVLTDTKYLYSTSWFRKNPGTTDWERMSIGGRYVESVNKGAKSFSLRIKDLTVADSATYICRAWTSFEEQVKDVYGAGTVLTVN |
| DL89 | TRVDQTPRTATKEETGESLTINCVLTDTSYALSATSWFRKNPGTTDWERMSIGGRYVESVNKGAKSFSLRIKDLTVADSATYICRAAWPFMIEETTDVYGAGTVLTVN |

```
HS1  TRVDQTPRTATKETGESLTINCVLIDFSYGLFSTSWFRKNPGTTDWERMSIGGRYVESVNKGAKSFSLRIKDLTVADSATYYCKAMGNHEWDIWWWWYDGAGTVLTVN
HS2  TRVDQTPRTATKETGESLTINCVLIDFEYGLSATSWFRKNPGTTDWERMSIGGRYVESVNKGAKSFSLRIKDLTVADSATYYCKARRMGHGRLMYDGAGTVLTVN
HS3  ASVNQTPRTATKETGESLTINCVLIDFSYALSSTSWFRKNPGTTDWERMSIGGRYVESVNKGAKSFSLRIKDLTVADSATYYCRAIDDPVWIEWLWDVYGAGTVLTVN
```

Fig. 15(a)

```
RG1  TRVDQTPRTATKETGESLTINCVLIDFSYGLFATSWFRKNPGTTDWERMSIGGRYVESVNKGAKSFSLRIKDLTVADSATYYCKARAPKRPIHGKLIVPWDGAGTVLTVN
RG2  TRVDQTPRTATKETGESLTINCVLIDFTVGLYSTSWFRKNPGTTDWERMSIGGRYVESVNKGAKSFSLRIKDLTVADSATYYCKAYVIRALPAWWDGAGTVLTVN
RG3  TRVDQTPRTATKETGESLTINCVLIDFDYSLFATSWFRKNPGTTDWERMSIGGRYVESVNKGAKSFSLRIKDLTVADSATYYCKALVQWIKWWVVWDGAGTVLTVN
RG4  TRVDQTPRTATKETGESLTINCVLIDFSIGLYSTSWFRKNPGTTDWERMSIGGRYVESVNKGAKSFSLRIKDLTVADSATYYCKAVFVVHGTETIATGVYDGAGTVLTVN
RG5  TRVDQTPRTATKETGESLTINCVLIDFGYSWYSTSWFRKNPGTTDWERMSIGGRYVESVNKGAKSFSLRIKDLTVADSATYYCRARQEAVWLRQEEDVYGAGTVLTVN
RG6  TRVDQTPRTATKETGESLTINCVLIDFLSQTWSWFRKNPGTTDWERMSIGGRYVESVNKGAKSFSLRIKDLTVADSATYYCRA
```

Fig. 15(b)

```
04E02  TRVDQTPRTATKETGESLTINCVLIDTKNLWQPTSWFRKNPGTTDWERMSIGGRYVESVNKGAKSFSLRIKDLTVADSATYYCKAPMQSSWVHWYDGAGTVLTVN
04E03  ASVNQTPRTATKETGESLTINCVLIDTTFPHMSTSWFRKNPGTTDWERMSIGGRYVESVNKGAKSFSLRIKDLTVADSATYYCKAKSNERVMDVYGAGTVLTVN
04E08  ASVNQTPRTATKETGESLTINCVVTGAROTWERTYWYRKNPGSSNQERISISGRYVESVNKRTMSFSLRIKDLTVADSATYYCRAVQMSHQQNMHGYGAGTVLTVN
05F02  TRVDQTPRTATKETGESLTINCVLIDTSYSLFSTSWFRKNPGTTDWERMSIGGRYVESVNKGAKSFSLRIKDLTVADSATYYCKAMMIFFYMVYDGAGTVLTVN
01A02  TRVDQTPRTATKETGESLTINCVLIDTDYSLFATSWFRKNPGTTDWERMSIGGRYVESVNKGAKSFSLRIKDLTVADSATYYCRAQMFVHQKQDYYGAGTVLTVN
01E10  TRVDQTPRTATKETGESLTINCVLIDTSYALFSTSWFRKNPGTTDWERMSIGGRYVESVNKGAKSFSLRIKDLTVADSATYYCKAPMWEKFVQSWYDGAGTVLTVN
```

Fig. 16

| Source | CDR1 | CDR3 |
|---|---|---|
| 2V | SYGLYS | QSLAISTRSYWY |
| 5V | SYAWSS | YRMESIAGRGYDV |
| | | |
| A1 | GYGWFA | DMWPKNTKYSPDV |
| CC3 | EYGLFS | LGWWPPAFPHWY |
| AG2 | RYALYS | NEMMPPMDV |
| AG12 | SYGWFS | QAAIPDFPRYV |
| C4 | GYGLFS | LGWIPPEFPHWY |
| B3 | EYALFS | HVDPLAWLDV |
| B5 | WQHWTH | YHMLDGWDV |
| C2 | SYGLYS | KHFSQLQPFLNDV |
| C11 | KYALFS | NWLMHPMDV |
| D1 | GYALFA | AKETFAHVYPWY |
| E1 | YPHWWQW | RAHRKEQWRDV |
| E6 | TPHWWRW | NQPGLSPHDV |
| E10 | GYAWFS | SVAIPQWPRDV |
| F10 | DYALFS | NEMMKPYDV |
| G1 | WPAWSN | YHKQYGWDV |
| G2 | EYGWFA | YWHYVFMDV |
| H3 | FPIWSH | WEMLVGWDV |
| AA1 | KYALFA | NESMKPMDV |
| BF3 | GYGWFA | DVWPHSVMDDPDV |
| CF1 | DYGLYA | FQLGFLGWY |
| AE5 | VQWWIP | PMFPYVSNVWRDV |
| AF3 | WPTFDH | FHRVVGWDV |
| CA1 | WQHWTH | WHGRVGWDV |
| DA4 | GYSWFA | KIAIPSFPYDV |
| DA6 | KYALFA | NEWMLPFDV |
| DC8 | SYGLYS | KHFSQLQPFLNDV |
| DE5 | GYGLFS | IWSSRPFWWEWY |

Fig. 17

| | | |
|---|---|---|
| DL1 | RYALSA | ADWWTAFDV |
| DL2 | WSVWYT | AFPNWWFWYEPDV |
| DL3 | PSHEFF | AHKLSXGFDDV |
| DL4 | TPQWWT | ALWWSWWPYDV |
| DL5 | RYGWYS | ANGFQDSFADV |
| DL6 | DYGWYS | ANGLARSMADV |
| DL7 | NYGWYS | ANGWARSYEDV |
| DL8 | GYALFS | AWFPYWVQNMMDV |
| DL9 | GYALYS | AWIPYLVRDMRDV |
| DL10 | RYALFA | AWQPYNVDSIWDV |
| DL11 | RYALFA | AWQPYNVDSIWDV |
| DL12 | SYGLSA | AWVPYSVDSMWDV |
| DL13 | DYALSS | AWWPNWVSNSWDV |
| DL14 | FIPWLH | DKAWEVENWAIKHWWY |
| DL15 | GYSWFS | DWNWWWADKMEDV |
| DL16 | NYGWYA | DYWWNPKDV |
| DL17 | DHYWVA | EFHPQGGWSSQDV |
| DL18 | WWSWWA | ENYWDSWFWAPDV |
| DL19 | GYSLFS | EQWSWMSWWPWDV |
| DL20 | NYGWYS | ESFVHIWTWY |
| DL21 | RYALFA | ETWTWWWPLMEDV |
| DL22 | GYAWYS | EVWQWWIPWKNDV |
| DL23 | NYSWFA | GHKYATGYXDV |

Fig. 17
(continued)

| Source | CDR1 | CDR3 |
|---|---|---|
| DL24 | NYSWFA | GHKYAXGCPDV |
| DL25 | GYSWFS | GMFWAWWPWYQDV |
| DL26 | NYGLFS | GTWWFWPLLDV |
| DL27 | WWSWWD | GVLPWSPWGYWDV |
| DL28 | WHPWWV | GWMVSWPFYDV |
| DL29 | WWWWHQ | HSSIWGWREDV |
| DL30 | NYALSA | HSYVWWWGYYTDV |
| DL31 | DATWFH | IWWPSAYYNWADV |
| DL32 | WWPWYT | LGTWNPWWPDV |
| DL33 | GYAWFA | MHPWWPFSHWWDV |
| DL34 | ESPWWY | MQWWWWQVYDV |
| DL35 | GYGLSA | NVFHWWAWWQHDV |
| DL36 | RYSLYS | PFAGMATYADV |
| DL37 | SYGLSA | PFPSPTSIWDV |
| DL38 | SYALYS | PHEGQTHYADV |
| DL39 | RYALYS | PHEKQSHYEDV |
| DL40 | YQMWGR | PHLQQSTPMDV |
| DL41 | KYSLFS | PHRGQRSFEDV |
| DL42 | NYSLYS | PHSNMSTYSDV |
| DL43 | LASMGL | PHSSMSHYNDV |
| DL44 | LTPSGS | PHTLAKTYSDV |
| DL45 | EEVFGK | PLHGVANMWDV |
| DL46 | EQVFGK | PLRHVAHMWDV |
| DL47 | EQVFGK | PLRHVANMWDV |
| DL48 | KYGLAS | PPDFFQESQNWDV |
| DL49 | MSIPEA | PTAYQHSIWDV |
| DL50 | RYALYS | PYAGMQSYSDV |
| DL51 | EYGWFS | PYHDATGMQDV |

Fig. 17
(continued)

| | | |
|---|---|---|
| DL52 | ETMSGR | PYTEARNIWDV |
| DL53 | EYAWFS | QSVSWLFPWRSDV |
| DL54 | GYALFS | RKQHWYWWWGDDV |
| DL55 | NYPLYS | RTCNYVADY |
| DL56 | PFWQHR | SDGWAHAFDDV |
| DL57 | CDVCPG | SHRVRSTYEDV |
| DL58 | WYWWWK | SLFPLQWMTDV |
| DL59 | SYALYA | SLTWPFKWWAPDV |
| DL60 | SYAWFS | SLWDWWWPEDL |
| DL61 | EYGWYA | SNGYQQAWQDV |
| DL62 | WLPWWQ | SSPWWGWGWDV |
| DL63 | GYAWFS | SVPTTWWWYGNDV |
| DL64 | GYAWYA | SVWWWTWPMDV |
| DL65 | SYALYA | SVYQWWWPVPADV |
| DL66 | GYALSS | SWWPYWVETMDDV |
| DL67 | THQWVE | SWYWPWDWYQPDV |
| DL70 | WMPWDT | TQWEAFSWWWKDV |
| DL71 | GYSWFA | TVWAWMWPIDV |
| DL72 | SYALSS | TWTPYWVDTIWDV |
| DL73 | FASSHH | VHPFSRVENIWDV |
| DL74 | PQQWFQ | VNWYKWDDV |
| DL75 | SEFHHH | VPMYRRNTWEEDV |
| DL76 | SEFHHH | VPMYWRNTWEEDV |
| DL77 | NYSWFS | VPWFEQWWEIWY |
| DL78 | NYSLYA | VWFPYFISDMWDV |
| DL79 | RYALAS | VWHPFTVTNMPDV |
| DL80 | GYALFS | VWIPWWVFDMWDV |
| DL81 | DYGLYA | VWKPYMVVHLWDV |
| DL82 | GYALAS | VWMPFMVRTPGDV |
| DL83 | DYSLFS | VWMPYTVVDSSDV |

Fig. 17
(continued)

| Source | CDR1 | CDR3 |
|---|---|---|
| DL84 | KYALFS | VWQPYEVVHMWDV |
| DL85 | RYALFA | VYAMPKWY |
| DL86 | GYGLFS | WGWWWWWPQDV |
| DL87 | WWPWLT | WVPYWTAWYDV |
| DL88 | KYLYST | WTSFEEQVKDV |
| DL89 | SYALSA | AWWPFMIEETTDV |
| HS1 | SYGLFS | MGNHEWDIWWWWW |
| HS2 | EYGLSA | RRMGHGRLW |
| HS3 | SYALSS | TIDPVWIEWLWDV |
| RG1 | SYGLFA | RAPKRPWHGKLTVPWY |
| RG2 | NYGLYS | YVIYRALPAWWY |
| RG3 | DYSLFA | LVQWIKWWVVWY |
| RG4 | SYGLYS | VFVVHKGTETIATGW |
| RG5 | GYSWYS | NDVTKHGDV |
| RG6 | ISQTWV | RQHAVWLRQEFDV |
| 4E02 | KNLWQP | FMQSSWVHWYD |
| 4E03 | FPHWST | KSNIRVMDV |
| 4E08 | RQTWER | VGMSHQQWMHGV |
| 5F02 | SYSLFS | MMWIFFYMWY |
| 1A02 | DYSLFA | QMWYWHQKQDV |
| 1E10 | SYALFS | PMPWGKFVQSWY |

Fig. 17
(continued)

SEQUENCE LISTING

```
<160> NUMBER OF SEQ ID NOS: 470

<210> SEQ ID NO 1
<211> LENGTH: 27
<212> TYPE: PRT
<213> ORGANISM: Artificial sequence
<220> FEATURE:
<223> OTHER INFORMATION: Synthetic sequence: A in Formula II of PCT/
      EP2014/058251
<220> FEATURE:
<221> NAME/KEY: VARIANT
<222> LOCATION: (24)..(27)
<223> OTHER INFORMATION: In an embodiment, Xaa at location 24 is Leu and
      Xaa Xaa at location 26-27 is Asp Thr
<220> FEATURE:
<221> NAME/KEY: VARIANT
<222> LOCATION: (24)..(27)
<223> OTHER INFORMATION: In an embodiment, Xaa at location 24 is Val and
      Xaa Xaa at location 26-27 is Gly Ala

<400> SEQUENCE: 1

Thr Arg Val Asp Gln Thr Pro Arg Thr Ala Thr Lys Glu Thr Gly Glu
1               5                   10                  15

Ser Leu Thr Ile Asn Cys Val Xaa Thr Xaa Xaa
            20                  25

<210> SEQ ID NO 2
<211> LENGTH: 52
<212> TYPE: PRT
<213> ORGANISM: Artificial sequence
<220> FEATURE:
<223> OTHER INFORMATION: Synthetic sequence: B in Formula II of PCT/
      EP2014/058251
<220> FEATURE:
<221> NAME/KEY: VARIANT
<222> LOCATION: (49)..(51)
<223> OTHER INFORMATION: In an embodiment, Xaa at location 49 is Tyr and
      Xaa at location 51 is Lys
<220> FEATURE:
<221> NAME/KEY: VARIANT
<222> LOCATION: (49)..(51)
<223> OTHER INFORMATION: In an embodiment, Xaa at location 49 is Ile and
      Xaa at location 51 is Arg

<400> SEQUENCE: 2

Thr Ser Trp Phe Arg Lys Asn Pro Gly Thr Thr Asp Trp Glu Arg Met
1               5                   10                  15

Ser Ile Gly Gly Arg Tyr Val Glu Ser Val Asn Lys Gly Ala Lys Ser
            20                  25                  30

Phe Ser Leu Arg Ile Lys Asp Leu Thr Val Ala Asp Ser Ala Thr Tyr
```

```
                    35                  40                  45
Xaa Cys Xaa Ala
        50

<210> SEQ ID NO 3
<211> LENGTH: 10
<212> TYPE: PRT
<213> ORGANISM: Artificial sequence
<220> FEATURE:
<223> OTHER INFORMATION: Synthetic sequence: C in Formula II of PCT/
      EP2014/058251

<400> SEQUENCE: 3

Asp Gly Ala Gly Thr Val Leu Thr Val Asn
1               5                   10

<210> SEQ ID NO 4
<211> LENGTH: 27
<212> TYPE: PRT
<213> ORGANISM: Artificial sequence
<220> FEATURE:
<223> OTHER INFORMATION: Synthetic sequence: A in Formula II of PCT/
      EP2014/058251
<220> FEATURE:
<221> NAME/KEY: VARIANT
<222> LOCATION: (24)..(27)
<223> OTHER INFORMATION: In an embodiment, Xaa at location 24 is Leu and
      Xaa Xaa at location 26-27 is Asp Thr
<220> FEATURE:
<221> NAME/KEY: VARIANT
<222> LOCATION: (24)..(27)
<223> OTHER INFORMATION: In an embodiment, Xaa at location 24 is Val and
      Xaa Xaa at location 26-27 is Gly Ala

<400> SEQUENCE: 4

Ala Ser Val Asn Gln Thr Pro Arg Thr Ala Thr Lys Glu Thr Gly Glu
1               5                   10                  15

Ser Leu Thr Ile Asn Cys Val Xaa Thr Xaa Xaa
            20                  25

<210> SEQ ID NO 5
<211> LENGTH: 52
<212> TYPE: PRT
<213> ORGANISM: Artificial sequence
<220> FEATURE:
<223> OTHER INFORMATION: Synthetic sequence: B in Formula II of PCT/
      EP2014/058251
<220> FEATURE:
<221> NAME/KEY: VARIANT
<222> LOCATION: (49)..(51)
<223> OTHER INFORMATION: In an embodiment, Xaa at location 49 is Tyr and
      Xaa at location 51 is Lys
<220> FEATURE:
<221> NAME/KEY: VARIANT
<222> LOCATION: (49)..(51)
<223> OTHER INFORMATION: In an embodiment, Xaa at location 49 is Ile and
      Xaa at location 51 is Arg

<400> SEQUENCE: 5

Thr Tyr Trp Tyr Arg Lys Asn Pro Gly Ser Ser Asn Gln Glu Arg Ile
1               5                   10                  15

Ser Ile Ser Gly Arg Tyr Val Glu Ser Val Asn Lys Arg Thr Met Ser
            20                  25                  30

Phe Ser Leu Arg Ile Lys Asp Leu Thr Val Ala Asp Ser Ala Thr Tyr
        35                  40                  45

Xaa Cys Xaa Ala
    50
```

<210> SEQ ID NO 6
<211> LENGTH: 10
<212> TYPE: PRT
<213> ORGANISM: Artificial sequence
<220> FEATURE:
<223> OTHER INFORMATION: Synthetic sequence: C in Formula II of PCT/
      EP2014/058251

<400> SEQUENCE: 6

```
Tyr Gly Ala Gly Thr Val Leu Thr Val Asn
1               5                   10
```

<210> SEQ ID NO 7
<211> LENGTH: 26
<212> TYPE: PRT
<213> ORGANISM: Artificial sequence
<220> FEATURE:
<223> OTHER INFORMATION: Synthetic sequence: A in Formula II of PCT/
      EP2014/058251

<400> SEQUENCE: 7

```
Ala Arg Val Asp Gln Thr Pro Gln Thr Ile Thr Lys Glu Thr Gly Glu
1               5                   10                  15

Ser Leu Thr Ile Asn Cys Val Leu Arg Asp
            20                  25
```

<210> SEQ ID NO 8
<211> LENGTH: 52
<212> TYPE: PRT
<213> ORGANISM: Artificial sequence
<220> FEATURE:
<223> OTHER INFORMATION: Synthetic sequence: B in Formula II of PCT/
      EP2014/058251
<220> FEATURE:
<221> NAME/KEY: VARIANT
<222> LOCATION: (7)..(8)
<223> OTHER INFORMATION: In an embodiment, Xaa Xaa at location 7-8 is
      Lys Ser
<220> FEATURE:
<221> NAME/KEY: VARIANT
<222> LOCATION: (7)..(8)
<223> OTHER INFORMATION: In an embodiment, Xaa Xaa at location 7-8 is
      Asn Pro

<400> SEQUENCE: 8

```
Thr Tyr Trp Tyr Arg Lys Xaa Xaa Gly Ser Thr Asn Glu Glu Ser Ile
1               5                   10                  15

Ser Lys Gly Gly Arg Tyr Val Glu Thr Val Asn Ser Gly Ser Lys Ser
            20                  25                  30

Phe Ser Leu Arg Ile Lys Asp Leu Thr Val Ala Asp Ser Ala Thr Tyr
        35                  40                  45

Ile Cys Arg Ala
    50
```

<210> SEQ ID NO 9
<211> LENGTH: 321
<212> TYPE: DNA
<213> ORGANISM: Artificial sequence
<220> FEATURE:
<223> OTHER INFORMATION: Synthetic sequence: Nucleotide sequence of
      clone 2V of PCT/EP2014/058251

<400> SEQUENCE: 9

```
acaagagtag accaaacacc aagaacggca acgaaagaga caggagaatc cctgaccatc    60
aactgcgtcc taactgatac cagctatggt ttgtacagca catcctggtt ccggaaaaat   120
```

```
ccgggtacaa cagactggga acgcatgtcg attggcggcc gatatgtcga atcagtcaac    180
aagggagcaa agtcattttc tctgcgaatc aaggacctaa cagttgcaga cagtgccacg    240
tattattgca aagctcaaag cctcgcaatc agtacgcgct cttactggta tgacggagct    300
ggcaccgtgc tgactgtgaa c                                              321
```

<210> SEQ ID NO 10
<211> LENGTH: 107
<212> TYPE: PRT
<213> ORGANISM: Artificial sequence
<220> FEATURE:
<223> OTHER INFORMATION: Synthetic sequence: Amino acid sequence of
      clone 2V of PCT/EP2014/058251

<400> SEQUENCE: 10

```
Thr Arg Val Asp Gln Thr Pro Arg Thr Ala Thr Lys Glu Thr Gly Glu
1               5                   10                  15

Ser Leu Thr Ile Asn Cys Val Leu Thr Asp Thr Ser Tyr Gly Leu Tyr
                20                  25                  30

Ser Thr Ser Trp Phe Arg Lys Asn Pro Gly Thr Thr Asp Trp Glu Arg
            35                  40                  45

Met Ser Ile Gly Gly Arg Tyr Val Glu Ser Val Asn Lys Gly Ala Lys
    50                  55                  60

Ser Phe Ser Leu Arg Ile Lys Asp Leu Thr Val Ala Asp Ser Ala Thr
65                  70                  75                  80

Tyr Tyr Cys Lys Ala Gln Ser Leu Ala Ile Ser Thr Arg Ser Tyr Trp
                85                  90                  95

Tyr Asp Gly Ala Gly Thr Val Leu Thr Val Asn
            100                 105
```

<210> SEQ ID NO 11
<211> LENGTH: 324
<212> TYPE: DNA
<213> ORGANISM: Artificial sequence
<220> FEATURE:
<223> OTHER INFORMATION: Synthetic sequence: Nucleotide sequence of
      clone 5V of PCT/EP2014/058251

<400> SEQUENCE: 11

```
gcaagtgtaa accaaacacc aagaacggca acgaaagaga caggcgaatc cctgaccatc    60
aactgcgttg taactggtgc cagctatgct tggagcagca catactggta ccggaaaaat    120
ccgggttcat caaaccagga gcggatatcg attagcggcc gatatgttga atcagtcaac    180
aagcgaacaa tgtcattttc tctgcgaatc aaggacctaa cagttgcaga cagtgcgacg    240
tatatctgca gagcttatcg gatggagtcc atagctggaa ggggttacga tgtctacgga    300
gctggcaccg tgctgactgt gaac                                           324
```

<210> SEQ ID NO 12
<211> LENGTH: 108
<212> TYPE: PRT
<213> ORGANISM: Artificial sequence
<220> FEATURE:
<223> OTHER INFORMATION: Synthetic sequence: Amino acid sequence of
      clone 5V of PCT/EP2014/058251

<400> SEQUENCE: 12

```
Ala Ser Val Asn Gln Thr Pro Arg Thr Ala Thr Lys Glu Thr Gly Glu
1               5                   10                  15

Ser Leu Thr Ile Asn Cys Val Val Thr Gly Ala Ser Tyr Ala Trp Ser
                20                  25                  30
```

Ser Thr Tyr Trp Tyr Arg Lys Asn Pro Gly Ser Ser Asn Gln Glu Arg
            35                  40                  45

Ile Ser Ile Ser Gly Arg Tyr Val Glu Ser Val Asn Lys Arg Thr Met
     50                  55                  60

Ser Phe Ser Leu Arg Ile Lys Asp Leu Thr Val Ala Asp Ser Ala Thr
 65                 70                  75                  80

Tyr Ile Cys Arg Ala Tyr Arg Met Glu Ser Ile Ala Gly Arg Gly Tyr
                 85                  90                  95

Asp Val Tyr Gly Ala Gly Thr Val Leu Thr Val Asn
            100                 105

<210> SEQ ID NO 13
<211> LENGTH: 27
<212> TYPE: DNA
<213> ORGANISM: Artificial sequence
<220> FEATURE:
<223> OTHER INFORMATION: Synthetic sequence: Primer sequence used in
      preparation of library

<400> SEQUENCE: 13
aacacaatta atggtcaggc tttcacc                                           27

<210> SEQ ID NO 14
<211> LENGTH: 27
<212> TYPE: DNA
<213> ORGANISM: Artificial sequence
<220> FEATURE:
<223> OTHER INFORMATION: Synthetic sequence: Primer sequence used in
      preparation of library

<400> SEQUENCE: 14
ataggttgcg ctatctgcaa cggtcag                                           27

<210> SEQ ID NO 15
<211> LENGTH: 72
<212> TYPE: DNA
<213> ORGANISM: Artificial sequence
<220> FEATURE:
<223> OTHER INFORMATION: Synthetic sequence: Primer sequence used in
      preparation of library

<400> SEQUENCE: 15
ctgaccatta attgtgttct gaccgatacc rrktatgstt kgtwckccac cagctggttt       60
cgtaaaaatc cg                                                           72

<210> SEQ ID NO 16
<211> LENGTH: 72
<212> TYPE: DNA
<213> ORGANISM: Artificial sequence
<220> FEATURE:
<223> OTHER INFORMATION: Synthetic sequence: Primer sequence used in
      preparation of library

<400> SEQUENCE: 16
ctgaccatta attgtgttct gaccgatacc rrktatkctt kgtwckccac cagctggttt       60
cgtaaaaatc cg                                                           72

<210> SEQ ID NO 17
<211> LENGTH: 72
<212> TYPE: DNA
<213> ORGANISM: Artificial sequence
<220> FEATURE:
<223> OTHER INFORMATION: Synthetic sequence: Primer sequence used in preparation of library

<400> SEQUENCE: 17
ctgaccatta attgtgttct gaccgatacc rrktatgstt kgkctkccac cagctggttt     60
cgtaaaaatc cg                                                         72

<210> SEQ ID NO 18
<211> LENGTH: 72
<212> TYPE: DNA
<213> ORGANISM: Artificial sequence
<220> FEATURE:
<223> OTHER INFORMATION: Synthetic sequence: Primer sequence used in
      preparation of library

<400> SEQUENCE: 18
ctgaccatta attgtgttct gaccgatacc trmtrmtrmt ggtrmtrmac cagctggttt     60
cgtaaaaatc cg                                                         72

<210> SEQ ID NO 19
<211> LENGTH: 72
<212> TYPE: DNA
<213> ORGANISM: Artificial sequence
<220> FEATURE:
<223> OTHER INFORMATION: Synthetic sequence: Primer sequence used in
      preparation of library

<400> SEQUENCE: 19
ctgaccatta attgtgttct gaccgatacc trmtrmtrmt rmtrmtrmac cagctggttt     60
cgtaaaaatc cg                                                         72

<210> SEQ ID NO 20
<211> LENGTH: 66
<212> TYPE: DNA
<213> ORGANISM: Artificial sequence
<220> FEATURE:
<223> OTHER INFORMATION: Synthetic sequence: Primer sequence used in
      preparation of library

<400> SEQUENCE: 20
gcaacctatt actgtaaagc atrmtrmtrm trmtrmtrmt ggtatgatgg tgcaggcacc     60
gttctg                                                                66

<210> SEQ ID NO 21
<211> LENGTH: 72
<212> TYPE: DNA
<213> ORGANISM: Artificial sequence
<220> FEATURE:
<223> OTHER INFORMATION: Synthetic sequence: Primer sequence used in
      preparation of library

<400> SEQUENCE: 21
gcaacctatt actgtaaagc atrmtrmtrm trmtrmtrmt rmtrmtggta tgatggtgca     60
ggcaccgttc tg                                                         72

<210> SEQ ID NO 22
<211> LENGTH: 78
<212> TYPE: DNA
<213> ORGANISM: Artificial sequence
<220> FEATURE:
<223> OTHER INFORMATION: Synthetic sequence: Primer sequence used in
      preparation of library

<400> SEQUENCE: 22

```
gcaacctatt actgtaaagc atrmtrmtrm trmtrmtrmt rmtrmtrmtr mtggtatgat    60
ggtgcaggca ccgttctg                                                  78
```

<210> SEQ ID NO 23
<211> LENGTH: 84
<212> TYPE: DNA
<213> ORGANISM: Artificial sequence
<220> FEATURE:
<223> OTHER INFORMATION: Synthetic sequence: Primer sequence used in
      preparation of library

<400> SEQUENCE: 23

```
gcaacctatt actgtaaagc atrmtrmtrm trmtrmtrmt rmtrmtrmtr mtrmtrmtgg    60
tatgatggtg caggcaccgt tctg                                           84
```

<210> SEQ ID NO 24
<211> LENGTH: 90
<212> TYPE: DNA
<213> ORGANISM: Artificial sequence
<220> FEATURE:
<223> OTHER INFORMATION: Synthetic sequence: Primer sequence used in
      preparation of library

<400> SEQUENCE: 24

```
gcaacctatt actgtaaagc atrmtrmtrm trmtrmtrmt rmtrmtrmtr mtrmtrmtrm    60
trmtggtatg atggtgcagg caccgttctg                                     90
```

<210> SEQ ID NO 25
<211> LENGTH: 72
<212> TYPE: DNA
<213> ORGANISM: Artificial sequence
<220> FEATURE:
<223> OTHER INFORMATION: Synthetic sequence: Primer sequence used in
      preparation of library

<400> SEQUENCE: 25

```
ctgaccatta attgtgttgt taccggtgca rrktatgstt kgtwckccac ctattggtat    60
cgtaaaaatc cg                                                        72
```

<210> SEQ ID NO 26
<211> LENGTH: 72
<212> TYPE: DNA
<213> ORGANISM: Artificial sequence
<220> FEATURE:
<223> OTHER INFORMATION: Synthetic sequence: Primer sequence used in
      preparation of library

<400> SEQUENCE: 26

```
ctgaccatta attgtgttgt taccggtgca rrktatkctt kgtwckccac ctattggtat    60
cgtaaaaatc cg                                                        72
```

<210> SEQ ID NO 27
<211> LENGTH: 72
<212> TYPE: DNA
<213> ORGANISM: Artificial sequence
<220> FEATURE:
<223> OTHER INFORMATION: Synthetic sequence: Primer sequence used in
      preparation of library

<400> SEQUENCE: 27

```
ctgaccatta attgtgttgt taccggtgca rrktatgstt kgkctkccac ctattggtat    60
cgtaaaaatc cg                                                        72
```

<210> SEQ ID NO 28
<211> LENGTH: 72
<212> TYPE: DNA
<213> ORGANISM: Artificial sequence
<220> FEATURE:
<223> OTHER INFORMATION: Synthetic sequence: Primer sequence used in
      preparation of library

<400> SEQUENCE: 28
ctgaccatta attgtgttgt taccggtgca trmtrmtrmt ggtrmtrmac ctattggtat    60
cgtaaaaatc cg                                                       72

<210> SEQ ID NO 29
<211> LENGTH: 72
<212> TYPE: DNA
<213> ORGANISM: Artificial sequence
<220> FEATURE:
<223> OTHER INFORMATION: Synthetic sequence: Primer sequence used in
      preparation of library

<400> SEQUENCE: 29
ctgaccatta attgtgttgt taccggtgca trmtrmtrmt rmtrmtrmac ctattggtat    60
cgtaaaaatc cg                                                       72

<210> SEQ ID NO 30
<211> LENGTH: 69
<212> TYPE: DNA
<213> ORGANISM: Artificial sequence
<220> FEATURE:
<223> OTHER INFORMATION: Synthetic sequence: Primer sequence used in
      preparation of library

<400> SEQUENCE: 30
gcaacctata tctgtcgtgc ctrmtrmtrm trmtrmtrmt rmgatgttta tggtgcaggc    60
accgttctg                                                           69

<210> SEQ ID NO 31
<211> LENGTH: 75
<212> TYPE: DNA
<213> ORGANISM: Artificial sequence
<220> FEATURE:
<223> OTHER INFORMATION: Synthetic sequence: Primer sequence used in
      preparation of library

<400> SEQUENCE: 31
gcaacctata tctgtcgtgc ctrmtrmtrm trmtrmtrmt rmtrmtrmga tgtttatggt    60
gcaggcaccg ttctg                                                    75

<210> SEQ ID NO 32
<211> LENGTH: 81
<212> TYPE: DNA
<213> ORGANISM: Artificial sequence
<220> FEATURE:
<223> OTHER INFORMATION: Synthetic sequence: Primer sequence used in
      preparation of library

<400> SEQUENCE: 32
gcaacctata tctgtcgtgc ctrmtrmtrm trmtrmtrmt rmtrmtrmtr mtrmgatgtt    60
tatggtgcag gcaccgttct g                                             81

<210> SEQ ID NO 33
<211> LENGTH: 113
<212> TYPE: PRT

```
<213> ORGANISM: Artificial sequence
<220> FEATURE:
<223> OTHER INFORMATION: Synthetic sequence: Library framework
      combination 2V2V2V
<220> FEATURE:
<221> NAME/KEY: VARIANT
<222> LOCATION: (28)..(34)
<223> OTHER INFORMATION: Up to 2 amino acids may be present or absent;
      represents a CDR1 region of 5, 6, or 7 amino acid residues
<220> FEATURE:
<221> NAME/KEY: VARIANT
<222> LOCATION: (87)..(103)
<223> OTHER INFORMATION: Up to 9 amino acids may be present or absent;
      represents a CDR3 region of 8, 9, 10, 11, 12, 13, 14, 15, 16, or
      17 amino acid residues

<400> SEQUENCE: 33

Thr Arg Val Asp Gln Thr Pro Arg Thr Ala Thr Lys Glu Thr Gly Glu
1               5                   10                  15

Ser Leu Thr Ile Asn Cys Val Leu Thr Asp Thr Xaa Xaa Xaa Xaa Xaa
                20                  25                  30

Xaa Xaa Thr Ser Trp Phe Arg Lys Asn Pro Gly Thr Thr Asp Trp Glu
            35                  40                  45

Arg Met Ser Ile Gly Gly Arg Tyr Val Glu Ser Val Asn Lys Gly Ala
        50                  55                  60

Lys Ser Phe Ser Leu Arg Ile Lys Asp Leu Thr Val Ala Asp Ser Ala
65                  70                  75                  80

Thr Tyr Tyr Cys Lys Ala Xaa Xaa Xaa Xaa Xaa Xaa Xaa Xaa Xaa Xaa
                85                  90                  95

Xaa Xaa Xaa Xaa Xaa Xaa Xaa Asp Gly Ala Gly Thr Val Leu Thr Val
            100                 105                 110

Asn

<210> SEQ ID NO 34
<211> LENGTH: 113
<212> TYPE: PRT
<213> ORGANISM: Artificial sequence
<220> FEATURE:
<223> OTHER INFORMATION: Synthetic sequence: Library framework
      combination 2V2V5V
<220> FEATURE:
<221> NAME/KEY: VARIANT
<222> LOCATION: (28)..(34)
<223> OTHER INFORMATION: Up to 2 amino acids may be present or absent;
      represents a CDR1 region of 5, 6, or 7 amino acid residues
<220> FEATURE:
<221> NAME/KEY: VARIANT
<222> LOCATION: (87)..(103)
<223> OTHER INFORMATION: Up to 9 amino acids may be present or absent;
      represents a CDR3 region of 8, 9, 10, 11, 12, 13, 14, 15, 16, or
      17 amino acid residues

<400> SEQUENCE: 34

Thr Arg Val Asp Gln Thr Pro Arg Thr Ala Thr Lys Glu Thr Gly Glu
1               5                   10                  15

Ser Leu Thr Ile Asn Cys Val Leu Thr Asp Thr Xaa Xaa Xaa Xaa Xaa
                20                  25                  30

Xaa Xaa Thr Ser Trp Phe Arg Lys Asn Pro Gly Thr Thr Asp Trp Glu
            35                  40                  45

Arg Met Ser Ile Gly Gly Arg Tyr Val Glu Ser Val Asn Lys Gly Ala
        50                  55                  60

Lys Ser Phe Ser Leu Arg Ile Lys Asp Leu Thr Val Ala Asp Ser Ala
65                  70                  75                  80

Thr Tyr Ile Cys Arg Ala Xaa Xaa Xaa Xaa Xaa Xaa Xaa Xaa Xaa Xaa
```

```
                    85                  90                  95
Xaa Xaa Xaa Xaa Xaa Xaa Xaa Tyr Gly Ala Gly Thr Val Leu Thr Val
                100                 105                 110

Asn

<210> SEQ ID NO 35
<211> LENGTH: 113
<212> TYPE: PRT
<213> ORGANISM: Artificial sequence
<220> FEATURE:
<223> OTHER INFORMATION: Synthetic sequence: Library framework
      combination 2V5V2V
<220> FEATURE:
<221> NAME/KEY: VARIANT
<222> LOCATION: (28)..(34)
<223> OTHER INFORMATION: Up to 2 amino acids may be present or absent;
      represents a CDR1 region of 5, 6, or 7 amino acid residues
<220> FEATURE:
<221> NAME/KEY: VARIANT
<222> LOCATION: (87)..(103)
<223> OTHER INFORMATION: Up to 9 amino acids may be present or absent;
      represents a CDR3 region of 8, 9, 10, 11, 12, 13, 14, 15, 16, or
      17 amino acid residues

<400> SEQUENCE: 35

Thr Arg Val Asp Gln Thr Pro Arg Thr Ala Thr Lys Glu Thr Gly Glu
1               5                   10                  15

Ser Leu Thr Ile Asn Cys Val Val Thr Gly Ala Xaa Xaa Xaa Xaa Xaa
                20                  25                  30

Xaa Xaa Thr Tyr Trp Tyr Arg Lys Asn Pro Gly Ser Ser Asn Gln Glu
            35                  40                  45

Arg Ile Ser Ile Ser Gly Arg Tyr Val Glu Ser Val Asn Lys Arg Thr
50                  55                  60

Met Ser Phe Ser Leu Arg Ile Lys Asp Leu Thr Val Ala Asp Ser Ala
65                  70                  75                  80

Thr Tyr Tyr Cys Lys Ala Xaa Xaa Xaa Xaa Xaa Xaa Xaa Xaa Xaa Xaa
                85                  90                  95

Xaa Xaa Xaa Xaa Xaa Xaa Xaa Asp Gly Ala Gly Thr Val Leu Thr Val
                100                 105                 110

Asn

<210> SEQ ID NO 36
<211> LENGTH: 113
<212> TYPE: PRT
<213> ORGANISM: Artificial sequence
<220> FEATURE:
<223> OTHER INFORMATION: Synthetic sequence: Library framework
      combination 2V5V5V
<220> FEATURE:
<221> NAME/KEY: VARIANT
<222> LOCATION: (28)..(34)
<223> OTHER INFORMATION: Up to 2 amino acids may be present or absent;
      represents a CDR1 region of 5, 6, or 7 amino acid residues
<220> FEATURE:
<221> NAME/KEY: VARIANT
<222> LOCATION: (87)..(103)
<223> OTHER INFORMATION: Up to 9 amino acids may be present or absent;
      represents a CDR3 region of 8, 9, 10, 11, 12, 13, 14, 15, 16, or
      17 amino acid residues

<400> SEQUENCE: 36

Thr Arg Val Asp Gln Thr Pro Arg Thr Ala Thr Lys Glu Thr Gly Glu
1               5                   10                  15

Ser Leu Thr Ile Asn Cys Val Val Thr Gly Ala Xaa Xaa Xaa Xaa Xaa
                20                  25                  30
```

```
Xaa Xaa Thr Tyr Trp Tyr Arg Lys Asn Pro Gly Ser Ser Asn Gln Glu
        35                  40                  45

Arg Ile Ser Ile Ser Gly Arg Tyr Val Glu Ser Val Asn Lys Arg Thr
 50                  55                  60

Met Ser Phe Ser Leu Arg Ile Lys Asp Leu Thr Val Ala Asp Ser Ala
 65                  70                  75                  80

Thr Tyr Ile Cys Arg Ala Xaa Xaa Xaa Xaa Xaa Xaa Xaa Xaa Xaa
                 85                  90                  95

Xaa Xaa Xaa Xaa Xaa Xaa Xaa Tyr Gly Ala Gly Thr Val Leu Thr Val
            100                 105                 110

Asn
```

<210> SEQ ID NO 37
<211> LENGTH: 113
<212> TYPE: PRT
<213> ORGANISM: Artificial sequence
<220> FEATURE:
<223> OTHER INFORMATION: Synthetic sequence: Library framework
      combination 5V5V5V
<220> FEATURE:
<221> NAME/KEY: VARIANT
<222> LOCATION: (28)..(34)
<223> OTHER INFORMATION: Up to 2 amino acids may be present or absent;
      represents a CDR1 region of 5, 6, or 7 amino acid residues
<220> FEATURE:
<221> NAME/KEY: VARIANT
<222> LOCATION: (87)..(103)
<223> OTHER INFORMATION: Up to 9 amino acids may be present or absent;
      represents a CDR3 region of 8, 9, 10, 11, 12, 13, 14, 15, 16, or
      17 amino acid residues

<400> SEQUENCE: 37

```
Ala Ser Val Asn Gln Thr Pro Arg Thr Ala Thr Lys Glu Thr Gly Glu
 1               5                  10                  15

Ser Leu Thr Ile Asn Cys Val Val Thr Gly Ala Xaa Xaa Xaa Xaa Xaa
             20                  25                  30

Xaa Xaa Thr Tyr Trp Tyr Arg Lys Asn Pro Gly Ser Ser Asn Gln Glu
        35                  40                  45

Arg Ile Ser Ile Ser Gly Arg Tyr Val Glu Ser Val Asn Lys Arg Thr
 50                  55                  60

Met Ser Phe Ser Leu Arg Ile Lys Asp Leu Thr Val Ala Asp Ser Ala
 65                  70                  75                  80

Thr Tyr Ile Cys Arg Ala Xaa Xaa Xaa Xaa Xaa Xaa Xaa Xaa Xaa
                 85                  90                  95

Xaa Xaa Xaa Xaa Xaa Xaa Xaa Tyr Gly Ala Gly Thr Val Leu Thr Val
            100                 105                 110

Asn
```

<210> SEQ ID NO 38
<211> LENGTH: 113
<212> TYPE: PRT
<213> ORGANISM: Artificial sequence
<220> FEATURE:
<223> OTHER INFORMATION: Synthetic sequence: Library framework
      combination 5V5V2V
<220> FEATURE:
<221> NAME/KEY: VARIANT
<222> LOCATION: (28)..(34)
<223> OTHER INFORMATION: Up to 2 amino acids may be present or absent;
      represents a CDR1 region of 5, 6, or 7 amino acid residues
<220> FEATURE:
<221> NAME/KEY: VARIANT
<222> LOCATION: (87)..(103)

<223> OTHER INFORMATION: Up to 9 amino acids may be present or absent;
      represents a CDR3 region of 8, 9, 10, 11, 12, 13, 14, 15, 16, or
      17 amino acid residues

<400> SEQUENCE: 38

Ala Ser Val Asn Gln Thr Pro Arg Thr Ala Thr Lys Glu Thr Gly Glu
1               5                   10                  15

Ser Leu Thr Ile Asn Cys Val Val Thr Gly Ala Xaa Xaa Xaa Xaa Xaa
            20                  25                  30

Xaa Xaa Thr Tyr Trp Tyr Arg Lys Asn Pro Gly Ser Ser Asn Gln Glu
        35                  40                  45

Arg Ile Ser Ile Ser Gly Arg Tyr Val Glu Ser Val Asn Lys Arg Thr
50                  55                  60

Met Ser Phe Ser Leu Arg Ile Lys Asp Leu Thr Val Ala Asp Ser Ala
65                  70                  75                  80

Thr Tyr Tyr Cys Lys Ala Xaa Xaa Xaa Xaa Xaa Xaa Xaa Xaa Xaa Xaa
                85                  90                  95

Xaa Xaa Xaa Xaa Xaa Xaa Xaa Asp Gly Ala Gly Thr Val Leu Thr Val
            100                 105                 110

Asn

<210> SEQ ID NO 39
<211> LENGTH: 113
<212> TYPE: PRT
<213> ORGANISM: Artificial sequence
<220> FEATURE:
<223> OTHER INFORMATION: Synthetic sequence: Library framework
      combination 5V2V5V
<220> FEATURE:
<221> NAME/KEY: VARIANT
<222> LOCATION: (28)..(34)
<223> OTHER INFORMATION: Up to 2 amino acids may be present or absent;
      represents a CDR1 region of 5, 6, or 7 amino acid residues
<220> FEATURE:
<221> NAME/KEY: VARIANT
<222> LOCATION: (87)..(103)
<223> OTHER INFORMATION: Up to 9 amino acids may be present or absent;
      represents a CDR3 region of 8, 9, 10, 11, 12, 13, 14, 15, 16, or
      17 amino acid residues

<400> SEQUENCE: 39

Ala Ser Val Asn Gln Thr Pro Arg Thr Ala Thr Lys Glu Thr Gly Glu
1               5                   10                  15

Ser Leu Thr Ile Asn Cys Val Leu Thr Asp Thr Xaa Xaa Xaa Xaa Xaa
            20                  25                  30

Xaa Xaa Thr Ser Trp Phe Arg Lys Asn Pro Gly Thr Thr Asp Trp Glu
        35                  40                  45

Arg Met Ser Ile Gly Gly Arg Tyr Val Glu Ser Val Asn Lys Gly Ala
50                  55                  60

Lys Ser Phe Ser Leu Arg Ile Lys Asp Leu Thr Val Ala Asp Ser Ala
65                  70                  75                  80

Thr Tyr Ile Cys Arg Ala Xaa Xaa Xaa Xaa Xaa Xaa Xaa Xaa Xaa Xaa
                85                  90                  95

Xaa Xaa Xaa Xaa Xaa Xaa Xaa Tyr Gly Ala Gly Thr Val Leu Thr Val
            100                 105                 110

Asn

<210> SEQ ID NO 40
<211> LENGTH: 113
<212> TYPE: PRT
<213> ORGANISM: Artificial sequence

```
<220> FEATURE:
<223> OTHER INFORMATION: Synthetic sequence: Library framework
      combination 5V2V2V
<220> FEATURE:
<221> NAME/KEY: VARIANT
<222> LOCATION: (28)..(34)
<223> OTHER INFORMATION: Up to 2 amino acids may be present or absent;
      represents a CDR1 region of 5, 6, or 7 amino acid residues
<220> FEATURE:
<221> NAME/KEY: VARIANT
<222> LOCATION: (87)..(103)
<223> OTHER INFORMATION: Up to 9 amino acids may be present or absent;
      represents a CDR3 region of 8, 9, 10, 11, 12, 13, 14, 15, 16, or
      17 amino acid residues

<400> SEQUENCE: 40

Ala Ser Val Asn Gln Thr Pro Arg Thr Ala Thr Lys Glu Thr Gly Glu
 1               5                  10                  15

Ser Leu Thr Ile Asn Cys Val Leu Thr Asp Thr Xaa Xaa Xaa Xaa Xaa
                20                  25                  30

Xaa Xaa Thr Ser Trp Phe Arg Lys Asn Pro Gly Thr Thr Asp Trp Glu
             35                  40                  45

Arg Met Ser Ile Gly Gly Arg Tyr Val Glu Ser Val Asn Lys Gly Ala
 50                  55                  60

Lys Ser Phe Ser Leu Arg Ile Lys Asp Leu Thr Val Ala Asp Ser Ala
 65                  70                  75                  80

Thr Tyr Tyr Cys Lys Ala Xaa Xaa Xaa Xaa Xaa Xaa Xaa Xaa Xaa Xaa
                 85                  90                  95

Xaa Xaa Xaa Xaa Xaa Xaa Xaa Asp Gly Ala Gly Thr Val Leu Thr Val
            100                 105                 110

Asn

<210> SEQ ID NO 41
<211> LENGTH: 108
<212> TYPE: PRT
<213> ORGANISM: Artificial sequence
<220> FEATURE:
<223> OTHER INFORMATION: Synthetic sequence: Anti-mICOSL antigen
      specific antigen binding molecule (VNAR)

<400> SEQUENCE: 41

Ala Ser Val Asn Gln Thr Pro Arg Thr Ala Thr Lys Glu Thr Gly Glu
 1               5                  10                  15

Ser Leu Thr Ile Asn Cys Val Leu Thr Asp Thr Gly Tyr Gly Trp Phe
                20                  25                  30

Ala Thr Ser Trp Phe Arg Lys Asn Pro Gly Thr Thr Asp Trp Glu Arg
             35                  40                  45

Met Ser Ile Gly Gly Arg Tyr Val Glu Ser Val Asn Lys Gly Ala Lys
 50                  55                  60

Ser Phe Ser Leu Arg Ile Lys Asp Leu Thr Val Ala Asp Ser Ala Thr
 65                  70                  75                  80

Tyr Ile Cys Arg Ala Asp Met Trp Pro Lys Asn Thr Lys Tyr Ser Pro
                 85                  90                  95

Asp Val Tyr Gly Ala Gly Thr Val Leu Thr Val Asn
            100                 105

<210> SEQ ID NO 42
<211> LENGTH: 107
<212> TYPE: PRT
<213> ORGANISM: Artificial sequence
<220> FEATURE:
<223> OTHER INFORMATION: Synthetic sequence: Anti-mICOSL antigen
``` specific antigen binding molecule (VNAR)

<400> SEQUENCE: 42

Thr Arg Val Asp Gln Thr Pro Arg Thr Ala Thr Lys Glu Thr Gly Glu
1               5                   10                  15

Ser Leu Thr Ile Asn Cys Val Leu Thr Asp Thr Glu Tyr Gly Leu Phe
            20                  25                  30

Ser Thr Ser Trp Phe Arg Lys Asn Pro Gly Thr Thr Asp Trp Glu Arg
        35                  40                  45

Met Ser Ile Gly Gly Arg Tyr Val Glu Ser Val Asn Lys Gly Ala Lys
    50                  55                  60

Ser Phe Ser Leu Arg Ile Lys Asp Leu Thr Val Ala Asp Ser Ala Thr
65                  70                  75                  80

Tyr Tyr Cys Lys Ala Leu Gly Trp Trp Pro Ala Phe Pro His Trp
                85                  90                  95

Tyr Asp Gly Ala Gly Thr Val Leu Thr Val Asn
            100                 105

<210> SEQ ID NO 43
<211> LENGTH: 104
<212> TYPE: PRT
<213> ORGANISM: Artificial sequence
<220> FEATURE:
<223> OTHER INFORMATION: Synthetic sequence: Anti-mICOSL antigen
      specific antigen binding molecule (VNAR)

<400> SEQUENCE: 43

Thr Arg Val Asp Gln Thr Pro Arg Thr Ala Thr Lys Glu Thr Gly Glu
1               5                   10                  15

Ser Leu Thr Ile Asn Cys Val Leu Thr Asp Thr Arg Tyr Ala Leu Tyr
            20                  25                  30

Ser Thr Ser Trp Phe Arg Lys Asn Pro Gly Thr Thr Asp Trp Glu Arg
        35                  40                  45

Met Ser Ile Gly Gly Arg Tyr Val Glu Ser Val Asn Lys Gly Ala Lys
    50                  55                  60

Ser Phe Ser Leu Arg Ile Lys Asp Leu Thr Val Ala Asp Ser Ala Thr
65                  70                  75                  80

Tyr Ile Cys Arg Ala Asn Glu Met Met Pro Pro Met Asp Val Tyr Gly
                85                  90                  95

Ala Gly Thr Val Leu Thr Val Asn
            100

<210> SEQ ID NO 44
<211> LENGTH: 106
<212> TYPE: PRT
<213> ORGANISM: Artificial sequence
<220> FEATURE:
<223> OTHER INFORMATION: Synthetic sequence: Anti-mICOSL antigen
      specific antigen binding molecule (VNAR)

<400> SEQUENCE: 44

Thr Arg Val Asp Gln Thr Pro Arg Thr Ala Thr Lys Glu Thr Gly Glu
1               5                   10                  15

Ser Leu Thr Ile Asn Cys Val Leu Thr Asp Thr Ser Tyr Gly Trp Phe
            20                  25                  30

Ser Thr Ser Trp Phe Arg Lys Asn Pro Gly Thr Thr Asp Trp Glu Arg
        35                  40                  45

Met Ser Ile Gly Gly Arg Tyr Val Glu Ser Val Asn Lys Gly Ala Lys
    50                  55                  60

Ser Phe Ser Leu Arg Ile Lys Asp Leu Thr Val Ala Asp Ser Ala Thr
65                  70                  75                  80

Tyr Ile Cys Arg Ala Gln Ala Ala Ile Pro Asp Phe Pro Arg Tyr Val
                85                  90                  95

Tyr Gly Ala Gly Thr Val Leu Thr Val Asn
            100                 105

<210> SEQ ID NO 45
<211> LENGTH: 107
<212> TYPE: PRT
<213> ORGANISM: Artificial sequence
<220> FEATURE:
<223> OTHER INFORMATION: Synthetic sequence: Anti-mlCOSL antigen
      specific antigen binding molecule (VNAR)

<400> SEQUENCE: 45

Thr Arg Val Asp Gln Thr Pro Arg Thr Ala Thr Lys Glu Thr Gly Glu
1               5                   10                  15

Ser Leu Thr Ile Asn Cys Val Leu Thr Asp Thr Gly Tyr Gly Leu Phe
                20                  25                  30

Ser Thr Ser Trp Phe Arg Lys Asn Pro Gly Thr Thr Asp Trp Glu Arg
            35                  40                  45

Met Ser Ile Gly Gly Arg Tyr Val Glu Ser Val Asn Lys Gly Ala Lys
        50                  55                  60

Ser Phe Ser Leu Arg Ile Lys Asp Leu Thr Val Ala Asp Ser Ala Thr
65                  70                  75                  80

Tyr Tyr Cys Lys Ala Leu Gly Trp Ile Pro Pro Glu Phe Pro His Trp
                85                  90                  95

Tyr Asp Gly Ala Gly Thr Val Leu Thr Val Asn
            100                 105

<210> SEQ ID NO 46
<211> LENGTH: 105
<212> TYPE: PRT
<213> ORGANISM: Artificial sequence
<220> FEATURE:
<223> OTHER INFORMATION: Synthetic sequence: Anti-mlCOSL antigen
      specific antigen binding molecule (VNAR)

<400> SEQUENCE: 46

Ala Ser Val Asn Gln Thr Pro Arg Thr Ala Thr Lys Glu Thr Gly Glu
1               5                   10                  15

Ser Leu Thr Ile Asn Cys Val Leu Thr Asp Thr Glu Tyr Ala Leu Phe
                20                  25                  30

Ser Thr Ser Trp Phe Arg Lys Asn Pro Gly Thr Thr Asp Trp Glu Arg
            35                  40                  45

Met Ser Ile Gly Gly Arg Tyr Val Glu Ser Val Asn Lys Gly Ala Lys
        50                  55                  60

Ser Phe Ser Leu Arg Ile Lys Asp Leu Thr Val Ala Asp Ser Ala Thr
65                  70                  75                  80

Tyr Ile Cys Arg Ala His Val Asp Pro Leu Ala Trp Leu Asp Val Tyr
                85                  90                  95

Gly Ala Gly Thr Val Leu Thr Val Asn
            100                 105

<210> SEQ ID NO 47
<211> LENGTH: 104
<212> TYPE: PRT
<213> ORGANISM: Artificial sequence
<220> FEATURE:
<223> OTHER INFORMATION: Synthetic sequence: Anti-mICOSL antigen
    specific antigen binding molecule (VNAR)

<400> SEQUENCE: 47

Ala Ser Val Asn Gln Thr Pro Arg Thr Ala Thr Lys Glu Thr Gly Glu
1               5                   10                  15

Ser Leu Thr Ile Asn Cys Val Leu Thr Asp Thr Trp Gln His Trp Thr
            20                  25                  30

His Thr Ser Trp Phe Arg Lys Asn Pro Gly Thr Thr Asp Trp Glu Arg
        35                  40                  45

Met Ser Ile Gly Gly Arg Tyr Val Glu Ser Val Asn Lys Gly Ala Lys
    50                  55                  60

Ser Phe Ser Leu Arg Ile Lys Asp Leu Thr Val Ala Asp Ser Ala Thr
65                  70                  75                  80

Tyr Ile Cys Arg Ala Tyr His Met Leu Asp Gly Trp Asp Val Tyr Gly
                85                  90                  95

Ala Gly Thr Val Leu Thr Val Asn
            100

<210> SEQ ID NO 48
<211> LENGTH: 108
<212> TYPE: PRT
<213> ORGANISM: Artificial sequence
<220> FEATURE:
<223> OTHER INFORMATION: Synthetic sequence: Anti-mICOSL antigen
    specific antigen binding molecule (VNAR)

<400> SEQUENCE: 48

Ala Ser Val Asn Gln Thr Pro Arg Thr Ala Thr Lys Glu Thr Gly Glu
1               5                   10                  15

Ser Leu Thr Ile Asn Cys Val Leu Thr Asp Thr Ser Tyr Gly Leu Tyr
            20                  25                  30

Ser Thr Ser Trp Phe Arg Lys Asn Pro Gly Thr Thr Asp Trp Glu Arg
        35                  40                  45

Met Ser Ile Gly Gly Arg Tyr Val Glu Ser Val Asn Lys Gly Ala Lys
    50                  55                  60

Ser Phe Ser Leu Arg Ile Lys Asp Leu Thr Val Ala Asp Ser Ala Thr
65                  70                  75                  80

Tyr Ile Cys Arg Ala Lys His Phe Ser Gln Leu Gln Pro Phe Leu Asn
                85                  90                  95

Asp Val Tyr Gly Ala Gly Thr Val Leu Thr Val Asn
            100                 105

<210> SEQ ID NO 49
<211> LENGTH: 104
<212> TYPE: PRT
<213> ORGANISM: Artificial sequence
<220> FEATURE:
<223> OTHER INFORMATION: Synthetic sequence: Anti-mICOSL antigen
    specific antigen binding molecule (VNAR)

<400> SEQUENCE: 49

Thr Arg Val Asp Gln Thr Pro Arg Thr Ala Thr Lys Glu Thr Gly Glu
1               5                   10                  15

Ser Leu Thr Ile Asn Cys Val Leu Thr Asp Thr Lys Tyr Ala Leu Phe
            20                  25                  30

Ser Thr Ser Trp Phe Arg Lys Asn Pro Gly Thr Thr Asp Trp Glu Arg
        35                  40                  45

-continued

```
Met Ser Ile Gly Gly Arg Tyr Val Glu Ser Val Asn Lys Gly Ala Lys
 50                  55                  60

Ser Phe Ser Leu Arg Ile Lys Asp Leu Thr Val Ala Asp Ser Ala Thr
 65                  70                  75                  80

Tyr Ile Cys Arg Ala Asn Trp Leu Met His Pro Met Asp Val Tyr Gly
                 85                  90                  95

Ala Gly Thr Val Leu Thr Val Asn
                100

<210> SEQ ID NO 50
<211> LENGTH: 107
<212> TYPE: PRT
<213> ORGANISM: Artificial sequence
<220> FEATURE:
<223> OTHER INFORMATION: Synthetic sequence: Anti-mlCOSL antigen
      specific antigen binding molecule (VNAR)

<400> SEQUENCE: 50

Thr Arg Val Asp Gln Thr Pro Arg Thr Ala Thr Lys Glu Thr Gly Glu
 1               5                  10                  15

Ser Leu Thr Ile Asn Cys Val Leu Thr Asp Thr Gly Tyr Ala Leu Phe
                 20                  25                  30

Ala Thr Ser Trp Phe Arg Lys Asn Pro Gly Thr Thr Asp Trp Glu Arg
             35                  40                  45

Met Ser Ile Gly Gly Arg Tyr Val Glu Ser Val Asn Lys Gly Ala Lys
 50                  55                  60

Ser Phe Ser Leu Arg Ile Lys Asp Leu Thr Val Ala Asp Ser Ala Thr
 65                  70                  75                  80

Tyr Tyr Cys Lys Ala Ala Lys Glu Thr Phe Ala His Val Tyr Pro Trp
                 85                  90                  95

Tyr Asp Gly Ala Gly Thr Val Leu Thr Val Asn
                100                 105

<210> SEQ ID NO 51
<211> LENGTH: 107
<212> TYPE: PRT
<213> ORGANISM: Artificial sequence
<220> FEATURE:
<223> OTHER INFORMATION: Synthetic sequence: Anti-mlCOSL antigen
      specific antigen binding molecule (VNAR)

<400> SEQUENCE: 51

Thr Arg Val Asp Gln Thr Pro Arg Thr Ala Thr Lys Glu Thr Gly Glu
 1               5                  10                  15

Ser Leu Thr Ile Asn Cys Val Leu Thr Asp Thr Tyr Pro His Trp Trp
                 20                  25                  30

Gln Trp Thr Ser Trp Phe Arg Lys Asn Pro Gly Thr Thr Asp Trp Glu
             35                  40                  45

Arg Met Ser Ile Gly Gly Arg Tyr Val Glu Ser Val Asn Lys Gly Ala
 50                  55                  60

Lys Ser Phe Ser Leu Arg Ile Lys Asp Leu Thr Val Ala Asp Ser Ala
 65                  70                  75                  80

Thr Tyr Ile Cys Arg Ala Arg Ala His Arg Lys Glu Gln Trp Arg Asp
                 85                  90                  95

Val Tyr Gly Ala Gly Thr Val Leu Thr Val Asn
                100                 105

<210> SEQ ID NO 52
<211> LENGTH: 106
```

```
<212> TYPE: PRT
<213> ORGANISM: Artificial sequence
<220> FEATURE:
<223> OTHER INFORMATION: Synthetic sequence: Anti-mlCOSL antigen
      specific antigen binding molecule (VNAR)

<400> SEQUENCE: 52

Ala Ser Val Asn Gln Thr Pro Arg Thr Ala Thr Lys Glu Thr Gly Glu
1               5                   10                  15

Ser Leu Thr Ile Asn Cys Val Leu Thr Asp Thr Thr Pro His Trp Trp
            20                  25                  30

Arg Trp Thr Ser Trp Phe Arg Lys Asn Pro Gly Thr Thr Asp Trp Glu
        35                  40                  45

Arg Met Ser Ile Gly Gly Arg Tyr Val Glu Ser Val Asn Lys Gly Ala
    50                  55                  60

Lys Ser Phe Ser Leu Arg Ile Lys Asp Leu Thr Val Ala Asp Ser Ala
65                  70                  75                  80

Thr Tyr Ile Cys Arg Ala Asn Gln Pro Gly Leu Ser Pro His Asp Val
                85                  90                  95

Tyr Gly Ala Gly Thr Val Leu Thr Val Asn
            100                 105

<210> SEQ ID NO 53
<211> LENGTH: 106
<212> TYPE: PRT
<213> ORGANISM: Artificial sequence
<220> FEATURE:
<223> OTHER INFORMATION: Synthetic sequence: Anti-mlCOSL antigen
      specific antigen binding molecule (VNAR)

<400> SEQUENCE: 53

Ala Arg Val Asp Gln Thr Pro Arg Thr Ala Thr Lys Glu Thr Gly Glu
1               5                   10                  15

Ser Leu Thr Ile Asn Cys Val Leu Thr Asp Thr Gly Tyr Ala Trp Phe
            20                  25                  30

Ser Thr Ser Trp Phe Arg Lys Asn Pro Gly Thr Thr Asp Trp Glu Arg
        35                  40                  45

Met Ser Ile Gly Gly Arg Tyr Val Glu Ser Val Asn Lys Gly Ala Lys
    50                  55                  60

Ser Phe Ser Leu Arg Ile Lys Asp Leu Thr Val Ala Asp Ser Ala Thr
65                  70                  75                  80

Tyr Ile Cys Arg Ala Ser Val Ala Ile Pro Gln Trp Pro Arg Asp Val
                85                  90                  95

Tyr Gly Ala Gly Thr Val Leu Thr Val Asn
            100                 105

<210> SEQ ID NO 54
<211> LENGTH: 104
<212> TYPE: PRT
<213> ORGANISM: Artificial sequence
<220> FEATURE:
<223> OTHER INFORMATION: Synthetic sequence: Anti-mlCOSL antigen
      specific antigen binding molecule (VNAR)

<400> SEQUENCE: 54

Ala Ser Val Asn Gln Thr Pro Arg Thr Ala Thr Lys Glu Thr Gly Glu
1               5                   10                  15

Ser Leu Thr Ile Asn Cys Val Leu Thr Asp Asp Tyr Ala Leu Phe
            20                  25                  30

Ser Thr Ser Trp Phe Arg Lys Asn Pro Gly Thr Thr Asp Trp Glu Arg
```

```
            35                  40                  45
Met Ser Ile Gly Gly Arg Tyr Val Glu Ser Val Asn Lys Gly Ala Lys
 50                  55                  60

Ser Phe Ser Leu Arg Ile Lys Asp Leu Thr Val Ala Asp Ser Ala Thr
65                  70                  75                  80

Tyr Ile Cys Arg Ala Asn Glu Met Met Lys Pro Tyr Asp Val Tyr Gly
                 85                  90                  95

Ala Gly Thr Val Leu Thr Val Asn
                100
```

<210> SEQ ID NO 55
<211> LENGTH: 104
<212> TYPE: PRT
<213> ORGANISM: Artificial sequence
<220> FEATURE:
<223> OTHER INFORMATION: Synthetic sequence: Anti-mICOSL antigen
    specific antigen binding molecule (VNAR)

<400> SEQUENCE: 55

```
Ala Ser Val Asn Gln Thr Pro Arg Thr Ala Thr Lys Glu Thr Gly Glu
 1               5                  10                  15

Ser Leu Thr Ile Asn Cys Val Leu Thr Asp Thr Trp Pro Ala Trp Ser
                20                  25                  30

Asn Thr Ser Trp Phe Arg Lys Asn Pro Gly Thr Asp Trp Glu Arg
             35                  40                  45

Met Ser Ile Gly Gly Arg Tyr Val Glu Ser Val Asn Lys Gly Ala Lys
 50                  55                  60

Ser Phe Ser Leu Arg Ile Lys Asp Leu Thr Val Ala Asp Ser Ala Thr
65                  70                  75                  80

Tyr Ile Cys Arg Ala Tyr His Lys Gln Tyr Gly Trp Asp Val Tyr Gly
                 85                  90                  95

Ala Gly Thr Val Leu Thr Val Asn
                100
```

<210> SEQ ID NO 56
<211> LENGTH: 104
<212> TYPE: PRT
<213> ORGANISM: Artificial sequence
<220> FEATURE:
<223> OTHER INFORMATION: Synthetic sequence: Anti-mICOSL antigen
    specific antigen binding molecule (VNAR)

<400> SEQUENCE: 56

```
Thr Arg Val Asp Gln Thr Pro Arg Thr Ala Thr Lys Glu Thr Gly Glu
 1               5                  10                  15

Ser Leu Thr Ile Asn Cys Val Val Thr Gly Ala Glu Tyr Gly Trp Phe
                20                  25                  30

Ala Thr Tyr Trp Tyr Arg Lys Asn Pro Gly Ser Ser Asn Gln Glu Arg
             35                  40                  45

Ile Ser Ile Ser Gly Arg Tyr Val Glu Ser Val Asn Lys Arg Thr Met
 50                  55                  60

Ser Phe Ser Leu Arg Ile Lys Asp Leu Thr Val Ala Asp Ser Ala Thr
65                  70                  75                  80

Tyr Ile Cys Arg Ala Tyr Trp His Tyr Val Phe Met Asp Val Tyr Gly
                 85                  90                  95

Ala Gly Thr Val Leu Thr Val Asn
                100
```

```
<210> SEQ ID NO 57
<211> LENGTH: 104
<212> TYPE: PRT
<213> ORGANISM: Artificial sequence
<220> FEATURE:
<223> OTHER INFORMATION: Synthetic sequence: Anti-mlCOSL antigen
      specific antigen binding molecule (VNAR)

<400> SEQUENCE: 57

Ala Ser Val Asn Gln Thr Pro Arg Thr Ala Thr Lys Glu Thr Gly Glu
1               5                   10                  15

Ser Leu Thr Ile Asn Cys Val Leu Thr Asp Thr Phe Pro Ile Trp Ser
            20                  25                  30

His Thr Ser Trp Phe Arg Lys Asn Pro Gly Thr Thr Asp Trp Glu Arg
        35                  40                  45

Met Ser Ile Gly Gly Arg Tyr Val Glu Ser Val Asn Lys Gly Ala Lys
    50                  55                  60

Ser Phe Ser Leu Arg Ile Lys Asp Leu Thr Val Ala Asp Ser Ala Thr
65                  70                  75                  80

Tyr Ile Cys Arg Ala Trp Glu Met Leu Val Gly Trp Asp Val Tyr Gly
                85                  90                  95

Ala Gly Thr Val Leu Thr Val Asn
            100

<210> SEQ ID NO 58
<211> LENGTH: 104
<212> TYPE: PRT
<213> ORGANISM: Artificial sequence
<220> FEATURE:
<223> OTHER INFORMATION: Synthetic sequence: Anti-mlCOSL antigen
      specific antigen binding molecule (VNAR)

<400> SEQUENCE: 58

Thr Arg Val Asp Gln Thr Pro Arg Thr Ala Thr Lys Glu Thr Gly Glu
1               5                   10                  15

Ser Leu Thr Ile Asn Cys Val Leu Thr Asp Thr Lys Tyr Ala Leu Phe
            20                  25                  30

Ala Thr Ser Trp Phe Arg Lys Asn Pro Gly Thr Thr Asp Trp Glu Arg
        35                  40                  45

Met Ser Ile Gly Gly Arg Tyr Val Glu Ser Val Asn Lys Gly Ala Lys
    50                  55                  60

Ser Phe Ser Leu Arg Ile Lys Asp Leu Thr Val Ala Asp Ser Ala Thr
65                  70                  75                  80

Tyr Ile Cys Arg Ala Asn Glu Ser Met Lys Pro Met Asp Val Tyr Gly
                85                  90                  95

Ala Gly Thr Val Leu Thr Val Asn
            100

<210> SEQ ID NO 59
<211> LENGTH: 108
<212> TYPE: PRT
<213> ORGANISM: Artificial sequence
<220> FEATURE:
<223> OTHER INFORMATION: Synthetic sequence: Anti-mlCOSL antigen
      specific antigen binding molecule (VNAR)

<400> SEQUENCE: 59

Thr Arg Val Asp Gln Thr Pro Arg Thr Ala Thr Lys Glu Thr Gly Glu
1               5                   10                  15

Ser Leu Thr Ile Asn Cys Val Leu Thr Asp Thr Gly Tyr Gly Trp Phe
            20                  25                  30
```

```
Ala Thr Ser Trp Phe Arg Lys Asn Pro Gly Thr Thr Asp Trp Glu Arg
            35                  40                  45

Met Ser Ile Gly Gly Arg Tyr Val Glu Ser Val Asn Lys Gly Ala Lys
 50                  55                  60

Ser Phe Ser Leu Arg Ile Lys Asp Leu Thr Val Ala Asp Ser Ala Thr
 65                  70                  75                  80

Tyr Ile Cys Arg Ala Asp Val Trp Pro His Ser Val Met Asp Asp Pro
                    85                  90                  95

Asp Val Tyr Gly Ala Gly Thr Val Leu Thr Val Asn
                100                 105

<210> SEQ ID NO 60
<211> LENGTH: 104
<212> TYPE: PRT
<213> ORGANISM: Artificial sequence
<220> FEATURE:
<223> OTHER INFORMATION: Synthetic sequence: Anti-mICOSL antigen
      specific antigen binding molecule (VNAR)

<400> SEQUENCE: 60

Thr Arg Val Asp Gln Thr Pro Arg Thr Ala Thr Lys Glu Thr Gly Glu
 1               5                  10                  15

Ser Leu Thr Ile Asn Cys Val Leu Thr Asp Thr Asp Tyr Gly Leu Tyr
                20                  25                  30

Ala Thr Ser Trp Phe Arg Gln Asn Pro Gly Thr Thr Asp Trp Glu Arg
            35                  40                  45

Met Ser Ile Gly Gly Arg Tyr Val Glu Ser Val Asn Lys Gly Ala Lys
 50                  55                  60

Ser Phe Ser Leu Arg Ile Lys Asp Leu Thr Val Ala Asp Ser Ala Thr
 65                  70                  75                  80

Tyr Tyr Cys Lys Ala Phe Gln Leu Gly Phe Leu Gly Trp Tyr Asp Gly
                    85                  90                  95

Ala Gly Thr Val Leu Thr Val Asn
                100

<210> SEQ ID NO 61
<211> LENGTH: 108
<212> TYPE: PRT
<213> ORGANISM: Artificial sequence
<220> FEATURE:
<223> OTHER INFORMATION: Synthetic sequence: Anti-mICOSL antigen
      specific antigen binding molecule (VNAR)

<400> SEQUENCE: 61

Ala Ser Val Asn Gln Thr Pro Arg Thr Ala Thr Lys Glu Thr Gly Glu
 1               5                  10                  15

Ser Leu Thr Ile Asn Cys Val Leu Thr Asp Thr Val Gln Trp Trp Ile
                20                  25                  30

Pro Thr Ser Trp Phe Arg Lys Asn Pro Gly Thr Thr Asp Trp Glu Arg
            35                  40                  45

Met Ser Ile Gly Gly Arg Tyr Val Glu Ser Val Asn Lys Gly Ala Lys
 50                  55                  60

Ser Phe Ser Leu Arg Ile Lys Asp Leu Thr Val Ala Asp Ser Ala Thr
 65                  70                  75                  80

Tyr Ile Cys Arg Ala Pro Met Phe Pro Tyr Val Ser Asn Val Trp Arg
                    85                  90                  95

Asp Val Tyr Gly Ala Gly Thr Val Leu Thr Val Asn
                100                 105
```

<210> SEQ ID NO 62
<211> LENGTH: 104
<212> TYPE: PRT
<213> ORGANISM: Artificial sequence
<220> FEATURE:
<223> OTHER INFORMATION: Synthetic sequence: Anti-mICOSL antigen
      specific antigen binding molecule (VNAR)

<400> SEQUENCE: 62

Ala Ser Val Asn Gln Thr Pro Arg Thr Ala Thr Lys Glu Thr Gly Glu
1               5                   10                  15

Ser Leu Thr Ile Asn Cys Val Leu Thr Asp Thr Trp Pro Thr Phe Asp
            20                  25                  30

His Thr Ser Trp Phe Arg Lys Asn Pro Gly Thr Thr Asp Trp Glu Arg
        35                  40                  45

Met Ser Ile Gly Gly Arg Tyr Val Glu Ser Val Asn Lys Gly Ala Lys
    50                  55                  60

Ser Phe Ser Leu Arg Ile Lys Asp Leu Thr Val Ala Asp Ser Ala Thr
65                  70                  75                  80

Tyr Ile Cys Arg Ala Phe His Arg Val Val Gly Trp Asp Val Tyr Gly
                85                  90                  95

Ala Gly Thr Val Leu Thr Val Asn
            100

<210> SEQ ID NO 63
<211> LENGTH: 104
<212> TYPE: PRT
<213> ORGANISM: Artificial sequence
<220> FEATURE:
<223> OTHER INFORMATION: Synthetic sequence: Anti-mICOSL antigen
      specific antigen binding molecule (VNAR)

<400> SEQUENCE: 63

Ala Ser Val Asn Gln Thr Pro Arg Thr Ala Thr Lys Glu Thr Gly Glu
1               5                   10                  15

Ser Leu Thr Ile Asn Cys Val Leu Thr Asp Thr Trp Gln His Trp Thr
            20                  25                  30

His Thr Ser Trp Phe Arg Lys Asn Pro Gly Thr Thr Asp Trp Glu Arg
        35                  40                  45

Met Ser Ile Gly Gly Arg Tyr Val Glu Ser Val Asn Lys Gly Ala Lys
    50                  55                  60

Ser Phe Ser Leu Arg Ile Lys Asp Leu Thr Val Ala Asp Ser Ala Thr
65                  70                  75                  80

Tyr Ile Cys Arg Ala Trp His Gly Arg Val Gly Trp Asp Val Tyr Gly
                85                  90                  95

Ala Gly Thr Val Leu Thr Val Asn
            100

<210> SEQ ID NO 64
<211> LENGTH: 106
<212> TYPE: PRT
<213> ORGANISM: Artificial sequence
<220> FEATURE:
<223> OTHER INFORMATION: Synthetic sequence: Anti-mICOSL antigen
      specific antigen binding molecule (VNAR)

<400> SEQUENCE: 64

Ala Ser Val Asn Gln Thr Pro Arg Thr Ala Thr Lys Glu Thr Gly Glu
1               5                   10                  15

```
Ser Leu Thr Ile Asn Cys Val Leu Thr Asp Thr Gly Tyr Ser Trp Phe
            20                  25                  30

Ala Thr Ser Trp Phe Arg Lys Asn Pro Gly Thr Thr Asp Trp Glu Arg
        35                  40                  45

Met Ser Ile Gly Gly Arg Tyr Val Glu Ser Val Asn Lys Gly Ala Lys
    50                  55                  60

Ser Phe Ser Leu Arg Ile Lys Asp Leu Thr Val Ala Asp Ser Ala Thr
65                  70                  75                  80

Tyr Ile Cys Arg Ala Lys Ile Ala Ile Pro Ser Phe Pro Tyr Asp Val
                85                  90                  95

Tyr Gly Ala Gly Thr Val Leu Thr Val Asn
                100                 105

<210> SEQ ID NO 65
<211> LENGTH: 104
<212> TYPE: PRT
<213> ORGANISM: Artificial sequence
<220> FEATURE:
<223> OTHER INFORMATION: Synthetic sequence: Anti-mICOSL antigen
      specific antigen binding molecule (VNAR)

<400> SEQUENCE: 65

Ala Ser Val Asn Gln Thr Pro Arg Thr Ala Thr Lys Glu Thr Gly Glu
1               5                   10                  15

Ser Leu Thr Ile Asn Cys Val Leu Thr Asp Thr Lys Tyr Ala Leu Phe
            20                  25                  30

Ala Thr Ser Trp Phe Arg Lys Asn Pro Gly Thr Thr Asp Trp Glu Arg
        35                  40                  45

Met Ser Ile Gly Gly Arg Tyr Val Glu Ser Val Asn Lys Gly Ala Lys
    50                  55                  60

Ser Phe Ser Leu Arg Ile Lys Asp Leu Thr Val Ala Asp Ser Ala Thr
65                  70                  75                  80

Tyr Ile Cys Arg Ala Asn Glu Trp Met Leu Pro Phe Asp Val Tyr Gly
                85                  90                  95

Ala Gly Thr Val Leu Thr Val Asn
                100

<210> SEQ ID NO 66
<211> LENGTH: 108
<212> TYPE: PRT
<213> ORGANISM: Artificial sequence
<220> FEATURE:
<223> OTHER INFORMATION: Synthetic sequence: Anti-mICOSL antigen
      specific antigen binding molecule (VNAR)

<400> SEQUENCE: 66

Ala Ser Val Asn Gln Thr Pro Arg Thr Ala Thr Lys Glu Thr Gly Glu
1               5                   10                  15

Ser Leu Thr Ile Asn Cys Val Leu Thr Asp Thr Ser Tyr Gly Leu Tyr
            20                  25                  30

Ser Thr Ser Trp Phe Arg Lys Asn Pro Gly Thr Thr Asp Trp Glu Arg
        35                  40                  45

Met Ser Ile Gly Gly Arg Tyr Val Glu Ser Val Asn Lys Gly Ala Lys
    50                  55                  60

Ser Phe Ser Leu Arg Ile Lys Asp Leu Thr Val Ala Asp Ser Ala Thr
65                  70                  75                  80

Tyr Ile Cys Arg Ala Lys His Phe Ser Gln Leu Gln Pro Phe Leu Asn
                85                  90                  95
```

Asp Val Tyr Gly Ala Gly Thr Val Leu Thr Val Asn
            100                 105

<210> SEQ ID NO 67
<211> LENGTH: 107
<212> TYPE: PRT
<213> ORGANISM: Artificial sequence
<220> FEATURE:
<223> OTHER INFORMATION: Synthetic sequence: Anti-mICOSL antigen
      specific antigen binding molecule (VNAR)

<400> SEQUENCE: 67

Ala Ser Val Asn Gln Thr Pro Arg Thr Ala Lys Glu Thr Gly Glu
1               5                   10                  15

Ser Leu Thr Ile Asn Cys Val Leu Thr Asp Thr Gly Tyr Gly Leu Phe
            20                  25                  30

Ser Thr Ser Trp Phe Arg Lys Asn Pro Gly Thr Thr Asp Trp Glu Arg
        35                  40                  45

Met Ser Ile Gly Gly Arg Tyr Val Glu Ser Val Asn Lys Gly Ala Lys
    50                  55                  60

Ser Phe Ser Leu Arg Ile Lys Asp Leu Thr Val Ala Asp Ser Ala Thr
65                  70                  75                  80

Tyr Tyr Cys Lys Ala Ile Trp Ser Ser Arg Pro Phe Trp Trp Glu Trp
                85                  90                  95

Tyr Asp Gly Ala Gly Thr Val Leu Thr Val Asn
            100                 105

<210> SEQ ID NO 68
<211> LENGTH: 104
<212> TYPE: PRT
<213> ORGANISM: Artificial sequence
<220> FEATURE:
<223> OTHER INFORMATION: Synthetic sequence: Anti-mDLL4 antigen
      specific antigen binding molecule (VNAR)

<400> SEQUENCE: 68

Thr Arg Val Asp Gln Thr Pro Arg Thr Ala Thr Lys Glu Thr Gly Glu
1               5                   10                  15

Ser Leu Thr Ile Asn Cys Val Leu Thr Asp Thr Arg Tyr Ala Leu Ser
            20                  25                  30

Ala Thr Ser Trp Phe Arg Lys Asn Pro Gly Thr Thr Asp Trp Glu Arg
        35                  40                  45

Met Ser Ile Gly Gly Arg Tyr Val Glu Ser Val Asn Lys Gly Ala Lys
    50                  55                  60

Ser Phe Ser Leu Arg Ile Lys Asp Leu Thr Val Ala Asp Ser Ala Thr
65                  70                  75                  80

Tyr Ile Cys Arg Ala Ala Asp Trp Trp Thr Ala Phe Asp Val Tyr Gly
                85                  90                  95

Ala Gly Thr Val Leu Thr Val Asn
            100

<210> SEQ ID NO 69
<211> LENGTH: 108
<212> TYPE: PRT
<213> ORGANISM: Artificial sequence
<220> FEATURE:
<223> OTHER INFORMATION: Synthetic sequence: Anti-mDLL4 antigen
      specific antigen binding molecule (VNAR)

<400> SEQUENCE: 69

Thr Arg Val Asp Gln Thr Pro Arg Thr Ala Thr Lys Glu Thr Gly Glu

```
  1               5                  10                 15
Ser Leu Thr Ile Asn Cys Val Leu Thr Asp Thr Trp Ser Val Trp Tyr
                20                 25                 30

Thr Thr Ser Trp Phe Arg Lys Asn Pro Gly Thr Thr Asp Trp Glu Arg
            35                 40                 45

Met Ser Ile Gly Gly Arg Tyr Val Glu Ser Val Asn Lys Gly Ala Lys
        50                 55                 60

Ser Phe Ser Leu Arg Ile Lys Asp Leu Thr Val Ala Asp Ser Ala Thr
65                 70                 75                 80

Tyr Ile Cys Arg Ala Ala Phe Pro Asn Trp Trp Phe Trp Tyr Glu Pro
                85                 90                 95

Asp Val Tyr Gly Ala Gly Thr Val Leu Thr Val Asn
                100                105

<210> SEQ ID NO 70
<211> LENGTH: 106
<212> TYPE: PRT
<213> ORGANISM: Artificial sequence
<220> FEATURE:
<223> OTHER INFORMATION: Synthetic sequence
<220> FEATURE:
<221> NAME/KEY: SITE
<222> LOCATION: (91)..(91)
<223> OTHER INFORMATION: Xaa is unknown

<400> SEQUENCE: 70

Ala Ser Val Asn Gln Thr Pro Arg Thr Ala Thr Lys Glu Thr Gly Glu
1               5                  10                 15

Ser Leu Thr Ile Asn Cys Val Leu Thr Asp Thr Pro Ser His Glu Phe
                20                 25                 30

Phe Thr Ser Trp Phe Arg Lys Asn Pro Gly Thr Thr Asp Trp Glu Arg
            35                 40                 45

Met Ser Ile Gly Gly Arg Tyr Val Glu Ser Val Asn Lys Gly Ala Lys
        50                 55                 60

Ser Phe Ser Leu Arg Ile Lys Asp Leu Thr Val Ala Asp Ser Ala Thr
65                 70                 75                 80

Tyr Ile Cys Arg Ala Ala His Lys Leu Ser Xaa Gly Phe Asp Asp Val
                85                 90                 95

Tyr Gly Ala Gly Thr Val Leu Thr Val Asn
            100                105

<210> SEQ ID NO 71
<211> LENGTH: 106
<212> TYPE: PRT
<213> ORGANISM: Artificial sequence
<220> FEATURE:
<223> OTHER INFORMATION: Synthetic sequence: Anti-mDLL4 antigen
      specific antigen binding molecule

<400> SEQUENCE: 71

Thr Arg Val Asp Gln Thr Pro Arg Thr Ala Thr Lys Glu Thr Gly Glu
1               5                  10                 15

Ser Leu Thr Ile Asn Cys Val Leu Thr Asp Thr Pro Gln Trp Trp
                20                 25                 30

Thr Thr Ser Trp Phe Arg Lys Asn Pro Gly Thr Thr Asp Trp Glu Arg
            35                 40                 45

Met Ser Ile Gly Gly Arg Tyr Val Glu Ser Val Asn Lys Gly Ala Lys
        50                 55                 60

Ser Phe Ser Leu Arg Ile Lys Asp Leu Thr Val Ala Asp Ser Ala Thr
```

```
                65                  70                  75                  80
Tyr Ile Cys Arg Ala Ala Leu Trp Trp Ser Trp Trp Pro Tyr Asp Val
                    85                  90                  95

Tyr Gly Ala Gly Thr Val Leu Thr Val Asn
            100                 105

<210> SEQ ID NO 72
<211> LENGTH: 106
<212> TYPE: PRT
<213> ORGANISM: Artificial sequence
<220> FEATURE:
<223> OTHER INFORMATION: Synthetic sequence: Anti-mDLL4 antigen
      specific antigen binding molecule

<400> SEQUENCE: 72

Ala Ser Val Asn Gln Thr Pro Arg Thr Ala Thr Lys Glu Thr Gly Glu
1               5                   10                  15

Ser Leu Thr Ile Asn Cys Val Leu Thr Asp Thr Arg Tyr Gly Trp Tyr
                20                  25                  30

Ser Thr Ser Trp Phe Arg Lys Asn Pro Gly Thr Thr Asp Trp Glu Arg
            35                  40                  45

Met Ser Ile Gly Gly Arg Tyr Val Glu Ser Val Asn Lys Gly Ala Lys
        50                  55                  60

Ser Phe Ser Leu Arg Ile Lys Asp Leu Thr Val Ala Asp Ser Ala Thr
65                  70                  75                  80

Tyr Ile Cys Arg Ala Ala Asn Gly Phe Gln Asp Ser Phe Ala Asp Val
                    85                  90                  95

Tyr Gly Ala Gly Thr Val Leu Thr Val Asn
            100                 105

<210> SEQ ID NO 73
<211> LENGTH: 106
<212> TYPE: PRT
<213> ORGANISM: Artificial sequence
<220> FEATURE:
<223> OTHER INFORMATION: Synthetic sequence: Anti-mDLL4 antigen
      specific antigen binding molecule

<400> SEQUENCE: 73

Ala Ser Val Asn Gln Thr Pro Arg Thr Ala Thr Lys Glu Thr Gly Glu
1               5                   10                  15

Ser Leu Thr Ile Asn Cys Val Leu Thr Asp Thr Asp Tyr Gly Trp Tyr
                20                  25                  30

Ser Thr Ser Trp Phe Arg Lys Asn Pro Gly Thr Thr Asp Trp Glu Arg
            35                  40                  45

Met Ser Ile Gly Gly Arg Tyr Val Glu Ser Val Asn Lys Gly Ala Lys
        50                  55                  60

Ser Phe Ser Leu Arg Ile Lys Asp Leu Thr Val Ala Asp Ser Ala Thr
65                  70                  75                  80

Tyr Ile Cys Arg Ala Ala Asn Gly Leu Ala Arg Ser Met Ala Asp Val
                    85                  90                  95

Tyr Gly Ala Gly Thr Val Leu Thr Val Asn
            100                 105

<210> SEQ ID NO 74
<211> LENGTH: 106
<212> TYPE: PRT
<213> ORGANISM: Artificial sequence
<220> FEATURE:
<223> OTHER INFORMATION: Synthetic sequence: Anti-mDLL4 antigen
``` specific antigen binding molecule

<400> SEQUENCE: 74

```
Ala Ser Val Asn Gln Thr Pro Arg Thr Ala Thr Lys Glu Thr Gly Glu
1               5                   10                  15

Ser Leu Thr Ile Asn Cys Val Leu Thr Asp Thr Asn Tyr Gly Trp Tyr
            20                  25                  30

Ser Thr Ser Trp Phe Arg Lys Asn Pro Gly Thr Thr Asp Trp Glu Arg
        35                  40                  45

Met Ser Ile Gly Gly Arg Tyr Val Glu Ser Val Asn Lys Gly Ala Lys
    50                  55                  60

Ser Phe Ser Leu Arg Ile Lys Asp Leu Thr Val Ala Asp Ser Ala Thr
65                  70                  75                  80

Tyr Ile Cys Arg Ala Ala Asn Gly Trp Ala Arg Ser Tyr Glu Asp Val
                85                  90                  95

Tyr Gly Ala Gly Thr Val Leu Thr Val Asn
            100                 105
```

<210> SEQ ID NO 75
<211> LENGTH: 108
<212> TYPE: PRT
<213> ORGANISM: Artificial sequence
<220> FEATURE:
<223> OTHER INFORMATION: Synthetic sequence: Anti-mDLL4 antigen specific antigen binding molecule

<400> SEQUENCE: 75

```
Thr Arg Val Asp Gln Thr Pro Arg Thr Ala Thr Lys Glu Thr Gly Glu
1               5                   10                  15

Ser Leu Thr Ile Asn Cys Val Leu Thr Asp Thr Gly Tyr Ala Leu Phe
            20                  25                  30

Ser Thr Ser Trp Phe Arg Lys Asn Pro Gly Thr Thr Asp Trp Glu Arg
        35                  40                  45

Met Ser Ile Gly Gly Arg Tyr Val Glu Ser Val Asn Lys Gly Ala Lys
    50                  55                  60

Ser Phe Ser Leu Arg Ile Lys Asp Leu Thr Val Ala Asp Ser Ala Thr
65                  70                  75                  80

Tyr Ile Cys Arg Ala Ala Trp Phe Pro Tyr Trp Val Gln Asn Met Met
                85                  90                  95

Asp Val Tyr Gly Ala Gly Thr Val Leu Thr Val Asn
            100                 105
```

<210> SEQ ID NO 76
<211> LENGTH: 108
<212> TYPE: PRT
<213> ORGANISM: Artificial sequence
<220> FEATURE:
<223> OTHER INFORMATION: Synthetic sequence: Anti-mDLL4 antigen specific antigen binding molecule

<400> SEQUENCE: 76

```
Thr Arg Val Asp Gln Thr Pro Arg Thr Ala Thr Lys Glu Thr Gly Glu
1               5                   10                  15

Ser Leu Thr Ile Asn Cys Val Leu Thr Asp Thr Gly Tyr Ala Leu Tyr
            20                  25                  30

Ser Thr Ser Trp Phe Arg Lys Asn Pro Gly Thr Thr Asp Trp Glu Arg
        35                  40                  45

Met Ser Ile Gly Gly Arg Tyr Val Glu Ser Val Asn Lys Gly Ala Lys
    50                  55                  60
```

Ser Phe Ser Leu Arg Ile Lys Asp Leu Thr Val Ala Asp Ser Ala Thr
65                  70                  75                  80

Tyr Ile Cys Arg Ala Ala Trp Ile Pro Tyr Leu Val Arg Asp Met Arg
            85                  90                  95

Asp Val Tyr Gly Ala Gly Thr Val Leu Thr Val Asn
            100                 105

<210> SEQ ID NO 77
<211> LENGTH: 108
<212> TYPE: PRT
<213> ORGANISM: Artificial sequence
<220> FEATURE:
<223> OTHER INFORMATION: Synthetic sequence: Anti-mDLL4 antigen specific
      antigen binding molecule

<400> SEQUENCE: 77

Thr Arg Val Asp Gln Thr Pro Arg Thr Ala Thr Lys Glu Thr Gly Glu
1               5                   10                  15

Ser Leu Thr Ile Asn Cys Val Leu Thr Asp Thr Arg Tyr Ala Leu Phe
            20                  25                  30

Ala Thr Ser Trp Phe Arg Lys Asn Pro Gly Thr Thr Asp Trp Glu Arg
        35                  40                  45

Met Ser Ile Gly Gly Arg Tyr Val Glu Ser Val Asn Lys Gly Ala Lys
    50                  55                  60

Ser Phe Ser Leu Arg Ile Lys Asp Leu Thr Val Ala Asp Ser Ala Thr
65                  70                  75                  80

Tyr Ile Cys Arg Ala Ala Trp Gln Pro Tyr Asn Val Asp Ser Ile Trp
            85                  90                  95

Asp Val Tyr Gly Ala Gly Thr Val Leu Thr Val Asn
            100                 105

<210> SEQ ID NO 78
<211> LENGTH: 108
<212> TYPE: PRT
<213> ORGANISM: Artificial sequence
<220> FEATURE:
<223> OTHER INFORMATION: Synthetic sequence: Anti-mDLL4 antigen specific
      antigen binding molecule

<400> SEQUENCE: 78

Thr Arg Val Asp Gln Thr Pro Arg Thr Ala Thr Lys Glu Thr Gly Glu
1               5                   10                  15

Ser Leu Thr Ile Asn Cys Val Leu Thr Asp Thr Arg Tyr Ala Leu Phe
            20                  25                  30

Ala Thr Ser Trp Phe Arg Lys Asn Pro Gly Thr Thr Asp Trp Glu Arg
        35                  40                  45

Met Ser Ile Gly Gly Arg Tyr Val Glu Ser Val Asn Lys Gly Ala Lys
    50                  55                  60

Ser Phe Ser Leu Arg Ile Lys Asp Leu Thr Val Ala Asp Ser Ala Thr
65                  70                  75                  80

Tyr Ile Cys Arg Ala Ala Trp Gln Pro Tyr Asn Val Asp Ser Ile Trp
            85                  90                  95

Asp Val Tyr Gly Ala Gly Thr Val Leu Thr Val Asn
            100                 105

<210> SEQ ID NO 79
<211> LENGTH: 108
<212> TYPE: PRT
<213> ORGANISM: Artificial sequence

```
<220> FEATURE:
<223> OTHER INFORMATION: Synthetic sequence: Anti-mDLL4 antigen specific
      antigen binding molecule

<400> SEQUENCE: 79

Thr Arg Val Asp Gln Thr Pro Arg Thr Ala Thr Lys Glu Thr Gly Glu
1               5                   10                  15

Ser Leu Thr Ile Asn Cys Val Leu Thr Asp Thr Ser Tyr Gly Leu Ser
                20                  25                  30

Ala Thr Ser Trp Phe Arg Lys Asn Pro Gly Thr Thr Asp Trp Glu Arg
            35                  40                  45

Met Ser Ile Gly Gly Arg Tyr Val Glu Ser Val Asn Lys Gly Ala Lys
    50                  55                  60

Ser Phe Ser Leu Arg Ile Lys Asp Leu Thr Val Ala Asp Ser Ala Thr
65                  70                  75                  80

Tyr Ile Cys Arg Ala Ala Trp Val Pro Tyr Ser Val Asp Ser Met Trp
                85                  90                  95

Asp Val Tyr Gly Ala Gly Thr Val Leu Thr Val Asn
            100                 105

<210> SEQ ID NO 80
<211> LENGTH: 108
<212> TYPE: PRT
<213> ORGANISM: Artificial sequence
<220> FEATURE:
<223> OTHER INFORMATION: Synthetic sequence: Anti-mDLL4 antigen specific
      antigen binding molecule

<400> SEQUENCE: 80

Thr Arg Val Asp Gln Thr Pro Arg Thr Ala Thr Lys Glu Thr Gly Glu
1               5                   10                  15

Ser Leu Thr Ile Asn Cys Val Leu Thr Asp Thr Asp Tyr Ala Leu Ser
                20                  25                  30

Ser Thr Ser Trp Phe Arg Lys Asn Pro Gly Thr Thr Asp Trp Glu Arg
            35                  40                  45

Met Ser Ile Gly Gly Arg Tyr Val Glu Ser Val Asn Lys Gly Ala Lys
    50                  55                  60

Ser Phe Ser Leu Arg Ile Lys Asp Leu Thr Val Ala Asp Ser Ala Thr
65                  70                  75                  80

Tyr Ile Cys Arg Ala Ala Trp Trp Pro Asn Trp Val Ser Asn Ser Trp
                85                  90                  95

Asp Val Tyr Gly Ala Gly Thr Val Leu Thr Val Asn
            100                 105

<210> SEQ ID NO 81
<211> LENGTH: 111
<212> TYPE: PRT
<213> ORGANISM: Artificial sequence
<220> FEATURE:
<223> OTHER INFORMATION: Synthetic sequence: Anti-mDLL4 antigen specific
      antigen binding molecule

<400> SEQUENCE: 81

Ala Ser Val Asn Gln Thr Pro Arg Thr Ala Thr Lys Glu Thr Gly Glu
1               5                   10                  15

Ser Leu Thr Ile Asn Cys Val Leu Thr Asp Thr Phe Ile Pro Trp Leu
                20                  25                  30

His Thr Ser Trp Phe Arg Lys Asn Pro Gly Thr Thr Asp Trp Glu Arg
            35                  40                  45
```

-continued

Met Ser Ile Gly Gly Arg Tyr Val Glu Ser Val Asn Lys Gly Ala Lys
 50                  55                  60

Ser Phe Ser Leu Arg Ile Lys Asp Leu Thr Val Ala Asp Ser Ala Thr
 65                  70                  75                  80

Tyr Tyr Cys Lys Ala Asp Lys Ala Trp Glu Val Glu Asn Trp Ala Ile
                 85                  90                  95

Lys His Trp Trp Tyr Asp Gly Ala Gly Thr Val Leu Thr Val Asn
                100                 105                 110

<210> SEQ ID NO 82
<211> LENGTH: 108
<212> TYPE: PRT
<213> ORGANISM: Artificial sequence
<220> FEATURE:
<223> OTHER INFORMATION: Synthetic sequence: Anti-mDLL4 antigen specific
      antigen binding molecule

<400> SEQUENCE: 82

Thr Arg Val Asp Gln Thr Pro Arg Thr Ala Thr Lys Glu Thr Gly Glu
 1               5                  10                  15

Ser Leu Thr Ile Asn Cys Val Leu Thr Asp Thr Gly Tyr Ser Trp Phe
                 20                  25                  30

Ser Thr Ser Trp Phe Arg Lys Asn Pro Gly Thr Thr Asp Trp Glu Arg
             35                  40                  45

Met Ser Ile Gly Gly Arg Tyr Val Glu Ser Val Asn Lys Gly Ala Lys
 50                  55                  60

Ser Phe Ser Leu Arg Ile Lys Asp Leu Thr Val Ala Asp Ser Ala Thr
 65                  70                  75                  80

Tyr Ile Cys Arg Ala Asp Trp Asn Trp Trp Ala Asp Lys Met Glu
                 85                  90                  95

Asp Val Tyr Gly Ala Gly Thr Val Leu Thr Val Asn
                100                 105

<210> SEQ ID NO 83
<211> LENGTH: 104
<212> TYPE: PRT
<213> ORGANISM: Artificial sequence
<220> FEATURE:
<223> OTHER INFORMATION: Synthetic sequence: Anti-mDLL4 antigen specific
      antigen binding molecule

<400> SEQUENCE: 83

Ala Ser Val Asn Gln Thr Pro Arg Thr Ala Thr Lys Glu Thr Gly Glu
 1               5                  10                  15

Ser Leu Thr Ile Asn Cys Val Leu Thr Asp Thr Asn Tyr Gly Trp Tyr
                 20                  25                  30

Ala Thr Ser Trp Phe Arg Lys Asn Pro Gly Thr Thr Asp Trp Glu Arg
             35                  40                  45

Met Ser Ile Gly Gly Arg Tyr Val Glu Ser Val Asn Lys Gly Ala Lys
 50                  55                  60

Ser Phe Ser Leu Arg Ile Lys Asp Leu Thr Val Ala Asp Ser Ala Thr
 65                  70                  75                  80

Tyr Ile Cys Arg Ala Asp Tyr Trp Trp Asn Pro Lys Asp Val Tyr Gly
                 85                  90                  95

Ala Gly Thr Val Leu Thr Val Asn
                100

<210> SEQ ID NO 84
<211> LENGTH: 108

<212> TYPE: PRT
<213> ORGANISM: Artificial sequence
<220> FEATURE:
<223> OTHER INFORMATION: Synthetic sequence: Anti-mDLL4 antigen specific
      antigen binding molecule

<400> SEQUENCE: 84

Ala Ser Val Asn Gln Thr Pro Arg Thr Ala Thr Lys Glu Thr Gly Glu
1               5                   10                  15

Ser Leu Thr Ile Asn Cys Val Leu Thr Asp Thr Asp His Tyr Trp Val
            20                  25                  30

Ala Thr Ser Trp Phe Arg Lys Asn Pro Gly Thr Thr Asp Trp Glu Arg
        35                  40                  45

Met Ser Ile Gly Gly Arg Tyr Val Glu Ser Val Asn Lys Gly Ala Lys
    50                  55                  60

Ser Phe Ser Leu Arg Ile Lys Asp Leu Thr Val Ala Asp Ser Ala Thr
65                  70                  75                  80

Tyr Ile Cys Arg Ala Glu Phe His Pro Gln Gly Gly Trp Ser Ser Gln
                85                  90                  95

Asp Val Tyr Gly Ala Gly Thr Val Leu Thr Val Asn
            100                 105

<210> SEQ ID NO 85
<211> LENGTH: 108
<212> TYPE: PRT
<213> ORGANISM: Artificial sequence
<220> FEATURE:
<223> OTHER INFORMATION: Synthetic sequence: Anti-mDLL4 antigen specific
      antigen binding molecule

<400> SEQUENCE: 85

Thr Arg Val Asp Gln Thr Pro Arg Thr Ala Thr Lys Glu Thr Gly Glu
1               5                   10                  15

Ser Leu Thr Ile Asn Cys Val Leu Thr Asp Thr Trp Trp Ser Trp Trp
            20                  25                  30

Ala Thr Ser Trp Phe Arg Lys Asn Pro Gly Thr Thr Asp Trp Glu Arg
        35                  40                  45

Met Ser Ile Gly Gly Arg Tyr Val Glu Ser Val Asn Lys Gly Ala Lys
    50                  55                  60

Ser Phe Ser Leu Arg Ile Lys Asp Leu Thr Val Ala Asp Ser Ala Thr
65                  70                  75                  80

Tyr Ile Cys Arg Ala Glu Asn Tyr Trp Asp Ser Trp Phe Ala Pro
                85                  90                  95

Asp Val Tyr Gly Ala Gly Thr Val Leu Thr Val Asn
            100                 105

<210> SEQ ID NO 86
<211> LENGTH: 108
<212> TYPE: PRT
<213> ORGANISM: Artificial sequence
<220> FEATURE:
<223> OTHER INFORMATION: Synthetic sequence: Anti-mDLL4 antigen specific
      antigen binding molecule

<400> SEQUENCE: 86

Thr Arg Val Asp Gln Thr Pro Arg Thr Ala Thr Lys Glu Thr Gly Glu
1               5                   10                  15

Ser Leu Thr Ile Asn Cys Val Leu Thr Asp Gly Tyr Ser Leu Phe
            20                  25                  30

Ser Thr Ser Trp Phe Arg Lys Asn Pro Gly Thr Thr Asp Trp Glu Arg

```
                35                  40                  45
Met Ser Ile Gly Gly Arg Tyr Val Glu Ser Val Asn Lys Gly Ala Lys
 50                  55                  60
Ser Phe Ser Leu Arg Ile Lys Asp Leu Thr Val Ala Asp Ser Ala Thr
 65                  70                  75                  80
Tyr Ile Cys Arg Ala Glu Gln Trp Ser Trp Met Ser Trp Trp Pro Trp
                 85                  90                  95
Asp Val Tyr Gly Ala Gly Thr Val Leu Thr Val Asn
                100                 105

<210> SEQ ID NO 87
<211> LENGTH: 105
<212> TYPE: PRT
<213> ORGANISM: Artificial sequence
<220> FEATURE:
<223> OTHER INFORMATION: Synthetic sequence: Anti-mDLL4 antigen specific
      antigen binding molecule

<400> SEQUENCE: 87

Ala Ser Val Asn Gln Thr Pro Arg Thr Ala Thr Lys Glu Thr Gly Glu
  1               5                  10                  15
Ser Leu Thr Ile Asn Cys Val Leu Thr Asp Thr Asn Tyr Gly Trp Tyr
                 20                  25                  30
Ser Thr Ser Trp Phe Arg Lys Asn Pro Gly Thr Asp Trp Glu Arg
             35                  40                  45
Met Ser Ile Gly Gly Arg Tyr Val Glu Ser Val Asn Lys Gly Ala Lys
 50                  55                  60
Ser Phe Ser Leu Arg Ile Lys Asp Leu Thr Val Ala Asp Ser Ala Thr
 65                  70                  75                  80
Tyr Tyr Cys Lys Ala Glu Ser Phe Val His Ile Trp Thr Trp Tyr Asp
                 85                  90                  95
Gly Ala Gly Thr Val Leu Thr Val Asn
                100                 105

<210> SEQ ID NO 88
<211> LENGTH: 108
<212> TYPE: PRT
<213> ORGANISM: Artificial sequence
<220> FEATURE:
<223> OTHER INFORMATION: Synthetic sequence: Anti-mDLL4 antigen specific
      antigen binding molecule

<400> SEQUENCE: 88

Thr Arg Val Asp Gln Thr Pro Arg Thr Ala Thr Lys Glu Thr Gly Glu
  1               5                  10                  15
Ser Leu Thr Ile Asn Cys Val Leu Thr Asp Thr Arg Tyr Ala Leu Phe
                 20                  25                  30
Ala Thr Ser Trp Phe Arg Lys Asn Pro Gly Thr Asp Trp Glu Arg
             35                  40                  45
Met Ser Ile Gly Gly Arg Tyr Val Glu Ser Val Asn Lys Gly Ala Lys
 50                  55                  60
Ser Phe Ser Leu Arg Ile Lys Asp Leu Thr Val Ala Asp Ser Ala Thr
 65                  70                  75                  80
Tyr Ile Cys Arg Ala Glu Thr Trp Thr Trp Trp Pro Leu Met Glu
             85                  90                  95
Asp Val Tyr Gly Ala Gly Thr Val Leu Thr Val Asn
                100                 105
```

-continued

<210> SEQ ID NO 89
<211> LENGTH: 108
<212> TYPE: PRT
<213> ORGANISM: Artificial sequence
<220> FEATURE:
<223> OTHER INFORMATION: Synthetic sequence: Anti-mDLL4 antigen specific
      antigen binding molecule

<400> SEQUENCE: 89

Ala Ser Val Asn Gln Thr Pro Arg Thr Ala Thr Lys Glu Thr Gly Glu
1               5                   10                  15

Ser Leu Thr Ile Asn Cys Val Leu Thr Asp Thr Gly Tyr Ala Trp Tyr
            20                  25                  30

Ser Thr Ser Trp Phe Arg Lys Asn Pro Gly Thr Thr Asp Trp Glu Arg
        35                  40                  45

Met Ser Ile Gly Gly Arg Tyr Val Glu Ser Val Asn Lys Gly Ala Lys
    50                  55                  60

Ser Phe Ser Leu Arg Ile Lys Asp Leu Thr Val Ala Asp Ser Ala Thr
65                  70                  75                  80

Tyr Ile Cys Arg Ala Glu Val Trp Gln Trp Trp Ile Pro Trp Lys Asn
                85                  90                  95

Asp Val Tyr Gly Ala Gly Thr Val Leu Thr Val Asn
            100                 105

<210> SEQ ID NO 90
<211> LENGTH: 106
<212> TYPE: PRT
<213> ORGANISM: Artificial sequence
<220> FEATURE:
<223> OTHER INFORMATION: Synthetic sequence: Anti-mDLL4 antigen specific
      antigen binding molecule
<220> FEATURE:
<221> NAME/KEY: SITE
<222> LOCATION: (94)..(94)
<223> OTHER INFORMATION: Xaa is unknown

<400> SEQUENCE: 90

Ala Ser Val Asn Gln Thr Pro Arg Thr Ala Thr Lys Glu Thr Gly Glu
1               5                   10                  15

Ser Leu Thr Ile Asn Cys Val Leu Thr Asp Thr Asn Tyr Ser Trp Phe
            20                  25                  30

Ala Thr Ser Trp Phe Arg Lys Asn Pro Gly Thr Thr Asp Trp Glu Arg
        35                  40                  45

Met Ser Ile Gly Gly Arg Tyr Val Glu Ser Val Asn Lys Gly Ala Lys
    50                  55                  60

Ser Phe Ser Leu Arg Ile Lys Asp Leu Thr Val Ala Asp Ser Ala Thr
65                  70                  75                  80

Tyr Ile Cys Arg Ala Gly His Lys Tyr Ala Thr Gly Tyr Xaa Asp Val
                85                  90                  95

Tyr Gly Ala Gly Thr Val Leu Thr Val Asn
            100                 105

<210> SEQ ID NO 91
<211> LENGTH: 106
<212> TYPE: PRT
<213> ORGANISM: Artificial sequence
<220> FEATURE:
<223> OTHER INFORMATION: Synthetic sequence: Anti-mDLL4 antigen specific
      antigen binding molecule
<220> FEATURE:
<221> NAME/KEY: SITE
<222> LOCATION: (91)..(91)
<223> OTHER INFORMATION: Xaa is unknown

<400> SEQUENCE: 91

Ala Ser Val Asn Gln Thr Pro Arg Thr Ala Thr Lys Glu Thr Gly Glu
1               5                   10                  15

Ser Leu Thr Ile Asn Cys Val Leu Thr Asp Thr Asn Tyr Ser Trp Phe
            20                  25                  30

Ala Thr Ser Trp Phe Arg Lys Asn Pro Gly Thr Thr Asp Trp Glu Arg
        35                  40                  45

Met Ser Ile Gly Gly Arg Tyr Val Glu Ser Val Asn Lys Gly Ala Lys
    50                  55                  60

Ser Phe Ser Leu Arg Ile Lys Asp Leu Thr Val Ala Asp Ser Ala Thr
65                  70                  75                  80

Tyr Ile Cys Arg Ala Gly His Lys Tyr Ala Xaa Gly Cys Pro Asp Val
                85                  90                  95

Tyr Gly Ala Gly Thr Val Leu Thr Val Asn
            100                 105

<210> SEQ ID NO 92
<211> LENGTH: 108
<212> TYPE: PRT
<213> ORGANISM: Artificial sequence
<220> FEATURE:
<223> OTHER INFORMATION: Synthetic sequence: Anti-mDLL4 antigen specific
      antigen binding molecule

<400> SEQUENCE: 92

Thr Arg Val Asp Gln Thr Pro Arg Thr Ala Thr Lys Glu Thr Gly Glu
1               5                   10                  15

Ser Leu Thr Ile Asn Cys Val Leu Thr Asp Thr Gly Tyr Ser Trp Phe
            20                  25                  30

Ser Thr Ser Trp Phe Arg Lys Asn Pro Gly Thr Thr Asp Trp Glu Arg
        35                  40                  45

Met Ser Ile Gly Gly Arg Tyr Val Glu Ser Val Asn Lys Gly Ala Lys
    50                  55                  60

Ser Phe Ser Leu Arg Ile Lys Asp Leu Thr Val Ala Asp Ser Ala Thr
65                  70                  75                  80

Tyr Ile Cys Arg Ala Gly Met Phe Trp Ala Trp Trp Pro Trp Tyr Gln
                85                  90                  95

Asp Val Tyr Gly Ala Gly Thr Val Leu Thr Val Asn
            100                 105

<210> SEQ ID NO 93
<211> LENGTH: 106
<212> TYPE: PRT
<213> ORGANISM: Artificial sequence
<220> FEATURE:
<223> OTHER INFORMATION: Synthetic sequence: Anti-mDLL4 antigen specific
      antigen binding molecule

<400> SEQUENCE: 93

Thr Arg Val Asp Gln Thr Pro Arg Thr Ala Thr Lys Glu Thr Gly Glu
1               5                   10                  15

Ser Leu Thr Ile Asn Cys Val Leu Thr Asp Thr Asn Tyr Gly Leu Phe
            20                  25                  30

Ser Thr Ser Trp Phe Arg Lys Asn Pro Gly Thr Thr Asp Trp Glu Arg
        35                  40                  45

Met Ser Ile Gly Gly Arg Tyr Val Glu Ser Val Asn Lys Gly Ala Lys
    50                  55                  60

Ser Phe Ser Leu Arg Ile Lys Asp Leu Thr Val Ala Asp Ser Ala Thr
65                  70                  75                  80

Tyr Ile Cys Arg Ala Gly Thr Trp Trp Phe Trp Pro Leu Leu Asp Val
                85                  90                  95

Tyr Gly Ala Gly Thr Val Leu Thr Val Asn
            100                 105

<210> SEQ ID NO 94
<211> LENGTH: 108
<212> TYPE: PRT
<213> ORGANISM: Artificial sequence
<220> FEATURE:
<223> OTHER INFORMATION: Synthetic sequence: Anti-mDLL4 antigen specific
      antigen binding molecule

<400> SEQUENCE: 94

Ala Ser Val Asn Gln Thr Pro Arg Thr Ala Thr Lys Glu Thr Gly Glu
1               5                   10                  15

Ser Leu Thr Ile Asn Cys Val Leu Thr Asp Thr Trp Ser Trp Trp
            20                  25                  30

Asp Thr Ser Trp Phe Arg Lys Asn Pro Gly Thr Thr Asp Trp Glu Arg
            35                  40                  45

Met Ser Ile Gly Gly Arg Tyr Val Glu Ser Val Asn Lys Gly Ala Lys
        50                  55                  60

Ser Phe Ser Leu Arg Ile Lys Asp Leu Thr Val Ala Asp Ser Ala Thr
65                  70                  75                  80

Tyr Ile Cys Arg Ala Gly Val Leu Pro Trp Ser Pro Trp Gly Tyr Trp
                85                  90                  95

Asp Val Tyr Gly Ala Gly Thr Val Leu Thr Val Asn
            100                 105

<210> SEQ ID NO 95
<211> LENGTH: 106
<212> TYPE: PRT
<213> ORGANISM: Artificial sequence
<220> FEATURE:
<223> OTHER INFORMATION: Synthetic sequence: Anti-mDLL4 antigen specific
      antigen binding molecule

<400> SEQUENCE: 95

Thr Arg Val Asp Gln Thr Pro Arg Thr Ala Thr Lys Glu Thr Gly Glu
1               5                   10                  15

Ser Leu Thr Ile Asn Cys Val Leu Thr Asp Thr Trp His Pro Trp Trp
            20                  25                  30

Val Thr Ser Trp Phe Arg Lys Asn Pro Gly Thr Thr Asp Trp Glu Arg
            35                  40                  45

Met Ser Ile Gly Gly Arg Tyr Val Glu Ser Val Asn Lys Gly Ala Lys
        50                  55                  60

Ser Phe Ser Leu Arg Ile Lys Asp Leu Thr Val Ala Asp Ser Ala Thr
65                  70                  75                  80

Tyr Ile Cys Arg Ala Gly Trp Met Val Ser Trp Pro Phe Tyr Asp Val
                85                  90                  95

Tyr Gly Ala Gly Thr Val Leu Thr Val Asn
            100                 105

<210> SEQ ID NO 96
<211> LENGTH: 106
<212> TYPE: PRT
<213> ORGANISM: Artificial sequence
<220> FEATURE:

<223> OTHER INFORMATION: Synthetic sequence: Anti-mDLL4 antigen specific
     antigen binding molecule

<400> SEQUENCE: 96

Ala Ser Val Asn Gln Thr Pro Arg Thr Ala Thr Lys Glu Thr Gly Glu
1               5                   10                  15

Ser Leu Thr Ile Asn Cys Val Leu Thr Asp Thr Trp Trp Trp His
            20                  25                  30

Gln Thr Ser Trp Phe Arg Lys Asn Pro Gly Thr Thr Asp Trp Glu Arg
        35                  40                  45

Met Ser Ile Gly Gly Arg Tyr Val Glu Ser Val Asn Lys Gly Ala Lys
    50                  55                  60

Ser Phe Ser Leu Arg Ile Lys Asp Leu Thr Val Ala Asp Ser Ala Thr
65                  70                  75                  80

Tyr Ile Cys Arg Ala His Ser Ser Ile Trp Gly Trp Arg Glu Asp Val
                85                  90                  95

Tyr Gly Ala Gly Thr Val Leu Thr Val Asn
            100                 105

<210> SEQ ID NO 97
<211> LENGTH: 108
<212> TYPE: PRT
<213> ORGANISM: Artificial sequence
<220> FEATURE:
<223> OTHER INFORMATION: Synthetic sequence: Anti-mDLL4 antigen specific
     antigen binding molecule

<400> SEQUENCE: 97

Ala Ser Val Asn Gln Thr Pro Arg Thr Ala Thr Lys Glu Thr Gly Glu
1               5                   10                  15

Ser Leu Thr Ile Asn Cys Val Leu Thr Asp Thr Asn Tyr Ala Leu Ser
            20                  25                  30

Ala Thr Ser Trp Phe Arg Lys Asn Pro Gly Thr Thr Asp Trp Glu Arg
        35                  40                  45

Met Ser Ile Gly Gly Arg Tyr Val Glu Ser Val Asn Lys Gly Ala Lys
    50                  55                  60

Ser Phe Ser Leu Arg Ile Lys Asp Leu Thr Val Ala Asp Ser Ala Thr
65                  70                  75                  80

Tyr Ile Cys Arg Ala His Ser Tyr Val Trp Trp Trp Gly Tyr Tyr Thr
                85                  90                  95

Asp Val Tyr Gly Ala Gly Thr Val Leu Thr Val Asn
            100                 105

<210> SEQ ID NO 98
<211> LENGTH: 108
<212> TYPE: PRT
<213> ORGANISM: Artificial sequence
<220> FEATURE:
<223> OTHER INFORMATION: Synthetic sequence: Anti-mDLL4 antigen specific
     antigen binding molecule

<400> SEQUENCE: 98

Thr Arg Val Asp Gln Thr Pro Arg Thr Ala Thr Lys Glu Thr Gly Glu
1               5                   10                  15

Ser Leu Thr Ile Asn Cys Val Leu Thr Asp Thr Asp Ala Thr Trp Phe
            20                  25                  30

His Thr Ser Trp Phe Arg Lys Asn Pro Gly Thr Thr Asp Trp Glu Arg
        35                  40                  45

Met Ser Ile Gly Gly Arg Tyr Val Glu Ser Val Asn Lys Gly Ala Lys

```
                 50                  55                  60

Ser Phe Ser Leu Arg Ile Lys Asp Leu Thr Val Ala Asp Ser Ala Thr
 65                  70                  75                  80

Tyr Ile Cys Arg Ala Ile Trp Trp Pro Ser Ala Tyr Tyr Asn Trp Ala
                     85                  90                  95

Asp Val Tyr Gly Ala Gly Thr Val Leu Thr Val Asn
                100                 105
```

<210> SEQ ID NO 99
<211> LENGTH: 106
<212> TYPE: PRT
<213> ORGANISM: Artificial sequence
<220> FEATURE:
<223> OTHER INFORMATION: Synthetic sequence: Anti-mDLL4 antigen specific
      antigen binding molecule

<400> SEQUENCE: 99

```
Ala Ser Val Asn Gln Thr Pro Arg Thr Ala Thr Lys Glu Thr Gly Glu
 1               5                  10                  15

Ser Leu Thr Ile Asn Cys Val Leu Thr Asp Thr Trp Trp Pro Trp Tyr
                20                  25                  30

Thr Thr Ser Trp Phe Arg Lys Asn Pro Gly Thr Thr Asp Trp Glu Arg
            35                  40                  45

Met Ser Ile Gly Gly Arg Tyr Val Glu Ser Val Asn Lys Gly Ala Lys
 50                  55                  60

Ser Phe Ser Leu Arg Ile Lys Asp Leu Thr Val Ala Asp Ser Ala Thr
 65                  70                  75                  80

Tyr Ile Cys Arg Ala Leu Gly Thr Trp Asn Pro Trp Trp Pro Asp Val
                     85                  90                  95

Tyr Gly Ala Gly Thr Val Leu Thr Val Asn
                100                 105
```

<210> SEQ ID NO 100
<211> LENGTH: 108
<212> TYPE: PRT
<213> ORGANISM: Artificial sequence
<220> FEATURE:
<223> OTHER INFORMATION: Synthetic sequence: Anti-mDLL4 antigen specific
      antigen binding molecule

<400> SEQUENCE: 100

```
Ala Ser Val Asn Gln Thr Pro Arg Thr Ala Thr Lys Glu Thr Gly Glu
 1               5                  10                  15

Ser Leu Thr Ile Asn Cys Val Leu Thr Asp Gly Tyr Ala Trp Phe
                20                  25                  30

Ala Thr Ser Trp Phe Arg Lys Asn Pro Gly Thr Thr Asp Trp Glu Arg
            35                  40                  45

Met Ser Ile Gly Gly Arg Tyr Val Glu Ser Val Asn Lys Gly Ala Lys
 50                  55                  60

Ser Phe Ser Leu Arg Ile Lys Asp Leu Thr Val Ala Asp Ser Ala Thr
 65                  70                  75                  80

Tyr Ile Cys Arg Ala Met His Pro Trp Trp Pro Phe Ser His Trp Trp
                     85                  90                  95

Asp Val Tyr Gly Ala Gly Thr Val Leu Thr Val Asn
                100                 105
```

<210> SEQ ID NO 101
<211> LENGTH: 106
<212> TYPE: PRT

<213> ORGANISM: Artificial sequence
<220> FEATURE:
<223> OTHER INFORMATION: Synthetic sequence: Anti-mDLL4 antigen specific
      antigen binding molecule

<400> SEQUENCE: 101

Ala Ser Val Asn Gln Thr Pro Arg Thr Ala Thr Lys Glu Thr Gly Glu
1               5                   10                  15

Ser Leu Thr Ile Asn Cys Val Leu Thr Asp Thr Glu Ser Pro Trp Trp
            20                  25                  30

Tyr Thr Ser Trp Phe Arg Lys Asn Pro Gly Thr Thr Asp Trp Glu Arg
        35                  40                  45

Met Ser Ile Gly Gly Arg Tyr Val Glu Ser Val Asn Lys Gly Ala Lys
    50                  55                  60

Ser Phe Ser Leu Arg Ile Lys Asp Leu Thr Val Ala Asp Ser Ala Thr
65                  70                  75                  80

Tyr Ile Cys Arg Ala Met Gln Trp Trp Trp Gln Val Tyr Asp Val
                85                  90                  95

Tyr Gly Ala Gly Thr Val Leu Thr Val Asn
            100                 105

<210> SEQ ID NO 102
<211> LENGTH: 108
<212> TYPE: PRT
<213> ORGANISM: Artificial sequence
<220> FEATURE:
<223> OTHER INFORMATION: Synthetic sequence: Anti-mDLL4 antigen specific
      antigen binding molecule

<400> SEQUENCE: 102

Ala Ser Val Asn Gln Thr Pro Arg Thr Ala Thr Lys Glu Thr Gly Glu
1               5                   10                  15

Ser Leu Thr Ile Asn Cys Val Leu Thr Asp Thr Gly Tyr Gly Leu Ser
            20                  25                  30

Ala Thr Ser Trp Phe Arg Lys Asn Pro Gly Thr Thr Asp Trp Glu Arg
        35                  40                  45

Met Ser Ile Gly Gly Arg Tyr Val Glu Ser Val Asn Lys Gly Ala Lys
    50                  55                  60

Ser Phe Ser Leu Arg Ile Lys Asp Leu Thr Val Ala Asp Ser Ala Thr
65                  70                  75                  80

Tyr Ile Cys Arg Ala Asn Val Phe His Trp Trp Ala Trp Trp Gln His
                85                  90                  95

Asp Val Tyr Gly Ala Gly Thr Val Leu Thr Val Asn
            100                 105

<210> SEQ ID NO 103
<211> LENGTH: 106
<212> TYPE: PRT
<213> ORGANISM: Artificial sequence
<220> FEATURE:
<223> OTHER INFORMATION: Synthetic sequence: Anti-mDLL4 antigen specific
      antigen binding molecule

<400> SEQUENCE: 103

Ala Ser Val Asn Gln Thr Pro Arg Thr Ala Thr Lys Glu Thr Gly Glu
1               5                   10                  15

Ser Leu Thr Ile Asn Cys Val Leu Thr Asp Thr Arg Tyr Ser Leu Tyr
            20                  25                  30

Ser Thr Ser Trp Phe Arg Lys Asn Pro Gly Thr Thr Asp Trp Glu Arg
        35                  40                  45

Met Ser Ile Gly Gly Arg Tyr Val Glu Ser Val Asn Lys Gly Ala Lys
            50                  55                  60

Ser Phe Ser Leu Arg Ile Lys Asp Leu Thr Val Ala Asp Ser Ala Thr
 65                  70                  75                  80

Tyr Ile Cys Arg Ala Pro Phe Ala Gly Met Thr Tyr Ala Asp Val
                85                  90                  95

Tyr Gly Ala Gly Thr Val Leu Thr Val Asn
                100                 105

<210> SEQ ID NO 104
<211> LENGTH: 106
<212> TYPE: PRT
<213> ORGANISM: Artificial sequence
<220> FEATURE:
<223> OTHER INFORMATION: Synthetic sequence: Anti-mDLL4 antigen specific
      antigen binding molecule

<400> SEQUENCE: 104

Thr Arg Val Asp Gln Thr Pro Arg Thr Ala Thr Lys Glu Thr Gly Glu
 1                   5                  10                  15

Ser Leu Thr Ile Asn Cys Val Leu Thr Asp Thr Ser Tyr Gly Leu Ser
                20                  25                  30

Ala Thr Ser Trp Phe Arg Lys Asn Pro Gly Thr Thr Asp Trp Glu Arg
             35                  40                  45

Met Ser Ile Gly Gly Arg Tyr Val Glu Ser Val Asn Lys Gly Ala Lys
            50                  55                  60

Ser Phe Ser Leu Arg Ile Lys Asp Leu Thr Val Ala Asp Ser Ala Thr
 65                  70                  75                  80

Tyr Ile Cys Arg Ala Pro Phe Pro Ser Pro Thr Ser Ile Trp Asp Val
                85                  90                  95

Tyr Gly Ala Gly Thr Val Leu Thr Val Asn
                100                 105

<210> SEQ ID NO 105
<211> LENGTH: 106
<212> TYPE: PRT
<213> ORGANISM: Artificial sequence
<220> FEATURE:
<223> OTHER INFORMATION: Synthetic sequence: Anti-mDLL4 antigen specific
      antigen binding molecule

<400> SEQUENCE: 105

Thr Arg Val Asp Gln Thr Pro Arg Thr Ala Thr Lys Glu Thr Gly Glu
 1                   5                  10                  15

Ser Leu Thr Ile Asn Cys Val Leu Thr Asp Thr Ser Tyr Ala Leu Tyr
                20                  25                  30

Ser Thr Ser Trp Phe Arg Lys Asn Pro Gly Thr Thr Asp Trp Glu Arg
             35                  40                  45

Met Ser Ile Gly Gly Arg Tyr Val Glu Ser Val Asn Lys Gly Ala Lys
            50                  55                  60

Ser Phe Ser Leu Arg Ile Lys Asp Leu Thr Val Ala Asp Ser Ala Thr
 65                  70                  75                  80

Tyr Ile Cys Arg Ala Pro His Glu Gly Gln Thr His Tyr Ala Asp Val
                85                  90                  95

Tyr Gly Ala Gly Thr Val Leu Thr Val Asn
                100                 105

<210> SEQ ID NO 106

```
<211> LENGTH: 106
<212> TYPE: PRT
<213> ORGANISM: Artificial sequence
<220> FEATURE:
<223> OTHER INFORMATION: Synthetic sequence: Anti-mDLL4 antigen specific
      antigen binding molecule

<400> SEQUENCE: 106

Thr Arg Val Asp Gln Thr Pro Arg Thr Ala Thr Lys Glu Thr Gly Glu
1               5                   10                  15

Ser Leu Thr Ile Asn Cys Val Leu Thr Asp Thr Arg Tyr Ala Leu Tyr
            20                  25                  30

Ser Thr Ser Trp Phe Arg Lys Asn Pro Gly Thr Thr Asp Trp Glu Arg
        35                  40                  45

Met Ser Ile Gly Gly Arg Tyr Val Glu Ser Val Asn Lys Gly Ala Lys
    50                  55                  60

Ser Phe Ser Leu Arg Ile Lys Asp Leu Thr Val Ala Asp Ser Ala Thr
65                  70                  75                  80

Tyr Ile Cys Arg Ala Pro His Glu Lys Gln Ser His Tyr Glu Asp Val
                85                  90                  95

Tyr Gly Ala Gly Thr Val Leu Thr Val Asn
            100                 105

<210> SEQ ID NO 107
<211> LENGTH: 106
<212> TYPE: PRT
<213> ORGANISM: Artificial sequence
<220> FEATURE:
<223> OTHER INFORMATION: Synthetic sequence: Anti-mDLL4 antigen specific
      antigen binding molecule

<400> SEQUENCE: 107

Thr Arg Val Asp Gln Thr Pro Arg Thr Ala Thr Lys Glu Thr Gly Glu
1               5                   10                  15

Ser Leu Thr Ile Asn Cys Val Leu Thr Asp Thr Tyr Gln Met Trp Gly
            20                  25                  30

Arg Thr Ser Trp Phe Arg Lys Asn Pro Gly Thr Thr Asp Trp Glu Arg
        35                  40                  45

Met Ser Ile Gly Gly Arg Tyr Val Glu Ser Val Asn Lys Gly Ala Lys
    50                  55                  60

Ser Phe Ser Leu Arg Ile Lys Asp Leu Thr Val Ala Asp Ser Ala Thr
65                  70                  75                  80

Tyr Ile Cys Arg Ala Pro His Leu Gln Gln Ser Thr Pro Met Asp Val
                85                  90                  95

Tyr Gly Ala Gly Thr Val Leu Thr Val Asn
            100                 105

<210> SEQ ID NO 108
<211> LENGTH: 106
<212> TYPE: PRT
<213> ORGANISM: Artificial sequence
<220> FEATURE:
<223> OTHER INFORMATION: Synthetic sequence: Anti-mDLL4 antigen specific
      antigen binding molecule

<400> SEQUENCE: 108

Thr Arg Val Asp Gln Thr Pro Arg Thr Ala Thr Lys Glu Thr Gly Glu
1               5                   10                  15

Ser Leu Thr Ile Asn Cys Val Leu Thr Asp Thr Lys Tyr Ser Leu Phe
            20                  25                  30
```

Ser Thr Ser Trp Phe Arg Lys Asn Pro Gly Thr Thr Asp Trp Glu Arg
            35                  40                  45

Met Ser Ile Gly Gly Arg Tyr Val Glu Ser Val Asn Lys Gly Ala Lys
 50                  55                  60

Ser Phe Ser Leu Arg Ile Lys Asp Leu Thr Val Ala Asp Ser Ala Thr
 65                  70                  75                  80

Tyr Ile Cys Arg Ala Pro His Arg Gly Gln Arg Ser Phe Glu Asp Val
                 85                  90                  95

Tyr Gly Ala Gly Thr Val Leu Thr Val Asn
                100                 105

<210> SEQ ID NO 109
<211> LENGTH: 106
<212> TYPE: PRT
<213> ORGANISM: Artificial sequence
<220> FEATURE:
<223> OTHER INFORMATION: Synthetic sequence: Anti-mDLL4 antigen specific
      antigen binding molecule

<400> SEQUENCE: 109

Ala Ser Val Asn Gln Thr Pro Arg Thr Ala Thr Lys Glu Thr Gly Glu
 1               5                  10                  15

Ser Leu Thr Ile Asn Cys Val Leu Thr Asp Thr Asn Tyr Ser Leu Tyr
                20                  25                  30

Ser Thr Ser Trp Phe Arg Lys Asn Pro Gly Thr Thr Asp Trp Glu Arg
            35                  40                  45

Met Ser Ile Gly Gly Arg Tyr Val Glu Ser Val Asn Lys Gly Ala Lys
 50                  55                  60

Ser Phe Ser Leu Arg Ile Lys Asp Leu Thr Val Ala Asp Ser Ala Thr
 65                  70                  75                  80

Tyr Ile Cys Arg Ala Pro His Ser Asn Met Ser Thr Tyr Ser Asp Val
                 85                  90                  95

Tyr Gly Ala Gly Thr Val Leu Thr Val Asn
                100                 105

<210> SEQ ID NO 110
<211> LENGTH: 106
<212> TYPE: PRT
<213> ORGANISM: Artificial sequence
<220> FEATURE:
<223> OTHER INFORMATION: Synthetic sequence: Anti-mDLL4 antigen specific
      antigen binding molecule

<400> SEQUENCE: 110

Thr Arg Val Asp Gln Thr Pro Arg Thr Ala Thr Lys Glu Thr Gly Glu
 1               5                  10                  15

Ser Leu Thr Ile Asn Cys Val Leu Thr Asp Thr Leu Ala Ser Met Gly
                20                  25                  30

Leu Thr Ser Trp Phe Arg Lys Asn Pro Gly Thr Thr Asp Trp Glu Arg
            35                  40                  45

Met Ser Ile Gly Gly Arg Tyr Val Glu Ser Val Asn Lys Gly Ala Lys
 50                  55                  60

Ser Phe Ser Leu Arg Ile Lys Asp Leu Thr Val Ala Asp Ser Ala Thr
 65                  70                  75                  80

Tyr Ile Cys Arg Ala Pro His Ser Ser Met Ser His Tyr Asn Asp Val
                 85                  90                  95

Tyr Gly Ala Gly Thr Val Leu Thr Val Asn
                100                 105

<210> SEQ ID NO 111
<211> LENGTH: 106
<212> TYPE: PRT
<213> ORGANISM: Artificial sequence
<220> FEATURE:
<223> OTHER INFORMATION: Synthetic sequence: Anti-mDLL4 antigen specific antigen binding molecule

<400> SEQUENCE: 111

```
Ala Ser Val Asn Gln Thr Pro Arg Thr Ala Thr Lys Glu Thr Gly Glu
1               5                   10                  15

Ser Leu Thr Ile Asn Cys Val Leu Thr Asp Thr Leu Thr Pro Ser Gly
            20                  25                  30

Ser Thr Ser Trp Phe Arg Lys Asn Pro Gly Thr Thr Asp Trp Glu Arg
        35                  40                  45

Met Ser Ile Gly Gly Arg Tyr Val Glu Ser Val Asn Lys Gly Ala Lys
    50                  55                  60

Ser Phe Ser Leu Arg Ile Lys Asp Leu Thr Val Ala Asp Ser Ala Thr
65                  70                  75                  80

Tyr Ile Cys Arg Ala Pro His Thr Leu Ala Lys Thr Tyr Ser Asp Val
                85                  90                  95

Tyr Gly Ala Gly Thr Val Leu Thr Val Asn
            100                 105
```

<210> SEQ ID NO 112
<211> LENGTH: 106
<212> TYPE: PRT
<213> ORGANISM: Artificial sequence
<220> FEATURE:
<223> OTHER INFORMATION: Synthetic sequence: Anti-mDLL4 antigen specific antigen binding molecule

<400> SEQUENCE: 112

```
Thr Arg Val Asp Gln Thr Pro Arg Thr Ala Thr Lys Glu Thr Gly Glu
1               5                   10                  15

Ser Leu Thr Ile Asn Cys Val Leu Thr Asp Thr Glu Glu Val Phe Gly
            20                  25                  30

Lys Thr Ser Trp Phe Arg Lys Asn Pro Gly Thr Thr Asp Trp Glu Arg
        35                  40                  45

Met Ser Ile Gly Gly Arg Tyr Val Glu Ser Val Asn Lys Gly Ala Lys
    50                  55                  60

Ser Phe Ser Leu Arg Ile Lys Asp Leu Thr Val Ala Asp Ser Ala Thr
65                  70                  75                  80

Tyr Ile Cys Arg Ala Pro Leu His Gly Val Ala Asn Met Trp Asp Val
                85                  90                  95

Tyr Gly Ala Gly Thr Val Leu Thr Val Asn
            100                 105
```

<210> SEQ ID NO 113
<211> LENGTH: 106
<212> TYPE: PRT
<213> ORGANISM: Artificial sequence
<220> FEATURE:
<223> OTHER INFORMATION: Synthetic sequence: Anti-mDLL4 antigen specific antigen binding molecule

<400> SEQUENCE: 113

```
Thr Arg Val Asp Gln Thr Pro Arg Thr Ala Thr Lys Glu Thr Gly Glu
1               5                   10                  15

Ser Leu Thr Ile Asn Cys Val Leu Thr Asp Thr Glu Gln Val Phe Gly
```

```
            20                  25                  30
Lys Thr Ser Trp Phe Arg Lys Asn Pro Gly Thr Thr Asp Trp Glu Arg
        35                  40                  45

Met Ser Ile Gly Gly Arg Tyr Val Glu Ser Val Asn Lys Gly Ala Lys
 50                  55                  60

Ser Phe Ser Leu Arg Ile Lys Asp Leu Thr Val Ala Asp Ser Ala Thr
 65                  70                  75                  80

Tyr Ile Cys Arg Ala Pro Leu Arg His Val Ala His Met Trp Asp Val
                 85                  90                  95

Tyr Gly Ala Gly Thr Val Leu Thr Val Asn
                100                 105

<210> SEQ ID NO 114
<211> LENGTH: 106
<212> TYPE: PRT
<213> ORGANISM: Artificial sequence
<220> FEATURE:
<223> OTHER INFORMATION: Synthetic sequence: Anti-mDLL4 antigen specific
      antigen binding molecule

<400> SEQUENCE: 114

Thr Arg Val Asp Gln Thr Pro Arg Thr Ala Thr Lys Glu Thr Gly Glu
 1               5                  10                  15

Ser Leu Thr Ile Asn Cys Val Leu Thr Asp Thr Glu Gln Val Phe Gly
                20                  25                  30

Lys Thr Ser Trp Phe Arg Lys Asn Pro Gly Thr Thr Asp Trp Glu Arg
        35                  40                  45

Met Ser Ile Gly Gly Arg Tyr Val Glu Ser Val Asn Lys Gly Ala Lys
 50                  55                  60

Ser Phe Ser Leu Arg Ile Lys Asp Leu Thr Val Ala Asp Ser Ala Thr
 65                  70                  75                  80

Tyr Ile Cys Arg Ala Pro Leu Arg His Val Ala Asn Met Trp Asp Val
                 85                  90                  95

Tyr Gly Ala Gly Thr Val Leu Thr Val Asn
                100                 105

<210> SEQ ID NO 115
<211> LENGTH: 108
<212> TYPE: PRT
<213> ORGANISM: Artificial sequence
<220> FEATURE:
<223> OTHER INFORMATION: Synthetic sequence: Anti-mDLL4 antigen specific
      antigen binding molecule

<400> SEQUENCE: 115

Thr Arg Val Asp Gln Thr Pro Arg Thr Ala Thr Lys Glu Thr Gly Glu
 1               5                  10                  15

Ser Leu Thr Ile Asn Cys Val Leu Thr Asp Thr Lys Tyr Gly Leu Ala
                20                  25                  30

Ser Thr Ser Trp Phe Arg Lys Asn Pro Gly Thr Thr Asp Trp Glu Arg
        35                  40                  45

Met Ser Ile Gly Gly Arg Tyr Val Glu Ser Val Asn Lys Gly Ala Lys
 50                  55                  60

Ser Phe Ser Leu Arg Ile Lys Asp Leu Thr Val Ala Asp Ser Ala Thr
 65                  70                  75                  80

Tyr Ile Cys Arg Ala Pro Pro Asp Phe Phe Gln Glu Ser Gln Asn Trp
                 85                  90                  95

Asp Val Tyr Gly Ala Gly Thr Val Leu Thr Val Asn
```

<210> SEQ ID NO 116
<211> LENGTH: 106
<212> TYPE: PRT
<213> ORGANISM: Artificial sequence
<220> FEATURE:
<223> OTHER INFORMATION: Synthetic sequence: Anti-mDLL4 antigen specific
      antigen binding molecule

<400> SEQUENCE: 116

Thr Arg Val Asp Gln Thr Pro Arg Thr Ala Thr Lys Glu Thr Gly Glu
1               5                   10                  15

Ser Leu Thr Ile Asn Cys Val Leu Thr Asp Thr Met Ser Ile Pro Glu
            20                  25                  30

Ala Thr Ser Trp Phe Arg Lys Asn Pro Gly Thr Thr Asp Trp Glu Arg
        35                  40                  45

Met Ser Ile Gly Gly Arg Tyr Val Glu Ser Val Asn Lys Gly Ala Lys
    50                  55                  60

Ser Phe Ser Leu Arg Ile Lys Asp Leu Thr Val Ala Asp Ser Ala Thr
65                  70                  75                  80

Tyr Ile Cys Arg Ala Pro Thr Ala Tyr Gln His Ser Ile Trp Asp Val
                85                  90                  95

Tyr Gly Ala Gly Thr Val Leu Thr Val Asn
                100                 105

<210> SEQ ID NO 117
<211> LENGTH: 106
<212> TYPE: PRT
<213> ORGANISM: Artificial sequence
<220> FEATURE:
<223> OTHER INFORMATION: Synthetic sequence: Anti-mDLL4 antigen specific
      antigen binding molecule

<400> SEQUENCE: 117

Ala Ser Val Asn Gln Thr Pro Arg Thr Ala Thr Lys Glu Thr Gly Glu
1               5                   10                  15

Ser Leu Thr Ile Asn Cys Val Leu Thr Asp Thr Arg Tyr Ala Leu Tyr
            20                  25                  30

Ser Thr Ser Trp Phe Arg Lys Asn Pro Gly Thr Thr Asp Trp Glu Arg
        35                  40                  45

Met Ser Ile Gly Gly Arg Tyr Val Glu Ser Val Asn Lys Gly Ala Lys
    50                  55                  60

Ser Phe Ser Leu Arg Ile Lys Asp Leu Thr Val Ala Asp Ser Ala Thr
65                  70                  75                  80

Tyr Ile Cys Arg Ala Pro Tyr Ala Gly Met Gln Ser Tyr Ser Asp Val
                85                  90                  95

Tyr Gly Ala Gly Thr Val Leu Thr Val Asn
                100                 105

<210> SEQ ID NO 118
<211> LENGTH: 106
<212> TYPE: PRT
<213> ORGANISM: Artificial sequence
<220> FEATURE:
<223> OTHER INFORMATION: Synthetic sequence: Anti-mDLL4 antigen specific
      antigen binding molecule

<400> SEQUENCE: 118

Ala Ser Val Asn Gln Thr Pro Arg Thr Ala Thr Lys Glu Thr Gly Glu
1               5                   10                  15

```
Ser Leu Thr Ile Asn Cys Val Leu Thr Asp Thr Glu Tyr Gly Trp Phe
            20                  25                  30

Ser Thr Ser Trp Phe Arg Lys Asn Pro Gly Thr Thr Asp Trp Glu Arg
        35                  40                  45

Met Ser Ile Gly Gly Arg Tyr Val Glu Ser Val Asn Lys Gly Ala Lys
 50                  55                  60

Ser Phe Ser Leu Arg Ile Lys Asp Leu Thr Val Ala Asp Ser Ala Thr
 65                  70                  75                  80

Tyr Ile Cys Arg Ala Pro Tyr His Asp Ala Thr Gly Met Gln Asp Val
                 85                  90                  95

Tyr Gly Ala Gly Thr Val Leu Thr Val Asn
                100                 105

<210> SEQ ID NO 119
<211> LENGTH: 106
<212> TYPE: PRT
<213> ORGANISM: Artificial sequence
<220> FEATURE:
<223> OTHER INFORMATION: Synthetic sequence: Anti-mDLL4 antigen specific
      antigen binding molecule

<400> SEQUENCE: 119

Ala Ser Val Asn Gln Thr Pro Arg Thr Ala Thr Lys Glu Thr Gly Glu
1               5                  10                  15

Ser Leu Thr Ile Asn Cys Val Leu Thr Asp Thr Glu Thr Met Ser Gly
            20                  25                  30

Arg Thr Ser Trp Phe Arg Lys Asn Pro Gly Thr Thr Asp Trp Glu Arg
        35                  40                  45

Met Ser Ile Gly Gly Arg Tyr Val Glu Ser Val Asn Lys Gly Ala Lys
 50                  55                  60

Ser Phe Ser Leu Arg Ile Lys Asp Leu Thr Val Ala Asp Ser Ala Thr
 65                  70                  75                  80

Tyr Ile Cys Arg Ala Pro Tyr Thr Glu Ala Arg Asn Ile Trp Asp Val
                 85                  90                  95

Tyr Gly Ala Gly Thr Val Leu Thr Val Asn
                100                 105

<210> SEQ ID NO 120
<211> LENGTH: 108
<212> TYPE: PRT
<213> ORGANISM: Artificial sequence
<220> FEATURE:
<223> OTHER INFORMATION: Synthetic sequence: Anti-mDLL4 antigen specific
      antigen binding molecule

<400> SEQUENCE: 120

Thr Arg Val Asp Gln Thr Pro Arg Thr Ala Thr Lys Glu Thr Gly Glu
1               5                  10                  15

Ser Leu Thr Ile Asn Cys Val Leu Thr Asp Thr Glu Tyr Ala Trp Phe
            20                  25                  30

Ser Thr Ser Trp Phe Arg Lys Asn Pro Gly Thr Thr Asp Trp Glu Arg
        35                  40                  45

Met Ser Ile Gly Gly Arg Tyr Val Glu Ser Val Asn Lys Gly Ala Lys
 50                  55                  60

Ser Phe Ser Leu Arg Ile Lys Asp Leu Thr Val Ala Asp Ser Ala Thr
 65                  70                  75                  80

Tyr Ile Cys Arg Ala Gln Ser Val Ser Trp Leu Phe Pro Trp Arg Ser
                 85                  90                  95
```

Asp Val Tyr Gly Ala Gly Thr Val Leu Thr Val Asn
            100                 105

<210> SEQ ID NO 121
<211> LENGTH: 108
<212> TYPE: PRT
<213> ORGANISM: Artificial sequence
<220> FEATURE:
<223> OTHER INFORMATION: Synthetic sequence: Anti-mDLL4 antigen specific
      antigen binding molecule

<400> SEQUENCE: 121

Ala Ser Val Asn Gln Thr Pro Arg Thr Ala Thr Lys Glu Thr Gly Glu
1               5                   10                  15

Ser Leu Thr Ile Asn Cys Val Leu Thr Asp Thr Gly Tyr Ala Leu Phe
            20                  25                  30

Ser Thr Ser Trp Phe Arg Lys Asn Pro Gly Thr Thr Asp Trp Glu Arg
        35                  40                  45

Met Ser Ile Gly Gly Arg Tyr Val Glu Ser Val Asn Lys Gly Ala Lys
50                  55                  60

Ser Phe Ser Leu Arg Ile Lys Asp Leu Thr Val Ala Asp Ser Ala Thr
65                  70                  75                  80

Tyr Ile Cys Arg Ala Arg Lys Gln His Trp Tyr Trp Trp Gly Asp
                85                  90                  95

Asp Val Tyr Gly Ala Gly Thr Val Leu Thr Val Asn
            100                 105

<210> SEQ ID NO 122
<211> LENGTH: 104
<212> TYPE: PRT
<213> ORGANISM: Artificial sequence
<220> FEATURE:
<223> OTHER INFORMATION: Synthetic sequence: Anti-mDLL4 antigen specific
      antigen binding molecule

<400> SEQUENCE: 122

Ala Ser Val Asp Gln Thr Pro Arg Thr Ala Thr Lys Glu Thr Gly Glu
1               5                   10                  15

Ser Leu Thr Ile Asn Cys Val Leu Thr Asp Thr Asn Tyr Pro Leu Tyr
            20                  25                  30

Ser Thr Tyr Trp Tyr Arg Lys Asp Pro Gly Ser Ser Asn Lys Glu Gln
        35                  40                  45

Ile Ser Ile Ser Gly Arg Tyr Val Glu Ser Val Asn Lys Gly Thr Lys
50                  55                  60

Ser Phe Ser Leu Arg Ile Lys Asp Leu Thr Val Ala Asp Ser Ala Thr
65                  70                  75                  80

Tyr Ile Cys Arg Ala Arg Thr Cys Asn Tyr Val Ala Asp Tyr Tyr Gly
                85                  90                  95

Ala Gly Thr Val Leu Thr Val Asn
            100

<210> SEQ ID NO 123
<211> LENGTH: 106
<212> TYPE: PRT
<213> ORGANISM: Artificial sequence
<220> FEATURE:
<223> OTHER INFORMATION: Synthetic sequence: Anti-mDLL4 antigen specific
      antigen binding molecule

<400> SEQUENCE: 123

```
Ala Ser Val Asn Gln Thr Pro Arg Thr Ala Thr Lys Glu Thr Gly Glu
1               5                   10                  15

Ser Leu Thr Ile Asn Cys Val Leu Thr Asp Thr Pro Phe Trp Gln His
            20                  25                  30

Arg Thr Ser Trp Phe Arg Lys Asn Pro Gly Thr Thr Asp Trp Glu Arg
        35                  40                  45

Met Ser Ile Gly Gly Arg Tyr Val Glu Ser Val Asn Lys Gly Ala Lys
    50                  55                  60

Ser Phe Ser Leu Arg Ile Lys Asp Leu Thr Val Ala Asp Ser Ala Thr
65              70                  75                  80

Tyr Ile Cys Arg Ala Ser Asp Gly Trp Ala His Ala Phe Asp Asp Val
                85                  90                  95

Tyr Gly Ala Gly Thr Val Leu Thr Val Asn
                100                 105
```

<210> SEQ ID NO 124
<211> LENGTH: 106
<212> TYPE: PRT
<213> ORGANISM: Artificial sequence
<220> FEATURE:
<223> OTHER INFORMATION: Synthetic sequence: Anti-mDLL4 antigen specific antigen binding molecule

<400> SEQUENCE: 124

```
Ala Ser Val Asn Gln Thr Pro Arg Thr Ala Thr Lys Glu Thr Gly Glu
1               5                   10                  15

Ser Leu Thr Ile Asn Cys Val Leu Thr Asp Thr Cys Asp Val Cys Pro
            20                  25                  30

Gly Thr Ser Trp Phe Arg Lys Asn Pro Gly Thr Thr Asp Trp Glu Arg
        35                  40                  45

Met Ser Ile Gly Gly Arg Tyr Val Glu Ser Val Asn Lys Gly Ala Lys
    50                  55                  60

Ser Phe Ser Leu Arg Ile Lys Asp Leu Thr Val Ala Asp Ser Ala Thr
65              70                  75                  80

Tyr Ile Cys Arg Ala Ser His Arg Val Arg Ser Thr Tyr Glu Asp Val
                85                  90                  95

Tyr Gly Ala Gly Thr Val Leu Thr Val Asn
                100                 105
```

<210> SEQ ID NO 125
<211> LENGTH: 106
<212> TYPE: PRT
<213> ORGANISM: Artificial sequence
<220> FEATURE:
<223> OTHER INFORMATION: Synthetic sequence: Anti-mDLL4 antigen specific antigen binding molecule

<400> SEQUENCE: 125

```
Ala Ser Val Asn Gln Thr Pro Arg Thr Ala Thr Lys Glu Thr Gly Glu
1               5                   10                  15

Ser Leu Thr Ile Asn Cys Val Leu Thr Asp Thr Trp Tyr Trp Trp Trp
            20                  25                  30

Lys Thr Ser Trp Phe Arg Lys Asn Pro Gly Thr Thr Asp Trp Glu Arg
        35                  40                  45

Met Ser Ile Gly Gly Arg Tyr Val Glu Ser Val Asn Lys Gly Ala Lys
    50                  55                  60

Ser Phe Ser Leu Arg Ile Lys Asp Leu Thr Val Ala Asp Ser Ala Thr
65              70                  75                  80
```

Tyr Ile Cys Arg Ala Ser Leu Phe Pro Leu Gln Trp Met Thr Asp Val
                85                  90                  95

Tyr Gly Ala Gly Thr Val Leu Thr Val Asn
            100                 105

<210> SEQ ID NO 126
<211> LENGTH: 108
<212> TYPE: PRT
<213> ORGANISM: Artificial sequence
<220> FEATURE:
<223> OTHER INFORMATION: Synthetic sequence: Anti-mDLL4 antigen specific
      antigen binding molecule

<400> SEQUENCE: 126

Ala Ser Val Asn Gln Thr Pro Arg Thr Ala Thr Lys Glu Thr Gly Glu
1               5                   10                  15

Ser Leu Thr Ile Asn Cys Val Leu Thr Asp Thr Ser Tyr Ala Leu Tyr
                20                  25                  30

Ala Thr Ser Trp Phe Arg Lys Asn Pro Gly Thr Asp Trp Glu Arg
            35                  40                  45

Met Ser Ile Gly Gly Arg Tyr Val Glu Ser Val Asn Lys Gly Ala Lys
        50                  55                  60

Ser Phe Ser Leu Arg Ile Lys Asp Leu Thr Val Ala Asp Ser Ala Thr
65                  70                  75                  80

Tyr Ile Cys Arg Ala Ser Leu Thr Trp Pro Phe Lys Trp Trp Ala Pro
                85                  90                  95

Asp Val Tyr Gly Ala Gly Thr Val Leu Thr Val Asn
            100                 105

<210> SEQ ID NO 127
<211> LENGTH: 106
<212> TYPE: PRT
<213> ORGANISM: Artificial sequence
<220> FEATURE:
<223> OTHER INFORMATION: Synthetic sequence: Anti-mDLL4 antigen specific
      antigen binding molecule

<400> SEQUENCE: 127

Ala Ser Val Asn Gln Thr Pro Arg Thr Ala Thr Lys Glu Thr Gly Glu
1               5                   10                  15

Ser Leu Thr Ile Asn Cys Val Leu Thr Asp Thr Ser Tyr Ala Trp Phe
                20                  25                  30

Ser Thr Ser Trp Phe Arg Lys Asn Pro Gly Thr Asp Trp Glu Arg
        35                  40                  45

Met Ser Ile Gly Gly Arg Tyr Val Glu Ser Val Asn Lys Gly Ala Lys
        50                  55                  60

Ser Phe Ser Leu Arg Ile Lys Asp Leu Thr Val Ala Asp Ser Ala Thr
65                  70                  75                  80

Tyr Ile Cys Arg Ala Ser Leu Trp Asp Trp Trp Pro Glu Asp Leu
                85                  90                  95

Tyr Gly Ala Gly Thr Val Leu Thr Val Asn
            100                 105

<210> SEQ ID NO 128
<211> LENGTH: 106
<212> TYPE: PRT
<213> ORGANISM: Artificial sequence
<220> FEATURE:
<223> OTHER INFORMATION: Synthetic sequence: Anti-mDLL4 antigen specific
      antigen binding molecule -continued

```
<400> SEQUENCE: 128

Ala Ser Val Asn Gln Thr Pro Arg Thr Ala Thr Lys Glu Thr Gly Glu
1               5                   10                  15

Ser Leu Thr Ile Asn Cys Val Leu Thr Asp Thr Glu Tyr Gly Trp Tyr
            20                  25                  30

Ala Thr Ser Trp Phe Arg Lys Asn Pro Gly Thr Thr Asp Trp Glu Arg
        35                  40                  45

Met Ser Ile Gly Gly Arg Tyr Val Glu Ser Val Asn Lys Gly Ala Lys
    50                  55                  60

Ser Phe Ser Leu Arg Ile Lys Asp Leu Thr Val Ala Asp Ser Ala Thr
65                  70                  75                  80

Tyr Ile Cys Arg Ala Ser Asn Gly Tyr Gln Gln Ala Trp Gln Asp Val
                85                  90                  95

Tyr Gly Ala Gly Thr Val Leu Thr Val Asn
            100                 105

<210> SEQ ID NO 129
<211> LENGTH: 106
<212> TYPE: PRT
<213> ORGANISM: Artificial sequence
<220> FEATURE:
<223> OTHER INFORMATION: Synthetic sequence: Anti-mDLL4 antigen specific
      antigen binding molecule

<400> SEQUENCE: 129

Ala Ser Val Asn Gln Thr Pro Arg Thr Ala Thr Lys Glu Thr Gly Glu
1               5                   10                  15

Ser Leu Thr Ile Asn Cys Val Leu Thr Asp Thr Trp Leu Pro Trp Trp
            20                  25                  30

Gln Thr Ser Trp Phe Arg Lys Asn Pro Gly Thr Thr Asp Trp Glu Arg
        35                  40                  45

Met Ser Ile Gly Gly Arg Tyr Val Glu Ser Val Asn Lys Gly Ala Lys
    50                  55                  60

Ser Phe Ser Leu Arg Ile Lys Asp Leu Thr Val Ala Asp Ser Ala Thr
65                  70                  75                  80

Tyr Ile Cys Arg Ala Ser Ser Pro Trp Trp Gly Trp Gly Trp Asp Val
                85                  90                  95

Tyr Gly Ala Gly Thr Val Leu Thr Val Asn
            100                 105

<210> SEQ ID NO 130
<211> LENGTH: 108
<212> TYPE: PRT
<213> ORGANISM: Artificial sequence
<220> FEATURE:
<223> OTHER INFORMATION: Synthetic sequence: Anti-mDLL4 antigen specific
      antigen binding molecule

<400> SEQUENCE: 130

Ala Ser Val Asn Gln Thr Pro Arg Thr Ala Thr Lys Glu Thr Gly Glu
1               5                   10                  15

Ser Leu Thr Ile Asn Cys Val Leu Thr Asp Thr Gly Tyr Ala Trp Phe
            20                  25                  30

Ser Thr Ser Trp Phe Arg Lys Asn Pro Gly Thr Thr Asp Trp Glu Arg
        35                  40                  45

Met Ser Ile Gly Gly Arg Tyr Val Glu Ser Val Asn Lys Gly Ala Lys
    50                  55                  60

Ser Phe Ser Leu Arg Ile Lys Asp Leu Thr Val Ala Asp Ser Ala Thr
```

```
                65                  70                  75                  80
Tyr Ile Cys Arg Ala Ser Val Pro Thr Thr Trp Trp Trp Tyr Gly Asn
                    85                  90                  95

Asp Val Tyr Gly Ala Gly Thr Val Leu Thr Val Asn
                100                 105

<210> SEQ ID NO 131
<211> LENGTH: 106
<212> TYPE: PRT
<213> ORGANISM: Artificial sequence
<220> FEATURE:
<223> OTHER INFORMATION: Synthetic sequence: Anti-mDLL4 antigen specific
      antigen binding molecule

<400> SEQUENCE: 131

Thr Arg Val Asp Gln Thr Pro Arg Thr Ala Thr Lys Glu Thr Gly Glu
1               5                   10                  15

Ser Leu Thr Ile Asn Cys Val Leu Thr Asp Thr Gly Tyr Ala Trp Tyr
                20                  25                  30

Ala Thr Ser Trp Phe Arg Lys Asn Pro Gly Thr Thr Asp Trp Glu Arg
            35                  40                  45

Met Ser Ile Gly Gly Arg Tyr Val Glu Ser Val Asn Lys Gly Ala Lys
        50                  55                  60

Ser Phe Ser Leu Arg Ile Lys Asp Leu Thr Val Ala Asp Ser Ala Thr
65                  70                  75                  80

Tyr Ile Cys Arg Ala Ser Val Trp Trp Thr Trp Pro Met Asp Val
                    85                  90                  95

Tyr Gly Ala Gly Thr Val Leu Thr Val Asn
                100                 105

<210> SEQ ID NO 132
<211> LENGTH: 108
<212> TYPE: PRT
<213> ORGANISM: Artificial sequence
<220> FEATURE:
<223> OTHER INFORMATION: Synthetic sequence: Anti-mDLL4 antigen specific
      antigen binding molecule

<400> SEQUENCE: 132

Ala Ser Val Asn Gln Thr Pro Arg Thr Ala Thr Lys Glu Thr Gly Glu
1               5                   10                  15

Ser Leu Thr Ile Asn Cys Val Leu Thr Asp Thr Ser Tyr Ala Leu Tyr
                20                  25                  30

Ala Thr Ser Trp Phe Arg Lys Asn Pro Gly Thr Thr Asp Trp Glu Arg
            35                  40                  45

Met Ser Ile Gly Gly Arg Tyr Val Glu Ser Val Asn Lys Gly Ala Lys
        50                  55                  60

Ser Phe Ser Leu Arg Ile Lys Asp Leu Thr Val Ala Asp Ser Ala Thr
65                  70                  75                  80

Tyr Ile Cys Arg Ala Ser Val Tyr Gln Trp Trp Pro Val Pro Ala
                    85                  90                  95

Asp Val Tyr Gly Ala Gly Thr Val Leu Thr Val Asn
                100                 105

<210> SEQ ID NO 133
<211> LENGTH: 108
<212> TYPE: PRT
<213> ORGANISM: Artificial sequence
<220> FEATURE:
<223> OTHER INFORMATION: Synthetic sequence: Anti-mDLL4 antigen specific
``` antigen binding molecule

<400> SEQUENCE: 133

Thr Arg Val Asp Gln Thr Pro Arg Thr Ala Thr Lys Glu Thr Gly Glu
1               5                   10                  15

Ser Leu Thr Ile Asn Cys Val Leu Thr Asp Thr Gly Tyr Ala Leu Ser
            20                  25                  30

Ser Thr Ser Trp Phe Arg Lys Asn Pro Gly Thr Thr Asp Trp Glu Arg
        35                  40                  45

Met Ser Ile Gly Gly Arg Tyr Val Glu Ser Val Asn Lys Gly Ala Lys
    50                  55                  60

Ser Phe Ser Leu Arg Ile Lys Asp Leu Thr Val Ala Asp Ser Ala Thr
65                  70                  75                  80

Tyr Ile Cys Arg Ala Ser Trp Trp Pro Tyr Trp Val Glu Thr Met Asp
                85                  90                  95

Asp Val Tyr Gly Ala Gly Thr Val Leu Thr Val Asn
            100                 105

<210> SEQ ID NO 134
<211> LENGTH: 108
<212> TYPE: PRT
<213> ORGANISM: Artificial sequence
<220> FEATURE:
<223> OTHER INFORMATION: Synthetic sequence: Anti-mDLL4 antigen specific
      antigen binding molecule

<400> SEQUENCE: 134

Thr Arg Val Asp Gln Thr Pro Arg Thr Ala Thr Lys Glu Thr Gly Glu
1               5                   10                  15

Ser Leu Thr Ile Asn Cys Val Leu Thr Asp Thr Thr His Gln Trp Val
            20                  25                  30

Glu Thr Ser Trp Phe Arg Lys Asn Pro Gly Thr Thr Asp Trp Glu Arg
        35                  40                  45

Met Ser Ile Gly Gly Arg Tyr Val Glu Ser Val Asn Lys Gly Ala Lys
    50                  55                  60

Ser Phe Ser Leu Arg Ile Lys Asp Leu Thr Val Ala Asp Ser Ala Thr
65                  70                  75                  80

Tyr Ile Cys Arg Ala Ser Trp Tyr Trp Pro Trp Asp Trp Tyr Gln Pro
                85                  90                  95

Asp Val Tyr Gly Ala Gly Thr Val Leu Thr Val Asn
            100                 105

<210> SEQ ID NO 135
<211> LENGTH: 108
<212> TYPE: PRT
<213> ORGANISM: Artificial sequence
<220> FEATURE:
<223> OTHER INFORMATION: Synthetic sequence: Anti-mDLL4 antigen specific
      antigen binding molecule

<400> SEQUENCE: 135

Thr Arg Val Asp Gln Thr Pro Arg Thr Ala Thr Lys Glu Thr Gly Glu
1               5                   10                  15

Ser Leu Thr Ile Asn Cys Val Leu Thr Asp Thr Trp Met Pro Trp Asp
            20                  25                  30

Thr Thr Ser Trp Phe Arg Lys Asn Pro Gly Thr Thr Asp Trp Glu Arg
        35                  40                  45

Met Ser Ile Gly Gly Arg Tyr Val Glu Ser Val Asn Lys Gly Ala Lys
    50                  55                  60

```
Ser Phe Ser Leu Arg Ile Lys Asp Leu Thr Val Ala Asp Ser Ala Thr
 65                  70                  75                  80

Tyr Ile Cys Arg Ala Thr Gln Trp Glu Ala Phe Ser Trp Trp Trp Lys
                 85                  90                  95

Asp Val Tyr Gly Ala Gly Thr Val Leu Thr Val Asn
                100                 105
```

<210> SEQ ID NO 136
<211> LENGTH: 106
<212> TYPE: PRT
<213> ORGANISM: Artificial sequence
<220> FEATURE:
<223> OTHER INFORMATION: Synthetic sequence: Anti-mDLL4 antigen specific
      antigen binding molecule

<400> SEQUENCE: 136

```
Thr Arg Val Asp Gln Thr Pro Arg Thr Ala Thr Lys Glu Thr Gly Glu
 1               5                  10                  15

Ser Leu Thr Ile Asn Cys Val Leu Thr Asp Thr Gly Tyr Ser Trp Phe
                 20                  25                  30

Ala Thr Ser Trp Phe Arg Lys Asn Pro Gly Thr Thr Asp Trp Glu Arg
             35                  40                  45

Met Ser Ile Gly Gly Arg Tyr Val Glu Ser Val Asn Lys Gly Ala Lys
         50                  55                  60

Ser Phe Ser Leu Arg Ile Lys Asp Leu Thr Val Ala Asp Ser Ala Thr
 65                  70                  75                  80

Tyr Ile Cys Arg Ala Thr Val Trp Ala Trp Met Trp Pro Ile Asp Val
                 85                  90                  95

Tyr Gly Ala Gly Thr Val Leu Thr Val Asn
                100                 105
```

<210> SEQ ID NO 137
<211> LENGTH: 108
<212> TYPE: PRT
<213> ORGANISM: Artificial sequence
<220> FEATURE:
<223> OTHER INFORMATION: Synthetic sequence: Anti-mDLL4 antigen specific
      antigen binding molecule

<400> SEQUENCE: 137

```
Thr Arg Val Asp Gln Thr Pro Arg Thr Ala Thr Lys Glu Thr Gly Glu
 1               5                  10                  15

Ser Leu Thr Ile Asn Cys Val Leu Thr Asp Thr Ser Tyr Ala Leu Ser
                 20                  25                  30

Ser Thr Ser Trp Phe Arg Lys Asn Pro Gly Thr Thr Asp Trp Glu Arg
             35                  40                  45

Met Ser Ile Gly Gly Arg Tyr Val Glu Ser Val Asn Lys Gly Ala Lys
         50                  55                  60

Ser Phe Ser Leu Arg Ile Lys Asp Leu Thr Val Ala Asp Ser Ala Thr
 65                  70                  75                  80

Tyr Ile Cys Arg Ala Thr Trp Thr Pro Tyr Trp Val Asp Thr Ile Trp
                 85                  90                  95

Asp Val Tyr Gly Ala Gly Thr Val Leu Thr Val Asn
                100                 105
```

<210> SEQ ID NO 138
<211> LENGTH: 108
<212> TYPE: PRT
<213> ORGANISM: Artificial sequence
<220> FEATURE:
<223> OTHER INFORMATION: Synthetic sequence: Anti-mDLL4 antigen specific
      antigen binding molecule

<400> SEQUENCE: 138

```
Ala Ser Val Asn Gln Thr Pro Arg Thr Ala Thr Lys Glu Thr Gly Glu
1               5                   10                  15

Ser Leu Thr Ile Asn Cys Val Leu Thr Asp Thr Phe Ala Ser Ser His
            20                  25                  30

His Thr Ser Trp Phe Arg Lys Asn Pro Gly Thr Thr Asp Trp Glu Arg
        35                  40                  45

Met Ser Ile Gly Gly Arg Tyr Val Glu Ser Val Asn Lys Gly Ala Lys
    50                  55                  60

Ser Phe Ser Leu Arg Ile Lys Asp Leu Thr Val Ala Asp Ser Ala Thr
65                  70                  75                  80

Tyr Ile Cys Arg Ala Val His Pro Phe Ser Arg Val Glu Asn Ile Trp
                85                  90                  95

Asp Val Tyr Gly Ala Gly Thr Val Leu Thr Val Asn
            100                 105
```

<210> SEQ ID NO 139
<211> LENGTH: 104
<212> TYPE: PRT
<213> ORGANISM: Artificial sequence
<220> FEATURE:
<223> OTHER INFORMATION: Synthetic sequence: Anti-mDLL4 antigen specific
      antigen binding molecule

<400> SEQUENCE: 139

```
Thr Arg Val Asp Gln Thr Pro Arg Thr Ala Thr Lys Glu Thr Gly Glu
1               5                   10                  15

Ser Leu Thr Ile Asn Cys Val Leu Thr Asp Thr Pro Gln Gln Trp Phe
            20                  25                  30

Gln Thr Ser Trp Phe Arg Lys Asn Pro Gly Thr Thr Asp Trp Glu Arg
        35                  40                  45

Met Ser Ile Gly Gly Arg Tyr Val Glu Ser Val Asn Lys Gly Ala Lys
    50                  55                  60

Ser Phe Ser Leu Arg Ile Lys Asp Leu Thr Val Ala Asp Ser Ala Thr
65                  70                  75                  80

Tyr Ile Cys Arg Ala Val Asn Trp Tyr Lys Trp Asp Asp Val Tyr Gly
                85                  90                  95

Ala Gly Thr Val Leu Thr Val Asn
            100
```

<210> SEQ ID NO 140
<211> LENGTH: 108
<212> TYPE: PRT
<213> ORGANISM: Artificial sequence
<220> FEATURE:
<223> OTHER INFORMATION: Synthetic sequence: Anti-mDLL4 antigen specific
      antigen binding molecule

<400> SEQUENCE: 140

```
Thr Arg Val Asp Gln Thr Pro Arg Thr Ala Thr Lys Glu Thr Gly Glu
1               5                   10                  15

Ser Leu Thr Ile Asn Cys Val Leu Thr Asp Thr Ser Glu Phe His His
            20                  25                  30

His Thr Ser Trp Phe Arg Lys Asn Pro Gly Thr Thr Asp Trp Glu Arg
        35                  40                  45
```

Met Ser Ile Gly Gly Arg Tyr Val Glu Ser Val Asn Lys Gly Ala Lys
                50                  55                  60

Ser Phe Ser Leu Arg Ile Lys Asp Leu Thr Val Ala Asp Ser Ala Thr
 65                  70                  75                  80

Tyr Ile Cys Arg Ala Val Pro Met Tyr Arg Arg Asn Thr Trp Glu Glu
                         85                  90                  95

Asp Val Tyr Gly Ala Gly Thr Val Leu Thr Val Asn
                100                 105

<210> SEQ ID NO 141
<211> LENGTH: 108
<212> TYPE: PRT
<213> ORGANISM: Artificial sequence
<220> FEATURE:
<223> OTHER INFORMATION: Synthetic sequence: Anti-mDLL4 antigen specific
      antigen binding molecule

<400> SEQUENCE: 141

Thr Arg Val Asp Gln Thr Pro Arg Thr Ala Thr Lys Glu Thr Gly Glu
 1               5                  10                  15

Ser Leu Thr Ile Asn Cys Val Leu Thr Asp Thr Ser Glu Phe His His
                20                  25                  30

His Thr Ser Trp Phe Arg Lys Asn Pro Gly Thr Thr Asp Trp Glu Arg
            35                  40                  45

Met Ser Ile Gly Gly Arg Tyr Val Glu Ser Val Asn Lys Gly Ala Lys
 50                  55                  60

Ser Phe Ser Leu Arg Ile Lys Asp Leu Thr Val Ala Asp Ser Ala Thr
 65                  70                  75                  80

Tyr Ile Cys Arg Ala Val Pro Met Tyr Trp Arg Asn Thr Trp Glu Glu
                 85                  90                  95

Asp Val Tyr Gly Ala Gly Thr Val Leu Thr Val Asn
                100                 105

<210> SEQ ID NO 142
<211> LENGTH: 107
<212> TYPE: PRT
<213> ORGANISM: Artificial sequence
<220> FEATURE:
<223> OTHER INFORMATION: Synthetic sequence: Anti-mDLL4 antigen specific
      antigen binding molecule

<400> SEQUENCE: 142

Ala Ser Val Asn Gln Thr Pro Arg Thr Ala Thr Lys Glu Thr Gly Glu
 1               5                  10                  15

Ser Leu Thr Ile Asn Cys Val Leu Thr Asp Thr Asn Tyr Ser Trp Phe
                20                  25                  30

Ser Thr Ser Trp Phe Arg Lys Asn Pro Gly Thr Thr Asp Trp Glu Arg
            35                  40                  45

Met Ser Ile Gly Gly Arg Tyr Val Glu Ser Val Asn Lys Gly Ala Lys
 50                  55                  60

Ser Phe Ser Leu Arg Ile Lys Asp Leu Thr Val Ala Asp Ser Ala Thr
 65                  70                  75                  80

Tyr Tyr Cys Lys Ala Val Pro Trp Phe Glu Gln Trp Trp Glu Ile Trp
                 85                  90                  95

Tyr Asp Gly Ala Gly Thr Val Leu Thr Val Asn
                100                 105

<210> SEQ ID NO 143
<211> LENGTH: 108

```
<212> TYPE: PRT
<213> ORGANISM: Artificial sequence
<220> FEATURE:
<223> OTHER INFORMATION: Synthetic sequence: Anti-mDLL4 antigen specific
      antigen binding molecule

<400> SEQUENCE: 143

Thr Arg Val Asp Gln Thr Pro Arg Thr Ala Thr Lys Glu Thr Gly Glu
1               5                   10                  15

Ser Leu Thr Ile Asn Cys Val Leu Thr Asp Thr Asn Tyr Ser Leu Tyr
            20                  25                  30

Ala Thr Ser Trp Phe Arg Lys Asn Pro Gly Thr Thr Asp Trp Glu Arg
        35                  40                  45

Met Ser Ile Gly Gly Arg Tyr Val Glu Ser Val Asn Lys Gly Ala Lys
    50                  55                  60

Ser Phe Ser Leu Arg Ile Lys Asp Leu Thr Val Ala Asp Ser Ala Thr
65                  70                  75                  80

Tyr Ile Cys Arg Ala Val Trp Phe Pro Tyr Phe Ile Ser Asp Met Trp
                85                  90                  95

Asp Val Tyr Gly Ala Gly Thr Val Leu Thr Val Asn
            100                 105

<210> SEQ ID NO 144
<211> LENGTH: 108
<212> TYPE: PRT
<213> ORGANISM: Artificial sequence
<220> FEATURE:
<223> OTHER INFORMATION: Synthetic sequence: Anti-mDLL4 antigen specific
      antigen binding molecule

<400> SEQUENCE: 144

Thr Arg Val Asp Gln Thr Pro Arg Thr Ala Thr Lys Glu Thr Gly Glu
1               5                   10                  15

Ser Leu Thr Ile Asn Cys Val Leu Thr Asp Thr Arg Tyr Ala Leu Ala
            20                  25                  30

Ser Thr Ser Trp Phe Arg Lys Asn Pro Gly Thr Thr Asp Trp Glu Arg
        35                  40                  45

Met Ser Ile Gly Gly Arg Tyr Val Glu Ser Val Asn Lys Gly Ala Lys
    50                  55                  60

Ser Phe Ser Leu Arg Ile Lys Asp Leu Thr Val Ala Asp Ser Ala Thr
65                  70                  75                  80

Tyr Ile Cys Arg Ala Val Trp His Pro Phe Thr Val Thr Asn Met Pro
                85                  90                  95

Asp Val Tyr Gly Ala Gly Thr Val Leu Thr Val Asn
            100                 105

<210> SEQ ID NO 145
<211> LENGTH: 108
<212> TYPE: PRT
<213> ORGANISM: Artificial sequence
<220> FEATURE:
<223> OTHER INFORMATION: Synthetic sequence: Anti-mDLL4 antigen specific
      antigen binding molecule

<400> SEQUENCE: 145

Thr Arg Val Asp Gln Thr Pro Arg Thr Ala Thr Lys Glu Thr Gly Glu
1               5                   10                  15

Ser Leu Thr Ile Asn Cys Val Leu Thr Asp Gly Tyr Ala Leu Phe
            20                  25                  30

Ser Thr Ser Trp Phe Arg Lys Asn Pro Gly Thr Thr Asp Trp Glu Arg
```

```
                35                  40                  45
Met Ser Ile Gly Gly Arg Tyr Val Glu Ser Val Asn Lys Gly Ala Lys
 50                  55                  60
Ser Phe Ser Leu Arg Ile Lys Asp Leu Thr Val Ala Asp Ser Ala Thr
 65                  70                  75                  80
Tyr Ile Cys Arg Ala Val Trp Ile Pro Trp Trp Val Phe Asp Met Trp
                 85                  90                  95
Asp Val Tyr Gly Ala Gly Thr Val Leu Thr Val Asn
            100                 105
```

<210> SEQ ID NO 146
<211> LENGTH: 108
<212> TYPE: PRT
<213> ORGANISM: Artificial sequence
<220> FEATURE:
<223> OTHER INFORMATION: Synthetic sequence: Anti-mDLL4 antigen specific
      antigen binding molecule

<400> SEQUENCE: 146

```
Thr Arg Val Asp Gln Thr Pro Arg Thr Ala Thr Lys Glu Thr Gly Glu
  1               5                  10                  15
Ser Leu Thr Ile Asn Cys Val Leu Thr Asp Thr Asp Tyr Gly Leu Tyr
                 20                  25                  30
Ala Thr Ser Trp Phe Arg Lys Asn Pro Gly Thr Thr Asp Trp Glu Arg
             35                  40                  45
Met Ser Ile Gly Gly Arg Tyr Val Glu Ser Val Asn Lys Gly Ala Lys
 50                  55                  60
Ser Phe Ser Leu Arg Ile Lys Asp Leu Thr Val Ala Asp Ser Ala Thr
 65                  70                  75                  80
Tyr Ile Cys Arg Ala Val Trp Lys Pro Tyr Met Val Val His Leu Trp
                 85                  90                  95
Asp Val Tyr Gly Ala Gly Thr Val Leu Thr Val Asn
            100                 105
```

<210> SEQ ID NO 147
<211> LENGTH: 108
<212> TYPE: PRT
<213> ORGANISM: Artificial sequence
<220> FEATURE:
<223> OTHER INFORMATION: Synthetic sequence: Anti-mDLL4 antigen specific
      antigen binding molecule

<400> SEQUENCE: 147

```
Thr Arg Val Asp Gln Thr Pro Arg Thr Ala Thr Lys Glu Thr Gly Glu
  1               5                  10                  15
Ser Leu Thr Ile Asn Cys Val Leu Thr Asp Thr Gly Tyr Ala Leu Ala
                 20                  25                  30
Ser Thr Ser Trp Phe Arg Lys Asn Pro Gly Thr Thr Asp Trp Glu Arg
             35                  40                  45
Met Ser Ile Gly Gly Arg Tyr Val Glu Ser Val Asn Lys Gly Ala Lys
 50                  55                  60
Ser Phe Ser Leu Arg Ile Lys Asp Leu Thr Val Ala Asp Ser Ala Thr
 65                  70                  75                  80
Tyr Ile Cys Arg Ala Val Trp Met Pro Phe Met Val Arg Thr Pro Gly
                 85                  90                  95
Asp Val Tyr Gly Ala Gly Thr Val Leu Thr Val Asn
            100                 105
```

```
<210> SEQ ID NO 148
<211> LENGTH: 108
<212> TYPE: PRT
<213> ORGANISM: Artificial sequence
<220> FEATURE:
<223> OTHER INFORMATION: Synthetic sequence: Anti-mDLL4 antigen specific
      antigen binding molecule

<400> SEQUENCE: 148

Thr Arg Val Asp Gln Thr Pro Arg Thr Ala Thr Lys Glu Thr Gly Glu
1               5                   10                  15

Ser Leu Thr Ile Asn Cys Val Leu Thr Asp Thr Asp Tyr Ser Leu Phe
                20                  25                  30

Ser Thr Ser Trp Phe Arg Lys Asn Pro Gly Thr Thr Asp Trp Glu Arg
            35                  40                  45

Met Ser Ile Gly Gly Arg Tyr Val Glu Ser Val Asn Lys Gly Ala Lys
    50                  55                  60

Ser Phe Ser Leu Arg Ile Lys Asp Leu Thr Val Ala Asp Ser Ala Thr
65                  70                  75                  80

Tyr Ile Cys Arg Ala Val Trp Met Pro Tyr Thr Val Val Asp Ser Ser
                85                  90                  95

Asp Val Tyr Gly Ala Gly Thr Val Leu Thr Val Asn
            100                 105

<210> SEQ ID NO 149
<211> LENGTH: 108
<212> TYPE: PRT
<213> ORGANISM: Artificial sequence
<220> FEATURE:
<223> OTHER INFORMATION: Synthetic sequence: Anti-mDLL4 antigen specific
      antigen binding molecule

<400> SEQUENCE: 149

Thr Arg Val Asp Gln Thr Pro Arg Thr Ala Thr Lys Glu Thr Gly Glu
1               5                   10                  15

Ser Leu Thr Ile Asn Cys Val Leu Thr Asp Thr Lys Tyr Ala Leu Phe
                20                  25                  30

Ser Thr Ser Trp Phe Arg Lys Asn Pro Gly Thr Thr Asp Trp Glu Arg
            35                  40                  45

Met Ser Ile Gly Gly Arg Tyr Val Glu Ser Val Asn Lys Gly Ala Lys
    50                  55                  60

Ser Phe Ser Leu Arg Ile Lys Asp Leu Thr Val Ala Asp Ser Ala Thr
65                  70                  75                  80

Tyr Ile Cys Arg Ala Val Trp Gln Pro Tyr Glu Val Val His Met Trp
                85                  90                  95

Asp Val Tyr Gly Ala Gly Thr Val Leu Thr Val Asn
            100                 105

<210> SEQ ID NO 150
<211> LENGTH: 103
<212> TYPE: PRT
<213> ORGANISM: Artificial sequence
<220> FEATURE:
<223> OTHER INFORMATION: Synthetic sequence: Anti-mDLL4 antigen specific
      antigen binding molecule

<400> SEQUENCE: 150

Thr Arg Val Asp Gln Thr Pro Arg Thr Ala Thr Lys Glu Thr Gly Glu
1               5                   10                  15

Ser Leu Thr Ile Asn Cys Val Leu Thr Asp Thr Arg Tyr Ala Leu Phe
                20                  25                  30
```

```
Ala Thr Ser Trp Phe Arg Lys Asn Pro Gly Thr Thr Asp Trp Glu Arg
        35                  40                  45

Met Ser Ile Gly Gly Arg Tyr Val Glu Ser Val Asn Lys Gly Ala Lys
 50                  55                  60

Ser Phe Ser Leu Arg Ile Lys Asp Leu Thr Val Ala Asp Ser Ala Thr
 65                  70                  75                  80

Tyr Tyr Cys Lys Ala Val Tyr Ala Met Pro Lys Trp Tyr Asp Gly Ala
                85                  90                  95

Gly Thr Val Leu Thr Val Asn
            100
```

<210> SEQ ID NO 151
<211> LENGTH: 106
<212> TYPE: PRT
<213> ORGANISM: Artificial sequence
<220> FEATURE:
<223> OTHER INFORMATION: Synthetic sequence: Anti-mDLL4 antigen specific
      antigen binding molecule

<400> SEQUENCE: 151

```
Thr Arg Val Asp Gln Thr Pro Arg Thr Ala Thr Lys Glu Thr Gly Glu
 1               5                  10                  15

Ser Leu Thr Ile Asn Cys Val Leu Thr Asp Thr Gly Tyr Gly Leu Phe
                20                  25                  30

Ser Thr Ser Trp Phe Arg Lys Asn Pro Gly Thr Thr Asp Trp Glu Arg
        35                  40                  45

Met Ser Ile Gly Gly Arg Tyr Val Glu Ser Val Asn Lys Gly Ala Lys
 50                  55                  60

Ser Phe Ser Leu Arg Ile Lys Asp Leu Thr Val Ala Asp Ser Ala Thr
 65                  70                  75                  80

Tyr Ile Cys Arg Ala Trp Gly Trp Trp Trp Trp Pro Gln Asp Val
                85                  90                  95

Tyr Gly Ala Gly Thr Val Leu Thr Val Asn
            100                 105
```

<210> SEQ ID NO 152
<211> LENGTH: 106
<212> TYPE: PRT
<213> ORGANISM: Artificial sequence
<220> FEATURE:
<223> OTHER INFORMATION: Synthetic sequence: Anti-mDLL4 antigen specific
      antigen binding molecule

<400> SEQUENCE: 152

```
Ala Ser Val Asn Gln Thr Pro Arg Thr Ala Thr Lys Glu Thr Gly Glu
 1               5                  10                  15

Ser Leu Thr Ile Asn Cys Val Leu Thr Asp Thr Trp Trp Pro Trp Leu
                20                  25                  30

Thr Thr Ser Trp Phe Arg Lys Asn Pro Gly Thr Thr Asp Trp Glu Arg
        35                  40                  45

Met Ser Ile Gly Gly Arg Tyr Val Glu Ser Val Asn Lys Gly Ala Lys
 50                  55                  60

Ser Phe Ser Leu Arg Ile Lys Asp Leu Thr Val Ala Asp Ser Ala Thr
 65                  70                  75                  80

Tyr Ile Cys Arg Ala Trp Val Pro Tyr Trp Thr Ala Trp Tyr Asp Val
                85                  90                  95

Tyr Gly Ala Gly Thr Val Leu Thr Val Asn
            100                 105
```

<210> SEQ ID NO 153
<211> LENGTH: 105
<212> TYPE: PRT
<213> ORGANISM: Artificial sequence
<220> FEATURE:
<223> OTHER INFORMATION: Synthetic sequence: Anti-mDLL4 antigen specific
      antigen binding molecule

<400> SEQUENCE: 153

Ala Ser Val Asn Gln Thr Pro Arg Thr Ala Thr Lys Glu Thr Gly Glu
1               5                   10                  15

Ser Leu Thr Ile Asn Cys Val Leu Thr Asp Thr Lys Tyr Leu Tyr Ser
            20                  25                  30

Thr Ser Trp Phe Arg Lys Asn Pro Gly Thr Thr Asp Trp Glu Arg Met
        35                  40                  45

Ser Ile Gly Gly Arg Tyr Val Glu Ser Val Asn Lys Gly Ala Lys Ser
    50                  55                  60

Phe Ser Leu Arg Ile Lys Asp Leu Thr Val Ala Asp Ser Ala Thr Tyr
65                  70                  75                  80

Ile Cys Arg Ala Trp Thr Ser Phe Glu Glu Gln Val Lys Asp Val Tyr
                85                  90                  95

Gly Ala Gly Thr Val Leu Thr Val Asn
            100                 105

<210> SEQ ID NO 154
<211> LENGTH: 108
<212> TYPE: PRT
<213> ORGANISM: Artificial sequence
<220> FEATURE:
<223> OTHER INFORMATION: Synthetic sequence: Anti-mDLL4 antigen specific
      antigen binding molecule

<400> SEQUENCE: 154

Thr Arg Val Asp Gln Thr Pro Arg Thr Ala Thr Lys Glu Thr Gly Glu
1               5                   10                  15

Ser Leu Thr Ile Asn Cys Val Leu Thr Asp Thr Ser Tyr Ala Leu Ser
            20                  25                  30

Ala Thr Ser Trp Phe Arg Lys Asn Pro Gly Thr Thr Asp Trp Glu Arg
        35                  40                  45

Met Ser Ile Gly Gly Arg Tyr Val Glu Ser Val Asn Lys Gly Ala Lys
    50                  55                  60

Ser Phe Ser Leu Arg Ile Lys Asp Leu Thr Val Ala Asp Ser Ala Thr
65                  70                  75                  80

Tyr Ile Cys Arg Ala Ala Trp Trp Pro Phe Met Ile Glu Glu Thr Thr
                85                  90                  95

Asp Val Tyr Gly Ala Gly Thr Val Leu Thr Val Asn
            100                 105

<210> SEQ ID NO 155
<211> LENGTH: 109
<212> TYPE: PRT
<213> ORGANISM: Artificial sequence
<220> FEATURE:
<223> OTHER INFORMATION: Synthetic sequence: Anti-HSA antigen specific
      antigen binding molecule (VNAR)

<400> SEQUENCE: 155

Thr Arg Val Asp Gln Thr Pro Arg Thr Ala Thr Lys Glu Thr Gly Glu
1               5                   10                  15

```
Ser Leu Thr Ile Asn Cys Val Leu Thr Asp Thr Ser Tyr Gly Leu Phe
            20                  25                  30

Ser Thr Ser Trp Phe Arg Lys Asn Pro Gly Thr Thr Asp Trp Glu Arg
        35                  40                  45

Met Ser Ile Gly Gly Arg Tyr Val Glu Ser Val Asn Lys Gly Ala Lys
 50                  55                  60

Ser Phe Ser Leu Arg Ile Lys Asp Leu Thr Val Ala Asp Ser Ala Thr
 65                  70                  75                  80

Tyr Tyr Cys Lys Ala Met Gly Asn His Glu Trp Asp Ile Trp Trp Trp
             85                  90                  95

Trp Trp Tyr Asp Gly Ala Gly Thr Val Leu Thr Val Asn
            100                 105
```

```
<210> SEQ ID NO 156
<211> LENGTH: 105
<212> TYPE: PRT
<213> ORGANISM: Artificial sequence
<220> FEATURE:
<223> OTHER INFORMATION: Synthetic sequence: Anti-HSA antigen specific
      antigen binding molecule (VNAR)

<400> SEQUENCE: 156

Thr Arg Val Asp Gln Thr Pro Arg Thr Ala Thr Lys Glu Thr Gly Glu
1               5                   10                  15

Ser Leu Thr Ile Asn Cys Val Leu Thr Asp Thr Glu Tyr Gly Leu Ser
            20                  25                  30

Ala Thr Ser Trp Phe Arg Lys Asn Pro Gly Thr Thr Asp Trp Glu Arg
        35                  40                  45

Met Ser Ile Gly Gly Arg Tyr Val Glu Ser Val Asn Lys Gly Ala Lys
 50                  55                  60

Ser Phe Ser Leu Arg Ile Lys Asp Leu Thr Val Ala Asp Ser Ala Thr
 65                  70                  75                  80

Tyr Tyr Cys Lys Ala Arg Arg Met Gly His Gly Arg Leu Trp Tyr Asp
             85                  90                  95

Gly Ala Gly Thr Val Leu Thr Val Asn
                100                 105
```

```
<210> SEQ ID NO 157
<211> LENGTH: 108
<212> TYPE: PRT
<213> ORGANISM: Artificial sequence
<220> FEATURE:
<223> OTHER INFORMATION: Synthetic sequence: Anti-HSA antigen specific
      antigen binding molecule (VNAR)

<400> SEQUENCE: 157

Ala Ser Val Asn Gln Thr Pro Arg Thr Ala Thr Lys Glu Thr Gly Glu
1               5                   10                  15

Ser Leu Thr Ile Asn Cys Val Leu Thr Asp Thr Ser Tyr Ala Leu Ser
            20                  25                  30

Ser Thr Ser Trp Phe Arg Lys Asn Pro Gly Thr Thr Asp Trp Glu Arg
        35                  40                  45

Met Ser Ile Gly Gly Arg Tyr Val Glu Ser Val Asn Lys Gly Ala Lys
 50                  55                  60

Ser Phe Ser Leu Arg Ile Lys Asp Leu Thr Val Ala Asp Ser Ala Thr
 65                  70                  75                  80

Tyr Ile Cys Arg Ala Thr Ile Asp Pro Val Trp Ile Glu Trp Leu Trp
             85                  90                  95
```

Asp Val Tyr Gly Ala Gly Thr Val Leu Thr Val Asn
            100                 105

<210> SEQ ID NO 158
<211> LENGTH: 111
<212> TYPE: PRT
<213> ORGANISM: Artificial sequence
<220> FEATURE:
<223> OTHER INFORMATION: Synthetic sequence: Anti-hRAGE antigen specific
      antigen binding molecule (VNAR)

<400> SEQUENCE: 158

Thr Arg Val Asp Gln Thr Pro Arg Thr Ala Thr Lys Glu Thr Gly Glu
1               5                   10                  15

Ser Leu Thr Ile Asn Cys Val Leu Thr Asp Thr Ser Tyr Gly Leu Phe
            20                  25                  30

Ala Thr Ser Trp Phe Arg Lys Asn Pro Gly Thr Thr Asp Trp Glu Arg
        35                  40                  45

Met Ser Ile Gly Gly Arg Tyr Val Glu Ser Val Asn Lys Gly Ala Lys
    50                  55                  60

Ser Phe Ser Leu Arg Ile Lys Asp Leu Thr Val Ala Asp Ser Ala Thr
65                  70                  75                  80

Tyr Tyr Cys Lys Ala Arg Ala Pro Lys Arg Pro Trp His Gly Lys Leu
                85                  90                  95

Thr Val Pro Trp Tyr Asp Gly Ala Gly Thr Val Leu Thr Val Asn
            100                 105                 110

<210> SEQ ID NO 159
<211> LENGTH: 107
<212> TYPE: PRT
<213> ORGANISM: Artificial sequence
<220> FEATURE:
<223> OTHER INFORMATION: Synthetic sequence: Anti-hRAGE antigen specific
      antigen binding molecule (VNAR)

<400> SEQUENCE: 159

Thr Arg Val Asp Gln Thr Pro Arg Thr Ala Thr Lys Glu Thr Gly Glu
1               5                   10                  15

Ser Leu Thr Ile Asn Cys Val Leu Thr Asp Thr Asn Tyr Gly Leu Tyr
            20                  25                  30

Ser Thr Ser Trp Phe Arg Lys Asn Pro Gly Thr Thr Asp Trp Glu Arg
        35                  40                  45

Met Ser Ile Gly Gly Arg Tyr Val Glu Ser Val Asn Lys Gly Ala Lys
    50                  55                  60

Ser Phe Ser Leu Arg Ile Lys Asp Leu Thr Val Ala Asp Ser Ala Thr
65                  70                  75                  80

Tyr Tyr Cys Lys Ala Tyr Val Ile Tyr Arg Ala Leu Pro Ala Trp Trp
                85                  90                  95

Tyr Asp Gly Ala Gly Thr Val Leu Thr Val Asn
            100                 105

<210> SEQ ID NO 160
<211> LENGTH: 107
<212> TYPE: PRT
<213> ORGANISM: Artificial sequence
<220> FEATURE:
<223> OTHER INFORMATION: Synthetic sequence: Anti-hRAGE antigen specific
      antigen binding molecule (VNAR)

<400> SEQUENCE: 160

Thr Arg Val Asp Gln Thr Pro Arg Thr Ala Thr Lys Glu Thr Gly Glu

```
                1               5                  10                 15
Ser Leu Thr Ile Asn Cys Val Leu Thr Asp Thr Asp Tyr Ser Leu Phe
                20                  25                 30

Ala Thr Ser Trp Phe Arg Lys Asn Pro Gly Thr Thr Asp Trp Glu Arg
            35                  40                  45

Met Ser Ile Gly Gly Arg Tyr Val Glu Ser Val Asn Lys Gly Ala Lys
            50                  55                  60

Ser Phe Ser Leu Arg Ile Lys Asp Leu Thr Val Ala Asp Ser Ala Thr
65                  70                  75                  80

Tyr Tyr Cys Lys Ala Leu Val Gln Trp Ile Lys Trp Trp Val Trp
                85                  90                  95

Tyr Asp Gly Ala Gly Thr Val Leu Thr Val Asn
                100                 105
```

<210> SEQ ID NO 161
<211> LENGTH: 111
<212> TYPE: PRT
<213> ORGANISM: Artificial sequence
<220> FEATURE:
<223> OTHER INFORMATION: Synthetic sequence: Anti-hRAGE antigen specific
      antigen binding molecule (VNAR)

<400> SEQUENCE: 161

```
Thr Arg Val Asp Gln Thr Pro Arg Thr Ala Thr Lys Glu Thr Gly Glu
1               5                  10                 15

Ser Leu Thr Ile Asn Cys Val Leu Thr Asp Thr Ser Tyr Gly Leu Tyr
                20                  25                 30

Ser Thr Ser Trp Phe Arg Lys Asn Pro Gly Thr Thr Asp Trp Glu Arg
            35                  40                  45

Met Ser Ile Gly Gly Arg Tyr Val Glu Ser Val Asn Lys Gly Ala Lys
            50                  55                  60

Ser Phe Ser Leu Arg Ile Lys Asp Leu Thr Val Ala Asp Ser Ala Thr
65                  70                  75                  80

Tyr Tyr Cys Lys Ala Val Phe Val Val His Lys Gly Thr Glu Thr Ile
                85                  90                  95

Ala Thr Gly Trp Tyr Asp Gly Ala Gly Thr Val Leu Thr Val Asn
            100                 105                 110
```

<210> SEQ ID NO 162
<211> LENGTH: 104
<212> TYPE: PRT
<213> ORGANISM: Artificial sequence
<220> FEATURE:
<223> OTHER INFORMATION: Synthetic sequence: Anti-hRAGE antigen specific
      antigen binding molecule (VNAR)

<400> SEQUENCE: 162

```
Thr Arg Val Asp Gln Thr Pro Arg Thr Ala Thr Lys Glu Thr Gly Glu
1               5                  10                 15

Ser Leu Thr Ile Asn Cys Val Leu Thr Asp Thr Gly Tyr Ser Trp Tyr
                20                  25                 30

Ser Thr Ser Trp Phe Arg Lys Asn Pro Gly Thr Thr Asp Trp Glu Arg
            35                  40                  45

Met Ser Ile Gly Gly Arg Tyr Val Glu Ser Val Asn Lys Gly Ala Lys
            50                  55                  60

Ser Phe Ser Leu Arg Ile Lys Asp Leu Thr Val Ala Asp Ser Ala Thr
65                  70                  75                  80

Tyr Tyr Cys Arg Ala Asn Asp Val Thr Lys His Gly Asp Val Tyr Gly
```

Ala Gly Thr Val Leu Thr Val Asn
            100

<210> SEQ ID NO 163
<211> LENGTH: 107
<212> TYPE: PRT
<213> ORGANISM: Artificial sequence
<220> FEATURE:
<223> OTHER INFORMATION: Synthetic sequence: Anti-hRAGE antigen specific
      antigen binding molecule (VNAR)

<400> SEQUENCE: 163

Thr Arg Val Asp Gln Thr Pro Arg Thr Ala Thr Lys Glu Thr Gly Glu
1               5                   10                  15

Ser Leu Thr Ile Asn Cys Val Leu Thr Asp Thr Ile Ser Gln Thr Trp
            20                  25                  30

Val Ser Trp Phe Arg Lys Asn Pro Gly Thr Thr Asp Trp Glu Arg Met
        35                  40                  45

Ser Ile Gly Gly Arg Tyr Val Glu Ser Val Asn Lys Gly Ala Lys Ser
    50                  55                  60

Phe Ser Leu Arg Ile Lys Asp Leu Thr Val Ala Asp Ser Ala Thr Tyr
65                  70                  75                  80

Tyr Cys Arg Ala Arg Gln His Ala Val Trp Leu Arg Gln Glu Phe Asp
                85                  90                  95

Val Tyr Gly Ala Gly Thr Val Leu Thr Val Asn
            100                 105

<210> SEQ ID NO 164
<211> LENGTH: 106
<212> TYPE: PRT
<213> ORGANISM: Artificial sequence
<220> FEATURE:
<223> OTHER INFORMATION: Synthetic sequence: Anti-TNF-alpha antigen
      specific antigen binding molecule (VNAR)

<400> SEQUENCE: 164

Thr Arg Val Asp Gln Thr Pro Arg Thr Ala Thr Lys Glu Thr Gly Glu
1               5                   10                  15

Ser Leu Thr Ile Asn Cys Val Leu Thr Asp Thr Lys Asn Leu Trp Gln
            20                  25                  30

Pro Thr Ser Trp Phe Arg Lys Asn Pro Gly Thr Thr Asp Trp Glu Arg
        35                  40                  45

Met Ser Ile Gly Gly Arg Tyr Val Glu Ser Val Asn Lys Gly Ala Lys
    50                  55                  60

Ser Phe Ser Leu Arg Ile Lys Asp Leu Thr Val Ala Asp Ser Ala Thr
65                  70                  75                  80

Tyr Tyr Cys Lys Ala Phe Met Gln Ser Ser Trp Val His Trp Tyr Asp
                85                  90                  95

Asp Gly Ala Gly Thr Val Leu Thr Val Asn
            100                 105

<210> SEQ ID NO 165
<211> LENGTH: 104
<212> TYPE: PRT
<213> ORGANISM: Artificial sequence
<220> FEATURE:
<223> OTHER INFORMATION: Synthetic sequence: Anti-TNF-alpha antigen
      specific antigen binding molecule (VNAR)

<400> SEQUENCE: 165

```
Ala Ser Val Asn Gln Thr Pro Arg Thr Ala Thr Lys Glu Thr Gly Glu
1               5                   10                  15

Ser Leu Thr Ile Asn Cys Val Leu Thr Asp Thr Phe Pro His Trp Ser
                20                  25                  30

Thr Thr Ser Trp Phe Arg Lys Asn Pro Gly Thr Thr Asp Trp Glu Arg
            35                  40                  45

Met Ser Ile Gly Gly Arg Tyr Val Glu Ser Val Asn Lys Gly Ala Lys
    50                  55                  60

Ser Phe Ser Leu Arg Ile Lys Asp Leu Thr Val Ala Asp Ser Ala Thr
65              70                  75                  80

Tyr Ile Cys Arg Ala Lys Ser Asn Ile Arg Val Met Asp Val Tyr Gly
                85                  90                  95

Ala Gly Thr Val Leu Thr Val Asn
                100

<210> SEQ ID NO 166
<211> LENGTH: 107
<212> TYPE: PRT
<213> ORGANISM: Artificial sequence
<220> FEATURE:
<223> OTHER INFORMATION: Synthetic sequence: Anti-TNF-alpha antigen
      specific antigen binding molecule (VNAR)

<400> SEQUENCE: 166

Ala Ser Val Asn Gln Thr Pro Arg Thr Ala Thr Lys Glu Thr Gly Glu
1               5                   10                  15

Ser Leu Thr Ile Asn Cys Val Val Thr Gly Ala Arg Gln Thr Trp Glu
                20                  25                  30

Arg Thr Tyr Trp Tyr Arg Lys Asn Pro Gly Ser Ser Asn Gln Glu Arg
            35                  40                  45

Ile Ser Ile Ser Gly Arg Tyr Val Glu Ser Val Asn Lys Arg Thr Met
    50                  55                  60

Ser Phe Ser Leu Arg Ile Lys Asp Leu Thr Val Ala Asp Ser Ala Thr
65              70                  75                  80

Tyr Ile Cys Arg Ala Val Gly Met Ser His Gln Gln Trp Met His Gly
                85                  90                  95

Val Tyr Gly Ala Gly Thr Val Leu Thr Val Asn
                100                 105

<210> SEQ ID NO 167
<211> LENGTH: 105
<212> TYPE: PRT
<213> ORGANISM: Artificial sequence
<220> FEATURE:
<223> OTHER INFORMATION: Synthetic sequence: Anti-TNF-alpha antigen
      specific antigen binding molecule (VNAR)

<400> SEQUENCE: 167

Thr Arg Val Asp Gln Thr Pro Arg Thr Ala Thr Lys Glu Thr Gly Glu
1               5                   10                  15

Ser Leu Thr Ile Asn Cys Val Leu Thr Asp Thr Ser Tyr Ser Leu Phe
                20                  25                  30

Ser Thr Ser Trp Phe Arg Lys Asn Pro Gly Thr Thr Asp Trp Glu Arg
            35                  40                  45

Met Ser Ile Gly Gly Arg Tyr Val Glu Ser Val Asn Lys Gly Ala Lys
    50                  55                  60

Ser Phe Ser Leu Arg Ile Lys Asp Leu Thr Val Ala Asp Ser Ala Thr
65              70                  75                  80
```

```
Tyr Tyr Cys Lys Ala Met Met Trp Ile Phe Phe Tyr Met Trp Tyr Asp
                85                  90                  95

Gly Ala Gly Thr Val Leu Thr Val Asn
            100                 105

<210> SEQ ID NO 168
<211> LENGTH: 106
<212> TYPE: PRT
<213> ORGANISM: Artificial sequence
<220> FEATURE:
<223> OTHER INFORMATION: Synthetic sequence: Anti-TNF-alpha antigen
      specific antigen binding molecule (VNAR)

<400> SEQUENCE: 168

Thr Arg Val Asp Gln Thr Pro Arg Thr Ala Thr Lys Glu Thr Gly Glu
1               5                   10                  15

Ser Leu Thr Ile Asn Cys Val Leu Thr Asp Thr Asp Tyr Ser Leu Phe
            20                  25                  30

Ala Thr Ser Trp Phe Arg Lys Asn Pro Gly Thr Thr Asp Trp Glu Arg
        35                  40                  45

Met Ser Ile Gly Gly Arg Tyr Val Glu Ser Val Asn Lys Gly Ala Lys
    50                  55                  60

Ser Phe Ser Leu Arg Ile Lys Asp Leu Thr Val Ala Asp Ser Ala Thr
65                  70                  75                  80

Tyr Ile Cys Arg Ala Gln Met Trp Tyr Trp His Gln Lys Gln Asp Val
                85                  90                  95

Tyr Gly Ala Gly Thr Val Leu Thr Val Asn
            100                 105

<210> SEQ ID NO 169
<211> LENGTH: 107
<212> TYPE: PRT
<213> ORGANISM: Artificial sequence
<220> FEATURE:
<223> OTHER INFORMATION: Synthetic sequence: Anti-TNF-alpha antigen
      specific antigen binding molecule (VNAR)

<400> SEQUENCE: 169

Thr Arg Val Asp Gln Thr Pro Arg Thr Ala Thr Lys Glu Thr Gly Glu
1               5                   10                  15

Ser Leu Thr Ile Asn Cys Val Leu Thr Asp Thr Ser Tyr Ala Leu Phe
            20                  25                  30

Ser Thr Ser Trp Phe Arg Lys Asn Pro Gly Thr Thr Asp Trp Glu Arg
        35                  40                  45

Met Ser Ile Gly Gly Arg Tyr Val Glu Ser Val Asn Lys Gly Ala Lys
    50                  55                  60

Ser Phe Ser Leu Arg Ile Lys Asp Leu Thr Val Ala Asp Ser Ala Thr
65                  70                  75                  80

Tyr Tyr Cys Lys Ala Pro Met Pro Trp Gly Lys Phe Val Gln Ser Trp
                85                  90                  95

Tyr Asp Gly Ala Gly Thr Val Leu Thr Val Asn
            100                 105

<210> SEQ ID NO 170
<211> LENGTH: 6
<212> TYPE: PRT
<213> ORGANISM: Artificial sequence
<220> FEATURE:
<223> OTHER INFORMATION: Synthetic sequence: CDR1 domain
```

```
<400> SEQUENCE: 170

Ser Tyr Gly Leu Tyr Ser
1               5

<210> SEQ ID NO 171
<211> LENGTH: 6
<212> TYPE: PRT
<213> ORGANISM: Artificial sequence
<220> FEATURE:
<223> OTHER INFORMATION: Synthetic sequence: CDR1 domain

<400> SEQUENCE: 171

Ser Tyr Ala Trp Ser Ser
1               5

<210> SEQ ID NO 172
<211> LENGTH: 6
<212> TYPE: PRT
<213> ORGANISM: Artificial sequence
<220> FEATURE:
<223> OTHER INFORMATION: Synthetic sequence: CDR1 domain

<400> SEQUENCE: 172

Gly Tyr Gly Trp Phe Ala
1               5

<210> SEQ ID NO 173
<211> LENGTH: 6
<212> TYPE: PRT
<213> ORGANISM: Artificial sequence
<220> FEATURE:
<223> OTHER INFORMATION: Synthetic sequence: CDR1 domain

<400> SEQUENCE: 173

Glu Tyr Gly Leu Phe Ser
1               5

<210> SEQ ID NO 174
<211> LENGTH: 6
<212> TYPE: PRT
<213> ORGANISM: Artificial sequence
<220> FEATURE:
<223> OTHER INFORMATION: Synthetic sequence: CDR1 domain

<400> SEQUENCE: 174

Arg Tyr Ala Leu Tyr Ser
1               5

<210> SEQ ID NO 175
<211> LENGTH: 6
<212> TYPE: PRT
<213> ORGANISM: Artificial sequence
<220> FEATURE:
<223> OTHER INFORMATION: Synthetic sequence: CDR1 domain

<400> SEQUENCE: 175

Ser Tyr Gly Trp Phe Ser
1               5

<210> SEQ ID NO 176
<211> LENGTH: 6
<212> TYPE: PRT
<213> ORGANISM: Artificial sequence
<220> FEATURE:
<223> OTHER INFORMATION: Synthetic sequence: CDR1 domain

<400> SEQUENCE: 176
```

```
Gly Tyr Gly Leu Phe Ser
1               5
```

<210> SEQ ID NO 177
<211> LENGTH: 6
<212> TYPE: PRT
<213> ORGANISM: Artificial sequence
<220> FEATURE:
<223> OTHER INFORMATION: Synthetic sequence: CDR1 domain

<400> SEQUENCE: 177

```
Glu Tyr Ala Leu Phe Ser
1               5
```

<210> SEQ ID NO 178
<211> LENGTH: 6
<212> TYPE: PRT
<213> ORGANISM: Artificial sequence
<220> FEATURE:
<223> OTHER INFORMATION: Synthetic sequence: CDR1 domain

<400> SEQUENCE: 178

```
Trp Gln His Trp Thr His
1               5
```

<210> SEQ ID NO 179
<211> LENGTH: 6
<212> TYPE: PRT
<213> ORGANISM: Artificial sequence
<220> FEATURE:
<223> OTHER INFORMATION: Synthetic sequence: CDR1 domain

<400> SEQUENCE: 179

```
Ser Tyr Gly Leu Tyr Ser
1               5
```

<210> SEQ ID NO 180
<211> LENGTH: 6
<212> TYPE: PRT
<213> ORGANISM: Artificial sequence
<220> FEATURE:
<223> OTHER INFORMATION: Synthetic sequence: CDR1 domain

<400> SEQUENCE: 180

```
Lys Tyr Ala Leu Phe Ser
1               5
```

<210> SEQ ID NO 181
<211> LENGTH: 6
<212> TYPE: PRT
<213> ORGANISM: Artificial sequence
<220> FEATURE:
<223> OTHER INFORMATION: Synthetic sequence: CDR1 domain

<400> SEQUENCE: 181

```
Gly Tyr Ala Leu Phe Ala
1               5
```

<210> SEQ ID NO 182
<211> LENGTH: 7
<212> TYPE: PRT
<213> ORGANISM: Artificial sequence
<220> FEATURE:
<223> OTHER INFORMATION: Synthetic sequence: CDR1 domain

<400> SEQUENCE: 182

Tyr Pro His Trp Trp Gln Trp
1               5

<210> SEQ ID NO 183
<211> LENGTH: 7
<212> TYPE: PRT
<213> ORGANISM: Artificial sequence
<220> FEATURE:
<223> OTHER INFORMATION: Synthetic sequence: CDR1 domain

<400> SEQUENCE: 183

Thr Pro His Trp Trp Arg Trp
1               5

<210> SEQ ID NO 184
<211> LENGTH: 6
<212> TYPE: PRT
<213> ORGANISM: Artificial sequence
<220> FEATURE:
<223> OTHER INFORMATION: Synthetic sequence: CDR1 domain

<400> SEQUENCE: 184

Gly Tyr Ala Trp Phe Ser
1               5

<210> SEQ ID NO 185
<211> LENGTH: 6
<212> TYPE: PRT
<213> ORGANISM: Artificial sequence
<220> FEATURE:
<223> OTHER INFORMATION: Synthetic sequence: CDR1 domain

<400> SEQUENCE: 185

Asp Tyr Ala Leu Phe Ser
1               5

<210> SEQ ID NO 186
<211> LENGTH: 6
<212> TYPE: PRT
<213> ORGANISM: Artificial sequence
<220> FEATURE:
<223> OTHER INFORMATION: Synthetic sequence: CDR1 domain

<400> SEQUENCE: 186

Trp Pro Ala Trp Ser Asn
1               5

<210> SEQ ID NO 187
<211> LENGTH: 6
<212> TYPE: PRT
<213> ORGANISM: Artificial sequence
<220> FEATURE:
<223> OTHER INFORMATION: Synthetic sequence: CDR1 domain

<400> SEQUENCE: 187

Glu Tyr Gly Trp Phe Ala
1               5

<210> SEQ ID NO 188
<211> LENGTH: 6
<212> TYPE: PRT
<213> ORGANISM: Artificial sequence
<220> FEATURE:
<223> OTHER INFORMATION: Synthetic sequence: CDR1 domain

<400> SEQUENCE: 188

Phe Pro Ile Trp Ser His

```
1               5
```

<210> SEQ ID NO 189
<211> LENGTH: 6
<212> TYPE: PRT
<213> ORGANISM: Artificial sequence
<220> FEATURE:
<223> OTHER INFORMATION: Synthetic sequence: CDR1 domain

<400> SEQUENCE: 189

```
Lys Tyr Ala Leu Phe Ala
1               5
```

<210> SEQ ID NO 190
<211> LENGTH: 6
<212> TYPE: PRT
<213> ORGANISM: Artificial sequence
<220> FEATURE:
<223> OTHER INFORMATION: Synthetic sequence: CDR1 domain

<400> SEQUENCE: 190

```
Gly Tyr Gly Trp Phe Ala
1               5
```

<210> SEQ ID NO 191
<211> LENGTH: 6
<212> TYPE: PRT
<213> ORGANISM: Artificial sequence
<220> FEATURE:
<223> OTHER INFORMATION: Synthetic sequence: CDR1 domain

<400> SEQUENCE: 191

```
Asp Tyr Gly Leu Tyr Ala
1               5
```

<210> SEQ ID NO 192
<211> LENGTH: 6
<212> TYPE: PRT
<213> ORGANISM: Artificial sequence
<220> FEATURE:
<223> OTHER INFORMATION: Synthetic sequence: CDR1 domain

<400> SEQUENCE: 192

```
Val Gln Trp Trp Ile Pro
1               5
```

<210> SEQ ID NO 193
<211> LENGTH: 6
<212> TYPE: PRT
<213> ORGANISM: Artificial sequence
<220> FEATURE:
<223> OTHER INFORMATION: Synthetic sequence: CDR1 domain

<400> SEQUENCE: 193

```
Trp Pro Thr Phe Asp His
1               5
```

<210> SEQ ID NO 194
<211> LENGTH: 6
<212> TYPE: PRT
<213> ORGANISM: Artificial sequence
<220> FEATURE:
<223> OTHER INFORMATION: Synthetic sequence: CDR1 domain

<400> SEQUENCE: 194

```
Trp Gln His Trp Thr His
1               5
```

```
<210> SEQ ID NO 195
<211> LENGTH: 6
<212> TYPE: PRT
<213> ORGANISM: Artificial sequence
<220> FEATURE:
<223> OTHER INFORMATION: Synthetic sequence: CDR1 domain

<400> SEQUENCE: 195

Gly Tyr Ser Trp Phe Ala
1               5

<210> SEQ ID NO 196
<211> LENGTH: 6
<212> TYPE: PRT
<213> ORGANISM: Artificial sequence
<220> FEATURE:
<223> OTHER INFORMATION: Synthetic sequence: CDR1 domain

<400> SEQUENCE: 196

Lys Tyr Ala Leu Phe Ala
1               5

<210> SEQ ID NO 197
<211> LENGTH: 6
<212> TYPE: PRT
<213> ORGANISM: Artificial sequence
<220> FEATURE:
<223> OTHER INFORMATION: Synthetic sequence: CDR1 domain

<400> SEQUENCE: 197

Ser Tyr Gly Leu Tyr Ser
1               5

<210> SEQ ID NO 198
<211> LENGTH: 6
<212> TYPE: PRT
<213> ORGANISM: Artificial sequence
<220> FEATURE:
<223> OTHER INFORMATION: Synthetic sequence: CDR1 domain

<400> SEQUENCE: 198

Gly Tyr Gly Leu Phe Ser
1               5

<210> SEQ ID NO 199
<211> LENGTH: 6
<212> TYPE: PRT
<213> ORGANISM: Artificial sequence
<220> FEATURE:
<223> OTHER INFORMATION: Synthetic sequence: CDR1 domain

<400> SEQUENCE: 199

Arg Tyr Ala Leu Ser Ala
1               5

<210> SEQ ID NO 200
<211> LENGTH: 6
<212> TYPE: PRT
<213> ORGANISM: Artificial sequence
<220> FEATURE:
<223> OTHER INFORMATION: Synthetic sequence: CDR1 domain

<400> SEQUENCE: 200

Trp Ser Val Trp Tyr Thr
1               5
```

```
<210> SEQ ID NO 201
<211> LENGTH: 6
<212> TYPE: PRT
<213> ORGANISM: Artificial sequence
<220> FEATURE:
<223> OTHER INFORMATION: Synthetic sequence: CDR1 domain

<400> SEQUENCE: 201

Pro Ser His Glu Phe Phe
1               5

<210> SEQ ID NO 202
<211> LENGTH: 6
<212> TYPE: PRT
<213> ORGANISM: Artificial sequence
<220> FEATURE:
<223> OTHER INFORMATION: Synthetic sequence: CDR1 domain

<400> SEQUENCE: 202

Thr Pro Gln Trp Trp Thr
1               5

<210> SEQ ID NO 203
<211> LENGTH: 6
<212> TYPE: PRT
<213> ORGANISM: Artificial sequence
<220> FEATURE:
<223> OTHER INFORMATION: Synthetic sequence: CDR1 domain

<400> SEQUENCE: 203

Arg Tyr Gly Trp Tyr Ser
1               5

<210> SEQ ID NO 204
<211> LENGTH: 6
<212> TYPE: PRT
<213> ORGANISM: Artificial sequence
<220> FEATURE:
<223> OTHER INFORMATION: Synthetic sequence: CDR1 domain

<400> SEQUENCE: 204

Asp Tyr Gly Trp Tyr Ser
1               5

<210> SEQ ID NO 205
<211> LENGTH: 6
<212> TYPE: PRT
<213> ORGANISM: Artificial sequence
<220> FEATURE:
<223> OTHER INFORMATION: Synthetic sequence: CDR1 domain

<400> SEQUENCE: 205

Asn Tyr Gly Trp Tyr Ser
1               5

<210> SEQ ID NO 206
<211> LENGTH: 6
<212> TYPE: PRT
<213> ORGANISM: Artificial sequence
<220> FEATURE:
<223> OTHER INFORMATION: Synthetic sequence: CDR1 domain

<400> SEQUENCE: 206

Gly Tyr Ala Leu Phe Ser
1               5
```

```
<210> SEQ ID NO 207
<211> LENGTH: 6
<212> TYPE: PRT
<213> ORGANISM: Artificial sequence
<220> FEATURE:
<223> OTHER INFORMATION: Synthetic sequence: CDR1 domain

<400> SEQUENCE: 207

Gly Tyr Ala Leu Tyr Ser
1               5

<210> SEQ ID NO 208
<211> LENGTH: 6
<212> TYPE: PRT
<213> ORGANISM: Artificial sequence
<220> FEATURE:
<223> OTHER INFORMATION: Synthetic sequence: CDR1 domain

<400> SEQUENCE: 208

Arg Tyr Ala Leu Phe Ala
1               5

<210> SEQ ID NO 209
<211> LENGTH: 6
<212> TYPE: PRT
<213> ORGANISM: Artificial sequence
<220> FEATURE:
<223> OTHER INFORMATION: Synthetic sequence: CDR1 domain

<400> SEQUENCE: 209

Ser Tyr Gly Leu Ser Ala
1               5

<210> SEQ ID NO 210
<211> LENGTH: 6
<212> TYPE: PRT
<213> ORGANISM: Artificial sequence
<220> FEATURE:
<223> OTHER INFORMATION: Synthetic sequence: CDR1 domain

<400> SEQUENCE: 210

Asp Tyr Ala Leu Ser Ser
1               5

<210> SEQ ID NO 211
<211> LENGTH: 6
<212> TYPE: PRT
<213> ORGANISM: Artificial sequence
<220> FEATURE:
<223> OTHER INFORMATION: Synthetic sequence: CDR1 domain

<400> SEQUENCE: 211

Phe Ile Pro Trp Leu His
1               5

<210> SEQ ID NO 212
<211> LENGTH: 6
<212> TYPE: PRT
<213> ORGANISM: Artificial sequence
<220> FEATURE:
<223> OTHER INFORMATION: Synthetic sequence: CDR1 domain

<400> SEQUENCE: 212

Gly Tyr Ser Trp Phe Ser
1               5

<210> SEQ ID NO 213
```

```
<211> LENGTH: 6
<212> TYPE: PRT
<213> ORGANISM: Artificial sequence
<220> FEATURE:
<223> OTHER INFORMATION: Synthetic sequence: CDR1 domain

<400> SEQUENCE: 213

Asn Tyr Gly Trp Tyr Ala
1               5

<210> SEQ ID NO 214
<211> LENGTH: 6
<212> TYPE: PRT
<213> ORGANISM: Artificial sequence
<220> FEATURE:
<223> OTHER INFORMATION: Synthetic sequence: CDR1 domain

<400> SEQUENCE: 214

Asp His Tyr Trp Val Ala
1               5

<210> SEQ ID NO 215
<211> LENGTH: 6
<212> TYPE: PRT
<213> ORGANISM: Artificial sequence
<220> FEATURE:
<223> OTHER INFORMATION: Synthetic sequence: CDR1 domain

<400> SEQUENCE: 215

Trp Trp Ser Trp Trp Ala
1               5

<210> SEQ ID NO 216
<211> LENGTH: 6
<212> TYPE: PRT
<213> ORGANISM: Artificial sequence
<220> FEATURE:
<223> OTHER INFORMATION: Synthetic sequence: CDR1 domain

<400> SEQUENCE: 216

Gly Tyr Ser Leu Phe Ser
1               5

<210> SEQ ID NO 217
<211> LENGTH: 6
<212> TYPE: PRT
<213> ORGANISM: Artificial sequence
<220> FEATURE:
<223> OTHER INFORMATION: Synthetic sequence: CDR1 domain

<400> SEQUENCE: 217

Asn Tyr Gly Trp Tyr Ser
1               5

<210> SEQ ID NO 218
<211> LENGTH: 6
<212> TYPE: PRT
<213> ORGANISM: Artificial sequence
<220> FEATURE:
<223> OTHER INFORMATION: Synthetic sequence: CDR1 domain

<400> SEQUENCE: 218

Arg Tyr Ala Leu Phe Ala
1               5

<210> SEQ ID NO 219
<211> LENGTH: 6
```

```
<212> TYPE: PRT
<213> ORGANISM: Artificial sequence
<220> FEATURE:
<223> OTHER INFORMATION: Synthetic sequence: CDR1 domain

<400> SEQUENCE: 219

Gly Tyr Ala Trp Tyr Ser
1               5

<210> SEQ ID NO 220
<211> LENGTH: 6
<212> TYPE: PRT
<213> ORGANISM: Artificial sequence
<220> FEATURE:
<223> OTHER INFORMATION: Synthetic sequence: CDR1 domain

<400> SEQUENCE: 220

Asn Tyr Ser Trp Phe Ala
1               5

<210> SEQ ID NO 221
<211> LENGTH: 6
<212> TYPE: PRT
<213> ORGANISM: Artificial sequence
<220> FEATURE:
<223> OTHER INFORMATION: Synthetic sequence: CDR1 domain

<400> SEQUENCE: 221

Asn Tyr Ser Trp Phe Ala
1               5

<210> SEQ ID NO 222
<211> LENGTH: 6
<212> TYPE: PRT
<213> ORGANISM: Artificial sequence
<220> FEATURE:
<223> OTHER INFORMATION: Synthetic sequence: CDR1 domain

<400> SEQUENCE: 222

Gly Tyr Ser Trp Phe Ser
1               5

<210> SEQ ID NO 223
<211> LENGTH: 6
<212> TYPE: PRT
<213> ORGANISM: Artificial sequence
<220> FEATURE:
<223> OTHER INFORMATION: Synthetic sequence: CDR1 domain

<400> SEQUENCE: 223

Asn Tyr Gly Leu Phe Ser
1               5

<210> SEQ ID NO 224
<211> LENGTH: 6
<212> TYPE: PRT
<213> ORGANISM: Artificial sequence
<220> FEATURE:
<223> OTHER INFORMATION: Synthetic sequence: CDR1 domain

<400> SEQUENCE: 224

Trp Trp Ser Trp Trp Asp
1               5

<210> SEQ ID NO 225
<211> LENGTH: 6
<212> TYPE: PRT
```

<213> ORGANISM: Artificial sequence
<220> FEATURE:
<223> OTHER INFORMATION: Synthetic sequence: CDR1 domain

<400> SEQUENCE: 225

Trp His Pro Trp Trp Val
1               5

<210> SEQ ID NO 226
<211> LENGTH: 6
<212> TYPE: PRT
<213> ORGANISM: Artificial sequence
<220> FEATURE:
<223> OTHER INFORMATION: Synthetic sequence: CDR1 domain

<400> SEQUENCE: 226

Trp Trp Trp Trp His Gln
1               5

<210> SEQ ID NO 227
<211> LENGTH: 6
<212> TYPE: PRT
<213> ORGANISM: Artificial sequence
<220> FEATURE:
<223> OTHER INFORMATION: Synthetic sequence: CDR1 domain

<400> SEQUENCE: 227

Asn Tyr Ala Leu Ser Ala
1               5

<210> SEQ ID NO 228
<211> LENGTH: 6
<212> TYPE: PRT
<213> ORGANISM: Artificial sequence
<220> FEATURE:
<223> OTHER INFORMATION: Synthetic sequence: CDR1 domain

<400> SEQUENCE: 228

Asp Ala Thr Trp Phe His
1               5

<210> SEQ ID NO 229
<211> LENGTH: 6
<212> TYPE: PRT
<213> ORGANISM: Artificial sequence
<220> FEATURE:
<223> OTHER INFORMATION: Synthetic sequence: CDR1 domain

<400> SEQUENCE: 229

Trp Trp Pro Trp Tyr Thr
1               5

<210> SEQ ID NO 230
<211> LENGTH: 6
<212> TYPE: PRT
<213> ORGANISM: Artificial sequence
<220> FEATURE:
<223> OTHER INFORMATION: Synthetic sequence: CDR1 domain

<400> SEQUENCE: 230

Gly Tyr Ala Trp Phe Ala
1               5

<210> SEQ ID NO 231
<211> LENGTH: 6
<212> TYPE: PRT
<213> ORGANISM: Artificial sequence

```
<220> FEATURE:
<223> OTHER INFORMATION: Synthetic sequence: CDR1 domain

<400> SEQUENCE: 231

Glu Ser Pro Trp Trp Tyr
1               5

<210> SEQ ID NO 232
<211> LENGTH: 6
<212> TYPE: PRT
<213> ORGANISM: Artificial sequence
<220> FEATURE:
<223> OTHER INFORMATION: Synthetic sequence: CDR1 domain

<400> SEQUENCE: 232

Gly Tyr Gly Leu Ser Ala
1               5

<210> SEQ ID NO 233
<211> LENGTH: 6
<212> TYPE: PRT
<213> ORGANISM: Artificial sequence
<220> FEATURE:
<223> OTHER INFORMATION: Synthetic sequence: CDR1 domain

<400> SEQUENCE: 233

Arg Tyr Ser Leu Tyr Ser
1               5

<210> SEQ ID NO 234
<211> LENGTH: 6
<212> TYPE: PRT
<213> ORGANISM: Artificial sequence
<220> FEATURE:
<223> OTHER INFORMATION: Synthetic sequence: CDR1 domain

<400> SEQUENCE: 234

Ser Tyr Gly Leu Ser Ala
1               5

<210> SEQ ID NO 235
<211> LENGTH: 6
<212> TYPE: PRT
<213> ORGANISM: Artificial sequence
<220> FEATURE:
<223> OTHER INFORMATION: Synthetic sequence: CDR1 domain

<400> SEQUENCE: 235

Ser Tyr Ala Leu Tyr Ser
1               5

<210> SEQ ID NO 236
<211> LENGTH: 6
<212> TYPE: PRT
<213> ORGANISM: Artificial sequence
<220> FEATURE:
<223> OTHER INFORMATION: Synthetic sequence: CDR1 domain

<400> SEQUENCE: 236

Arg Tyr Ala Leu Tyr Ser
1               5

<210> SEQ ID NO 237
<211> LENGTH: 6
<212> TYPE: PRT
<213> ORGANISM: Artificial sequence
<220> FEATURE:
```

<223> OTHER INFORMATION: Synthetic sequence: CDR1 domain

<400> SEQUENCE: 237

Tyr Gln Met Trp Gly Arg
1               5

<210> SEQ ID NO 238
<211> LENGTH: 6
<212> TYPE: PRT
<213> ORGANISM: Artificial sequence
<220> FEATURE:
<223> OTHER INFORMATION: Synthetic sequence: CDR1 domain

<400> SEQUENCE: 238

Lys Tyr Ser Leu Phe Ser
1               5

<210> SEQ ID NO 239
<211> LENGTH: 6
<212> TYPE: PRT
<213> ORGANISM: Artificial sequence
<220> FEATURE:
<223> OTHER INFORMATION: Synthetic sequence: CDR1 domain

<400> SEQUENCE: 239

Asn Tyr Ser Leu Tyr Ser
1               5

<210> SEQ ID NO 240
<211> LENGTH: 6
<212> TYPE: PRT
<213> ORGANISM: Artificial sequence
<220> FEATURE:
<223> OTHER INFORMATION: Synthetic sequence: CDR1 domain

<400> SEQUENCE: 240

Leu Ala Ser Met Gly Leu
1               5

<210> SEQ ID NO 241
<211> LENGTH: 6
<212> TYPE: PRT
<213> ORGANISM: Artificial sequence
<220> FEATURE:
<223> OTHER INFORMATION: Synthetic sequence: CDR1 domain

<400> SEQUENCE: 241

Leu Thr Pro Ser Gly Ser
1               5

<210> SEQ ID NO 242
<211> LENGTH: 6
<212> TYPE: PRT
<213> ORGANISM: Artificial sequence
<220> FEATURE:
<223> OTHER INFORMATION: Synthetic sequence: CDR1 domain

<400> SEQUENCE: 242

Glu Glu Val Phe Gly Lys
1               5

<210> SEQ ID NO 243
<211> LENGTH: 6
<212> TYPE: PRT
<213> ORGANISM: Artificial sequence
<220> FEATURE:
<223> OTHER INFORMATION: Synthetic sequence: CDR1 domain

<400> SEQUENCE: 243

Glu Gln Val Phe Gly Lys
1               5

<210> SEQ ID NO 244
<211> LENGTH: 6
<212> TYPE: PRT
<213> ORGANISM: Artificial sequence
<220> FEATURE:
<223> OTHER INFORMATION: Synthetic sequence: CDR1 domain

<400> SEQUENCE: 244

Lys Tyr Gly Leu Ala Ser
1               5

<210> SEQ ID NO 245
<211> LENGTH: 6
<212> TYPE: PRT
<213> ORGANISM: Artificial sequence
<220> FEATURE:
<223> OTHER INFORMATION: Synthetic sequence: CDR1 domain

<400> SEQUENCE: 245

Met Ser Ile Pro Glu Ala
1               5

<210> SEQ ID NO 246
<211> LENGTH: 6
<212> TYPE: PRT
<213> ORGANISM: Artificial sequence
<220> FEATURE:
<223> OTHER INFORMATION: Synthetic sequence: CDR1 domain

<400> SEQUENCE: 246

Arg Tyr Ala Leu Tyr Ser
1               5

<210> SEQ ID NO 247
<211> LENGTH: 6
<212> TYPE: PRT
<213> ORGANISM: Artificial sequence
<220> FEATURE:
<223> OTHER INFORMATION: Synthetic sequence: CDR1 domain

<400> SEQUENCE: 247

Glu Tyr Gly Trp Phe Ser
1               5

<210> SEQ ID NO 248
<211> LENGTH: 6
<212> TYPE: PRT
<213> ORGANISM: Artificial sequence
<220> FEATURE:
<223> OTHER INFORMATION: Synthetic sequence: CDR1 domain

<400> SEQUENCE: 248

Glu Thr Met Ser Gly Arg
1               5

<210> SEQ ID NO 249
<211> LENGTH: 6
<212> TYPE: PRT
<213> ORGANISM: Artificial sequence
<220> FEATURE:
<223> OTHER INFORMATION: Synthetic sequence: CDR1 domain

```
<400> SEQUENCE: 249

Glu Tyr Ala Trp Phe Ser
1               5

<210> SEQ ID NO 250
<211> LENGTH: 6
<212> TYPE: PRT
<213> ORGANISM: Artificial sequence
<220> FEATURE:
<223> OTHER INFORMATION: Synthetic sequence: CDR1 domain

<400> SEQUENCE: 250

Gly Tyr Ala Leu Phe Ser
1               5

<210> SEQ ID NO 251
<211> LENGTH: 6
<212> TYPE: PRT
<213> ORGANISM: Artificial sequence
<220> FEATURE:
<223> OTHER INFORMATION: Synthetic sequence: CDR1 domain

<400> SEQUENCE: 251

Asn Tyr Pro Leu Tyr Ser
1               5

<210> SEQ ID NO 252
<211> LENGTH: 6
<212> TYPE: PRT
<213> ORGANISM: Artificial sequence
<220> FEATURE:
<223> OTHER INFORMATION: Synthetic sequence: CDR1 domain

<400> SEQUENCE: 252

Pro Phe Trp Gln His Arg
1               5

<210> SEQ ID NO 253
<211> LENGTH: 6
<212> TYPE: PRT
<213> ORGANISM: Artificial sequence
<220> FEATURE:
<223> OTHER INFORMATION: Synthetic sequence: CDR1 domain

<400> SEQUENCE: 253

Cys Asp Val Cys Pro Gly
1               5

<210> SEQ ID NO 254
<211> LENGTH: 6
<212> TYPE: PRT
<213> ORGANISM: Artificial sequence
<220> FEATURE:
<223> OTHER INFORMATION: Synthetic sequence: CDR1 domain

<400> SEQUENCE: 254

Trp Tyr Trp Trp Trp Lys
1               5

<210> SEQ ID NO 255
<211> LENGTH: 6
<212> TYPE: PRT
<213> ORGANISM: Artificial sequence
<220> FEATURE:
<223> OTHER INFORMATION: Synthetic sequence: CDR1 domain

<400> SEQUENCE: 255
```

Ser Tyr Ala Leu Tyr Ala
1               5

<210> SEQ ID NO 256
<211> LENGTH: 6
<212> TYPE: PRT
<213> ORGANISM: Artificial sequence
<220> FEATURE:
<223> OTHER INFORMATION: Synthetic sequence: CDR1 domain

<400> SEQUENCE: 256

Ser Tyr Ala Trp Phe Ser
1               5

<210> SEQ ID NO 257
<211> LENGTH: 6
<212> TYPE: PRT
<213> ORGANISM: Artificial sequence
<220> FEATURE:
<223> OTHER INFORMATION: Synthetic sequence: CDR1 domain

<400> SEQUENCE: 257

Glu Tyr Gly Trp Tyr Ala
1               5

<210> SEQ ID NO 258
<211> LENGTH: 6
<212> TYPE: PRT
<213> ORGANISM: Artificial sequence
<220> FEATURE:
<223> OTHER INFORMATION: Synthetic sequence: CDR1 domain

<400> SEQUENCE: 258

Trp Leu Pro Trp Trp Gln
1               5

<210> SEQ ID NO 259
<211> LENGTH: 6
<212> TYPE: PRT
<213> ORGANISM: Artificial sequence
<220> FEATURE:
<223> OTHER INFORMATION: Synthetic sequence: CDR1 domain

<400> SEQUENCE: 259

Gly Tyr Ala Trp Phe Ser
1               5

<210> SEQ ID NO 260
<211> LENGTH: 6
<212> TYPE: PRT
<213> ORGANISM: Artificial sequence
<220> FEATURE:
<223> OTHER INFORMATION: Synthetic sequence: CDR1 domain

<400> SEQUENCE: 260

Gly Tyr Ala Trp Tyr Ala
1               5

<210> SEQ ID NO 261
<211> LENGTH: 6
<212> TYPE: PRT
<213> ORGANISM: Artificial sequence
<220> FEATURE:
<223> OTHER INFORMATION: Synthetic sequence: CDR1 domain

<400> SEQUENCE: 261

Ser Tyr Ala Leu Tyr Ala
1               5

<210> SEQ ID NO 262
<211> LENGTH: 6
<212> TYPE: PRT
<213> ORGANISM: Artificial sequence
<220> FEATURE:
<223> OTHER INFORMATION: Synthetic sequence: CDR1 domain

<400> SEQUENCE: 262

Gly Tyr Ala Leu Ser Ser
1               5

<210> SEQ ID NO 263
<211> LENGTH: 6
<212> TYPE: PRT
<213> ORGANISM: Artificial sequence
<220> FEATURE:
<223> OTHER INFORMATION: Synthetic sequence: CDR1 domain

<400> SEQUENCE: 263

Thr His Gln Trp Val Glu
1               5

<210> SEQ ID NO 264
<211> LENGTH: 6
<212> TYPE: PRT
<213> ORGANISM: Artificial sequence
<220> FEATURE:
<223> OTHER INFORMATION: Synthetic sequence: CDR1 domain

<400> SEQUENCE: 264

Trp Met Pro Trp Asp Thr
1               5

<210> SEQ ID NO 265
<211> LENGTH: 6
<212> TYPE: PRT
<213> ORGANISM: Artificial sequence
<220> FEATURE:
<223> OTHER INFORMATION: Synthetic sequence: CDR1 domain

<400> SEQUENCE: 265

Gly Tyr Ser Trp Phe Ala
1               5

<210> SEQ ID NO 266
<211> LENGTH: 6
<212> TYPE: PRT
<213> ORGANISM: Artificial sequence
<220> FEATURE:
<223> OTHER INFORMATION: Synthetic sequence: CDR1 domain

<400> SEQUENCE: 266

Ser Tyr Ala Leu Ser Ser
1               5

<210> SEQ ID NO 267
<211> LENGTH: 6
<212> TYPE: PRT
<213> ORGANISM: Artificial sequence
<220> FEATURE:
<223> OTHER INFORMATION: Synthetic sequence: CDR1 domain

<400> SEQUENCE: 267

Phe Ala Ser Ser His His

<210> SEQ ID NO 268
<211> LENGTH: 6
<212> TYPE: PRT
<213> ORGANISM: Artificial sequence
<220> FEATURE:
<223> OTHER INFORMATION: Synthetic sequence: CDR1 domain

<400> SEQUENCE: 268

Pro Gln Gln Trp Phe Gln
1               5

<210> SEQ ID NO 269
<211> LENGTH: 6
<212> TYPE: PRT
<213> ORGANISM: Artificial sequence
<220> FEATURE:
<223> OTHER INFORMATION: Synthetic sequence: CDR1 domain

<400> SEQUENCE: 269

Ser Glu Phe His His His
1               5

<210> SEQ ID NO 270
<211> LENGTH: 6
<212> TYPE: PRT
<213> ORGANISM: Artificial sequence
<220> FEATURE:
<223> OTHER INFORMATION: Synthetic sequence: CDR1 domain

<400> SEQUENCE: 270

Asn Tyr Ser Trp Phe Ser
1               5

<210> SEQ ID NO 271
<211> LENGTH: 6
<212> TYPE: PRT
<213> ORGANISM: Artificial sequence
<220> FEATURE:
<223> OTHER INFORMATION: Synthetic sequence: CDR1 domain

<400> SEQUENCE: 271

Asn Tyr Ser Leu Tyr Ala
1               5

<210> SEQ ID NO 272
<211> LENGTH: 6
<212> TYPE: PRT
<213> ORGANISM: Artificial sequence
<220> FEATURE:
<223> OTHER INFORMATION: Synthetic sequence: CDR1 domain

<400> SEQUENCE: 272

Arg Tyr Ala Leu Ala Ser
1               5

<210> SEQ ID NO 273
<211> LENGTH: 6
<212> TYPE: PRT
<213> ORGANISM: Artificial sequence
<220> FEATURE:
<223> OTHER INFORMATION: Synthetic sequence: CDR1 domain

<400> SEQUENCE: 273

Gly Tyr Ala Leu Phe Ser
1               5

```
<210> SEQ ID NO 274
<211> LENGTH: 6
<212> TYPE: PRT
<213> ORGANISM: Artificial sequence
<220> FEATURE:
<223> OTHER INFORMATION: Synthetic sequence: CDR1 domain

<400> SEQUENCE: 274

Asp Tyr Gly Leu Tyr Ala
1               5

<210> SEQ ID NO 275
<211> LENGTH: 6
<212> TYPE: PRT
<213> ORGANISM: Artificial sequence
<220> FEATURE:
<223> OTHER INFORMATION: Synthetic sequence: CDR1 domain

<400> SEQUENCE: 275

Gly Tyr Ala Leu Ala Ser
1               5

<210> SEQ ID NO 276
<211> LENGTH: 6
<212> TYPE: PRT
<213> ORGANISM: Artificial sequence
<220> FEATURE:
<223> OTHER INFORMATION: Synthetic sequence: CDR1 domain

<400> SEQUENCE: 276

Asp Tyr Ser Leu Phe Ser
1               5

<210> SEQ ID NO 277
<211> LENGTH: 6
<212> TYPE: PRT
<213> ORGANISM: Artificial sequence
<220> FEATURE:
<223> OTHER INFORMATION: Synthetic sequence: CDR1 domain

<400> SEQUENCE: 277

Lys Tyr Ala Leu Phe Ser
1               5

<210> SEQ ID NO 278
<211> LENGTH: 6
<212> TYPE: PRT
<213> ORGANISM: Artificial sequence
<220> FEATURE:
<223> OTHER INFORMATION: Synthetic sequence: CDR1 domain

<400> SEQUENCE: 278

Arg Tyr Ala Leu Phe Ala
1               5

<210> SEQ ID NO 279
<211> LENGTH: 6
<212> TYPE: PRT
<213> ORGANISM: Artificial sequence
<220> FEATURE:
<223> OTHER INFORMATION: Synthetic sequence: CDR1 domain

<400> SEQUENCE: 279

Gly Tyr Gly Leu Phe Ser
1               5
```

<210> SEQ ID NO 280
<211> LENGTH: 6
<212> TYPE: PRT
<213> ORGANISM: Artificial sequence
<220> FEATURE:
<223> OTHER INFORMATION: Synthetic sequence: CDR1 domain

<400> SEQUENCE: 280

Trp Trp Pro Trp Leu Thr
1               5

<210> SEQ ID NO 281
<211> LENGTH: 6
<212> TYPE: PRT
<213> ORGANISM: Artificial sequence
<220> FEATURE:
<223> OTHER INFORMATION: Synthetic sequence: CDR1 domain

<400> SEQUENCE: 281

Lys Tyr Leu Tyr Ser Thr
1               5

<210> SEQ ID NO 282
<211> LENGTH: 6
<212> TYPE: PRT
<213> ORGANISM: Artificial sequence
<220> FEATURE:
<223> OTHER INFORMATION: Synthetic sequence: CDR1 domain

<400> SEQUENCE: 282

Ser Tyr Ala Leu Ser Ala
1               5

<210> SEQ ID NO 283
<211> LENGTH: 6
<212> TYPE: PRT
<213> ORGANISM: Artificial sequence
<220> FEATURE:
<223> OTHER INFORMATION: Synthetic sequence: CDR1 domain

<400> SEQUENCE: 283

Ser Tyr Gly Leu Phe Ser
1               5

<210> SEQ ID NO 284
<211> LENGTH: 6
<212> TYPE: PRT
<213> ORGANISM: Artificial sequence
<220> FEATURE:
<223> OTHER INFORMATION: Synthetic sequence: CDR1 domain

<400> SEQUENCE: 284

Glu Tyr Gly Leu Ser Ala
1               5

<210> SEQ ID NO 285
<211> LENGTH: 6
<212> TYPE: PRT
<213> ORGANISM: Artificial sequence
<220> FEATURE:
<223> OTHER INFORMATION: Synthetic sequence: CDR1 domain

<400> SEQUENCE: 285

Ser Tyr Ala Leu Ser Ser
1               5

```
<210> SEQ ID NO 286
<211> LENGTH: 6
<212> TYPE: PRT
<213> ORGANISM: Artificial sequence
<220> FEATURE:
<223> OTHER INFORMATION: Synthetic sequence: CDR1 domain

<400> SEQUENCE: 286

Ser Tyr Gly Leu Phe Ala
1               5

<210> SEQ ID NO 287
<211> LENGTH: 6
<212> TYPE: PRT
<213> ORGANISM: Artificial sequence
<220> FEATURE:
<223> OTHER INFORMATION: Synthetic sequence: CDR1 domain

<400> SEQUENCE: 287

Asn Tyr Gly Leu Tyr Ser
1               5

<210> SEQ ID NO 288
<211> LENGTH: 6
<212> TYPE: PRT
<213> ORGANISM: Artificial sequence
<220> FEATURE:
<223> OTHER INFORMATION: Synthetic sequence: CDR1 domain

<400> SEQUENCE: 288

Asp Tyr Ser Leu Phe Ala
1               5

<210> SEQ ID NO 289
<211> LENGTH: 6
<212> TYPE: PRT
<213> ORGANISM: Artificial sequence
<220> FEATURE:
<223> OTHER INFORMATION: Synthetic sequence: CDR1 domain

<400> SEQUENCE: 289

Ser Tyr Gly Leu Tyr Ser
1               5

<210> SEQ ID NO 290
<211> LENGTH: 6
<212> TYPE: PRT
<213> ORGANISM: Artificial sequence
<220> FEATURE:
<223> OTHER INFORMATION: Synthetic sequence: CDR1 domain

<400> SEQUENCE: 290

Gly Tyr Ser Trp Tyr Ser
1               5

<210> SEQ ID NO 291
<211> LENGTH: 6
<212> TYPE: PRT
<213> ORGANISM: Artificial sequence
<220> FEATURE:
<223> OTHER INFORMATION: Synthetic sequence: CDR1 domain

<400> SEQUENCE: 291

Ile Ser Gln Thr Trp Val
1               5

<210> SEQ ID NO 292
```

```
<211> LENGTH: 6
<212> TYPE: PRT
<213> ORGANISM: Artificial sequence
<220> FEATURE:
<223> OTHER INFORMATION: Synthetic sequence: CDR1 domain

<400> SEQUENCE: 292

Lys Asn Leu Trp Gln Pro
1               5

<210> SEQ ID NO 293
<211> LENGTH: 6
<212> TYPE: PRT
<213> ORGANISM: Artificial sequence
<220> FEATURE:
<223> OTHER INFORMATION: Synthetic sequence: CDR1 domain

<400> SEQUENCE: 293

Phe Pro His Trp Ser Thr
1               5

<210> SEQ ID NO 294
<211> LENGTH: 6
<212> TYPE: PRT
<213> ORGANISM: Artificial sequence
<220> FEATURE:
<223> OTHER INFORMATION: Synthetic sequence: CDR1 domain

<400> SEQUENCE: 294

Arg Gln Thr Trp Glu Arg
1               5

<210> SEQ ID NO 295
<211> LENGTH: 6
<212> TYPE: PRT
<213> ORGANISM: Artificial sequence
<220> FEATURE:
<223> OTHER INFORMATION: Synthetic sequence: CDR1 domain

<400> SEQUENCE: 295

Ser Tyr Ser Leu Phe Ser
1               5

<210> SEQ ID NO 296
<211> LENGTH: 6
<212> TYPE: PRT
<213> ORGANISM: Artificial sequence
<220> FEATURE:
<223> OTHER INFORMATION: Synthetic sequence: CDR1 domain

<400> SEQUENCE: 296

Asp Tyr Ser Leu Phe Ala
1               5

<210> SEQ ID NO 297
<211> LENGTH: 6
<212> TYPE: PRT
<213> ORGANISM: Artificial sequence
<220> FEATURE:
<223> OTHER INFORMATION: Synthetic sequence: CDR1 domain

<400> SEQUENCE: 297

Ser Tyr Ala Leu Phe Ser
1               5

<210> SEQ ID NO 298
<211> LENGTH: 12
```

```
<212> TYPE: PRT
<213> ORGANISM: Artificial sequence
<220> FEATURE:
<223> OTHER INFORMATION: Synthetic sequence: CDR3 domain

<400> SEQUENCE: 298

Gln Ser Leu Ala Ile Ser Thr Arg Ser Tyr Trp Tyr
1               5                   10

<210> SEQ ID NO 299
<211> LENGTH: 13
<212> TYPE: PRT
<213> ORGANISM: Artificial sequence
<220> FEATURE:
<223> OTHER INFORMATION: Synthetic sequence: CDR3 domain

<400> SEQUENCE: 299

Tyr Arg Met Glu Ser Ile Ala Gly Arg Gly Tyr Asp Val
1               5                   10

<210> SEQ ID NO 300
<211> LENGTH: 13
<212> TYPE: PRT
<213> ORGANISM: Artificial sequence
<220> FEATURE:
<223> OTHER INFORMATION: Synthetic sequence: CDR3 domain

<400> SEQUENCE: 300

Asp Met Trp Pro Lys Asn Thr Lys Tyr Ser Pro Asp Val
1               5                   10

<210> SEQ ID NO 301
<211> LENGTH: 12
<212> TYPE: PRT
<213> ORGANISM: Artificial sequence
<220> FEATURE:
<223> OTHER INFORMATION: Synthetic sequence: CDR3 domain

<400> SEQUENCE: 301

Leu Gly Trp Trp Pro Pro Ala Phe Pro His Trp Tyr
1               5                   10

<210> SEQ ID NO 302
<211> LENGTH: 9
<212> TYPE: PRT
<213> ORGANISM: Artificial sequence
<220> FEATURE:
<223> OTHER INFORMATION: Synthetic sequence: CDR3 domain

<400> SEQUENCE: 302

Asn Glu Met Met Pro Pro Met Asp Val
1               5

<210> SEQ ID NO 303
<211> LENGTH: 11
<212> TYPE: PRT
<213> ORGANISM: Artificial sequence
<220> FEATURE:
<223> OTHER INFORMATION: Synthetic sequence: CDR3 domain

<400> SEQUENCE: 303

Gln Ala Ala Ile Pro Asp Phe Pro Arg Tyr Val
1               5                   10

<210> SEQ ID NO 304
<211> LENGTH: 12
<212> TYPE: PRT
```

```
<213> ORGANISM: Artificial sequence
<220> FEATURE:
<223> OTHER INFORMATION: Synthetic sequence: CDR3 domain

<400> SEQUENCE: 304

Leu Gly Trp Ile Pro Pro Glu Phe Pro His Trp Tyr
1               5                   10

<210> SEQ ID NO 305
<211> LENGTH: 10
<212> TYPE: PRT
<213> ORGANISM: Artificial sequence
<220> FEATURE:
<223> OTHER INFORMATION: Synthetic sequence: CDR3 domain

<400> SEQUENCE: 305

His Val Asp Pro Leu Ala Trp Leu Asp Val
1               5                   10

<210> SEQ ID NO 306
<211> LENGTH: 9
<212> TYPE: PRT
<213> ORGANISM: Artificial sequence
<220> FEATURE:
<223> OTHER INFORMATION: Synthetic sequence: CDR3 domain

<400> SEQUENCE: 306

Tyr His Met Leu Asp Gly Trp Asp Val
1               5

<210> SEQ ID NO 307
<211> LENGTH: 13
<212> TYPE: PRT
<213> ORGANISM: Artificial sequence
<220> FEATURE:
<223> OTHER INFORMATION: Synthetic sequence: CDR3 domain

<400> SEQUENCE: 307

Lys His Phe Ser Gln Leu Gln Pro Phe Leu Asn Asp Val
1               5                   10

<210> SEQ ID NO 308
<211> LENGTH: 9
<212> TYPE: PRT
<213> ORGANISM: Artificial sequence
<220> FEATURE:
<223> OTHER INFORMATION: Synthetic sequence: CDR3 domain

<400> SEQUENCE: 308

Asn Trp Leu Met His Pro Met Asp Val
1               5

<210> SEQ ID NO 309
<211> LENGTH: 12
<212> TYPE: PRT
<213> ORGANISM: Artificial sequence
<220> FEATURE:
<223> OTHER INFORMATION: Synthetic sequence: CDR3 domain

<400> SEQUENCE: 309

Ala Lys Glu Thr Phe Ala His Val Tyr Pro Trp Tyr
1               5                   10

<210> SEQ ID NO 310
<211> LENGTH: 11
<212> TYPE: PRT
<213> ORGANISM: Artificial sequence
```

```
<220> FEATURE:
<223> OTHER INFORMATION: Synthetic sequence: CDR3 domain

<400> SEQUENCE: 310

Arg Ala His Arg Lys Glu Gln Trp Arg Asp Val
1               5                   10

<210> SEQ ID NO 311
<211> LENGTH: 10
<212> TYPE: PRT
<213> ORGANISM: Artificial sequence
<220> FEATURE:
<223> OTHER INFORMATION: Synthetic sequence: CDR3 domain

<400> SEQUENCE: 311

Asn Gln Pro Gly Leu Ser Pro His Asp Val
1               5                   10

<210> SEQ ID NO 312
<211> LENGTH: 11
<212> TYPE: PRT
<213> ORGANISM: Artificial sequence
<220> FEATURE:
<223> OTHER INFORMATION: Synthetic sequence: CDR3 domain

<400> SEQUENCE: 312

Ser Val Ala Ile Pro Gln Trp Pro Arg Asp Val
1               5                   10

<210> SEQ ID NO 313
<211> LENGTH: 9
<212> TYPE: PRT
<213> ORGANISM: Artificial sequence
<220> FEATURE:
<223> OTHER INFORMATION: Synthetic sequence: CDR3 domain

<400> SEQUENCE: 313

Asn Glu Met Met Lys Pro Tyr Asp Val
1               5

<210> SEQ ID NO 314
<211> LENGTH: 9
<212> TYPE: PRT
<213> ORGANISM: Artificial sequence
<220> FEATURE:
<223> OTHER INFORMATION: Synthetic sequence: CDR3 domain

<400> SEQUENCE: 314

Tyr His Lys Gln Tyr Gly Trp Asp Val
1               5

<210> SEQ ID NO 315
<211> LENGTH: 9
<212> TYPE: PRT
<213> ORGANISM: Artificial sequence
<220> FEATURE:
<223> OTHER INFORMATION: Synthetic sequence: CDR3 domain

<400> SEQUENCE: 315

Tyr Trp His Tyr Val Phe Met Asp Val
1               5

<210> SEQ ID NO 316
<211> LENGTH: 9
<212> TYPE: PRT
<213> ORGANISM: Artificial sequence
<220> FEATURE:
```

<223> OTHER INFORMATION: Synthetic sequence: CDR3 domain

<400> SEQUENCE: 316

Trp Glu Met Leu Val Gly Trp Asp Val
1               5

<210> SEQ ID NO 317
<211> LENGTH: 9
<212> TYPE: PRT
<213> ORGANISM: Artificial sequence
<220> FEATURE:
<223> OTHER INFORMATION: Synthetic sequence: CDR3 domain

<400> SEQUENCE: 317

Asn Glu Ser Met Lys Pro Met Asp Val
1               5

<210> SEQ ID NO 318
<211> LENGTH: 13
<212> TYPE: PRT
<213> ORGANISM: Artificial sequence
<220> FEATURE:
<223> OTHER INFORMATION: Synthetic sequence: CDR3 domain

<400> SEQUENCE: 318

Asp Val Trp Pro His Ser Val Met Asp Asp Pro Asp Val
1               5                   10

<210> SEQ ID NO 319
<211> LENGTH: 9
<212> TYPE: PRT
<213> ORGANISM: Artificial sequence
<220> FEATURE:
<223> OTHER INFORMATION: Synthetic sequence: CDR3 domain

<400> SEQUENCE: 319

Phe Gln Leu Gly Phe Leu Gly Trp Tyr
1               5

<210> SEQ ID NO 320
<211> LENGTH: 13
<212> TYPE: PRT
<213> ORGANISM: Artificial sequence
<220> FEATURE:
<223> OTHER INFORMATION: Synthetic sequence: CDR3 domain

<400> SEQUENCE: 320

Pro Met Phe Pro Tyr Val Ser Asn Val Trp Arg Asp Val
1               5                   10

<210> SEQ ID NO 321
<211> LENGTH: 9
<212> TYPE: PRT
<213> ORGANISM: Artificial sequence
<220> FEATURE:
<223> OTHER INFORMATION: Synthetic sequence: CDR3 domain

<400> SEQUENCE: 321

Phe His Arg Val Val Gly Trp Asp Val
1               5

<210> SEQ ID NO 322
<211> LENGTH: 9
<212> TYPE: PRT
<213> ORGANISM: Artificial sequence
<220> FEATURE:
<223> OTHER INFORMATION: Synthetic sequence: CDR3 domain

```
<400> SEQUENCE: 322

Trp His Gly Arg Val Gly Trp Asp Val
1               5

<210> SEQ ID NO 323
<211> LENGTH: 11
<212> TYPE: PRT
<213> ORGANISM: Artificial sequence
<220> FEATURE:
<223> OTHER INFORMATION: Synthetic sequence: CDR3 domain

<400> SEQUENCE: 323

Lys Ile Ala Ile Pro Ser Phe Pro Tyr Asp Val
1               5                   10

<210> SEQ ID NO 324
<211> LENGTH: 9
<212> TYPE: PRT
<213> ORGANISM: Artificial sequence
<220> FEATURE:
<223> OTHER INFORMATION: Synthetic sequence: CDR3 domain

<400> SEQUENCE: 324

Asn Glu Trp Met Leu Pro Phe Asp Val
1               5

<210> SEQ ID NO 325
<211> LENGTH: 13
<212> TYPE: PRT
<213> ORGANISM: Artificial sequence
<220> FEATURE:
<223> OTHER INFORMATION: Synthetic sequence: CDR3 domain

<400> SEQUENCE: 325

Lys His Phe Ser Gln Leu Gln Pro Phe Leu Asn Asp Val
1               5                   10

<210> SEQ ID NO 326
<211> LENGTH: 12
<212> TYPE: PRT
<213> ORGANISM: Artificial sequence
<220> FEATURE:
<223> OTHER INFORMATION: Synthetic sequence: CDR3 domain

<400> SEQUENCE: 326

Ile Trp Ser Ser Arg Pro Phe Trp Trp Glu Trp Tyr
1               5                   10

<210> SEQ ID NO 327
<211> LENGTH: 9
<212> TYPE: PRT
<213> ORGANISM: Artificial sequence
<220> FEATURE:
<223> OTHER INFORMATION: Synthetic sequence: CDR3 domain

<400> SEQUENCE: 327

Ala Asp Trp Trp Thr Ala Phe Asp Val
1               5

<210> SEQ ID NO 328
<211> LENGTH: 13
<212> TYPE: PRT
<213> ORGANISM: Artificial sequence
<220> FEATURE:
<223> OTHER INFORMATION: Synthetic sequence: CDR3 domain
```

```
<400> SEQUENCE: 328

Ala Phe Pro Asn Trp Trp Phe Trp Tyr Glu Pro Asp Val
1               5                   10

<210> SEQ ID NO 329
<211> LENGTH: 11
<212> TYPE: PRT
<213> ORGANISM: Artificial sequence
<220> FEATURE:
<223> OTHER INFORMATION: Synthetic sequence: CDR3 domain
<220> FEATURE:
<221> NAME/KEY: SITE
<222> LOCATION: (6)..(6)
<223> OTHER INFORMATION: Xaa is unknown

<400> SEQUENCE: 329

Ala His Lys Leu Ser Xaa Gly Phe Asp Asp Val
1               5                   10

<210> SEQ ID NO 330
<211> LENGTH: 11
<212> TYPE: PRT
<213> ORGANISM: Artificial sequence
<220> FEATURE:
<223> OTHER INFORMATION: Synthetic sequence: CDR3 domain

<400> SEQUENCE: 330

Ala Leu Trp Trp Ser Trp Trp Pro Tyr Asp Val
1               5                   10

<210> SEQ ID NO 331
<211> LENGTH: 11
<212> TYPE: PRT
<213> ORGANISM: Artificial sequence
<220> FEATURE:
<223> OTHER INFORMATION: Synthetic sequence: CDR3 domain

<400> SEQUENCE: 331

Ala Asn Gly Phe Gln Asp Ser Phe Ala Asp Val
1               5                   10

<210> SEQ ID NO 332
<211> LENGTH: 11
<212> TYPE: PRT
<213> ORGANISM: Artificial sequence
<220> FEATURE:
<223> OTHER INFORMATION: Synthetic sequence: CDR3 domain

<400> SEQUENCE: 332

Ala Asn Gly Leu Ala Arg Ser Met Ala Asp Val
1               5                   10

<210> SEQ ID NO 333
<211> LENGTH: 11
<212> TYPE: PRT
<213> ORGANISM: Artificial sequence
<220> FEATURE:
<223> OTHER INFORMATION: Synthetic sequence: CDR3 domain

<400> SEQUENCE: 333

Ala Asn Gly Trp Ala Arg Ser Tyr Glu Asp Val
1               5                   10

<210> SEQ ID NO 334
<211> LENGTH: 13
<212> TYPE: PRT
<213> ORGANISM: Artificial sequence
```

<220> FEATURE:
<223> OTHER INFORMATION: Synthetic sequence: CDR3 domain

<400> SEQUENCE: 334

Ala Trp Phe Pro Tyr Trp Val Gln Asn Met Met Asp Val
1               5                   10

<210> SEQ ID NO 335
<211> LENGTH: 13
<212> TYPE: PRT
<213> ORGANISM: Artificial sequence
<220> FEATURE:
<223> OTHER INFORMATION: Synthetic sequence: CDR3 domain

<400> SEQUENCE: 335

Ala Trp Ile Pro Tyr Leu Val Arg Asp Met Arg Asp Val
1               5                   10

<210> SEQ ID NO 336
<211> LENGTH: 13
<212> TYPE: PRT
<213> ORGANISM: Artificial sequence
<220> FEATURE:
<223> OTHER INFORMATION: Synthetic sequence: CDR3 domain

<400> SEQUENCE: 336

Ala Trp Gln Pro Tyr Asn Val Asp Ser Ile Trp Asp Val
1               5                   10

<210> SEQ ID NO 337
<211> LENGTH: 13
<212> TYPE: PRT
<213> ORGANISM: Artificial sequence
<220> FEATURE:
<223> OTHER INFORMATION: Synthetic sequence: CDR3 domain

<400> SEQUENCE: 337

Ala Trp Gln Pro Tyr Asn Val Asp Ser Ile Trp Asp Val
1               5                   10

<210> SEQ ID NO 338
<211> LENGTH: 13
<212> TYPE: PRT
<213> ORGANISM: Artificial sequence
<220> FEATURE:
<223> OTHER INFORMATION: Synthetic sequence: CDR3 domain

<400> SEQUENCE: 338

Ala Trp Val Pro Tyr Ser Val Asp Ser Met Trp Asp Val
1               5                   10

<210> SEQ ID NO 339
<211> LENGTH: 13
<212> TYPE: PRT
<213> ORGANISM: Artificial sequence
<220> FEATURE:
<223> OTHER INFORMATION: Synthetic sequence: CDR3 domain

<400> SEQUENCE: 339

Ala Trp Trp Pro Asn Trp Val Ser Asn Ser Trp Asp Val
1               5                   10

<210> SEQ ID NO 340
<211> LENGTH: 16
<212> TYPE: PRT
<213> ORGANISM: Artificial sequence
<220> FEATURE:

<223> OTHER INFORMATION: Synthetic sequence: CDR3 domain

<400> SEQUENCE: 340

Asp Lys Ala Trp Glu Val Glu Asn Trp Ala Ile Lys His Trp Trp Tyr
1               5                   10                  15

<210> SEQ ID NO 341
<211> LENGTH: 13
<212> TYPE: PRT
<213> ORGANISM: Artificial sequence
<220> FEATURE:
<223> OTHER INFORMATION: Synthetic sequence: CDR3 domain

<400> SEQUENCE: 341

Asp Trp Asn Trp Trp Trp Ala Asp Lys Met Glu Asp Val
1               5                   10

<210> SEQ ID NO 342
<211> LENGTH: 9
<212> TYPE: PRT
<213> ORGANISM: Artificial sequence
<220> FEATURE:
<223> OTHER INFORMATION: Synthetic sequence: CDR3 domain

<400> SEQUENCE: 342

Asp Tyr Trp Trp Asn Pro Lys Asp Val
1               5

<210> SEQ ID NO 343
<211> LENGTH: 13
<212> TYPE: PRT
<213> ORGANISM: Artificial sequence
<220> FEATURE:
<223> OTHER INFORMATION: Synthetic sequence: CDR3 domain

<400> SEQUENCE: 343

Glu Phe His Pro Gln Gly Gly Trp Ser Ser Gln Asp Val
1               5                   10

<210> SEQ ID NO 344
<211> LENGTH: 13
<212> TYPE: PRT
<213> ORGANISM: Artificial sequence
<220> FEATURE:
<223> OTHER INFORMATION: Synthetic sequence: CDR3 domain

<400> SEQUENCE: 344

Glu Asn Tyr Trp Asp Ser Trp Phe Trp Ala Pro Asp Val
1               5                   10

<210> SEQ ID NO 345
<211> LENGTH: 13
<212> TYPE: PRT
<213> ORGANISM: Artificial sequence
<220> FEATURE:
<223> OTHER INFORMATION: Synthetic sequence: CDR3 domain

<400> SEQUENCE: 345

Glu Gln Trp Ser Trp Met Ser Trp Trp Pro Trp Asp Val
1               5                   10

<210> SEQ ID NO 346
<211> LENGTH: 10
<212> TYPE: PRT
<213> ORGANISM: Artificial sequence
<220> FEATURE:
<223> OTHER INFORMATION: Synthetic sequence: CDR3 domain

```
<400> SEQUENCE: 346

Glu Ser Phe Val His Ile Trp Thr Trp Tyr
1               5                   10

<210> SEQ ID NO 347
<211> LENGTH: 13
<212> TYPE: PRT
<213> ORGANISM: Artificial sequence
<220> FEATURE:
<223> OTHER INFORMATION: Synthetic sequence: CDR3 domain

<400> SEQUENCE: 347

Glu Thr Trp Thr Trp Trp Trp Pro Leu Met Glu Asp Val
1               5                   10

<210> SEQ ID NO 348
<211> LENGTH: 13
<212> TYPE: PRT
<213> ORGANISM: Artificial sequence
<220> FEATURE:
<223> OTHER INFORMATION: Synthetic sequence: CDR3 domain

<400> SEQUENCE: 348

Glu Val Trp Gln Trp Trp Ile Pro Trp Lys Asn Asp Val
1               5                   10

<210> SEQ ID NO 349
<211> LENGTH: 11
<212> TYPE: PRT
<213> ORGANISM: Artificial sequence
<220> FEATURE:
<223> OTHER INFORMATION: Synthetic sequence: CDR3 domain
<220> FEATURE:
<221> NAME/KEY: SITE
<222> LOCATION: (9)..(9)
<223> OTHER INFORMATION: Xaa is unknown

<400> SEQUENCE: 349

Gly His Lys Tyr Ala Thr Gly Tyr Xaa Asp Val
1               5                   10

<210> SEQ ID NO 350
<211> LENGTH: 11
<212> TYPE: PRT
<213> ORGANISM: Artificial sequence
<220> FEATURE:
<223> OTHER INFORMATION: Synthetic sequence: CDR3 domain
<220> FEATURE:
<221> NAME/KEY: SITE
<222> LOCATION: (6)..(6)
<223> OTHER INFORMATION: Xaa is unknown

<400> SEQUENCE: 350

Gly His Lys Tyr Ala Xaa Gly Cys Pro Asp Val
1               5                   10

<210> SEQ ID NO 351
<211> LENGTH: 13
<212> TYPE: PRT
<213> ORGANISM: Artificial sequence
<220> FEATURE:
<223> OTHER INFORMATION: Synthetic sequence: CDR3 domain

<400> SEQUENCE: 351

Gly Met Phe Trp Ala Trp Trp Pro Trp Tyr Gln Asp Val
1               5                   10
```

<210> SEQ ID NO 352
<211> LENGTH: 11
<212> TYPE: PRT
<213> ORGANISM: Artificial sequence
<220> FEATURE:
<223> OTHER INFORMATION: Synthetic sequence: CDR3 domain

<400> SEQUENCE: 352

Gly Thr Trp Trp Phe Trp Pro Leu Leu Asp Val
1               5                   10

<210> SEQ ID NO 353
<211> LENGTH: 13
<212> TYPE: PRT
<213> ORGANISM: Artificial sequence
<220> FEATURE:
<223> OTHER INFORMATION: Synthetic sequence: CDR3 domain

<400> SEQUENCE: 353

Gly Val Leu Pro Trp Ser Pro Trp Gly Tyr Trp Asp Val
1               5                   10

<210> SEQ ID NO 354
<211> LENGTH: 11
<212> TYPE: PRT
<213> ORGANISM: Artificial sequence
<220> FEATURE:
<223> OTHER INFORMATION: Synthetic sequence: CDR3 domain

<400> SEQUENCE: 354

Gly Trp Met Val Ser Trp Pro Phe Tyr Asp Val
1               5                   10

<210> SEQ ID NO 355
<211> LENGTH: 11
<212> TYPE: PRT
<213> ORGANISM: Artificial sequence
<220> FEATURE:
<223> OTHER INFORMATION: Synthetic sequence: CDR3 domain

<400> SEQUENCE: 355

His Ser Ser Ile Trp Gly Trp Arg Glu Asp Val
1               5                   10

<210> SEQ ID NO 356
<211> LENGTH: 13
<212> TYPE: PRT
<213> ORGANISM: Artificial sequence
<220> FEATURE:
<223> OTHER INFORMATION: Synthetic sequence: CDR3 domain

<400> SEQUENCE: 356

His Ser Tyr Val Trp Trp Trp Gly Tyr Tyr Thr Asp Val
1               5                   10

<210> SEQ ID NO 357
<211> LENGTH: 13
<212> TYPE: PRT
<213> ORGANISM: Artificial sequence
<220> FEATURE:
<223> OTHER INFORMATION: Synthetic sequence: CDR3 domain

<400> SEQUENCE: 357

Ile Trp Trp Pro Ser Ala Tyr Tyr Asn Trp Ala Asp Val
1               5                   10

```
<210> SEQ ID NO 358
<211> LENGTH: 11
<212> TYPE: PRT
<213> ORGANISM: Artificial sequence
<220> FEATURE:
<223> OTHER INFORMATION: Synthetic sequence: CDR3 domain

<400> SEQUENCE: 358

Leu Gly Thr Trp Asn Pro Trp Trp Pro Asp Val
1               5                   10

<210> SEQ ID NO 359
<211> LENGTH: 13
<212> TYPE: PRT
<213> ORGANISM: Artificial sequence
<220> FEATURE:
<223> OTHER INFORMATION: Synthetic sequence: CDR3 domain

<400> SEQUENCE: 359

Met His Pro Trp Trp Pro Phe Ser His Trp Trp Asp Val
1               5                   10

<210> SEQ ID NO 360
<211> LENGTH: 11
<212> TYPE: PRT
<213> ORGANISM: Artificial sequence
<220> FEATURE:
<223> OTHER INFORMATION: Synthetic sequence: CDR3 domain

<400> SEQUENCE: 360

Met Gln Trp Trp Trp Trp Gln Val Tyr Asp Val
1               5                   10

<210> SEQ ID NO 361
<211> LENGTH: 13
<212> TYPE: PRT
<213> ORGANISM: Artificial sequence
<220> FEATURE:
<223> OTHER INFORMATION: Synthetic sequence: CDR3 domain

<400> SEQUENCE: 361

Asn Val Phe His Trp Trp Ala Trp Trp Gln His Asp Val
1               5                   10

<210> SEQ ID NO 362
<211> LENGTH: 11
<212> TYPE: PRT
<213> ORGANISM: Artificial sequence
<220> FEATURE:
<223> OTHER INFORMATION: Synthetic sequence: CDR3 domain

<400> SEQUENCE: 362

Pro Phe Ala Gly Met Ala Thr Tyr Ala Asp Val
1               5                   10

<210> SEQ ID NO 363
<211> LENGTH: 11
<212> TYPE: PRT
<213> ORGANISM: Artificial sequence
<220> FEATURE:
<223> OTHER INFORMATION: Synthetic sequence: CDR3 domain

<400> SEQUENCE: 363

Pro Phe Pro Ser Pro Thr Ser Ile Trp Asp Val
1               5                   10

<210> SEQ ID NO 364
```

```
<211> LENGTH: 11
<212> TYPE: PRT
<213> ORGANISM: Artificial sequence
<220> FEATURE:
<223> OTHER INFORMATION: Synthetic sequence: CDR3 domain

<400> SEQUENCE: 364

Pro His Glu Gly Gln Thr His Tyr Ala Asp Val
1               5                   10

<210> SEQ ID NO 365
<211> LENGTH: 11
<212> TYPE: PRT
<213> ORGANISM: Artificial sequence
<220> FEATURE:
<223> OTHER INFORMATION: Synthetic sequence: CDR3 domain

<400> SEQUENCE: 365

Pro His Glu Lys Gln Ser His Tyr Glu Asp Val
1               5                   10

<210> SEQ ID NO 366
<211> LENGTH: 11
<212> TYPE: PRT
<213> ORGANISM: Artificial sequence
<220> FEATURE:
<223> OTHER INFORMATION: Synthetic sequence: CDR3 domain

<400> SEQUENCE: 366

Pro His Leu Gln Gln Ser Thr Pro Met Asp Val
1               5                   10

<210> SEQ ID NO 367
<211> LENGTH: 11
<212> TYPE: PRT
<213> ORGANISM: Artificial sequence
<220> FEATURE:
<223> OTHER INFORMATION: Synthetic sequence: CDR3 domain

<400> SEQUENCE: 367

Pro His Arg Gly Gln Arg Ser Phe Glu Asp Val
1               5                   10

<210> SEQ ID NO 368
<211> LENGTH: 11
<212> TYPE: PRT
<213> ORGANISM: Artificial sequence
<220> FEATURE:
<223> OTHER INFORMATION: Synthetic sequence: CDR3 domain

<400> SEQUENCE: 368

Pro His Ser Asn Met Ser Thr Tyr Ser Asp Val
1               5                   10

<210> SEQ ID NO 369
<211> LENGTH: 11
<212> TYPE: PRT
<213> ORGANISM: Artificial sequence
<220> FEATURE:
<223> OTHER INFORMATION: Synthetic sequence: CDR3 domain

<400> SEQUENCE: 369

Pro His Ser Ser Met Ser His Tyr Asn Asp Val
1               5                   10

<210> SEQ ID NO 370
<211> LENGTH: 11
```

```
<212> TYPE: PRT
<213> ORGANISM: Artificial sequence
<220> FEATURE:
<223> OTHER INFORMATION: Synthetic sequence: CDR3 domain

<400> SEQUENCE: 370

Pro His Thr Leu Ala Lys Thr Tyr Ser Asp Val
1               5                   10

<210> SEQ ID NO 371
<211> LENGTH: 11
<212> TYPE: PRT
<213> ORGANISM: Artificial sequence
<220> FEATURE:
<223> OTHER INFORMATION: Synthetic sequence: CDR3 domain

<400> SEQUENCE: 371

Pro Leu His Gly Val Ala Asn Met Trp Asp Val
1               5                   10

<210> SEQ ID NO 372
<211> LENGTH: 11
<212> TYPE: PRT
<213> ORGANISM: Artificial sequence
<220> FEATURE:
<223> OTHER INFORMATION: Synthetic sequence: CDR3 domain

<400> SEQUENCE: 372

Pro Leu Arg His Val Ala His Met Trp Asp Val
1               5                   10

<210> SEQ ID NO 373
<211> LENGTH: 11
<212> TYPE: PRT
<213> ORGANISM: Artificial sequence
<220> FEATURE:
<223> OTHER INFORMATION: Synthetic sequence: CDR3 domain

<400> SEQUENCE: 373

Pro Leu Arg His Val Ala Asn Met Trp Asp Val
1               5                   10

<210> SEQ ID NO 374
<211> LENGTH: 13
<212> TYPE: PRT
<213> ORGANISM: Artificial sequence
<220> FEATURE:
<223> OTHER INFORMATION: Synthetic sequence: CDR3 domain

<400> SEQUENCE: 374

Pro Pro Asp Phe Phe Gln Glu Ser Gln Asn Trp Asp Val
1               5                   10

<210> SEQ ID NO 375
<211> LENGTH: 11
<212> TYPE: PRT
<213> ORGANISM: Artificial sequence
<220> FEATURE:
<223> OTHER INFORMATION: Synthetic sequence: CDR3 domain

<400> SEQUENCE: 375

Pro Thr Ala Tyr Gln His Ser Ile Trp Asp Val
1               5                   10

<210> SEQ ID NO 376
<211> LENGTH: 11
<212> TYPE: PRT
```

<213> ORGANISM: Artificial sequence
<220> FEATURE:
<223> OTHER INFORMATION: Synthetic sequence: CDR3 domain

<400> SEQUENCE: 376

Pro Tyr Ala Gly Met Gln Ser Tyr Ser Asp Val
1               5                   10

<210> SEQ ID NO 377
<211> LENGTH: 11
<212> TYPE: PRT
<213> ORGANISM: Artificial sequence
<220> FEATURE:
<223> OTHER INFORMATION: Synthetic sequence: CDR3 domain

<400> SEQUENCE: 377

Pro Tyr His Asp Ala Thr Gly Met Gln Asp Val
1               5                   10

<210> SEQ ID NO 378
<211> LENGTH: 11
<212> TYPE: PRT
<213> ORGANISM: Artificial sequence
<220> FEATURE:
<223> OTHER INFORMATION: Synthetic sequence: CDR3 domain

<400> SEQUENCE: 378

Pro Tyr Thr Glu Ala Arg Asn Ile Trp Asp Val
1               5                   10

<210> SEQ ID NO 379
<211> LENGTH: 13
<212> TYPE: PRT
<213> ORGANISM: Artificial sequence
<220> FEATURE:
<223> OTHER INFORMATION: Synthetic sequence: CDR3 domain

<400> SEQUENCE: 379

Gln Ser Val Ser Trp Leu Phe Pro Trp Arg Ser Asp Val
1               5                   10

<210> SEQ ID NO 380
<211> LENGTH: 13
<212> TYPE: PRT
<213> ORGANISM: Artificial sequence
<220> FEATURE:
<223> OTHER INFORMATION: Synthetic sequence: CDR3 domain

<400> SEQUENCE: 380

Arg Lys Gln His Trp Tyr Trp Trp Trp Gly Asp Asp Val
1               5                   10

<210> SEQ ID NO 381
<211> LENGTH: 9
<212> TYPE: PRT
<213> ORGANISM: Artificial sequence
<220> FEATURE:
<223> OTHER INFORMATION: Synthetic sequence: CDR3 domain

<400> SEQUENCE: 381

Arg Thr Cys Asn Tyr Val Ala Asp Tyr
1               5

<210> SEQ ID NO 382
<211> LENGTH: 11
<212> TYPE: PRT
<213> ORGANISM: Artificial sequence

```
<220> FEATURE:
<223> OTHER INFORMATION: Synthetic sequence: CDR3 domain

<400> SEQUENCE: 382

Ser Asp Gly Trp Ala His Ala Phe Asp Asp Val
1               5                   10

<210> SEQ ID NO 383
<211> LENGTH: 11
<212> TYPE: PRT
<213> ORGANISM: Artificial sequence
<220> FEATURE:
<223> OTHER INFORMATION: Synthetic sequence: CDR3 domain

<400> SEQUENCE: 383

Ser His Arg Val Arg Ser Thr Tyr Glu Asp Val
1               5                   10

<210> SEQ ID NO 384
<211> LENGTH: 11
<212> TYPE: PRT
<213> ORGANISM: Artificial sequence
<220> FEATURE:
<223> OTHER INFORMATION: Synthetic sequence: CDR3 domain

<400> SEQUENCE: 384

Ser Leu Phe Pro Leu Gln Trp Met Thr Asp Val
1               5                   10

<210> SEQ ID NO 385
<211> LENGTH: 13
<212> TYPE: PRT
<213> ORGANISM: Artificial sequence
<220> FEATURE:
<223> OTHER INFORMATION: Synthetic sequence: CDR3 domain

<400> SEQUENCE: 385

Ser Leu Thr Trp Pro Phe Lys Trp Trp Ala Pro Asp Val
1               5                   10

<210> SEQ ID NO 386
<211> LENGTH: 11
<212> TYPE: PRT
<213> ORGANISM: Artificial sequence
<220> FEATURE:
<223> OTHER INFORMATION: Synthetic sequence: CDR3 domain

<400> SEQUENCE: 386

Ser Leu Trp Asp Trp Trp Trp Pro Glu Asp Leu
1               5                   10

<210> SEQ ID NO 387
<211> LENGTH: 11
<212> TYPE: PRT
<213> ORGANISM: Artificial sequence
<220> FEATURE:
<223> OTHER INFORMATION: Synthetic sequence: CDR3 domain

<400> SEQUENCE: 387

Ser Asn Gly Tyr Gln Gln Ala Trp Gln Asp Val
1               5                   10

<210> SEQ ID NO 388
<211> LENGTH: 11
<212> TYPE: PRT
<213> ORGANISM: Artificial sequence
<220> FEATURE:
```

<223> OTHER INFORMATION: Synthetic sequence: CDR3 domain

<400> SEQUENCE: 388

Ser Ser Pro Trp Trp Gly Trp Gly Trp Asp Val
1               5                   10

<210> SEQ ID NO 389
<211> LENGTH: 13
<212> TYPE: PRT
<213> ORGANISM: Artificial sequence
<220> FEATURE:
<223> OTHER INFORMATION: Synthetic sequence: CDR3 domain

<400> SEQUENCE: 389

Ser Val Pro Thr Thr Trp Trp Trp Tyr Gly Asn Asp Val
1               5                   10

<210> SEQ ID NO 390
<211> LENGTH: 11
<212> TYPE: PRT
<213> ORGANISM: Artificial sequence
<220> FEATURE:
<223> OTHER INFORMATION: Synthetic sequence: CDR3 domain

<400> SEQUENCE: 390

Ser Val Trp Trp Trp Thr Trp Pro Met Asp Val
1               5                   10

<210> SEQ ID NO 391
<211> LENGTH: 13
<212> TYPE: PRT
<213> ORGANISM: Artificial sequence
<220> FEATURE:
<223> OTHER INFORMATION: Synthetic sequence: CDR3 domain

<400> SEQUENCE: 391

Ser Val Tyr Gln Trp Trp Trp Pro Val Pro Ala Asp Val
1               5                   10

<210> SEQ ID NO 392
<211> LENGTH: 13
<212> TYPE: PRT
<213> ORGANISM: Artificial sequence
<220> FEATURE:
<223> OTHER INFORMATION: Synthetic sequence: CDR3 domain

<400> SEQUENCE: 392

Ser Trp Trp Pro Tyr Trp Val Glu Thr Met Asp Asp Val
1               5                   10

<210> SEQ ID NO 393
<211> LENGTH: 13
<212> TYPE: PRT
<213> ORGANISM: Artificial sequence
<220> FEATURE:
<223> OTHER INFORMATION: Synthetic sequence: CDR3 domain

<400> SEQUENCE: 393

Ser Trp Tyr Trp Pro Trp Asp Trp Tyr Gln Pro Asp Val
1               5                   10

<210> SEQ ID NO 394
<211> LENGTH: 13
<212> TYPE: PRT
<213> ORGANISM: Artificial sequence
<220> FEATURE:
<223> OTHER INFORMATION: Synthetic sequence: CDR3 domain

```
<400> SEQUENCE: 394

Thr Gln Trp Glu Ala Phe Ser Trp Trp Trp Lys Asp Val
1               5                   10

<210> SEQ ID NO 395
<211> LENGTH: 11
<212> TYPE: PRT
<213> ORGANISM: Artificial sequence
<220> FEATURE:
<223> OTHER INFORMATION: Synthetic sequence: CDR3 domain

<400> SEQUENCE: 395

Thr Val Trp Ala Trp Met Trp Pro Ile Asp Val
1               5                   10

<210> SEQ ID NO 396
<211> LENGTH: 13
<212> TYPE: PRT
<213> ORGANISM: Artificial sequence
<220> FEATURE:
<223> OTHER INFORMATION: Synthetic sequence: CDR3 domain

<400> SEQUENCE: 396

Thr Trp Thr Pro Tyr Trp Val Asp Thr Ile Trp Asp Val
1               5                   10

<210> SEQ ID NO 397
<211> LENGTH: 13
<212> TYPE: PRT
<213> ORGANISM: Artificial sequence
<220> FEATURE:
<223> OTHER INFORMATION: Synthetic sequence: CDR3 domain

<400> SEQUENCE: 397

Val His Pro Phe Ser Arg Val Glu Asn Ile Trp Asp Val
1               5                   10

<210> SEQ ID NO 398
<211> LENGTH: 9
<212> TYPE: PRT
<213> ORGANISM: Artificial sequence
<220> FEATURE:
<223> OTHER INFORMATION: Synthetic sequence: CDR3 domain

<400> SEQUENCE: 398

Val Asn Trp Tyr Lys Trp Asp Asp Val
1               5

<210> SEQ ID NO 399
<211> LENGTH: 13
<212> TYPE: PRT
<213> ORGANISM: Artificial sequence
<220> FEATURE:
<223> OTHER INFORMATION: Synthetic sequence: CDR3 domain

<400> SEQUENCE: 399

Val Pro Met Tyr Arg Arg Asn Thr Trp Glu Glu Asp Val
1               5                   10

<210> SEQ ID NO 400
<211> LENGTH: 13
<212> TYPE: PRT
<213> ORGANISM: Artificial sequence
<220> FEATURE:
<223> OTHER INFORMATION: Synthetic sequence: CDR3 domain
```

```
<400> SEQUENCE: 400

Val Pro Met Tyr Trp Arg Asn Thr Trp Glu Glu Asp Val
1               5                   10

<210> SEQ ID NO 401
<211> LENGTH: 12
<212> TYPE: PRT
<213> ORGANISM: Artificial sequence
<220> FEATURE:
<223> OTHER INFORMATION: Synthetic sequence: CDR3 domain

<400> SEQUENCE: 401

Val Pro Trp Phe Glu Gln Trp Trp Glu Ile Trp Tyr
1               5                   10

<210> SEQ ID NO 402
<211> LENGTH: 13
<212> TYPE: PRT
<213> ORGANISM: Artificial sequence
<220> FEATURE:
<223> OTHER INFORMATION: Synthetic sequence: CDR3 domain

<400> SEQUENCE: 402

Val Trp Phe Pro Tyr Phe Ile Ser Asp Met Trp Asp Val
1               5                   10

<210> SEQ ID NO 403
<211> LENGTH: 13
<212> TYPE: PRT
<213> ORGANISM: Artificial sequence
<220> FEATURE:
<223> OTHER INFORMATION: Synthetic sequence: CDR3 domain

<400> SEQUENCE: 403

Val Trp His Pro Phe Thr Val Thr Asn Met Pro Asp Val
1               5                   10

<210> SEQ ID NO 404
<211> LENGTH: 13
<212> TYPE: PRT
<213> ORGANISM: Artificial sequence
<220> FEATURE:
<223> OTHER INFORMATION: Synthetic sequence: CDR3 domain

<400> SEQUENCE: 404

Val Trp Ile Pro Trp Trp Val Phe Asp Met Trp Asp Val
1               5                   10

<210> SEQ ID NO 405
<211> LENGTH: 13
<212> TYPE: PRT
<213> ORGANISM: Artificial sequence
<220> FEATURE:
<223> OTHER INFORMATION: Synthetic sequence: CDR3 domain

<400> SEQUENCE: 405

Val Trp Lys Pro Tyr Met Val Val His Leu Trp Asp Val
1               5                   10

<210> SEQ ID NO 406
<211> LENGTH: 13
<212> TYPE: PRT
<213> ORGANISM: Artificial sequence
<220> FEATURE:
<223> OTHER INFORMATION: Synthetic sequence: CDR3 domain

<400> SEQUENCE: 406
```

```
Val Trp Met Pro Phe Met Val Arg Thr Pro Gly Asp Val
1               5                   10
```

<210> SEQ ID NO 407
<211> LENGTH: 13
<212> TYPE: PRT
<213> ORGANISM: Artificial sequence
<220> FEATURE:
<223> OTHER INFORMATION: Synthetic sequence: CDR3 domain

<400> SEQUENCE: 407

```
Val Trp Met Pro Tyr Thr Val Val Asp Ser Ser Asp Val
1               5                   10
```

<210> SEQ ID NO 408
<211> LENGTH: 13
<212> TYPE: PRT
<213> ORGANISM: Artificial sequence
<220> FEATURE:
<223> OTHER INFORMATION: Synthetic sequence: CDR3 domain

<400> SEQUENCE: 408

```
Val Trp Gln Pro Tyr Glu Val Val His Met Trp Asp Val
1               5                   10
```

<210> SEQ ID NO 409
<211> LENGTH: 8
<212> TYPE: PRT
<213> ORGANISM: Artificial sequence
<220> FEATURE:
<223> OTHER INFORMATION: Synthetic sequence: CDR3 domain

<400> SEQUENCE: 409

```
Val Tyr Ala Met Pro Lys Trp Tyr
1               5
```

<210> SEQ ID NO 410
<211> LENGTH: 11
<212> TYPE: PRT
<213> ORGANISM: Artificial sequence
<220> FEATURE:
<223> OTHER INFORMATION: Synthetic sequence: CDR3 domain

<400> SEQUENCE: 410

```
Trp Gly Trp Trp Trp Trp Trp Pro Gln Asp Val
1               5                   10
```

<210> SEQ ID NO 411
<211> LENGTH: 11
<212> TYPE: PRT
<213> ORGANISM: Artificial sequence
<220> FEATURE:
<223> OTHER INFORMATION: Synthetic sequence: CDR3 domain

<400> SEQUENCE: 411

```
Trp Val Pro Tyr Trp Thr Ala Trp Tyr Asp Val
1               5                   10
```

<210> SEQ ID NO 412
<211> LENGTH: 11
<212> TYPE: PRT
<213> ORGANISM: Artificial sequence
<220> FEATURE:
<223> OTHER INFORMATION: Synthetic sequence: CDR3 domain

<400> SEQUENCE: 412

```
Trp Thr Ser Phe Glu Glu Gln Val Lys Asp Val
1               5                   10
```

<210> SEQ ID NO 413
<211> LENGTH: 13
<212> TYPE: PRT
<213> ORGANISM: Artificial sequence
<220> FEATURE:
<223> OTHER INFORMATION: Synthetic sequence: CDR3 domain

<400> SEQUENCE: 413

```
Ala Trp Trp Pro Phe Met Ile Glu Glu Thr Thr Asp Val
1               5                   10
```

<210> SEQ ID NO 414
<211> LENGTH: 13
<212> TYPE: PRT
<213> ORGANISM: Artificial sequence
<220> FEATURE:
<223> OTHER INFORMATION: Synthetic sequence: CDR3 domain

<400> SEQUENCE: 414

```
Met Gly Asn His Glu Trp Asp Ile Trp Trp Trp Trp Trp
1               5                   10
```

<210> SEQ ID NO 415
<211> LENGTH: 9
<212> TYPE: PRT
<213> ORGANISM: Artificial sequence
<220> FEATURE:
<223> OTHER INFORMATION: Synthetic sequence: CDR3 domain

<400> SEQUENCE: 415

```
Arg Arg Met Gly His Gly Arg Leu Trp
1               5
```

<210> SEQ ID NO 416
<211> LENGTH: 13
<212> TYPE: PRT
<213> ORGANISM: Artificial sequence
<220> FEATURE:
<223> OTHER INFORMATION: Synthetic sequence: CDR3 domain

<400> SEQUENCE: 416

```
Thr Ile Asp Pro Val Trp Ile Glu Trp Leu Trp Asp Val
1               5                   10
```

<210> SEQ ID NO 417
<211> LENGTH: 16
<212> TYPE: PRT
<213> ORGANISM: Artificial sequence
<220> FEATURE:
<223> OTHER INFORMATION: Synthetic sequence: CDR3 domain

<400> SEQUENCE: 417

```
Arg Ala Pro Lys Arg Pro Trp His Gly Lys Leu Thr Val Pro Trp Tyr
1               5                   10                  15
```

<210> SEQ ID NO 418
<211> LENGTH: 12
<212> TYPE: PRT
<213> ORGANISM: Artificial sequence
<220> FEATURE:
<223> OTHER INFORMATION: Synthetic sequence: CDR3 domain

<400> SEQUENCE: 418

```
Tyr Val Ile Tyr Arg Ala Leu Pro Ala Trp Trp Tyr
```

```
1               5                   10
```

<210> SEQ ID NO 419
<211> LENGTH: 12
<212> TYPE: PRT
<213> ORGANISM: Artificial sequence
<220> FEATURE:
<223> OTHER INFORMATION: Synthetic sequence: CDR3 domain

<400> SEQUENCE: 419

```
Leu Val Gln Trp Ile Lys Trp Trp Val Val Trp Tyr
1               5                   10
```

<210> SEQ ID NO 420
<211> LENGTH: 15
<212> TYPE: PRT
<213> ORGANISM: Artificial sequence
<220> FEATURE:
<223> OTHER INFORMATION: Synthetic sequence: CDR3 domain

<400> SEQUENCE: 420

```
Val Phe Val Val His Lys Gly Thr Glu Thr Ile Ala Thr Gly Trp
1               5                   10                  15
```

<210> SEQ ID NO 421
<211> LENGTH: 9
<212> TYPE: PRT
<213> ORGANISM: Artificial sequence
<220> FEATURE:
<223> OTHER INFORMATION: Synthetic sequence: CDR3 domain

<400> SEQUENCE: 421

```
Asn Asp Val Thr Lys His Gly Asp Val
1               5
```

<210> SEQ ID NO 422
<211> LENGTH: 13
<212> TYPE: PRT
<213> ORGANISM: Artificial sequence
<220> FEATURE:
<223> OTHER INFORMATION: Synthetic sequence: CDR3 domain

<400> SEQUENCE: 422

```
Arg Gln His Ala Val Trp Leu Arg Gln Glu Phe Asp Val
1               5                   10
```

<210> SEQ ID NO 423
<211> LENGTH: 11
<212> TYPE: PRT
<213> ORGANISM: Artificial sequence
<220> FEATURE:
<223> OTHER INFORMATION: Synthetic sequence: CDR3 domain

<400> SEQUENCE: 423

```
Phe Met Gln Ser Ser Trp Val His Trp Tyr Asp
1               5                   10
```

<210> SEQ ID NO 424
<211> LENGTH: 9
<212> TYPE: PRT
<213> ORGANISM: Artificial sequence
<220> FEATURE:
<223> OTHER INFORMATION: Synthetic sequence: CDR3 domain

<400> SEQUENCE: 424

```
Lys Ser Asn Ile Arg Val Met Asp Val
1               5
```

```
<210> SEQ ID NO 425
<211> LENGTH: 12
<212> TYPE: PRT
<213> ORGANISM: Artificial sequence
<220> FEATURE:
<223> OTHER INFORMATION: Synthetic sequence: CDR3 domain

<400> SEQUENCE: 425

Val Gly Met Ser His Gln Gln Trp Met His Gly Val
1               5                   10

<210> SEQ ID NO 426
<211> LENGTH: 10
<212> TYPE: PRT
<213> ORGANISM: Artificial sequence
<220> FEATURE:
<223> OTHER INFORMATION: Synthetic sequence: CDR3 domain

<400> SEQUENCE: 426

Met Met Trp Ile Phe Phe Tyr Met Trp Tyr
1               5                   10

<210> SEQ ID NO 427
<211> LENGTH: 11
<212> TYPE: PRT
<213> ORGANISM: Artificial sequence
<220> FEATURE:
<223> OTHER INFORMATION: Synthetic sequence: CDR3 domain

<400> SEQUENCE: 427

Gln Met Trp Tyr Trp His Gln Lys Gln Asp Val
1               5                   10

<210> SEQ ID NO 428
<211> LENGTH: 12
<212> TYPE: PRT
<213> ORGANISM: Artificial sequence
<220> FEATURE:
<223> OTHER INFORMATION: Synthetic sequence: CDR3 domain

<400> SEQUENCE: 428

Pro Met Pro Trp Gly Lys Phe Val Gln Ser Trp Tyr
1               5                   10

<210> SEQ ID NO 429
<211> LENGTH: 4
<212> TYPE: PRT
<213> ORGANISM: Artificial sequence
<220> FEATURE:
<223> OTHER INFORMATION: Synthetic sequence: Linker

<400> SEQUENCE: 429

Gly Gly Gly Gly
1

<210> SEQ ID NO 430
<211> LENGTH: 5
<212> TYPE: PRT
<213> ORGANISM: Artificial sequence
<220> FEATURE:
<223> OTHER INFORMATION: Synthetic sequence: Linker

<400> SEQUENCE: 430

Gly Gly Gly Gly Gly
1               5
```

```
<210> SEQ ID NO 431
<211> LENGTH: 5
<212> TYPE: PRT
<213> ORGANISM: Artificial sequence
<220> FEATURE:
<223> OTHER INFORMATION: Synthetic sequence: Linker

<400> SEQUENCE: 431

Gly Gly Gly Gly Ser
1               5

<210> SEQ ID NO 432
<211> LENGTH: 9
<212> TYPE: PRT
<213> ORGANISM: Artificial sequence
<220> FEATURE:
<223> OTHER INFORMATION: Synthetic sequence: Linker

<400> SEQUENCE: 432

Gly Gly Gly Gly Ser Gly Gly Gly Gly
1               5

<210> SEQ ID NO 433
<211> LENGTH: 15
<212> TYPE: PRT
<213> ORGANISM: Artificial sequence
<220> FEATURE:
<223> OTHER INFORMATION: Synthetic sequence: Linker

<400> SEQUENCE: 433

Gly Gly Gly Gly Ser Gly Gly Gly Gly Ser Gly Gly Gly Gly Ser
1               5                   10                  15

<210> SEQ ID NO 434
<211> LENGTH: 9
<212> TYPE: PRT
<213> ORGANISM: Artificial sequence
<220> FEATURE:
<223> OTHER INFORMATION: Synthetic sequence: Linker

<400> SEQUENCE: 434

Ala Ala Ala His His His His His His
1               5

<210> SEQ ID NO 435
<211> LENGTH: 2420
<212> TYPE: DNA
<213> ORGANISM: Ginglymostoma cirratum

<400> SEQUENCE: 435
ttttcacagt tctatcagtg cagaaacaat gaatatttc ttgctttcag tccttttagc        60
cttattacca tatgtcttta ctgagcgagt ggaccaaacg ccgagatcag tagcaaaggc       120 cgagggcaa gtactgacca tcaactgtgt cctacgcggt gcaaactacg aactggcgaa        180
gggcagcacg tgctggtatc gaaaaaaatc gggctcaaaa gttgaggaga gcataacgaa       240
aggtggacga tatgttgaaa cagttaacag cggatcaaag tccttttcct tgagaattaa      300
tgatctaacg attgaagacg ccggcgatta tcgttgcgca gcctgggaag ctgctgatat      360
gtgtatgtac ggggtctgca ctatttatcc cttctctggt gcatgcggat caggcactgc      420
cgtgactgtt actcctggaa taccgccttc tccaccaata gtcagtctcc tccactctgc      480
aactgaagaa cagagagcaa acagatttgt gcagctggtt tgtctaatca gcggatacta      540
tcccgaaaac attgcagtga gctggcagaa gaacacaaag accataactt ctggttttgc      600
```

```
aacaacatcc ccagtgaaaa cttcgagcaa tgacttcagc tgtgcaagtt tacttaaagt    660 gccccctacag gaatggagca ggggttctgt gtacagttgc caagtttctc attctgcaac   720
cagcagtaac cagaggaaag aaattcgatc aacatccgag atcgctgtat tactgaggga    780
tccaacagtt gaagaaatct ggatcgataa aagtgccact ctagtttgcg aagtgctctc    840
cacagtttcc gctggagtag tcgtctcttg gatggtaaat ggaaaagtaa ggaatgaagg    900
cgttcaaatg gaaccaacta aaatgagtgg aaaccaatat ctgacaatca gccgcttgac    960
cagcagcgtg gaagagtggc agagtggggt ggaatacact tgctccgcaa acaggatca   1020 atcgtccacc ccagtcgtaa acgaacacg aaaggcaaga gtcgaaccga caaaaccaca    1080
tctccgcctc cttcccccgt caccagaaga gattcaaagc accagctctg ctactctcac   1140
atgtttgata gaggattct atcctgacaa agtaagcgtt tcctggcaaa agatgatgt     1200 ttctgtgagc gcgaacgtca ccaatttccc cactgctctg aacaggacc tgaccttcag    1260 cacacggagc ctcctcaatt taactgcagt ggaatggaag agcggagcaa aatacacttg   1320
tactgcctca catccacctt cacaatccac ggtgaagagg gtcatcagga accagaaagt   1380
tgattgccgt cagacagaca tttctgtcag cctactgaag cctccgtttg aagagatttg   1440
gacgcaacag acagcgacca ttgtttgcga aatcgtttac agcgacttag aaaacatcaa   1500
agttttctgg caagtgaatg gggttgagag aagaaagga gtcgagacgc agaatcccga    1560
gtggagcgga agtaaatcca ccattgtgag caaactcaaa gtcatggcgt cggagtggga   1620
cagtggtacc gaatatgttt gcttggtaga agacagtgaa ttgccaacac cagtgaaagc   1680
ctctatcagg aaggcaaatg tcagccaaat gcatcctccc aaggtttatc tcctgcatcc   1740
atcgacggac gagattgaca ctgagaattc ggctaccctg atgtgtctag ccaccaactt   1800
tcacccagct gagatttacg ttggttggat ggcaaatgac actcttttgg attctgggta   1860
ccggacccaa gtagacagcg agaaggggag tggttccagc ttcgttaccg acagattgag   1920
actcacagcg gctgaatgga acagtgacac cacttactcc tgcttagtgg acatccgtc    1980 cctaaaccgg gatttaatca gaagtacaaa taaatctaac ggtaaaccgt cgtcagttaa   2040
tgtttcagtc gtactaagcg acactgttaa atcctgcaca taatttgttg tgattgatgg   2100
tttgttttcc atagataggt taatgctgtt cttgcgaaaa aaaactgttt aagcaactga   2160
accaatgcat ttcaattcat tgcacgcaat agtcacattt ccgatcagtg aacacttctg   2220 gaaaagaaa ctagccattg tcttaaattc tatctgttgg tgaaagataa ttattgttag    2280
atactgaaat acaagtgcaa cattgccagt gtaatcgttc tgaagataac ttgaagcttt   2340
cactccggta ctgaaagaac aggaagttat gtttcagtct gtatgtggct ccaataattg   2400
caataaatgc agaatgaaaa                                               2420
```

<210> SEQ ID NO 436
<211> LENGTH: 21
<212> TYPE: DNA
<213> ORGANISM: Artificial sequence
<220> FEATURE:
<223> OTHER INFORMATION: Synthetic sequence: Constant domain 1 primer

<400> SEQUENCE: 436
atagtatccg ctgattagac a                                               21

<210> SEQ ID NO 437
<211> LENGTH: 22
<212> TYPE: DNA

```
<213> ORGANISM: Artificial sequence
<220> FEATURE:
<223> OTHER INFORMATION: Synthetic sequence: Constant domain 1 primer

<400> SEQUENCE: 437
gagtggagga gactgactat tg                                              22

<210> SEQ ID NO 438
<211> LENGTH: 37
<212> TYPE: DNA
<213> ORGANISM: Artificial sequence
<220> FEATURE:
<223> OTHER INFORMATION: Synthetic sequence: Primer

<400> SEQUENCE: 438
ggccacgcgt cgactagtac tttttttttt tttttttt                             37

<210> SEQ ID NO 439
<211> LENGTH: 21
<212> TYPE: DNA
<213> ORGANISM: Artificial sequence
<220> FEATURE:
<223> OTHER INFORMATION: Synthetic sequence: Spiny dogfish 3' RACE
      primer

<400> SEQUENCE: 439
cggcaacgaa agagacagga g                                               21

<210> SEQ ID NO 440
<211> LENGTH: 23
<212> TYPE: DNA
<213> ORGANISM: Artificial sequence
<220> FEATURE:
<223> OTHER INFORMATION: Synthetic sequence: Spiny dogfish 3' RACE
      primer

<400> SEQUENCE: 440
gacaggagaa tccctgacca tca                                             23

<210> SEQ ID NO 441
<211> LENGTH: 25
<212> TYPE: DNA
<213> ORGANISM: Artificial sequence
<220> FEATURE:
<223> OTHER INFORMATION: Synthetic sequence: Spiny dogfish 3' RACE
      primer

<400> SEQUENCE: 441
gaatccctga ccatcaattg cgtcc                                           25

<210> SEQ ID NO 442
<211> LENGTH: 21
<212> TYPE: DNA
<213> ORGANISM: Artificial sequence
<220> FEATURE:
<223> OTHER INFORMATION: Synthetic sequence: Spiny dogfish 3' RACE
      primer

<400> SEQUENCE: 442
ctggtaccgg aaaaatccgg g                                               21

<210> SEQ ID NO 443
<211> LENGTH: 24
<212> TYPE: DNA
<213> ORGANISM: Artificial sequence
<220> FEATURE:
<223> OTHER INFORMATION: Synthetic sequence: Spiny dogfish 3' RACE
```

```
            primer

<400> SEQUENCE: 443
cattttctct gcgaatcaag gacc                                          24

<210> SEQ ID NO 444
<211> LENGTH: 24
<212> TYPE: DNA
<213> ORGANISM: Artificial sequence
<220> FEATURE:
<223> OTHER INFORMATION: Synthetic sequence: Spiny dogfish 3' RACE
      primer

<400> SEQUENCE: 444
ggtccttgat tcgcagagaa aatg                                          24

<210> SEQ ID NO 445
<211> LENGTH: 22
<212> TYPE: DNA
<213> ORGANISM: Artificial sequence
<220> FEATURE:
<223> OTHER INFORMATION: Synthetic sequence: Spiny dogfish 3' RACE
      primer

<400> SEQUENCE: 445
tacgtggcac tgtctgcaac tg                                            22

<210> SEQ ID NO 446
<211> LENGTH: 21
<212> TYPE: DNA
<213> ORGANISM: Artificial sequence
<220> FEATURE:
<223> OTHER INFORMATION: Synthetic sequence: Primer

<400> SEQUENCE: 446
gcctcctgcc tccatcgcca g                                             21

<210> SEQ ID NO 447
<211> LENGTH: 25
<212> TYPE: DNA
<213> ORGANISM: Artificial sequence
<220> FEATURE:
<223> OTHER INFORMATION: Synthetic sequence: Primer

<400> SEQUENCE: 447
gagaataaac aggatcacga gagcg                                         25

<210> SEQ ID NO 448
<211> LENGTH: 25
<212> TYPE: DNA
<213> ORGANISM: Artificial sequence
<220> FEATURE:
<223> OTHER INFORMATION: Synthetic sequence: Primer

<400> SEQUENCE: 448
ggagaatccc tgaccatcaa ctgcg                                         25

<210> SEQ ID NO 449
<211> LENGTH: 23
<212> TYPE: DNA
<213> ORGANISM: Artificial sequence
<220> FEATURE:
<223> OTHER INFORMATION: Synthetic sequence: Spiny dogfish 5' RACE
      primer

<400> SEQUENCE: 449
```
caccaatcat cagtctcctc tac                                               23

<210> SEQ ID NO 450
<211> LENGTH: 22
<212> TYPE: DNA
<213> ORGANISM: Artificial sequence
<220> FEATURE:
<223> OTHER INFORMATION: Synthetic sequence: Spiny dogfish 5' RACE
      primer

<400> SEQUENCE: 450
ctactctgca actgacgaac tg                                                22

<210> SEQ ID NO 451
<211> LENGTH: 24
<212> TYPE: DNA
<213> ORGANISM: Artificial sequence
<220> FEATURE:
<223> OTHER INFORMATION: Synthetic sequence: Spiny dogfish 5' RACE
      primer

<400> SEQUENCE: 451
ctcactccaa tgctttctgg ctgg                                              24

<210> SEQ ID NO 452
<211> LENGTH: 22
<212> TYPE: DNA
<213> ORGANISM: Artificial sequence
<220> FEATURE:
<223> OTHER INFORMATION: Synthetic sequence: Spiny dogfish 5' RACE
      primer

<400> SEQUENCE: 452
gtggtaaagc cagactgtat gg                                                22

<210> SEQ ID NO 453
<211> LENGTH: 23
<212> TYPE: DNA
<213> ORGANISM: Artificial sequence
<220> FEATURE:
<223> OTHER INFORMATION: Synthetic sequence: Spiny dogfish 5' RACE
      primer

<400> SEQUENCE: 453
ggtggagcta aagtctccgt tcg                                               23

<210> SEQ ID NO 454
<211> LENGTH: 23
<212> TYPE: DNA
<213> ORGANISM: Artificial sequence
<220> FEATURE:
<223> OTHER INFORMATION: Synthetic sequence: Spiny dogfish 5' RACE
      primer

<400> SEQUENCE: 454
cacttggcag ctgtacattg aac                                               23

<210> SEQ ID NO 455
<211> LENGTH: 24
<212> TYPE: DNA
<213> ORGANISM: Artificial sequence
<220> FEATURE:
<223> OTHER INFORMATION: Synthetic sequence: Spiny dogfish 5' RACE
      primer

<400> SEQUENCE: 455
ctaatttctt tccgttggtt actg                                              24

<210> SEQ ID NO 456
<211> LENGTH: 20
<212> TYPE: DNA
<213> ORGANISM: Artificial sequence
<220> FEATURE:
<223> OTHER INFORMATION: Synthetic sequence: Spiny dogfish 5' RACE
      primer

<400> SEQUENCE: 456
cttccacgct gctggtcaag                                               20

<210> SEQ ID NO 457
<211> LENGTH: 21
<212> TYPE: DNA
<213> ORGANISM: Artificial sequence
<220> FEATURE:
<223> OTHER INFORMATION: Synthetic sequence: Spiny dogfish 5' RACE
      primer

<400> SEQUENCE: 457
gaatctcctc tggcgatgga g                                             21

<210> SEQ ID NO 458
<211> LENGTH: 24
<212> TYPE: DNA
<213> ORGANISM: Artificial sequence
<220> FEATURE:
<223> OTHER INFORMATION: Synthetic sequence: Spiny dogfish 5' RACE
      primer

<400> SEQUENCE: 458
ctcttatcaa acaggtgaga gtag                                          24

<210> SEQ ID NO 459
<211> LENGTH: 22
<212> TYPE: DNA
<213> ORGANISM: Artificial sequence
<220> FEATURE:
<223> OTHER INFORMATION: Synthetic sequence: Spiny dogfish 5' RACE
      primer

<400> SEQUENCE: 459
cacatccacc ttcacaatcc ac                                            22

<210> SEQ ID NO 460
<211> LENGTH: 22
<212> TYPE: DNA
<213> ORGANISM: Artificial sequence
<220> FEATURE:
<223> OTHER INFORMATION: Synthetic sequence: Spiny dogfish 5' RACE
      primer

<400> SEQUENCE: 460
gtggattgtg aaggtggatg tg                                            22

<210> SEQ ID NO 461
<211> LENGTH: 20
<212> TYPE: DNA
<213> ORGANISM: Artificial sequence
<220> FEATURE:
<223> OTHER INFORMATION: Synthetic sequence: Spiny dogfish 5' RACE
      primer

<400> SEQUENCE: 461
ggcaatgcac tgtcttctac                                               20

<210> SEQ ID NO 462
<211> LENGTH: 23
<212> TYPE: DNA
<213> ORGANISM: Artificial sequence
<220> FEATURE:
<223> OTHER INFORMATION: Synthetic sequence: Spiny dogfish 5' RACE
      primer

<400> SEQUENCE: 462
caaaagggtg tcattggcca tcc                                              23

<210> SEQ ID NO 463
<211> LENGTH: 22
<212> TYPE: DNA
<213> ORGANISM: Artificial sequence
<220> FEATURE:
<223> OTHER INFORMATION: Synthetic sequence: Spiny dogfish 5' RACE
      primer

<400> SEQUENCE: 463
cccactaaac aggagtaagt gg                                               22

<210> SEQ ID NO 464
<211> LENGTH: 23
<212> TYPE: DNA
<213> ORGANISM: Artificial sequence
<220> FEATURE:
<223> OTHER INFORMATION: Synthetic sequence: Spiny dogfish primer used
      for Variable PCR

<400> SEQUENCE: 464
gcctgctggt gaagaaacaa tgc                                              23

<210> SEQ ID NO 465
<211> LENGTH: 24
<212> TYPE: DNA
<213> ORGANISM: Artificial sequence
<220> FEATURE:
<223> OTHER INFORMATION: Synthetic sequence: Spiny dogfish primer used
      for Variable PCR

<400> SEQUENCE: 465
atgcatattt tctgggtttc ggtc                                             24

<210> SEQ ID NO 466
<211> LENGTH: 23
<212> TYPE: DNA
<213> ORGANISM: Artificial sequence
<220> FEATURE:
<223> OTHER INFORMATION: Synthetic sequence: Spiny dogfish primer used
      for Variable PCR

<400> SEQUENCE: 466
cacttggcag ctgtacattg aac                                              23

<210> SEQ ID NO 467
<211> LENGTH: 22
<212> TYPE: DNA
<213> ORGANISM: Artificial sequence
<220> FEATURE:
<223> OTHER INFORMATION: Synthetic sequence: Spiny dogfish primer used
      for Variable PCR

<400> SEQUENCE: 467
ccctgctggt gaagaaacaa tg                                               22

```
<210> SEQ ID NO 468
<211> LENGTH: 22
<212> TYPE: DNA
<213> ORGANISM: Artificial sequence
<220> FEATURE:
<223> OTHER INFORMATION: Synthetic sequence: Spiny dogfish primer used
      for Variable PCR

<400> SEQUENCE: 468
ctttgctggt gaagaaacaa tg                                                  22

<210> SEQ ID NO 469
<211> LENGTH: 23
<212> TYPE: DNA
<213> ORGANISM: Artificial sequence
<220> FEATURE:
<223> OTHER INFORMATION: Synthetic sequence: Spiny dogfish primer used
      for Variable PCR

<400> SEQUENCE: 469
cacttggcag ctgtacattg aac                                                 23

<210> SEQ ID NO 470
<211> LENGTH: 4146
<212> TYPE: DNA
<213> ORGANISM: Ginglymostoma cirratum
<220> FEATURE:
<221> NAME/KEY: misc_feature
<222> LOCATION: (6)..(7)
<223> OTHER INFORMATION: n is a, c, g, or t
<220> FEATURE:
<221> NAME/KEY: misc_feature
<222> LOCATION: (1637)..(1637)
<223> OTHER INFORMATION: n is a, c, g, or t

<400> SEQUENCE: 470
gctggnnctc caccgcggtg gcggccgctc tagaactagt ggatccccg ggctgcagga        60 attcggcacg aggaaatttg gagtttgctg tttatagttc tatcagtgca gaaacaatga      120
atattttctt gctttcagtc cttttagcct tattaccata tgtctttact gctcgagtgg      180
accaaacacc gagatcagta acaaaggaga cgggcgaatc actgaccatc aactgtgtcc      240
tacgagatgc gagctatgca ttgggcagca cgtgctggta tcgaaaaaaa tcgggctcaa      300
caaacgagga gagcatatcg aaaggtggac gatatgttga acagttaac agcggatcaa       360 agtccttttc tttgagaatt aatgatctaa cagttgaaga cggtggcacg tatcgttgcg      420
gtgtctcccc gtgggggtgg ggccggagct gtgactaccc aagctgtgct caaagaccat     480
atgctgcatc ggagatggc actgccgtga ctgtgaatcc tggaataccg ccttctccac       540
caatagtcag tctcctccac tctgcaactg aagaacagag agcaaacaga tttgtgcagc     600
tggtttgtct aatcagcgga tactatcccg aaaacattgc agtgagctgg cagaagaaca     660
caaagaccat aacttctggt tttgcaacaa catccccagt gaaaacttcg agcaatgact     720
tcagctgtgc aagtttactt aaagtgcccc tacaggaatg gagcaggggt tctgtgtaca    780
gttgccaagt ttctcattct gcaaccagca gtaaccagag gaaagaaatt cgatcaacat     840
ccgagatcgc tgtattactg agggatccaa cagttgaaga aatctggatc gataaaagtg     900
ccactctagt ttgcgaagtg ctctccacag tttccgctgg agtagtcgtc tcttggatgg    960
taaatggaaa agtaaggaat gaaggcgttc aaatggaacc aactaaaatg agtggaaacc    1020
aatatctgac aatcagccgc ttgaccagca gcgtggaaga gtggcagagt gggtggaat     1080 acacttgctc cgcaaaacag gatcaatcgt ccaccccagt cgtaaaacga acacgaaagg   1140
```

```
caagagtcga accgacaaaa ccacatctcc gcctccttcc cccgtcacca gaagagattc    1200
aaagcaccag ctctgctact ctcacatgtt tgataagagg attctatcct gacaaagtaa    1260
gcgtttcctg gcaaaaagat gatgtttctg tgagcgcgaa cgtcaccaat ttccccactg    1320
ctctggaaca ggacctgacc ttcagcacac ggagcctcct caatttaact gcagtggaat    1380
ggaagagcgg agcaaaatac acttgtactg cctcacatcc accttcacaa tccacggtga    1440
agagggtcat caggaaccag aaagttgatt gccgtcagac agacatttct gtcagtctac    1500
tgaagcctcc gtttgaagag atttggacgc aacagacagc gaccattgtt tgcgaaatcg    1560
tttacagcga cttagaaaac atcaaagttt tctggcaagt gaatgggggtt gagagaaaga    1620 aaggagtcga gacgcanaat cccgagtgga gcggaagtaa atccaccatt gtgagcaaac    1680
tcaaagtcat ggcgtcggag tgggacagtg gtaccgaata tgtttgcttg gtagaagaca    1740
gtgaattgcc aacaccagtg aaagcctcta tcaggaaggc aaatgtcagc caaatgcatc    1800
ccccaaaggt ttatctcctg catccatcga cggacgagat tgacactgag aattcggcta    1860
ccctgatgtg tctagccacc aactttcacc cagctgagat ttacgttggt tggatggcaa    1920
atgacactct tttggattct gggtaccgga cccaagtaga cagcgagaag gggagtggtt    1980
ccagcttcgt taccagcaga ttgagactca cagcggctga atggaacagt gacaccactt    2040
actcctgctt agtgggacat ccgtccctaa accgggattt aatcagaagt acaaataaat    2100
ctaacgacac ccctgaaata atggaaagcc cggaagacca tggcacagaa gaagacgaac    2160
tagaaaatgt caatgaagac gccaacagtt cattatccat catgactttc gtgatcttgt    2220
ttattctcag tatgctgtac agcacatttg taactgtgct gaaggtgaac tgaccactgc    2280
tgttgaatag aaatacatct ggtttcatgg aaatcttatg actgaaaccc cattagatac    2340
tgatcgcaaa tggaattgaa tttatttttc ctctcaaccg tatcagctgt tccatggcat    2400
tgatcgcaaa tggaattgaa tttatttttc ctctcaaccg tatcagctgt tccatggcat    2460
tacttcagcg tgtgttccta cgtggtctca acttcggaat gagaactgct tgcatgtttt    2520
cggtcataga gtttgccttt gcttttttt ttagctgtta gttttcaaga aatcccactt    2580
aactgctaca agctgaggaa attacacttc cacaattcaa taaactgaag gtaaatcttg    2640
gaaatttgcc atgtgtcagt aaaacatttt gaaaagtgc agatgtatct gttgtaactg    2700
acgtgtcaga gatttataca atataacttt gagactcgta atcagataaa ctttcttcat    2760
agaaccagca gacaggctgt caaacatata atttttaccc aagagcattg ggtagataaa    2820
aacccattga tttcacaaga gggttcattc actcctatag aaaaaaagta catcatccaa    2880
atattgctaa gaaaattttg gaaatatacc tacaagaatg aactttcttc tcacaattgt    2940
tgttgttcat aacctgactg tgacagccga agtttattcc tgtttggcac ttttatttgc    3000
taagcactga ggctatcagt gctcaatgtg agtaataatg tcatttgcga gaaccagcag    3060
aggaaacgtt tgagaatatc ttcagttttt cactgcatac agaacccaga caacagttaa    3120
taaaaggtca tgtgttatat ccaatttgat tccatcctga cagtctcaag atttcacact    3180
ctcgtagaaa tcttataaat gctatatact gctattacta tccgtaatcg ccttgagaga    3240
ttatcgtggt ctcttttctt tatccactac aatctatgtc acgtcgagga ctgcactaca    3300
cttacatgca gaaaagtgtt gcaaatatga ttccttgttt caaccatgt ttacgaattc    3360 ccattaaata tgctgtcaga taatagttgc tccaaagcaa ttggtgtaag ggatatttc    3420 gaacacatta tgaaatgatt cgctgtctcg ctctaccaaa aaataaatga caaagcaaag    3480
gcaaacctgc aagagacatt gtgtaacatc gcagttaaca ttgaaatagc agatttcgct    3540
```

-continued

```
gctgtctatt gaactgcaaa tgttccaagt tactttgaaa gtgattagtt gttatatgag    3600
agaataaatc ttgttctgaa tgagtcaggg attcattctt gacaagaata ggctattcaa    3660
ccacttgtgc cattttttgtc ttttgtgaag cttctgtttg ttgactaccg tcactgttcc    3720
gatatgtatt tccaagcatt tgaatcaagt tcattaaaaa gattgtaatt cttgtaaatt    3780
acaaaaaagg aagtgtcaat aactttggaa acttgcaaaa aatttcccca aactgtggaa    3840
atataatgtt gccatgtata gatttaaata tgtctttgcc ttcaatgtta ctgttgtatt    3900
gttatttagt tatgaccttc atattctgtc aatgcagagg tgtgaaatgt aactgttatt    3960
atctccttca tgttgtcatt cattcaagtt ttgctgaaat cctggcctta aatcaagcac    4020
ttgttttcag aacgcaattt attgcagttt gttccaaaga gtgtgtcagt attcgcctca    4080
tatgtggtgc tccttgagca aataaaatca aattaatcat tttgtaaaaa aaaaaaaaaa    4140
aaaaaa                                                                4146
```

SYNTHETIC LIBRARY OF SPECIFIC BINDING MOLECULES

The present invention relates to a synthetic library of antigen specific binding molecules derived from a member of a species in the Elasmobranchii subclass, processes for the production thereof and specific antigen specific binding molecules isolated from said library.

The search for specific, increasingly efficacious, and diversified therapeutic weapons to combat diseases has utilised a myriad of distinct modalities. From the traditional small molecule to incrementally larger biologic pharmaceuticals, for example single binding domains (10-15 kDa) to full IgG (~150 kDa). Single domains currently under investigation as potential therapeutics include a wide variety of distinct protein scaffolds, all with their associated advantages and disadvantages.

Such single domain scaffolds can be derived from an array of proteins from distinct species. The immunoglobulin isotope novel antigen receptor (IgNAR) is a homodimeric heavy-chain complex originally found in the serum of the nurse shark (*Ginglymostoma cirratum*) and other sharks and ray species. IgNARs do not contain light chains. Each molecule consists of a single-variable domain (VNAR) and five constant domains (CNAR). The nomenclature in the literature refers to IgNARs as immunoglobulin isotope novel antigen receptors or immunoglobulin isotope new antigen receptors and the terms are synonymous.

In addition to the immunoglobulin or immunoglobulin-like shark variable novel antigen receptors (VNAR) (Fennell, B. J., et al., J Mol Biol, 2010. 400(2): p. 155-70), other examples are camelid variable heavy ($V_{HH}$) domains (Wesolowski, J., et al., Med Microbiol Immunol, 2009. 198(3): p. 157-74), engineered human variable heavy (VH) domains (Chen, W., et al., J Mol Biol, 2008. 382(3): p. 779-89) and constant heavy (CH2) (Dimitrov, D. S., MAbs, 2009. 1(1): p. 26-8), cytotoxic T-lymphocyte-associated protein 4 (CTLA4) (Nuttall, S. D., et al., Proteins, 1999. 36(2): p. 217-27) domains, Lamprey variable lymphocyte receptors (VLR) (Tasumi, S., et al., Proc Natl Acad Sci USA, 2009. 106(31): p. 12891-6). Similarities between the VNAR and Camelid Variable Heavy Chain (VHH) fragments include the presence of disulphide bonds and binding affinities in the nanomolar range.

There are also a host of 'non-immunoglobulin' domains which include as examples the fibronectin type III (FN3) (Bloom, L. and V. Calabro, Drug Discov Today, 2009. 14(19-20): p. 949-55), DARPins, Anticalins, and Affibodies (Gebauer, M. and A. Skerra, Curr Opin Chem Biol, 2009. 13(3): p. 245-55). Currently single domain biologics are the subject of intensive research toward their successful application as therapeutics to various distinct indications.

To date, there are three defined types of shark IgNAR known as I, II and III (FIG. 1). These have been categorized based on the position of non-canonical cysteine residues which are under strong selective pressure and are therefore rarely replaced.

All three types have the classical immunoglobulin canonical cysteines at positions 35 and 107 that stabilize the standard immunoglobulin fold, together with an invariant tryptophan at position 36. There is no defined CDR2 as such, but regions of sequence variation that compare more closely to TCR HV2 and HV4 have been defined in framework 2 and 3 respectively. Type I has germline encoded cysteine residues in framework 2 and framework 4 and an even number of additional cysteines within CDR3. Crystal structure studies of a Type I IgNAR isolated against and in complex with lysozyme enabled the contribution of these cysteine residues to be determined. Both the framework 2 and 4 cysteines form disulphide bridges with those in CDR3 forming a tightly packed structure within which the CDR3 loop is held tightly down towards the HV2 region. To date Type I IgNARs have only been identified in nurse sharks—all other elasmobranchs, including members of the same order have only Type II or variations of this type.

Type II IgNAR are defined as having a cysteine residue in CDR1 and CDR3 which form intra-molecular disulphide bonds that hold these two regions in close proximity, resulting in a protruding CDR3 (FIG. 2) that is conducive to binding pockets or grooves. Type I sequences typically have longer CDR3s than type II with an average of 21 and 15 residues respectively. This is believed to be due to a strong selective pressure for two or more cysteine residues in Type I CDR3 to associate with their framework 2 and 4 counterparts. Studies into the accumulation of somatic mutations show that there are a greater number of mutations in CDR1 of type II than type I, whereas HV2 regions of Type I show greater sequence variation than Type II. This evidence correlates well with the determined positioning of these regions within the antigen binding sites. A third IgNAR type known as Type III has been identified in neonates. This member of the IgNAR family lacks diversity within CDR3 due to the germline fusion of the D1 and D2 regions (which form CDR3) with the V-gene. Almost all known clones have a CDR3 length of 15 residues with little or no sequence diversity.

There are encouraging results from clinical trials of single domain binding molecules (Holliger, P. and P. J. Hudson, Nat Biotechnol, 2005. 23(9): p. 1126-36) that not only highlight their potential advantages but also the extent of investment in their application. Various rationales have been put forward for choosing small single domain scaffolds as opposed to the larger and more familiar biologic counterparts, for example full IgG's. Among the more widely cited are often the general presumption that as a consequence of their smaller size they may be more readily suited to crossing the blood brain barrier, and to targeting solid tumours through increased tissue penetration. Generally single domains reported for the camel and shark species are also suspected of forming structurally distinct paratopes and as a consequence they may facilitate targeting of clefts such as enzyme active sites.

It should however be noted that there is still a relative paucity of information with respect to many of these characteristics. Some single domains have demonstrated high intrinsic thermostability in addition to refolding propensity following denaturation. Such characteristics would be advantageous in the large scale process development activities generally required to bring biologic therapeutics to market. In addition these characteristics may make the single domain approaches more amenable to alternative modes of drug delivery. A consequence of using individual unit domain approaches mean it can also be applied to a 'building-block' synthesis lending to the potential for combined multidomain modalities with multiple distinct specificities.

Phage display allows the generation of large libraries of protein variants that can be rapidly sorted for those sequences that bind to a target antigen with high affinity. Nucleic acids encoding variant polypeptides are fused to a nucleic acid sequence encoding a viral coat protein. Libraries of antibodies or antigen binding polypeptides have been prepared in a number of ways including by altering a single gene by inserting random DNA sequences or by cloning a family of related genes. The library is then screened for expression of antibodies or antigen binding proteins with desired characteristics.

Phage display technology has several advantages over conventional hybridoma and recombinant methods for preparing antibodies with the desired characteristics. This technology allows the development of large libraries of antibodies with diverse sequences in less time and without the use of animals.

Isolation of high affinity antibodies from a library is dependent on the size of the library, the efficiency of production in bacterial cells and the diversity of the library. The size of the library is decreased by inefficiency of production due to improper folding of the antibody or antigen binding protein and the presence of stop codons. Expression in bacterial cells can be inhibited if the antibody or antigen binding domain is not properly folded. Expression can be improved by mutating residues in turns at the surface of the variable/constant interface, or at selected CDR residues. The sequence of the framework region is a factor in providing for proper folding when antibody phage libraries are produced in bacterial cells.

Generating a diverse library of antibodies or antigen binding proteins is also important to isolation of high affinity antibodies (see for example WO 03/102157, WO 03/014161, and WO 2005/118629). CDR3 regions are of interest in part because they often are found to participate in antigen binding.

The present invention concerns the Ig-like Novel Antigen Receptor variable domain (VNAR). Somewhat analogous (but different ancestral molecular lineage) to the camelid $V_{HH}$ domain, however the occurrence of literature reports describing phage-displayed library construction and specific binder selection are less frequent and rare using naïve shark repertoires (Nuttall, S. D., et al., FEBS Lett, 2002. 516(1-3): p. 80-6; Liu, J. L., et al., Mol Immunol, 2007. 44(7): p. 1775-8) by comparison. The majority of isolated VNAR domains to date appear to have been obtained from phage-displayed libraries constructed using tissues from target-immunised (Dooley, H., M. F. Flajnik, and A. J. Porter, Mol Immunol, 2003. 40(1): p. 25-33; Nuttall, S. D., et al., Proteins, 2004. 55(1): p. 187-97; and Dooley, H., et al., Proc Natl Acad Sci USA, 2006. 103(6): p. 1846-51), or 'naïve' non-immunised diversity combined with synthetic diversity targeted to Complementarity Determining Region 3 (CDR3) by PCR (Nuttall, S. D., et al., Mol Immunol, 2001. 38(4): p. 313-26; Nuttall, S. D., et al., Eur J Biochem, 2003. 270(17): p. 3543-54; and Liu, J. L., G. P. Anderson, and E. R. Goldman, BMC Biotechnol, 2007. 7: p. 78).

Shark immunisation-strategies are a powerful way to isolate high affinity, highly specific VNAR domains however this method presents some technical challenges such as long immunization schedules required and a general paucity of shark-species or isotype recognition reagents. Therefore, the present invention provides a synthetic VNAR library which can be used to effectively source potential VNAR therapeutics for any given target, in effect bypassing the aforementioned challenges. Ideally investigators should be able to use display library technologies to derive VNAR quickly, without the need for animals, in the same biologic drug discovery process that is currently widely employed for the isolation of human and mouse antibodies.

The present invention is based on the unexpected diversity, affinity, specificity and efficacy of VNARs isolated from a library created from two or more naturally occurring VNAR sequences from different isotypes within the same species and different isotypes across different Elasmobranchii species. This novel approach of fusing different isotype and different species frameworks together has the advantage of creating increased diversity within the library which would not be achieved using single framework libraries. Advantages include but are not limited to:

Additional diversity created within both CDR regions, both HV regions and framework regions through the fusion of different isotypes Additional diversity created within both CDR regions, both HV regions and framework regions through the fusion of different isotypes from different Elasmobranchii species Additional diversity created through directed mutagenesis using trinucleotide (TRM) oligos and random mutagenesis by the use of NNK oligos within both CDR regions.

Additional isotype diversity beyond the fused framework regions by using naturally occurring CDR1 regions in combination with NNK oligos as this results in the potential addition of a classical Type II cys pairing across CDR1 and CDR3.

Additional diversity through the use of different fixed lengths of diverse CDR3 regions Increased library size of >9×10$^{10}$ clones, which is two orders of magnitude larger than any shark library (naïve, immune or synthetic) previously reported The invention generally relates to libraries of antigen specific antigen binding molecules. The libraries include a plurality of different antigen specific antigen binding molecules, including domains and/or fragments thereof, generated by creating diversity in both the CDR regions and framework regions. In particular, diversity in CDR regions is designed to maximize the diversity while minimizing the structural perturbations of the VNAR sequences and domains of the antigen specific antigen binding molecules of the invention.

Such libraries provide combinatorial libraries useful for, for example, selecting and/or screening for synthetic VNAR clones with desirable activities such as binding affinities and avidities. These libraries are useful for identifying sequences that are capable of interacting with any of a wide variety of target antigens. For example, libraries comprising diversified VNAR polypeptides of the invention displayed on phage are particularly useful for, and provide a high throughput, efficient and automatable systems of, selecting and/or screening for antigen binding molecules of interest. The methods of the invention are designed to provide high affinity binders to target antigens with minimal changes to a source or template molecule and provide for good production yields when the antibody or antigens binding fragments are produced in cell culture.

The invention provides methods for generating and isolating novel VNARs or fragments thereof that preferably have a high affinity for a selected antigen. A plurality of different VNARs or VNAR domains are prepared by mutating (diversifying) one or more selected amino acid positions in a source template VNAR sequence to generate a diverse library of VNAR domains with variant amino acids at those positions. The amino acid positions are those that are solvent accessible, for example as determined by analyzing the structure of a source VNAR, and/or that are highly diverse among known and/or natural occurring VNAR polypeptides.

The invention also relates to fusion polypeptides of one or more antigen specific antigen binding molecules or domains (or parts thereof) and a heterologous protein such as a coat protein of a virus. The invention also relates to replicable expression vectors which include a gene encoding the fusion polypeptide, host cells containing the expression vectors, a virus which displays the fusion polypeptide on the surface of the virus, libraries of the virus displaying a plurality of different fusion polypeptides on the surface of the virus and If each Framework (FW) region is in a separate fragment then potentially 4 or 5 peptide domains may be prepared. In which case, the formula (III) is represented by:

P-Q-R-S where there are 4 separate peptide domains, where P-Q-R-S is FW1-CDR1-FW2-HV2-FW3a-HV4-FW3b-CDR3-FW4 and where each of P, Q, R and S represent the contiguous peptide domains; or

P-Q-R-S-T where there are 5 separate peptide domains where P-Q-R-S-T is FW1-CDR1-FW2-HV2-FW3a-HV4-FW3b-CDR3-FW4, and where each of P, Q, R, S and T represent the contiguous peptide domains.

Examples of contiguous peptide domains according to these alternative embodiments are shown in the Table below:

| No. | P | Q | R | S |
|---|---|---|---|---|
| 11 | FW1 | CDR1-FW2-HV2- | FW3a- | HV4-FW3b-CDR3-FW4 |
| 12 | FW1 | CDR1-FW2- | HV2-FW3a-HV4 | FW3b-CDR3-FW4 |
| 13 | FW1- CDR1 | FW2- HV2- FW3a-HV4- | FW3b- CDR3 | -FW4 |

| No. | P | Q | R | S | T |
|---|---|---|---|---|---|
| 14 | FW1 | CDR1-FW2-HV2- | FW3a- | HV4-FW3b | CDR3-FW4 |
| 15 | FW1 | CDR1-FW2- | HV2-FW3a-HV4 | FW3b- | CDR3-FW4 |
| 16 | FW1- CDR1 | FW2- HV2- | FW3a-HV4 | FW3b- CDR3 | -FW4 |

In one embodiment of this aspect of the invention, the two or more contiguous peptide domains are the three domains represented by FW1-CDR1-FW2-HV2-FW3a-HV4-FW3b-CDR3-FW4 are FW1, CDR1-FW2-HV2-FW3a-HV4-FW3b, and CDR3-FW4.

In this embodiment of the invention step (4) may be defined as being (4) amplifying DNA sequences encoding peptide domains FW1, CDR1-FW2-HV2-FW3a-HV4-FW3, and CDR3-FW4 from at least two heterologous DNA sequences selected in (3) in the presence of a plurality of heterologous oligomers complementary to CDR1 or CDR3 domains in sequences selected in (3) to form a plurality of amplified DNA sequences encoding peptide domains FW1, CDR1-FW2-HV2-FW3a-HV4-FW3, and CDR3-FW4. Consequently, step (5) according this embodiment of the invention can be defined as being ligating together said amplified DNA sequences encoding peptide domains FW1, CDR1-FW2-HV2-FW3a-HV4-FW3, and CDR3-FW4 to form DNA sequences encoding an antigen specific binding molecule having the peptide domain structure of formula (I);

In one embodiment of the invention, the template derived HV2 and HV4 loops within different contexts may be achieved through alternatively splicing PCR fragments encoding template derived HV2 and HV4 pairings with respectively derived FW1, and CDR1 and CDR3 fragments.

Selection of the DNA sequence from the database prepared in step (2) according to step (3) of the method of the first aspect of the invention can be made according to an analysis of the expressed amino acid sequences for the DNA sequences prepared. The translated DNA sequences can be examined in terms of amino acid (AA) content, relative positional conservation and frequency across the analysed population in addition to CDR3 length distribution.

From an analysis of the expressed DNA sequences in the database of natural sequences compared to expressed sequences from the library it is possible to select DNA sequences based upon the degree of natural content in either CDR1 and/or CDR3 and the relative diversity present in CDR1 and/or CDR3 also.

Natural sequence content is defined as a sequence identity of at least about 80%, 85%, 90% or 95%, for example about 80% to about 95%, or about 85% to about 90%, compared with a corresponding naturally expressed VNAR sequence. A high level of diversity is defined as a sequence identity of about 60% to about 75%, suitably about 65% to about 70%, where a diversity of about 60% to about 65% may be suitable compared to a corresponding naturally expressed VNAR sequence.

For example, it may be desirable to have a natural version of CDR1 and a high level of diversity on CDR3. The addition of cysteine residues can be achieved by using TRM oligonucleotides in the DNA amplification process.

Antigen specific antigen binding molecules of the invention may therefore be constructed of any of the amino acid sequences for the various regions disclosed herein according to the basic structure (as defined herein):

FW1-CDR1-FW2-HV2-FW3a-HV4-FW3b-CDR3-FW4 in which each of FW1, CDR1, FW2, HV2, FW3a, HV4, FW3b, CDR3, and FW4 represent a peptide sequence, where "FW" is a "Framework" region, "CDR1" is a "Complementarity Determining Region 1", "HV" is a "Hypervariable" region, and "CDR3" is a "Complementarity Determining Region 3". Examples of suitable peptide domain sequences are described herein.

The specific antigen binding molecules of the invention may be classified according to the general structure of the nomenclature for VNARs according to Liu et al (Liu et al Mol. Immunol. 44, 1775-1783 (2007) and Liu et al BMC Biotechnology, 7(78) doi:10.1186/1472-6750-7-78 (2007)).

In one embodiment of the invention, the amplification of DNA in step (4) is carried out in the presence of oligomers which encode a sequence of any amino acid except cysteine. In other words, the resulting CDR regions encoded by the amplified DNA will not include cysteine. However, in other embodiments cysteine may be present in the CDR regions.

All VNARs contain two canonical cys residues in FW1 and FW3 which create the classic immunoglobulin (Ig) fold. In addition, they are characterised by the addition of extra cysteine (cys) residues in the CDRs and FWs:

Type I: non-canonical cys residues in FW2 and FW4 in addition to two extra cys in CDR3—the FW-CDR3 pairings form a tightly constrained CDR3 structure.

Type II: non-canonical cys residues in CDR1 and CDR3 that create a disulphide bridge that results in the CDR3 being in a protruding position.

Type III: non-canonical cys residues as a Type II however they contain a conserved W in CDR1

All the above is based on nurse shark nomenclature. In the present invention other new isotypes have been isolated which are described as "type b" variants as follows:

Type IIb: no non-canonical cys residues in CDR1 and CDR3—resulting in a very flexible CDR3 (2V is an example of a type IIb variant).

Type IIIb: no non-canonical cys residues in CDR1 and CDR3 but does have the invariant W in CDR1 (5V is an example of a type IIIb variant).

It may be desirable to ensure that there are no non-canonical cysteine (C) residues in CDR1 and CDR3 which may provide for a more flexible CDR3 region. Such a structure may be referred to as a "Type IIb" isotype, following the general structure of nurse shark nomenclature for VNARs according to Liu et al (Liu et al Mol. Immunol. 44, 1775-1783 (2007) and Liu et al BMC Biotechnology, 7(78) doi:10.1186/1472-6750-7-78 (2007)).

In an alternative embodiment, it may also be desirable to ensure that there are no non-canonical cysteine (C) residues in CDR1 and CDR3, but also to have an invariant tryptophan (W) in CDR1. Such a structure may be referred to as a "Type IIIb" isotype, following the general structure of nurse shark nomenclature for VNARs according to Liu et al (cited above).

In one embodiment of the invention, the antigen specific antigen binding molecule may be a fusion of region FW1, CDR1, FW2, HV2, FW3a, HV4, FW3b, CDR3, and/or FW4 s from a type IIb and a type IIIb VNAR. The fused IIb and IIIb portions may be connected in either order as appropriate in order to form a VNAR structure.

In one embodiment of the invention, the selected DNA sequence may have the final three amino acid residues in domain FW3b as CKA, CRA, or CNA and first three amino acid residues of FW4 as Y or D/G or D/D or A. Other FW3b sequences may comprise variations such as CRG, CKV, CKT, and/or CHT.

Other alternative fusions of isotypes may also be made according to the present invention. For example, regions from a type I VNAR may be fused with a type III VNAR, or regions from a type I VNAR may be fused with a type II VNAR. Variations of isotype regions type I, type II and type III, such as described in the present invention, of type Ib, type IIb and type IIIb are also included. Fusions can also include any isotype fusion across VNAR families, i.e. isotype regions isolated from any species of Elasmobranchii. For example, a type II region from nurse shark fused with a type II region from dogfish, or a type IIb from Wobbegong fused with a type IIIb from dogfish.

In accordance with the present invention, the library may be created from two or more naturally occurring VNAR sequences from different isotypes within the same species and different isotypes across different Elasmobranchii species. This approach of fusing different isotype and different species frameworks together has the advantage of creating increased diversity within the library which would not be achieved using single framework libraries.

In one embodiment on the invention three different isotypes of VNAR domains from two different species of Elasmobranchii: *Squalus acanthias* and *Ginglymostoma cirratum* were combined. Framework fusion constructs were designed to incorporate type IIb and type IIIb VNAR domains from spiny dogfish and type II VNAR domains from nurse shark.

An additional embodiment of the invention is the incorporation of a cysteine (cys) residue to the CDR regions which increases the diversity by creating the potential for CDR1 to CDR3 disulphide bridging as seen in classical Type II VNAR domains.

In another embodiment of the invention, the step (1) of isolating RNA from a member of a species in the Elasmobranchii subclass may isolate RNA from a subject which has not been immunized previously, i.e. from a naïve or natural source of framework material. In other embodiments, the RNA can be sourced from a subject which has been immunized previously.

According to a second aspect of the invention, there is provided a process for the production of an antigen specific antigen binding molecule, comprising
  (1) selecting desired clones from the library prepared according to the first aspect of the invention;
  (2) isolating and purifying the antigen specific antigen binding molecules from these clones;
  (3) cloning the DNA sequences encoding the antigen specific antigen binding molecules into an expression vector; and
  (4) transforming a host to allow expression of the expression vector.

According to a third aspect of the invention, there is provided a method for the production of an antigen specific antigen binding molecule having a peptide domain structure represented by the following formula (I):

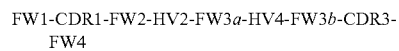

comprising
  (1) isolating RNA from a member of a species in the Elasmobranchii subclass;
  (2) amplifying DNA sequences from RNA obtained in (1) which encode antigen specific antigen binding molecules to create a database of DNA sequences encoding antigen specific binding molecules;
  (3) selecting a DNA sequence from the database prepared in (2);
  (4) amplifying DNA sequences encoding two or more contiguous peptide domains of FW1-CDR1-FW2-HV2-FW3a-HV4-FW3b-CDR3-FW4 wherein said two or more contiguous peptide domains when ligated encode an antigen specific antigen binding molecule of formula (I) and where said two or more contiguous peptide domains are from at least two heterologous DNA sequences selected in (3) in the presence of a plurality of heterologous oligomers complementary to CDR1 or CDR3 domains in sequences selected in (3) to form a plurality of amplified DNA sequences encoding an antigen specific antigen binding molecule of formula (I);
  (5) ligating together said amplified DNA sequences encoding peptide domains FW1, CDR1-FW2-HV2-FW3a-HV4-FW3, and CDR3-FW4 to form DNA sequences encoding an antigen specific binding molecule having the peptide domain structure of formula (I);
  (6) cloning the amplified DNA obtained in (5) into a display vector;
  (7) transforming a host with said display vector to produce a library of said antigen specific antigen binding molecules;
  (8) selecting a desired clone from the library;
  (9) isolating and purifying the antigen specific antigen binding molecule from the clone;

(10) cloning the DNA sequences encoding the antigen specific antigen binding molecule into an expression vector;
(11) transforming a host to allow expression of the expression vector.

In the methods of the invention, RNA may be isolated from one member or several different members of species in the Elasmobranchii subclass. References to a member of a species in the Elasmobranchii subclass therefore include references to one or more different members of a species in the Elasmobranchii subclass also. Step (1) of the third aspect of the invention may therefore comprise isolating RNA from a member or members of species in the Elasmobranchii subclass.

Selection of the DNA sequence in step (3) is as described in relation to the first aspect of the invention. This aspect of the invention therefore includes the production of a plurality of such molecules.

Combinations of contiguous peptide domains of FW1-CDR1-FW2-HV2-FW3a-HV4-FW3b-CDR3-FW4 in step (4) are as described in relation to the first aspect of the invention. Step (4) according to one embodiment of this aspect of the invention may be defined as amplifying DNA sequences encoding peptide domains FW1, CDR1-FW2-HV2-FW3a-HV4-FW3b, and CDR3-FW4 from at least two heterologous DNA sequences selected in (3) in the presence of a plurality of heterologous oligomers complementary to CDR1 or CDR3 domains in sequences selected in (3) to form a plurality of amplified DNA sequences encoding peptide domains FW1, CDR1-FW2-HV2-FW3a-HV4-FW3, and CDR3-FW4. Step (5) according this embodiment of the invention can be defined as being ligating together said amplified DNA sequences encoding peptide domains FW1, CDR1-FW2-HV2-FW3a-HV4-FW3, and CDR3-FW4 to form DNA sequences encoding an antigen specific binding molecule having the peptide domain structure of formula (I);

In another embodiment of the invention, the step (1) of isolating RNA from a member of a species in the Elasmobranchii subclass may isolate RNA from a subject which has not been immunized previously, i.e. from a naïve or natural source of framework material. In other embodiments, the RNA can be sourced from a subject which has been immunized previously.

In one embodiment of the invention, the amplification of DNA in step (4) is carried out in the presence of oligomers which encode a sequence of any amino acid except cysteine. In other words, the resulting CDR regions encoded by the amplified DNA will not include cysteine. However, in other embodiments cysteine may be present in the CDR regions.

According to a fourth aspect of the present invention, there is provided a process for the production of an antigen specific antigen binding molecule using a transformed host containing a library of expressible DNA sequences encoding a plurality of antigen specific antigen binding molecules wherein the library is created from at least two heterologous isotype NAR sequences, wherein the antigen specific antigen binding molecules comprise a plurality of domains of a variable region of the immunoglobulin isotype NAR found in a member of a species in the Elasmobranchii subclass.

In another embodiment of the invention, the step (1) of isolating RNA from a member of a species in the Elasmobranchii subclass may isolate RNA from a subject which has not been immunized previously, i.e. from a naïve or natural source of framework material. In other embodiments, the RNA can be sourced from a subject which has been immunized previously.

In one embodiment of the invention, the amplification of DNA in step (4) is carried out in the presence of oligomers which encode a sequence of any amino acid except cysteine. In other words, the resulting CDR regions encoded by the amplified DNA will not include cysteine. However, in other embodiments cysteine may be present in the CDR regions.

According to a fifth aspect of the invention, there is provided an antigen specific antigen binding molecule comprising an amino acid sequence represented by the formula (II)

A-X-B-Y-C (II)

wherein
A—is SEQ ID NO: 1, SEQ ID NO: 4 or SEQ ID NO: 7
X is a CDR1 region of 5, 6 or 7 amino acid residues
B—is SEQ ID NO: 2, SEQ ID NO: 5 or SEQ ID NO: 8
Y is a CDR3 region of 8, 9, 10, 11, 12, 13, 14, 15, 16, or 17 amino acid residues
C—is SEQ ID NO: 3 or SEQ ID NO: 6
or a sequence at least 50% homologous thereto,
in which

```
SEQ ID NO: 1 is
TRVDQTPRTATKETGESLTINCVLTDT,

TRVDQTPRTATKETGESLTINCVVTGA

SEQ ID NO: 2 is
TSWFRKNPGTTDWERMSIGGRYVESVNKGAKSFSLRIKDLTVA
DSATYYCKA
or

TSWFRKNPGTTDWERMSIGGRYVESVNKGAKSFSLRIKDLTVA
DSATYICRA

SEQ ID NO: 3 is
DGAGTVLTVN

SEQ ID NO: 4 is
ASVNQTPRTATKETGESLTINCVLTDT
or

ASVNQTPRTATKETGESLTINCVVTGA

SEQ ID NO: 5 is
TYWYRKNPGSSNQERISISGRYVESVNKRTMSFSLRIKDLTVA
DSATYYCKA
or

TYWYRKNPGSSNQERISISGRYVESVNKRTMSFSLRIKDLTVA
DSATYICRA

SEQ ID NO: 6 is
YGAGTVLTVN

SEQ ID NO: 7 is
ARVDQTPQTITKETGESLTINCVLRD,
and

SEQ ID NO: 8 is
TYWYRKKSGSTNEESISKGGRYVETVNSGSKSFSLRIKDLTVA
DSATYICRA
or

TYWYRKNPGSTNEESISKGGRYVETVNSGSKSFSLRIKDLTVA
DSATYICRA.
```

The amino acid sequences represented by A, X, B, Y and/or C may be derived from the same or different member of the Elasmobranchii subclass. The amino acid sequences represented by A, X, B, Y and/or C may also be derived from the same or different isotypes of VNAR sequences, e.g. type I, type II and/or type III (including type Ib, type IIb and type IIIb). Any generally suitable combination of source material is therefore possible.

In some embodiments of the invention, formula (II) A-X-B-Y-C may be composed of sequences in which elements A, B, and C are represented by (i) SEQ ID NO.s 1, 2, and 3; (ii) SEQ ID NO.s 1, 2, and 6; (iii) SEQ ID NO.s 1, 5, and 3; (iv) SEQ ID NO:s 1, 5 and 6; (v) SEQ ID NO.s 4, 5, and 6; (vi) SEQ ID NO:s 4, 5 and 3; (vii) SEQ ID NO:s 4, 2, and 6; (viii) SEQ ID NO.s 4, 2, and 3; (ix) SEQ ID NOs 7, 8 and 6; (x) SEQ ID NOs 1, 8 and 6.

Where A is SEQ ID NO: 1, B is SEQ ID NO: 2 and C is SEQ ID NO: 3, one embodiment of the sequence of formula (I) is SEQ ID NO: 10, where the CDR1 region is SYGLYS (SEQ ID NO: 170) and the CDR3 region is QSLAIST-RSYWY (SEQ ID NO: 298) as shown in FIG. 9.

Where A is SEQ ID NO: 4, B is SEQ ID NO: 5 and C is SEQ ID NO: 6, one embodiment of the sequence of formula (I) is SEQ ID NO: 12, where the CDR1 region is SYAWSS (SEQ ID NO: 171) and the CDR3 region is YRMESIAGR-GYDV (SEQ ID NO: 299) as shown in FIG. 9.

SEQ ID NO:s, 10 and 12 are as shown in FIG. 9 where the corresponding nucleic acid sequences encoding the protein sequences are shown also as SEQ ID No.s 9 and 11 respectively.

The CDR1 region may be any CDR1 region as shown in FIG. 17. The CDR3 region may be any CDR3 region as shown in FIG. 18.

Preferred antigen specific antigen binding molecules (peptides) of the invention and nucleic acid primer sequences used to prepare a library of the invention are shown in FIGS. 9 to 18.

In one embodiment of the invention, as represented by the sequences of the antigen specific antigen binding molecules of the invention shown in the figures, the framework regions may be derived from the clones designated as 2V and 5V, with sequences as shown in FIG. 11 and as SEQ ID No:s 9, 10, 11 and 12 (and described above with reference to SEQ ID No;s 1 to 8).

In one embodiment of this aspect of the invention, there is provided an antigen specific antigen binding molecule comprising an amino acid sequence represented by the formula (II)

A-X-B-Y-C (II)

wherein
A—is SEQ ID NO: 1 or SEQ ID NO: 4
X is a CDR1 region of 5, 6 or 7 amino acid residues
B—is SEQ ID NO: 2 or SEQ ID NO: 5
Y is a CDR3 region of 8, 9, 10, 11, 12, 13, 14, 15, 16, or 17 amino acid residues
C—is SEQ ID NO: 3 or SEQ ID NO: 6
or a sequence at least 50% homologous thereto,
in which

```
SEQ ID NO: 1 is
TRVDQTPRTATKETGESLTINCVLTDT,

TRVDQTPRTATKETGESLTINCVVTGA

SEQ ID NO: 2 is
TSWFRKNPGTTDWERMSIGGRYVESVNKGAKSFSLRIKDLTVA
DSATYYCKA
or

TSWFRKNPGTTDWERMSIGGRYVESVNKGAKSFSLRIKDLTVA
DSATYICRA

SEQ ID NO: 3 is
DGAGTVLTVN
```

-continued
```
SEQ ID NO: 4 is
ASVNQTPRTATKETGESLTINCVLTDT
or

ASVNQTPRTATKETGESLTINCVVTGA

SEQ ID NO: 5 is
TYWYRKNPGSSNQERISISGRYVESVNKRTMSFSLRIKDLTVA
DSATYYCKA
or

TYWYRKNPGSSNQERISISGRYVESVNKRTMSFSLRIKDLTVA
DSATYICRA

SEQ ID NO: 6 is
YGAGTVLTVN.
```

The amino acid sequences represented by A, X, B, Y and/or C may be derived from the same or different member of the Elasmobranchii subclass. The amino acid sequences represented by A, X, B, Y and/or C may also be derived from the same or different isotypes of VNAR sequences, e.g. type I, type II and/or type III (including type Ib, type IIb and type IIIb). Any generally suitable combination of source material is therefore possible.

In some embodiments of the invention, formula (II) A-X-B-Y-C may be composed of sequences in which elements A, B, and C are represented by (i) SEQ ID NO.s 1, 2, and 3; (ii) SEQ ID NO.s 1, 2, and 6; (iii) SEQ ID NO.s 1, 5, and 3; (iv) SEQ ID NO:s 1, 5 and 6; (v) SEQ ID NO.s 4, 5, and 6; (vi) SEQ ID NO:s 4, 5 and 3; (vii) SEQ ID NO:s 4, 2, and 6; (viii) SEQ ID NO.s 4, 2, and 3.

In the methods of the invention, RNA is isolated from a member of a species in the Elasmobranchii subclass which has not been immunized previously, a "naïve" subject. The Elasmobranchii subclass is a subclass of cartilaginous fish, including sharks, skates and rays. Generally suitable examples include sharks of the order Squaliformes, such as spiny dogfish (*Squalus acanthias*), and also the order Orectolobiformes, such as the nurse shark (*Ginglymostoma cirratum*).

RNA can be isolated from tissue samples, including whole blood, using standard molecular biological techniques as described herein.

Prior to building a library, a comprehensive cDNA sequence database can be prepared for the purposes of designing primers to amplify a repertoire representative of all the natural antigen specific antigen binding molecule (immunoglobulin isotope novel antigen receptor or IgNAR) transcripts in the tissue sample. One example of a library is a phage display library.

The database can be created by amplification of DNA sequences which encode antigen specific antigen binding molecules. Suitably, the process comprises a series of steps beginning with degenerate PCR to gain a partial sequence from which to design 3' RACE primers for use in "RACE" (Rapid Amplification of cDNA Ends). To isolate IgNAR encoding sequences degenerate PCR can be carried out using primers based on known nurse shark IgNAR sequences or other shark species. From these, the constant domains can be isolated and sequenced resulting in the design of 5'RACE primers to complete the full length IgNAR sequences from leader, through variable region to the constant domains.

Extracted RNA can be reverse transcribed to generate cDNA. cDNA synthesis from spiny dogfish tissue can be generated with constant domain 1 primers.

The native immunoglobulin isotope novel antigen receptor (IgNAR) is a homodimeric heavy-chain complex consists of a single-variable domain (VNAR) and five constant domains (CNAR). IgNAR sequences obtained by degenerate PCR techniques as described above can be analyzed and multiple primers designed for use in amplification of the 3' end of IgNAR transcripts (3'RACE). Total RNA can be isolated and 3' RACE performed. First strand cDNA can be synthesized from total RNA using a suitable primer. The first strand cDNA is used for PCR amplification. The PCR products can be cloned into a vector or TA cloned. The clones containing PCR products can then be sequenced.

The novel antigen receptor (NAR) encoding cDNAs using transmembrane specific primers can be isolated as follows. RNA can be extracted from spiny dogfish tissues as described above and reverse transcribed. First round PCRs can be carried out with the generated 3' RACE cDNA, a universal primer and a spiny dogfish IgNAR specific primer. The resultant PCR products can be cloned into a vector and sequenced.

NAR cDNA clones encoding 5' untranslated region, splice leader, variable domain and partial constant domains can be obtained as follows. Nucleotide sequences encoding the constant domains (isolated by 3'RACE as described above) for each species can be analyzed to identify conserved regions.

Primers may be designed in these regions of high identity and used for 5'RACE amplification of NAR encoding sequences as follows. Amplification of cDNA ends can be achieved using a 5' RACE system. Total RNA can be extracted from tissue and first strand cDNA synthesised using a gene specific primer and subsequently ligated to an oligo-dC tail. The dC-tailed cDNA can be used for PCR amplification in combination with a gene specific primer. Amplified products of the correct size can be purified and TA cloned or alternatively cloned into a vector. The clones containing PCR products can then be sequenced.

NAR cDNA clones encoding the splice leader region, variable domain, and partial constant domain 1 can be obtained by PCR amplification as follows. Sequences obtained by 5'RACE as described above can be analyzed to identify the splice leader sequence. The nucleotide sequences can be aligned and primers designed in regions of high nucleotide identity (designated forward primers). Similarly, sequences obtained by 3'RACE can be analyzed to identify regions of high nucleotide identity in the constant domain to design primers (designated reverse primers). PCR amplification to obtain NAR cDNA clones can be performed using these forward and reverse primers as follows.

RNA can be extracted from multiple spiny dogfish tissues as previously described. First strand cDNA can be synthesized from total RNA an oligo-dT primer. Forward and Reverse primers can be used to PCR amplify the NAR specific clones using from this cDNA. Amplified products of the correct size can be purified and TA cloned or alternatively cloned into a vector and sequenced.

Bioinformatic analyses can be performed to identify and characterize spiny dogfish IgNAR sequences. Identification of the open reading frame, and nucleotide sequence analysis of cDNA clones isolated as described, can enable the design of NAR-specific primers for each species to construct large libraries of NAR encoding clones. A nurse shark IgNAR protein sequence can serve as a template to define the IgNAR sequences from spiny dogfish. Sequentially, several seed spiny IgNAR sequences can be selected to generate a multiple sequence alignment. The open reading frame for each of the IgNAR cDNA sequences can be identified and translated to the amino acid sequence. The IgNAR amino acid sequences can then be aligned and compared to the known nurse shark IgNAR gene structure to identify the IgNAR domains (FW1, CDR1, FW2, HV2, FW3A, HV4, FW3B, CDR3 and FW4).

In one embodiment of the invention, clones 2V and 5V (sequences shown in FIG. 9) can be cloned into a display vector (for example a phagemid display vector) and used as library templates. Suitably, the selected templates show high levels of bacterial expression.

A comprehensive 'natural' spiny dogfish VNAR amino acid (AA) sequence database can be prepared using PCR amplified cDNA as described herein, which comprises full length unique cDNA VNAR clones from a range of different spiny dogfish animals and tissue types. The compiled translated VNAR domains can be examined in terms of amino acid (AA) content, relative positional conservation and frequency across the analysed population in addition to CDR3 length distribution. This analysis can therefore guide the synthetic library design.

Beginning at the CDR1 and CDR3 loops, it may be convenient to look at the content across these loops, the adjacent framework residues and the loop length range and distribution. Sequences within the database can be classified as unique clones according to length (n 100) pools. Overall CDR3 loop lengths ranging from 11 to 16 amino acids can be focused on as they corresponded to the average spiny dogfish CDR3 length of 13±2 amino acids.

According to the dual template design of the present invention, it is possible to modulate the FW3a positions-3, -2, & -1, immediately adjacent to the CDR 3 and thus represent either CKA or CRA motifs in the synthetic library. This approach may allow representation of up to 76% of the 'natural' amino acid (AA) sequence diversity as found in the database. The first three FW4 residues immediately after the CDR3 in the sequence database may comprise the DGA motif, and to a lesser extent YGA.

Within the CDR3 loop itself, the usage of specific joining or J-gene segments can introduce a bias for particular residues at C-terminal CDR3 end, especially the penultimate and ultimate residues.

PCR of respective template regions off plasmid-borne 2V and 5V sequences using specific mutagenic oligonucleotides can be performed PCR amplification. Each PCR product from three primary PCR product sets (fragments consisting FW1, CDR1-FW3, and CDR3-FW4, respectively) can be mixed as master mixes and subsequently joined by Splice-by-Overlap Extension (SOE) PCR.

SOE-PCR products can be digested with restriction endonuclease and ligated into similarly digested vector. Four template derived variant sub-libraries can be constructed by SOE-PCR and pools defined based on the origins of the CDR1-FW3 and CDR3-FW4 fragments used to construct them.

For all pools equal amounts of the FW1 fragments derived from both templates can be included with added oligonucleotide-directed synthetic diversity in both CDR1 and CDR3 loops. Host cells can then be transformed with ligated vector containing the appropriate inserts. In constructing the sub-libraries, suitably three sets of primary PCR products can be produced from each original template, where the templates can be divided into three distinct regions mostly comprising the framework 1 (FW1), CDR1 and CDR3. Defined CDR1 and CDR3 loop regions can be mutated using template-specific trinucleotide (TRM) oligomers. TRM oligonucleotides can be designed to incorporate any (AA) at a particular position at random with the exception of cysteine which was purposely omitted. In addition to the TRM oligos, additional template-specific CDR1-targeted oligos (for example, one, two or three) can be used for incorporating mutations.

The designed content can be decided upon using analysis of 'natural' spiny VNAR domain sequences and can be incorporated into the library using oligonucleotides with defined degenerate codons and direct homologue codons.

As discussed above, the present invention provides an improved synthetic library of VNARs (created from two or more naturally occurring VNAR sequences) and methods for the production thereof. From an extensive sequencing analyses of the VNAR repertoire of *Squalus acanthias*, two clones which show high levels of expression in prokaryotic systems were crystallised and used as the basis for the these libraries. The ELSS1 library is composed of two differing VNAR isotype (Type IIb and IIIb) frameworks from the same Elasmobranchii species, spiny dogfish (*Squalus acanthias*) which have been combined to create diversity across the frameworks (FW1, FW2, FW3a, FW3b and FW4) in addition to the diversity within the CDR1, HV2, HV4 and CDR3 regions as illustrated in FIG. 4. ELSS2 builds upon the creation of increased framework diversity by incorporating a third VNAR isotype (Type II) framework from a second species of Elasmobranchii, nurse shark (*Ginglymostoma cirratum*) as illustrated in FIG. 18.

A novel approach using overlapping PCR to create diversity within the framework regions was successfully achieved resulting in 2V/5V or 2V/5V/E9 hybrid sequences. Additional diversity was incorporated in both the CDR3 and CDR1 regions using defined TRM oligos to ensure the addition of desired amino acid types were incorporated or NNK oligos. In addition, the CDR1 diversity in ELSS1 was designed to represent that seen in the natural repertoire of *Squalus acanthias* and the lengths of the CDR3 designed were also based on the naturally occurring CDR3 sequences identified within the sequence database derived from these animals.

Using this design, synthetic shark variable NAR (VNAR) domain libraries (ELSS1 and ELSS2) were constructed incorporating a maximal level of functional diversity and improvements on previous synthetic/semi-synthetic library reports. Previous reported attempts to construct shark VNAR libraries typically utilised isolated natural diversity of VNAR framework (FW) regions 1 to 3, as derived from immune tissues. Such frameworks would then be coupled to synthetic diversity targeted to the CDR3 region, in effect creating semi-synthetic libraries.

In two additional distinct studies by Nuttall and Liu and their respective co-workers, the VNAR non-canonical cysteine residues were specifically introduced into the diversified CDR regions in an attempt to mimic previously observed Type II VNAR structures (Diaz, M., et al., Immunogenetics, 2002. 54(7): p. 501-12) characterised by CDR1-CDR3 disulphide linkage. A similar approach to the non-canonical cysteines was also central to the Shao library design, where they set out to maintain the original template non-canonical cysteine residues found in the FW2 and FW4 regions of the Type I VNAR structure. This was carried out through the biased introduction of complimentary cysteine residues in the synthetic CDR3.

Each of these design approaches are considered likely to lead to a high level of unpaired cysteine residues in the final library and thus compromise functional content and diversity within the final synthetic repertoire. Therefore, in contrast to previous designs, the present invention avoids the additional structural complexity posed by non-canonical cysteine residues. The repertoires of the spiny dogfish, specifically those that contained none of the non-canonical cysteine residues were mimicked in the method of the invention. One noted exception to this type of approach however was work described by Shao and co-workers (Shao, C. Y., C. J. Secombes, and A. J. Porter, Mol Immunol, 2007. 44(4): p. 656-65). This report described the fully synthetic and derived from a single template domain framework and included completely artificial diversity introduced into the CDR3 of the Type I nurse shark VNAR domain, clone 5A7. This clone was historically isolated from an immune-library and is specific for hen egg white lysozyme (HEL). Shao et al reported the identification of a solitary leptin binding VNAR with an intrinsically high degree of cross-reactivity to the original template binding partner, HEL.

Further distinguishing library design features of the present invention include:

Library Size

The final ELSS1 library size (>9×10$^{10}$), which is two orders of magnitude larger than any shark library (naïve, immune or synthetic) previously reported.

Diversity

The synthetic VNAR library of the invention is produced using a trinucleotide mix that gives equal representation to all amino acids at each randomized position, without adding cysteine. The synthetic library of the invention therefore provides trinucleotide diversity.

Tailored diversity in the synthetic library of the invention has been introduced, based on specific sequence database, into the VNAR CDR1, through the use of trinucleotide and 'homologue-scanning' oligonucleotides, targeted at this region. From detailed examination of the CDR1, it was noted that 'natural' diversity is relatively conserved at several key positions, especially the 2nd (57% Y or 33% C) and 4th (83% L or 13% W) positions (positions 29 and 31 in full VNAR sequence using Kabat numbering scheme).

Two contrasting mutagenesis approaches for the CDR1 were adopted. The full CDR1 randomization was carried out using custom trinucleotide (TRM) mixed codon oligonucleotides (Genelink), as described for the CDR3 loop. In contrast, the tailored (AA) content approach applied involved a refined modulation of defined CDR1 positions as guided by the 'natural' sequence analysis. Specifically, we aimed to incorporate as much as possible the defined 'natural' variability at each CDR1 position using specific degenerate and 'homolog residue' scan codons (Bostrom, J. and G. Fuh, Methods Mol Biol, 2009. 562: p. 17-35; Bostrom, J., et al., Methods Mol Biol, 2009. 525: p. 353-76, xiii).

Cysteine inclusion was avoided in ELSS1 for reasons previously discussed, irrespective of the fact that it was found at the 2nd position in 33% of the 'natural' database clones. Oligos were designed to introduce maintain the largest possible 'natural' contextual diversity as found in our sequence database with additional relevant tailoring of (AA) content. In the both the random and tailored strategies above, modulation of position 4 was included by maintaining, or not, a tryptophan residue (W). It is suspected that at this position either W or L side chains, at least as observed in the context of the 2V & 5V scaffolds, form hydrophobic interactions within the central domain core, in particular with framework residue F66.

The chosen CDR3 length variations which were included, a total of 8 randomized CDR3 lengths were added to cover the highest frequency length diversity range as observed in natural spiny dogfish NARs.

Library Design

The library design approach maintained CDR flanking residues that were suspected to be structurally important. Such motifs are analogous to those found in a host of similar Immunoglobulin (Ig) variable domains at the C-terminal end of the FW3b and CDR3. Observations to support this rationale were facilitated using the crystal structure models and additional bioinformatics analysis of spiny dogfish VNAR sequences. Having the crystal structures resolved for the two original template VNAR domains and their respective molecular models as shown (FIG. 3), the conserved N- and C-terminal CDR flanking residues observed in sequence database were mapped. Due to their proximity to CDR3 and their importance in other similar variable Ig domains, particular emphasis was placed on the last three FW3b residues and the first two FW4 residues. Residues in this region were generally found to be the more conserved.

Framework Fusion Scaffold Design

First synthetic VNAR library build using dual scaffold design based on sequences 2V and 5V (type IIb and IIIb) and the first library build using more than two VNAR isotype frameworks (2V, 5V in addition to the type II VNAR, E9) originating from two distinct Elasmobranchii species. Using two templates facilitated the introduction of additional structural diversity by shuffling key distinct Framework (FW) and Hypervariable (HV) loop regions. Thus in effect the resulting derived clones consisted of wild type and novel spliced hybrid scaffolds containing the supplementary CDR1 and CDR3 loop directed diversity. The template derived HV2 and HV4 loops within different contexts in ELSS1 was achieved through alternatively splicing PCR fragments encoding template derived HV2 and HV4 pairings with respectively derived FW1, and CDR1 and CDR3 fragments. In effect, this allowed us to incorporate six novel additional hybrid scaffolds consisting of hybrid template-derived sequence permutation.

Database analysis showed that the exact HV2 and HV4 amino acid (AA) sequences found on 2V template were observed in the largest comparative grouping of clones in the spiny VNAR database, corresponding to 33% (454/1364) and 38% (518/1364) of the population, respectively. The exact HV2 and HV4 sequences found on 5V were not found as frequently, with the exact HV4 observed in approximately 8% (111/1364) and HV2<1% (10/1364) of the database population. However, single amino variants of both HV loops were found in higher proportions of clones in the database. This implies that the 2V and 5V template HV regions are most probably germline encoded, or close to germline in sequence. In effect by shuffling this sequence space in the library design we simultaneously maintained commonly found 'natural' repertoire (i.e. derived from sequence 2V) and introduced additional synthetic variation through the generation of hybrid diversity. Further sequence diversity was incorporated by shuffling both template-derived FW1 regions.

The first 3-4 residues of the FW1 amino terminus can be critical in modulating binding characteristics for VNAR. N-terminal FW1 residues can have effects on binding characteristics of VNAR domains to their cognate antigens and when rationalised using available structural models it was not surprising, as invariably the early N-terminal residues map very closely to CDR1 and CDR3 loops, where paratope and target contacts are mediated. Here the advantage of the dual template design allowed a shuffle between distinct template-derived FW1 encoded regions. Thus overall the design approach employed could potentially yield eight distinct scaffolds onto which additional CDR1 and CDR3 loop diversity could be added.

Definitions

An antigen specific antigen binding molecule of the invention comprises amino acid sequence derived from a synthetic library of VNAR molecules prepared according to a method of the invention. The terms VNAR, IgNAR and NAR may be used interchangeably also.

Amino acids are represented herein as either a single letter code or as the three letter code or both.

The term "affinity purification" means the purification of a molecule based on a specific attraction or binding of the molecule to a chemical or binding partner to form a combination or complex which allows the molecule to be separated from impurities while remaining bound or attracted to the partner moiety.

The term "Complementarity Determining Regions" or CDRs (i.e., CDR1 and CDR3) refers to the amino acid residues of a VNAR domain the presence of which are necessary for antigen binding. Each VNAR typically has three CDR regions identified as CDR1 and CDR3. Each complementarity determining region may comprise amino acid residues from a "complementarity determining region" and/or those residues from a "hypervariable loop" (HV). In some instances, a complementarity determining region can include amino acids from both a CDR region and a hypervariable loop. According to the generally accepted nomenclature for VNAR molecules, a CDR2 region is not present.

"Framework regions" (FW) are those VNAR residues other than the CDR residues. Each VNAR typically has five framework regions identified as FW1, FW2, FW3a, FW3b and FW4.

A "codon set" refers to a set of different nucleotide triplet sequences used to encode desired variant amino acids. A set of oligonucleotides can be synthesized, for example, by solid phase synthesis, including sequences that represent all possible combinations of nucleotide triplets provided by the codon set and that will encode the desired group of amino acids. A standard form of codon designation is that of the IUB code, which is known in the art and described herein. A codon set is typically represented by 3 capital letters in italics, e.g. NNK, NNS, XYZ, DVK etc. A "non-random codon set" therefore refers to a codon set that encodes select amino acids that fulfill partially, preferably completely, the criteria for amino acid selection as described herein. Synthesis of oligonucleotides with selected nucleotide "degeneracy" at certain positions is well known in that art, for example the TRIM approach (Knappek et al.; J. Mol. Biol. (1999), 296, 57-86); Garrard & Henner, Gene (1993), 128, 103). Such sets of oligonucleotides having certain codon sets can be synthesized using commercial nucleic acid synthesizers (available from, for example, Applied Biosystems, Foster City, Calif.), or can be obtained commercially (for example, from Life Technologies, Rockville, Md.). A set of oligonucleotides synthesized having a particular codon set will typically include a plurality of oligonucleotides with different sequences, the differences established by the codon set within the overall sequence. Oligonucleotides used according to the present invention have sequences that allow for hybridization to a VNAR nucleic acid template and also may where convenient include restriction enzyme sites.

"Cell", "cell line", and "cell culture" are used interchangeably (unless the context indicates otherwise) and such designations include all progeny of a cell or cell line. Thus, for example, terms like "transformants" and "transformed cells" include the primary subject cell and cultures derived therefrom without regard for the number of transfers. It is also understood that all progeny may not be precisely identical in DNA content, due to deliberate or inadvertent mutations. Mutant progeny that have the same function or biological activity as screened for in the originally transformed cell are included.

"Control sequences" when referring to expression means DNA sequences necessary for the expression of an operably linked coding sequence in a particular host organism. The control sequences that are suitable for prokaryotes, for example, include a promoter, optionally an operator sequence, a ribosome binding site, etc. Eukaryotic cells use control sequences such as promoters, polyadenylation signals, and enhancers.

The term "coat protein" means a protein, at least a portion of which is present on the surface of the virus particle. From a functional perspective, a coat protein is any protein which associates with a virus particle during the viral assembly process in a host cell, and remains associated with the assembled virus until it infects another host cell.

The "detection limit" for a chemical entity in a particular assay is the minimum concentration of that entity which can be detected above the background level for that assay. For example, in the phage ELISA, the "detection limit" for a particular phage displaying a particular antigen binding fragment is the phage concentration at which the particular phage produces an ELISA signal above that produced by a control phage not displaying the antigen binding fragment.

A "fusion protein" and a "fusion polypeptide" refer to a polypeptide having two portions covalently linked together, where each of the portions is a polypeptide having a different property. The property may be a biological property, such as activity in vitro or in vivo. The property may also be a simple chemical or physical property, such as binding to a target antigen, catalysis of a reaction, etc. The two portions may be linked directly by a single peptide bond or through a peptide linker containing one or more amino acid residues. Generally, the two portions and the linker will be in reading frame with each other. Preferably, the two portions of the polypeptide are obtained from heterologous or different polypeptides.

The term "fusion protein" in this text means, in general terms, one or more proteins joined together by chemical means, including hydrogen bonds or salt bridges, or by peptide bonds through protein synthesis or both.

"Heterologous DNA" is any DNA that is introduced into a host cell. The DNA may be derived from a variety of sources including genomic DNA, cDNA, synthetic DNA and fusions or combinations of these. The DNA may include DNA from the same cell or cell type as the host or recipient cell or DNA from a different cell type, for example, from an allogenic or xenogenic source. The DNA may, optionally, include marker or selection genes, for example, antibiotic resistance genes, temperature resistance genes, etc.

A "highly diverse position" refers to a position of an amino acid located in the variable regions of the light and heavy chains that have a number of different amino acid represented at the position when the amino acid sequences of known and/or naturally occurring antibodies or antigen binding fragments are compared. The highly diverse positions are typically in the CDR regions.

"Identity" describes the relationship between two or more polypeptide sequences or two or more polynucleotide sequences, as determined by comparing the sequences. Identity also means the degree of sequence relatedness (homology) between polypeptide or polynucleotide sequences, as the case may be, as determined by the match between strings of such sequences. While there exist a number of methods to measure identity between two polypeptide or two polynucleotide sequences, methods commonly employed to determine identity are codified in computer programs. Preferred computer programs to determine identity between two sequences include, but are not limited to, GCG program package (Devereux, et al., Nucleic acids Research, 12, 387 (1984), BLASTP, BLASTN, and FASTA (Atschul et al., J. Molec. Biol. (1990) 215, 403).

Preferably, the amino acid sequence of the protein has at least 50% identity, using the default parameters of the BLAST computer program (Atschul et al., J. Mol. Biol. (1990) 215, 403-410) provided by HGMP (Human Genome Mapping Project), at the amino acid level, to the amino acid sequences disclosed herein.

More preferably, the protein sequence may have at least 55%, 60%, 65%, 66%, 67%, 68%, 69%, 70%, 75%, 80%, 85%, 90% and still more preferably 95% (still more preferably at least 96%, 97%, 98% or 99%) identity, at the nucleic acid or amino acid level, to the amino acid sequences as shown herein.

The protein may also comprise a sequence which has at least 50%, 55%, 60%, 65%, 66%, 67%, 68%, 69%, 70%, 75%, 80%, 85%, 90%, 95%, 96%, 97%, 98%, or 99% identity with a sequence disclosed herein, using the default parameters of the BLAST computer program provided by HGMP, thereto A "library" refers to a plurality of VNARs or VNAR fragment sequences (for example, polypeptides of the invention), or the nucleic acids that encode these sequences, the sequences being different in the combination of variant amino acids that are introduced into these sequences according to the methods of the invention.

"Ligation" is the process of forming phosphodiester bonds between two nucleic acid fragments. For ligation of the two fragments, the ends of the fragments must be compatible with each other. In some cases, the ends will be directly compatible after endonuclease digestion. However, it may be necessary first to convert the staggered ends commonly produced after endonuclease digestion to blunt ends to make them compatible for ligation. For blunting the ends, the DNA is treated in a suitable buffer for at least 15 minutes at 15° C. with about 10 units of the Klenow fragment of DNA polymerase I or T4 DNA polymerase in the presence of the four deoxyribonucleotide triphosphates. The DNA is then purified by phenol-chloroform extraction and ethanol precipitation or by silica purification. The DNA fragments that are to be ligated together are put in solution in about equimolar amounts. The solution will also contain ATP, ligase buffer, and a ligase such as T4 DNA ligase at about 10 units per 0.5 µg of DNA. If the DNA is to be ligated into a vector, the vector is first linearized by digestion with the appropriate restriction endonuclease(s). The linearized fragment is then treated with bacterial alkaline phosphatase or calf intestinal phosphatase to prevent self-ligation during the ligation step.

A "mutation" is a deletion, insertion, or substitution of a nucleotide(s) relative to a reference nucleotide sequence, such as a wild type sequence.

"Natural" or "naturally occurring" VNARs, refers to VNARs identified from a non-synthetic source, for example, from a tissue source obtained ex vivo, or from the serum of an animal of the Elasmobranchii subclass. These VNARs can include VNARs generated in any type of immune response, either natural or otherwise induced. Natural VNARs include the amino acid sequences, and the nucleotide sequences that constitute or encode these antibodies. As used herein, natural VNARs are different than "synthetic VNARs", synthetic VNARs referring to VNAR sequences that have been changed from a source or template sequence, for example, by the replacement, deletion, or addition, of an amino acid, or more than one amino acid, at a certain position with a different amino acid, the different amino acid providing an antibody sequence different from the source antibody sequence.

The term "nucleic acid construct" generally refers to any length of nucleic acid which may be DNA, cDNA or RNA such as mRNA obtained by cloning or produced by chemical synthesis. The DNA may be single or double stranded. Single stranded DNA may be the coding sense strand, or it may be the non-coding or anti-sense strand. For therapeutic use, the nucleic acid construct is preferably in a form capable of being expressed in the subject to be treated.

"Operably linked" when referring to nucleic acids means that the nucleic acids are placed in a functional relationship with another nucleic acid sequence. For example, DNA for a presequence or secretory leader is operably linked to DNA for a polypeptide if it is expressed as a preprotein that participates in the secretion of the polypeptide; a promotor or enhancer is operably linked to a coding sequence if it affects the transcription of the sequence; or a ribosome binding site is operably linked to a coding sequence if it is positioned so as to facilitate translation. Generally, "operably linked" means that the DNA sequences being linked are contiguous and, in the case of a secretory leader, contingent and in reading frame. However, enhancers do not have to be contiguous. Linking is accomplished by ligation at convenient restriction sites. If such sites do not exist, the synthetic oligonucleotide adapters or linkers are used in accord with conventional practice.

"Phage display" is a technique by which variant polypeptides are displayed as fusion proteins to at least a portion of coat protein on the surface of phage, e.g., filamentous phage, particles. Phage display technology allows for the preparation of large libraries of randomized protein variants which can be rapidly and efficiently sorted for those sequences that bind to a target antigen with high affinity. The display of peptide and protein libraries on phage can be used for screening millions of polypeptides for ones with specific binding properties. Polyvalent phage display methods have been used for displaying small random peptides and small proteins through fusions to the genes encoding coat proteins pIII, pVIII, pVI, pVII or pIX of filamentous phage.

A "phagemid" is a plasmid vector having a bacterial origin of replication, e.g., ColEI, and a copy of an intergenic region of a bacteriophage. The phagemid may be used on any known bacteriophage, including filamentous bacteriophage and lambdoid bacteriophage. The plasmid will also generally contain a selectable marker for antibiotic resistance. Segments of DNA cloned into these vectors can be propagated as plasmids. When cells harboring these vectors are provided with all genes necessary for the production of phage particles, the mode of replication of the plasmid changes to rolling circle replication to generate copies of one strand of the plasmid DNA and package phage particles. The phagemid may form infectious or non-infectious phage particles. This term includes phagemids which contain a phage coat protein gene or fragment thereof linked to a heterologous polypeptide gene as a gene fusion such that the heterologous polypeptide is displayed on the surface of the phage particle. An example of a phagemid display vector is pWRIL-1.

The term "phage vector" means a double stranded replicative form of a bacteriophage containing a heterologous gene and capable of replication. The phage vector has a phage origin of replication allowing phage replication and phage particle formation. The phage is preferably a filamentous bacteriophage, such as an M13, fl, fd, Pf3 phage or a derivative thereof, or a lambdoid phage, such as lambda, 21, phi80, phi81, or a derivative thereof.

The term "protein" means, in general terms, a plurality of amino acid residues joined together by peptide bonds. It is used interchangeably and means the same as peptide, oligopeptide, oligomer or polypeptide, and includes glycoproteins and derivatives thereof. The term "protein" is also intended to include fragments, analogues, variants and derivatives of a protein wherein the fragment, analogue, variant or derivative retains essentially the same biological activity or function as a reference protein. Examples of protein analogues and derivatives include peptide nucleic acids, and DARPins (Designed Ankyrin Repeat Proteins).

A fragment, analogue, variant or derivative of the protein may be at least 25 preferably 30 or 40, or up to 50 or 100, or 60 to 120 amino acids long, depending on the length of the original protein sequence from which it is derived. A length of 90 to 120, 100 to 110 amino acids may be convenient in some instances.

The fragment, derivative, variant or analogue of the protein may be (i) one in which one or more of the amino acid residues are substituted with a conserved or non-conserved amino acid residue (preferably, a conserved amino acid residue) and such substituted amino acid residue may or may not be one encoded by the genetic code, or (ii) one in which one or more of the amino acid residues includes a substituent group, or (iii) one in which the additional amino acids are fused to the mature polypeptide, such as a leader or auxiliary sequence which is employed for purification of the polypeptide. Such fragments, derivatives, variants and analogues are deemed to be within the scope of those skilled in the art from the teachings herein.

"Oligonucleotides" are short-length, single- or double-stranded polydeoxynucleotides that are chemically synthesized by known methods (such as phosphotriester, phosphite, or phosphoramidite chemistry, using solid-phase techniques). Further methods include the polymerase chain reaction (PCR) used if the entire nucleic acid sequence of the gene is known, or the sequence of the nucleic acid complementary to the coding strand is available. Alternatively, if the target amino acid sequence is known, one may infer potential nucleic acid sequences using known and preferred coding residues for each amino acid residue. The oligonucleotides can be purified on polyacrylamide gels or molecular sizing columns or by precipitation. DNA is "purified" when the DNA is separated from non-nucleic acid impurities (which may be polar, non-polar, ionic, etc.).

A "source" or "template" VNAR", as used herein, refers to a VNAR or VNAR antigen binding fragment whose antigen binding sequence serves as the template sequence upon which diversification according to the criteria described herein is performed. An antigen binding sequence generally includes within a VNAR preferably at least one CDR, preferably including framework regions.

A "transcription regulatory element" will contain one or more of the following components: an enhancer element, a promoter, an operator sequence, a repressor gene, and a transcription termination sequence.

"Transformation" means a process whereby a cell takes up DNA and becomes a "transformant". The DNA uptake may be permanent or transient. A "transformant" is a cell which has taken up and maintained DNA as evidenced by the expression of a phenotype associated with the DNA (e.g., antibiotic resistance conferred by a protein encoded by the DNA).

A "variant" or "mutant" of a starting or reference polypeptide (for example, a source VNAR or a CDR thereof), such as a fusion protein (polypeptide) or a heterologous polypeptide (heterologous to a phage), is a polypeptide that (1) has an amino acid sequence different from that of the starting or reference polypeptide and (2) was derived from the starting or reference polypeptide through either natural or artificial mutagenesis. Such variants include, for example, deletions from, and/or insertions into and/or substitutions of, residues within the amino acid sequence of the polypeptide of interest. For example, a fusion polypeptide of the invention generated using an oligonucleotide comprising a nonrandom codon set that encodes a sequence with a variant amino acid (with respect to the amino acid found at the corresponding position in a source VNAR or antigen binding fragment) would be a variant polypeptide with respect to a source VNAR or antigen binding fragment. Thus, a variant CDR refers to a CDR comprising a variant sequence with respect to a starting or reference polypeptide sequence (such as that of a source VNAR or antigen binding fragment). A variant amino acid, in this context, refers to an amino acid different from the amino acid at the corresponding position in a starting or reference polypeptide sequence (such as that of a source VNAR or antigen binding fragment). Any combination of deletion, insertion, and substitution may be made to arrive at the final variant or mutant construct, provided that the final construct possesses the desired functional characteristics. The amino acid changes also may alter post-translational processes of the polypeptide, such as changing the number or position of glycosylation sites.

A "wild-type" or "reference" sequence or the sequence of a "wild-type" or "reference" protein/polypeptide, such as a coat protein, or a CDR of a source VNAR, may be the reference sequence from which variant polypeptides are derived through the introduction of mutations. In general, the "wild-type" sequence for a given protein is the sequence that is most common in nature. Similarly, a "wild-type" gene sequence is the sequence for that gene which is most commonly found in nature. Mutations may be introduced into a "wild-type" gene (and thus the protein it encodes) either through natural processes or through man induced means. The products of such processes are "variant" or "mutant" forms of the original "wild-type" protein or gene.

Library Diversity

Amino acid positions in the CDR regions CDR1 and CDR3 can be each mutated using a non-random codon set encoding the commonly occurring amino acids at each position. In some embodiments, when a position in a CDR region is to be mutated, a codon set is selected that encodes preferably at least about 50%, preferably at least about 60%, preferably at least about 70%, preferably at least about 80%, preferably at least about 90%, preferably all the amino acids for that position. In some embodiments, when a position in a CDR region is to be mutated, a codon set is selected that encodes preferably from about 50% to about 100%, preferably from about 60% to about 95%, preferably from at least about 70% to about 90%, preferably from about 75% to about 90% of all the amino acids for that position.

The diversity of the library of the VNARs is designed to maximize diversity while minimizing structural perturbations of the VNAR to provide for increased ability to isolate high affinity antigen specific antigen binding molecules and to provide for such molecules that can be produced in high yield in cell culture. The number of positions mutated in the VNAR variable domain is minimized and the variant amino acids at each position are designed to include the commonly occurring amino acids at each position with the exception of cysteine, while suitably (where possible) excluding uncommonly occurring amino acids and stop codons.

The diversity in the library is designed by mutating those positions in at least one CDR using nonrandom codon sets. The nonrandom codon set preferably encodes at least a subset of the commonly occurring amino acids at those positions while minimizing non-target sequences such as cysteine and stop codons.

The nonrandom codon set for each position preferably encodes at least two amino acids and does not encode cysteine. Non-target amino acids at each position are minimized and cysteines and stop codons are generally and preferably excluded because they can adversely affect the structure.

As discussed above, the variant amino acids are encoded by nonrandom codon sets. A codon set is a set of different nucleotide triplet sequences which can be used to form a set of oligonucleotides used to encode the desired group of amino acids. A set of oligonucleotides can be synthesized, for example, by solid phase synthesis, containing sequences that represent all possible combinations of nucleotide triplets provided by the codon set and that will encode the desired group of amino acids. Synthesis of oligonucleotides with selected nucleotide "degeneracy" at certain positions is a standard procedure.

Such sets of nucleotides having certain codon sets can be synthesized using commercial nucleic acid synthesizers (available from, for example, Applied Biosystems, Foster City, Calif.), or can be obtained commercially (for example, from Gene Link Inc, Hawthorn, N.Y., or Life Technologies, Rockville, Md.). Therefore, a set of oligonucleotides synthesized having a particular codon set will typically include a plurality of oligonucleotides with different sequences, the differences established by the codon set within the overall sequence. Oligonucleotides, as used according to the invention, have sequences that allow for hybridization to a variable domain nucleic acid template and also can include restriction enzyme sites for cloning purposes.

Illustrative nonrandom codon sets encoding a group of amino acids comprising preferably at least about 50%, preferably at least about 60%, preferably at least about 70%, preferably at least about 80%, preferably at least about 90%, preferably all of the target amino acids for each position are also shown in FIG. 10(a).

In one embodiment, a polypeptide having a variant CDR1 and CDR3, or mixtures thereof is formed, wherein at least one variant CDR comprises a variant amino acid in at least one amino acid position, wherein the variant amino acid is encoded by a nonrandom codon set, and wherein at least 70% of the amino acids encoded by the nonrandom codon set are target amino acids for that position in known variable domain sequences. The variant amino acids at these positions are preferably encoded by codon sets as exemplified in FIG. 10(a).

An example of oligonucleotide derived diversity in relation to CDR1 is shown in FIG. 10(b) also.

Methods of substituting an amino acid of choice into a template nucleic acid are well established in the art, some of which are described herein. For example, libraries can be created by targeting amino acid positions in at least one CDR region for amino acid substitution with variant amino acids using the Kunkel method (Kunkel et al., Methods Enzymol. (1987), 154, 367-382).

A codon set is a set of different nucleotide triplet sequences used to encode desired variant amino acids. Codon sets can be represented using symbols to designate particular nucleotides or equimolar mixtures of nucleotides as shown in below according to the IUB code. Typically, a codon set is represented by three capital letters e.g. RRK, GST, TKG, TWC, KCC, KCT, and TRM in FIG. 10(a).

IUB Codes
- G Guanine
- A Adenine
- T Thymine
- C Cytosine
- R (A or G)
- Y (C or T)
- M (A or C)
- K (G or T)
- S (C or G)
- W (A or T)
- H (A or C or T)
- B (C or G or T)
- V (A or C or G)
- D (A or G or T) H
- N (A or C or G or T)

Oligonucleotide or primer sets can be synthesized using standard methods. A set of oligonucleotides can be synthesized, for example, by solid phase synthesis, containing sequences that represent all possible combinations of nucleotide triplets provided by the codon set and that will encode the desired group of amino acids.

Synthesis of oligonucleotides with selected nucleotide "degeneracy" at certain positions is well known in that art. Such sets of nucleotides having certain codon sets can be synthesized using commercial nucleic acid synthesizers (available from, for example, Applied Biosystems, Foster City, Calif.), or can be obtained commercially (for example, from Gene Link Inc, Hawthorn N.Y., or Life Technologies, Rockville, Md.). Therefore, a set of oligonucleotides synthesized having a particular codon set will typically include a plurality of oligonucleotides with different sequences, the differences established by the codon set within the overall sequence. Oligonucleotides, as used according to the invention, have sequences that allow for hybridization to a variable domain nucleic acid template and also can include restriction enzyme sites for cloning purposes.

In one method, nucleic acid sequences encoding variant amino acids can be created by oligonucleotide-mediated mutagenesis of a nucleic acid sequence encoding a source or template polypeptide such as the VNAR sequence 2V or 5V disclosed herein. This technique is well known in the art as described by Zoller et al. Nucleic Acids Res. (1987), 10, 6487-6504 (1987). Briefly, nucleic acid sequences encoding variant amino acids are created by hybridizing an oligonucleotide set encoding the desired codon sets to a DNA template, where the template is the single-stranded form of the plasmid containing a variable region nucleic acid template sequence. After hybridization, DNA polymerase is used to synthesize an entire second complementary strand of the template that will thus incorporate the oligonucleotide primer, and will contain the codon sets as provided by the oligonucleotide set.

Nucleic acids encoding other source or template molecules are known or can be readily determined. Generally, oligonucleotides of at least 25 nucleotides in length are used. An optimal oligonucleotide will have 12 to 15 nucleotides that are completely complementary to the template on either side of the nucleotide(s) coding for the mutation(s). This ensures that the oligonucleotide will hybridize properly to the single-stranded DNA template molecule. The oligonucleotides are readily synthesized using techniques known in the art such as that described by Crea et al., Proc. Nat'l. Acad. Sci. USA, (1987) 75: 5765).

The DNA template can be generated by those vectors that are either derived from bacteriophage M13 vectors (the commercially available M13mp18 and M13mp19 vectors are suitable), or those vectors that contain a single-stranded phage origin of replication as described by Viera et al., Methods Enzymol., (1987) 153, 3). Thus, the DNA that is to be mutated can be inserted into one of these vectors in order to generate single-stranded template.

To alter the native DNA sequence, the oligonucleotide is hybridized to the single stranded template under suitable hybridization conditions. A DNA polymerizing enzyme, usually T7 DNA polymerase or the Klenow fragment of DNA polymerase I, is then added to synthesize the complementary strand of the template using the oligonucleotide as a primer for synthesis. A heteroduplex molecule is thus formed such that one strand of DNA encodes the mutated form of coding sequence 1, and the other strand (the original template) encodes the native, unaltered sequence of coding sequence 1. This heteroduplex molecule is then transformed into a suitable host cell, usually a prokaryote such as E. coli JM101. After growing the cells, they are plated onto agarose plates and screened using the oligonucleotide primer radio-labelled with a $^{32}$-Phosphate to identify the bacterial colonies that contain the mutated DNA.

The method described immediately above may be modified such that a homoduplex molecule is created wherein both strands of the plasmid contain the mutation(s). The modifications are as follows: The single stranded oligonucleotide is annealed to the single-stranded template as described above. A mixture of three deoxyribonucleotides, deoxyriboadenosine (dATP), deoxyriboguanosine (dGTP), and deoxyribothymidine (dTT), is combined with a modified thiodeoxyribocytosine called dCTP-(aS) (which can be obtained from Amersham). This mixture is added to the template-oligonucleotide complex. Upon addition of DNA polymerase to this mixture, a strand of DNA identical to the template except for the mutated bases is generated. In addition, this new strand of DNA will contain dCTP-(aS) instead of dCTP, which serves to protect it from restriction endonuclease digestion. After the template strand of the double-stranded heteroduplex is nicked with an appropriate restriction enzyme, the template strand can be digested with ExoIII nuclease or another appropriate nuclease past the region that contains the site (s) to be mutagenized. The reaction is then stopped to leave a molecule that is only partially single-stranded. A complete double-stranded DNA homoduplex is then formed using DNA polymerase in the presence of all four deoxyribonucleotide triphosphates, ATP, and DNA ligase. This homoduplex molecule can then be transformed into a suitable host cell.

As indicated previously the sequence of the oligonucleotide set is of sufficient length to hybridize to the template nucleic acid and may also, but does not necessarily, contain restriction sites. The DNA template can be generated by those vectors that are either derived from bacteriophage M13 vectors or vectors that contain a single-stranded phage origin of replication as described by Viera et al. (Meth. Enzymol. (1987), 153, 3). Thus, the DNA that is to be mutated must be inserted into one of these vectors in order to generate a single-stranded template.

Oligonucleotide sets can be used in a polymerase chain reaction using a nucleic acid template sequence as the template to create nucleic acid cassettes. The nucleic acid template sequence can be any portion of a VNAR molecule (i.e., nucleic acid sequences encoding amino acids targeted for substitution). The nucleic acid template sequence is a portion of a double stranded DNA molecule having a first nucleic acid strand and complementary second nucleic acid strand. The nucleic acid template sequence contains at least a portion of a VNAR domain and has at least one CDR. In some cases, the nucleic acid template sequence contains more than one CDR. An upstream portion and a downstream portion of the nucleic acid template sequence can be targeted for hybridization with members of an upstream oligonucleotide set and a downstream oligonucleotide set.

A first oligonucleotide of the upstream primer set can hybridize to the first nucleic acid strand and a second oligonucleotide of the downstream primer set can hybridize to the second nucleic acid strand. The oligonucleotide primers can include one or more codon sets and be designed to hybridize to a portion of the nucleic acid template sequence. Use of these oligonucleotides can introduce two or more codon sets into the PCR product (i.e., the nucleic acid cassette) following PCR. The oligonucleotide primer that hybridizes to regions of the nucleic acid sequence encoding the VNAR domain includes portions that encode CDR residues that are targeted for amino acid substitution.

The upstream and downstream oligonucleotide sets can also be synthesized to include restriction sites within the oligonucleotide sequence. These restriction sites can facilitate the insertion of the nucleic acid cassettes (i.e., PCR reaction products) into an expression vector having additional VNAR sequences.

Protein Expression

Nucleic acid sequences encoding antigen specific antigen binding molecules of the invention may be present in a nucleic acid construct. Such nucleic acid constructs may be in the form of a vector, for example, an expression vector, and may include, among others, chromosomal, episomal and virus-derived vectors, for example, vectors derived from bacterial plasmids, from bacteriophage, from transposons, from yeast episomes, from insertion elements, from yeast chromosomal elements, from viruses such as baculo-viruses, papova-viruses, such as SV40, vaccinia viruses, adenoviruses, fowl pox viruses, pseudorabies viruses and retroviruses, and vectors derived from combinations thereof, such as those derived from plasmid and bacteriophage genetic elements, such as cosmids and phagemids. Generally, any vector suitable to maintain, propagate or express nucleic acid to express a polypeptide in a host, may be used for expression in this regard.

The nucleic acid construct may suitably include a promoter or other regulatory sequence which controls expression of the nucleic acid. Promoters and other regulatory sequences which control expression of a nucleic acid have been identified and are known in the art. The person skilled in the art will note that it may not be necessary to utilise the whole promoter or other regulatory sequence. Only the minimum essential regulatory element may be required and, in fact, such elements can be used to construct chimeric sequences or other promoters. The essential requirement is, of course, to retain the tissue and/or temporal specificity. The promoter may be any suitable known promoter, for example, the human cytomegalovirus (CMV) promoter, the CMV immediate early promoter, the HSV thymidine kinase, the early and late SV40 promoters or the promoters of retroviral LTRs, such as those of the Rous Sarcoma virus (RSV) and metallothionine promoters such as the mouse metallothionine-I promoter. The promoter may comprise the minimum comprised for promoter activity (such as a TATA element, optionally without enhancer element) for example, the minimum sequence of the CMV promoter. Preferably, the promoter is contiguous to the nucleic acid sequence.

As stated herein, the nucleic acid construct may be in the form of a vector. Vectors frequently include one or more expression markers which enable selection of cells transfected (or transformed) with them, and preferably, to enable a selection of cells containing vectors incorporating heterologous DNA. A suitable start and stop signal will generally be present.

The vector may be any suitable expression vector, such as pET. The vector may include such additional control sequences as desired, for example selectable markers (e.g. antibiotic resistance, fluorescence, etc.), transcriptional control sequences and promoters, including initiation and termination sequences.

The promoter may be any suitable promoter for causing expression of the protein encoded by a nucleic acid sequence of the invention, e.g. a CMV promoter, human phosphoglycerate kinase (hPGK) promoter.

Such vectors may be present in a host cell. Representative examples of appropriate host cells for expression of the nucleic acid construct of the invention include virus packaging cells which allow encapsulation of the nucleic acid into a viral vector; bacterial cells, such as Streptococci, Staphylococci, *E. coli, Streptomyces* and *Bacillus subtilis*; single cells, such as yeast cells, for example, *Saccharomyces cerevisiae*, and *Aspergillus* cells; insect cells such as *Drosophila* S2 and *Spodoptera* Sf9 cells, animal cells such as CHO, COS, C127, 3T3, PHK.293, and Bowes Melanoma cells and other suitable human cells; and plant cells e.g. *Arabidopsis thaliana*. Suitably, the host cell is a eukaryotic cell, such as a CHO cell or a HEK293 cell.

Introduction of an expression vector into the host cell can be achieved by calcium phosphate transfection, DEAE-dextran mediated transfection, microinjection, cationic—lipid-mediated transfection, electroporation, transduction, scrape loading, ballistic introduction, infection or other methods. Such methods are described in many standard laboratory manuals, such as Sambrook et al, Molecular Cloning, a Laboratory Manual, Second Edition, Cold Spring Harbor Laboratory Press, Cold Spring Harbor, N.Y. (1989).

Mature proteins can be expressed in host cells, including mammalian cells such as CHO cells, yeast, bacteria, or other cells under the control of appropriate promoters. Cell-free translation systems can be employed to produce such proteins using RNAs derived from the nucleic acid construct of the third aspect of the present invention. Appropriate cloning and expression vectors for use with prokaryotic and eukaryotic hosts are described by Sambrook et al, Molecular Cloning, a Laboratory Manual, Second Edition, Cold Spring Harbor Laboratory Press, Cold Spring Harbor, N.Y. (1989).

The invention also provides a host cell comprising any of the polynucleotides and/or vectors of the invention described herein. According to the invention, there is provided a process for the production of an antigen specific antigen binding molecule of the invention, comprising the step of expressing a nucleic acid sequence encoding said molecule in a suitable host cell as defined herein.

Proteins can be recovered and purified from recombinant cell cultures by standard methods including ammonium sulphate or ethanol precipitation, acid extraction, anion or cation exchange chromatography, phosphocellulose chromatography, hydrophobic interaction chromatography, affinity chromatography, hydroxyapatite chromatography, lectin and/or heparin chromatography. For therapy, the nucleic acid construct, e.g. in the form of a recombinant vector, may be purified by techniques known in the art, such as by means of column chromatography as described in Sambrook et al, Molecular Cloning, a Laboratory Manual, Second Edition, Cold Spring Harbor Laboratory Press, Cold Spring Harbor, N.Y. (1989).

This aspect of the invention therefore extends to processes for preparing a fusion protein of the invention comprising production of the fusion protein recombinantly by expression in a host cell, purification of the expressed fusion protein by means of peptide bond linkage, hydrogen or salt bond or chemical cross linking. In some embodiments of this aspect of the invention, the fusion protein could be prepared using hydrogen or salt bonds where the peptide is capable or multimerisation, for example dimerisation or trimerisation.

Protein Expression as a Library

In another aspect, the invention provides a library comprising a plurality of vectors of the invention, wherein the plurality of vectors encode a plurality of polypeptides. Accordingly, the invention provides a virus or viral particle (such as phage or phagemid particles) displaying a polypeptide of the invention on its surface. The invention also provides a library comprising a plurality of the viruses or viral particles of the invention, each virus or virus particle displaying a polypeptide of the invention. A library of the invention may comprise any number of distinct polypeptides (sequences), at least about $1\times10^8$, at least about $1\times10^9$, at least about $1\times10^{10}$ distinct sequences, more suitably at least about $9\times10^{10}$ sequences.

The invention also provides libraries containing a plurality of polypeptides, wherein each type of polypeptide is a polypeptide of the invention as described herein.

Nucleic acid cassettes can be cloned into any suitable vector for expression of a portion or the entire VNAR containing the targeted amino acid substitutions generated. The nucleic acid cassette can be cloned into a vector allowing production of a portion or the entire VNAR chain sequence fused to all or a portion of a viral coat protein (i.e., creating a fusion protein) and displayed on the surface of a particle or cell. While several types of vectors are available and may be used to practice this invention, phagemid vectors are the preferred vectors for use herein, as they may be constructed with relative ease, and can be readily amplified. Phagemid vectors generally contain a variety of components including promoters, signal sequences, phenotypic selection genes, origin of replication sites, and other necessary components.

In another embodiment, wherein a particular variant amino acid combination is to be expressed, the nucleic acid cassette contains a sequence that is able to encode all or a portion of the VNAR sequence, and is able to encode the variant amino acid combinations. For production of antigen specific antigen binding molecules containing these variant amino acids or combinations of variant amino acids, as in a library, the nucleic acid cassettes can be inserted into an expression vector containing additional VNAR sequence, for example all or portions of the various CDR, Framework and/or Hypervariable regions. These additional sequences can also be fused to other nucleic acids sequences, such as sequences which encode viral coat protein components and therefore allow production of a fusion protein.

One aspect of the invention includes a replicable expression vector comprising a nucleic acid sequence encoding a gene fusion, wherein the gene fusion encodes a fusion protein comprising a VNAR sequence and a second VNAR sequence, fused to all or a portion of a viral coat protein. Also included is a library of diverse replicable expression vectors comprising a plurality of gene fusions encoding a plurality of different fusion proteins including a plurality of VNAR sequences generated with diverse sequences as described above. The vectors can include a variety of components and are preferably constructed to allow for movement of VNAR sequences between different vectors and/or to provide for display of the fusion proteins in different formats.

Examples of vectors include phage vectors. The phage vector has a phage origin of replication allowing phage replication and phage particle formation. The phage is preferably a filamentous bacteriophage, such as an M13, fl, fd, Pf3 phage or a derivative thereof, or a lambdoid phage, such as lambda, 21, phi80, phi81, 82, 424, 434, etc., or a derivative thereof.

Examples of viral coat proteins include infectivity protein PIII, major coat protein PVIII, p3, Soc (T4), Hoc (T4), gpD (of bacteriophage lambda), minor bacteriophage coat protein 6 (pVI) (filamentous phage; Hufton et al, J Immunol Methods. (1999), 231, (1-2): 39-51), variants of the M13 bacteriophage major coat protein (P8) (Weiss et al, Protein Sci (2000) 9 (4): 647-54). The fusion protein can be displayed on the surface of a phage and suitable phage systems include M13K07 helper phage, M13R408, M13-VCS, and Phi X 174, pJuFo phage system (Pereboev at al J Virol. (2001); 75(15): 7107-13), and hyperphage (Rondot et al Nat Biotechnol. (2001); 19(1): 75-8). The preferred helper phage is M13K07, and the preferred coat protein is the M13 Phage gene III coat protein. The preferred host is *E. coli*, and protease deficient strains of *E. coli*. Vectors, such as the fth1 vector (Enshell-Seijffers et al, Nucleic Acids Res. (2001); 29(10): E50-0) can be useful for the expression of the fusion protein.

The expression vector also can have a secretory signal sequence fused to the DNA encoding each VNAR or fragment thereof. This sequence is typically located immediately 5' to the gene encoding the fusion protein, and will thus be transcribed at the amino terminus of the fusion protein. However, in certain cases, the signal sequence has been demonstrated to be located at positions other than 5' to the gene encoding the protein to be secreted. This sequence targets the protein to which it is attached across the inner membrane of the bacterial cell. The DNA encoding the signal sequence may be obtained as a restriction endonuclease fragment from any gene encoding a protein that has a signal sequence. Suitable prokaryotic signal sequences may be obtained from genes encoding, for example, LamB or OmpF (Wong et al, Gene, (1983) 68, 1931), MalE, PhoA and other genes.

A preferred prokaryotic signal sequence for practicing this invention is the *E. coli* heat-stable enterotoxin II (STII) signal sequence as described by Chang et al (Gene 55. 189 (1987)), and malE.

The vector also typically includes a promoter to drive expression of the fusion protein. Promoters most commonly used in prokaryotic vectors include the lac Z promoter system, the alkaline phosphatase pho A promoter (Ap), the bacteriophage XPL promoter (a temperature sensitive promoter), the tac promoter (a hybrid trp-lac promoter that is regulated by the lac repressor), the tryptophan promoter, and the bacteriophage T7 promoter. For general descriptions of promoters, see section 17 of Sambrook et al. supra. While these are the most commonly used promoters, other suitable microbial promoters may be used as well.

The vector can also include other nucleic acid sequences, for example, sequences encoding gD tags, c-Myc epitopes, poly-histidine tags, fluorescence proteins (e.g., GFP), or beta-galactosidase protein which can be useful for detection or purification of the fusion protein expressed on the surface of the phage or cell.

Nucleic acid sequences encoding, for example, a gD tag, also provide for positive or negative selection of cells or virus expressing the fusion protein. In some embodiments, the gD tag is preferably fused to a VNAR sequence which is not fused to the viral coat protein component. Nucleic acid sequences encoding, for example, a polyhistidine tag, are useful for identifying fusion proteins including VNAR sequences that bind to a specific antigen using immunohistochemistry. Tags useful for detection of antigen binding can be fused to either a VNAR sequence not fused to a viral coat protein component or a VNAR sequence fused to a viral coat protein component.

Another useful component of the vectors used to practice this invention is phenotypic selection genes. Typical phenotypic selection genes are those encoding proteins that confer antibiotic resistance upon the host cell. By way of illustration, the ampicillin resistance gene (Amp), and the tetracycline resistance gene ($Tet^r$) are readily employed for this purpose.

The vector can also include nucleic acid sequences containing unique restriction sites and suppressible stop codons. The unique restriction sites are useful for moving VNAR sequences between different vectors and expression systems. The suppressible stop codons are useful to control the level of expression of the fusion protein and to facilitate purification of soluble VNAR fragments. For example, an amber stop codon can be read as Gln in a supE host to enable phage display, while in a non-supE host it is read as a stop codon to produce soluble VNAR fragments without fusion to phage coat proteins. These synthetic sequences can be fused to one or more VNAR sequences in the vector.

It may be convenient to use vector systems that allow the nucleic acid encoding a sequence of interest, for example a CDR having variant amino acids, to be easily removed from the vector system and placed into another vector system. For example, appropriate restriction sites can be engineered in a vector system to facilitate the removal of the nucleic acid sequence encoding a VNAR. The restriction sequences are usually chosen to be unique in the vectors to facilitate efficient excision and ligation into new vectors. VNAR sequences can then be expressed from vectors without extraneous fusion sequences, such as viral coat proteins or other sequence tags.

Between nucleic acid encoding VNAR sequences (gene 1) and the viral coat protein component (gene 2), DNA encoding a termination or stop codon may be inserted, such termination codons including UAG (amber), UAA (ocher) and UGA (opel). (Microbiology, Davis et al., Harper & Row, New York, 1980, pp. 237, 245-47 and 374). The termination or stop codon expressed in a wild type host cell results in the synthesis of the gene 1 protein product without the gene 2 protein attached. However, growth in a suppressor host cell results in the synthesis of detectable quantities of fused protein. Such suppressor host cells are well known and described, such as *E. coli* suppressor strain (Bullock et al., BioTechniques 5: 376-379 (1987)). Any acceptable method may be used to place such a termination codon into the mRNA encoding the fusion polypeptide.

The suppressible codon may be inserted between the first gene encoding a VNAR sequence, and a second gene encoding at least a portion of a phage coat protein. Alternatively, the suppressible termination codon may be inserted adjacent to the fusion site by replacing the last amino acid triplet in the VNAR sequence or the first amino acid in the phage coat protein. The suppressible termination codon may be located at or after the C-terminal end of a dimerization domain. When the plasmid containing the suppressible codon is grown in a suppressor host cell, it results in the detectable production of a fusion polypeptide containing the polypeptide and the coat protein. When the plasmid is grown in a non-suppressor host cell, the VNAR sequence is synthesized substantially without fusion to the phage coat protein due to termination at the inserted suppressible triplet UAG, UAA, or UGA. In the non-suppressor cell the antibody variable domain is synthesized and secreted from the host cell due to the absence of the fused phage coat protein which otherwise anchored it to the host membrane.

In some embodiments, the CDR being diversified (randomized) may have a stop codon engineered in the template sequence (referred to herein as a "stop template"). This feature provides for detection and selection of successfully diversified sequences based on successful repair of the stop codon(s) in the template sequence due to incorporation of the oligonucleotide (s) comprising the sequence(s) for the variant amino acids of interest.

Antigen Specific Antigen Binding Molecules of the Invention

In certain embodiments of the invention, the antigen specific antigen binding molecule has an amino acid sequence selected from the group as shown in any one of FIG. 9, 11, 12, 13, 14, 15(*a*), 15(*b*), or 16.

In one embodiment of the invention, the antigen specific antigen binding molecule is an amino acid sequence as shown in any one of FIG. 9, 11, 12, 13, 14, 15(*a*), 15(*b*), or 16 or any variant, analogue, derivative or fragment thereof, including a sequence having 50% identity thereto, or at least 60%, 70%, 80%, 90%, 95% or 99% identity, using the default parameters of the BLAST computer program provided by HGMP, thereto. In one embodiment of the invention, the antigen specific antigen binding molecule is humanized. It may be convenient to provide for a humanized binding molecule of the invention with from about 20% to about 85% humanization, for example from about 25% to about 60% humanization.

The antigen specific antigen binding molecule may comprise additional N-terminal or C-terminal sequences which are cleaved off prior to use which may assist in purification and/or isolation during processes for the production of the molecule as described herein. For example, $(Ala)_3(His)_6$ at the C-terminal end of the molecule.

Also included within the invention are variants, analogues, derivatives and fragments having the amino acid sequence of the protein in which several e.g. 5 to 10, or 1 to 5, or 1 to 3, 2, 1 or no amino acid residues are substituted, deleted or added in any combination. Especially preferred among these are silent substitutions, additions and deletions, which do not alter the properties and activities of the protein of the present invention. Also especially preferred in this regard are conservative substitutions where the properties of a protein of the present invention are preserved in the variant form compared to the original form. Variants also include fusion proteins comprising an antigen specific antigen binding molecule according to the invention.

As discussed above, an example of a variant of the present invention includes a protein in which there is a substitution of one or more amino acids with one or more other amino acids. The skilled person is aware that various amino acids have similar properties. One or more such amino acids of a substance can often be substituted by one or more other such amino acids without interfering with or eliminating a desired activity of that substance. Such substitutions may be referred to as "non-conservative" amino acid substitutions.

Thus the amino acids glycine, alanine, valine, leucine and isoleucine can often be substituted for one another (amino acids having aliphatic side chains). Of these possible substitutions it is preferred that glycine and alanine are used to substitute for one another (since they have relatively short side chains) and that valine, leucine and isoleucine are used to substitute for one another (since they have larger aliphatic side chains which are hydrophobic). Other amino acids which can often be substituted for one another include: phenylalanine, tyrosine and tryptophan (amino acids having aromatic side chains); lysine, arginine and histidine (amino acids having basic side chains); aspartate and glutamate (amino acids having acidic side chains); asparagine and glutamine (amino acids having amide side chains); and cysteine and methionine (amino acids having sulphur containing side chains). Substitutions of this nature are often referred to as "conservative" or "semi-conservative" amino acid substitutions.

Amino acid deletions or insertions may also be made relative to the amino acid sequence for the fusion protein referred to above. Thus, for example, amino acids which do not have a substantial effect on the activity of the polypeptide, or at least which do not eliminate such activity, may be deleted. Such deletions can be advantageous since the overall length and the molecular weight of a polypeptide can be reduced whilst still retaining activity. This can enable the amount of polypeptide required for a particular purpose to be reduced—for example, dosage levels can be reduced.

Amino acid insertions relative to the sequence of the fusion protein above can also be made. This may be done to alter the properties of a substance of the present invention (e.g. to assist in identification, purification or expression, as explained above in relation to fusion proteins).

Amino acid changes relative to the sequence for the fusion protein of the invention can be made using any suitable technique e.g. by using site-directed mutagenesis.

It should be appreciated that amino acid substitutions or insertions within the scope of the present invention can be made using naturally occurring or non-naturally occurring amino acids. Whether or not natural or synthetic amino acids are used, it is preferred that only L-amino acids are present.

A protein according to the invention may have additional N-terminal and/or C-terminal amino acid sequences. Such sequences can be provided for various reasons, for example, glycosylation.

A fusion protein may comprise an antigen specific antigen binding molecule of the present invention fused to a heterologous peptide or protein sequence providing a structural element to the fusion protein. In other embodiments, the fusion protein may comprise an antigen specific antigen binding molecule of the present invention fused with a molecule having biological activity, i.e. a therapeutic protein having a pharmacologically useful activity. The molecule may be a peptide or protein sequence, or another biologically active molecule.

For example, the antigen specific antigen binding molecule may be fused to a heterologous peptide sequence which may be a poly-amino acid sequence, for example a plurality of histidine residues or a plurality of lysine residues (suitably 2, 3, 4, 5, or 6 residues), or an immunoglobulin domain (for example an Fc domain).

References to heterologous peptides sequences include sequences from other mammalian species, such as murine and human and any heterologous peptides sequences originated from other VNAR domains.

Where the fusion protein comprises an antigen specific antigen binding molecule of the present invention fused with a molecule having biological activity, a biologically active moiety may be a peptide or protein having biological activity such as an enzyme, immunoglobulin, cytokine or a fragment thereof. Alternatively, the biologically active molecule may be an antibiotic, an anti-cancer drug, an NSAID, a steroid, an analgesic, a toxin or other pharmaceutically active agent. Anti-cancer drugs may include cytotoxic or cytostatic drugs.

In some embodiments, the fusion protein may comprise an antigen specific antigen binding molecule of the invention fused to another immunoglobulin variable or constant region, or another antigen specific antigen binding molecule of the invention. In other words, fusions of antigen specific antigen binding molecules of the invention may be of variable length, e.g. dimers, trimers, tetramers, or higher order multimer (i.e. pentamers, hexamers, heptamers octamers, nonamers, or decamers, or greater). In specific embodiments this can be represented as a multimer of monomer VNAR subunits.

For example, where the VNAR CDRs are fused to an additional peptide sequence, the additional peptide sequence can provide for the interaction of one or more fusion polypeptides on the surface of the viral particle or cell. These peptide sequences can therefore be referred to as "dimerization domains". Dimerization domains may comprise at least one or more of a dimerization sequence, or at least one sequence comprising a cysteine residue or both. Suitable dimerization sequences include those of proteins having amphipathic alpha helices in which hydrophobic residues are regularly spaced and allow the formation of a dimer by interaction of the hydrophobic residues of each protein; such proteins and portions of proteins include, for example, leucine zipper regions.

Dimerization domains can also comprise one or more cysteine residues (e.g. as provided by inclusion of an antibody hinge sequence within the dimerization domain). The cysteine residues can provide for dimerization by formation of one or more disulfide bonds. In one embodiment, wherein a stop codon is present after the dimerization domain, the dimerization domain comprises at least one cysteine residue. The dimerization domains are preferably located between the antibody variable or constant domain and the viral coat protein component.

In fusion proteins of the present invention, the antigen specific antigen binding molecule may be directly fused or linked via a linker moiety to the other elements of the fusion protein. The linker may be a peptide, peptide nucleic acid, or polyamide linkage. Suitable peptide linkers may include a plurality of amino acid residues, for example, 4, 5, 6, 7, 8, 9, 10, 15, 20 or 25 amino acids, such as $(Gly)_4$ (SEQ ID NO: 429), $(Gly)_5$ (SEQ ID NO: 430), $(Gly)_4Ser$ (SEQ ID NO: 431), $(Gly)_4(Ser)(Gly)_4$ (SEQ ID NO: 432), or combinations thereof or a multimer thereof (for example a dimer, a trimer, or a tetramer, or greater). For example, a suitable linker may be $(GGGGS)_3$ (SEQ ID NO: 433). Alternative linkers include $(Ala)_3(His)_6$ (SEQ ID NO: 434) or multimers thereof. Also included is a sequence which has at least 50%, 60%, 70%, 80%, 90%, 95% or 99% identity, using the default parameters of the BLAST computer program provided by HGMP, thereto.

In some cases the vector encodes a single VNAR-phage polypeptide fused to a coat protein. In these cases the vector is considered to be "monocistronic", expressing one transcript under the control of a certain promoter.

Illustrative examples of such vectors utilize the alkaline phosphatase (AP) or Tac promoter to drive expression of a monocistronic sequence encoding VNAR regions, with a linker peptide between the domains. The cistronic sequence can be connected at the 5'-end to an E. coli malE or heat-stable enterotoxin II (STII) signal sequence and at its 3'end to all or a portion of a viral coat protein (for example, the pIII protein). The vector may further comprise a sequence encoding a dimerization domain (such as a leucine zipper) at its 3'-end, between the second variable domain sequence and the viral coat protein sequence. Fusion polypeptides comprising the dimerization domain are capable of dimerizing to form a complex of two polypeptides.

In other cases, the VNAR sequences (multiple VNAR sequences or fragments) can be expressed as separate polypeptides, the vector thus being "bicistronic", allowing the expression of separate transcripts. In these vectors, a suitable promoter, such as the Ptac or PhoA promoter, can be used to drive expression of a bicistronic message. A first cistron, encoding, for example, a first VNAR sequence, can be connected at the 5'-end to a E. coli malE or heat-stable enterotoxin II (STII) signal sequence and at the 3'-end to a nucleic acid sequence encoding a gD tag. A second cistron, encoding, for example, a second VNAR sequence, can be connected at its 5'-end to a E. coli malE or heat-stable enterotoxin II (STII) signal sequence and at the 3'-end to all or a portion of a viral coat protein.

An example vector can comprise, a suitable promoter, such as Ptac or PhoA (AP) promoter which drives expression of first cistron encoding a VNAR sequence operably linked at 5'-end to an E. coli malE or heat stable enterotoxin II (STII) signal sequence and at the 3'-end to a nucleic acid sequence encoding a gD tag. The second cistron encodes, for example, another VNAR sequence operatively linked at 5'-end to a E. coli malE or heat stable enterotoxin II (STII) signal sequence and at 3'-end has a dimerization domain comprising IgG hinge sequence and a leucine zipper sequence followed by at least a portion of viral coat protein.

Fusion polypeptides of a VNAR sequence can be displayed on the surface of a cell, virus, or phagemid particle in a variety of formats. These formats include single chain fragment and multivalent forms of these fragments. The multivalent forms may be a dimer, or a higher multimer. The multivalent forms of display may be convenient because they have more than one antigen binding site which generally results in the identification of lower affinity clones and also allows for more efficient sorting of rare clones during the selection process.

Vectors constructed as described in accordance with the invention are introduced into a host cell for amplification and/or expression. Vectors can be introduced into host cells using standard transformation methods including electroporation, calcium phosphate precipitation and the like. If the vector is an infectious particle such as a virus, the vector itself provides for entry into the host cell. Transfection of host cells containing a replicable expression vector which encodes the gene fusion and production of phage particles according to standard procedures provides phage particles in which the fusion protein is displayed on the surface of the phage particle.

Replicable expression vectors are introduced into host cells using a variety of methods. In one embodiment, vectors can be introduced into cells using. Cells are grown in culture in standard culture broth, optionally for about 6-48 hours (or to OD600=0.6-0.8) at about 37° C., and then the broth is centrifuged and the supernatant removed (e.g. decanted). Initial purification is preferably by resuspending the cell pellet in a buffer solution (e.g. 1.0 mM HEPES pH 7.4) followed by recentrifugation and removal of supernatant. The resulting cell pellet is resuspended in dilute glycerol (e.g. 5-20% v/v) and again recentrifuged to form a cell pellet and the supernatant removed. The final cell concentration is obtained by resuspending the cell pellet in water or dilute glycerol to the desired concentration.

The use of higher DNA concentrations during electroporation (about 10×) increases the transformation efficiency and increases the amount of DNA transformed into the host cells. The use of high cell concentrations also increases the efficiency (about 10×). The larger amount of transferred DNA produces larger libraries having greater diversity and representing a greater number of unique members of a combinatorial library. Transformed cells are generally selected by growth on antibiotic containing medium.

Use of phage display for identifying target antigen binders, with its various permutations and variations in methodology, are well established in the art. One approach involves constructing a family of variant replicable vectors containing a transcription regulatory element operably linked to a gene fusion encoding a fusion polypeptide, transforming suitable host cells, culturing the transformed cells to form phage particles which display the fusion polypeptide on the surface of the phage particle, followed by a process that entails selection or sorting by contacting the recombinant phage particles with a target antigen so that at least a portion of the population of particles bind to the target with the objective to increase and enrich the subsets of the particles which bind from particles relative to particles that do not bind in the process of selection. The selected pool can be amplified by infecting host cells for another round of sorting on the same target with different or same stringency. The resulting pool of variants is then screened against the target antigens to identify novel high affinity binding proteins.

These novel high affinity binding proteins can be useful as therapeutic agents as antagonists or agonists, and/or as diagnostic and research reagents.

Fusion polypeptides such as antibody variable domains comprising the variant amino acids can be expressed on the surface of a phage, phagemid particle or a cell and then selected and/or screened for the ability of members of the group of fusion polypeptides to bind a target antigen which is typically an antigen of interest.

Such fusion proteins may be prepared by any suitable route, including by recombinant techniques by expression in host cell or cell-free systems, as well as by chemical synthetic routes.

Selection of Library Members

The processes of selection for binders to target can also be include sorting on a generic protein having affinity for antibody variable domains such as protein L or a tag specific antibody which binds to antibody or antibody fragments displayed on phage, which can be used to enrich for library members that display correctly folded antibody fragments (fusion polypeptides).

Target proteins, such as receptors, may be isolated from natural sources or prepared by recombinant methods by procedures known in the art. Target antigens can include a number of molecules of therapeutic interest.

Two main strategies of selection (sorting) for affinity which can be are (i) the solid-support method or plate sorting or immobilized target sorting; and (ii) the solution-binding method.

For the solid support method, the target protein may be attached to a suitable solid or semi-solid matrix which are known in the art such as agarose beads, acrylamide beads, glass beads, cellulose, various acrylic copolymers, hydroxyalkyl methacrylate gels, polyacrylic and polymethacrylic copolymers, nylon, neutral and ionic carriers, etc.

After attachment of the target antigen to the matrix, the immobilized target is contacted with the library expressing the fusion polypeptides under conditions suitable for binding of at least a subset of the phage particle population with the immobilized target antigen. Normally, the conditions, including pH, ionic strength, temperature and the like will mimic physiological conditions. Bound particles ("binders") to the immobilized target are separated from those particles that do not bind to the target by washing. Wash conditions can be adjusted to result in removal of all but the high affinity binders. Binders may be dissociated from the immobilized target by a variety of methods. These methods include competitive dissociation using the wild-type ligand (e.g. excess target antigen), altering pH and/or ionic strength, and methods known in the art. Selection of binders typically involves elution from an affinity matrix with a suitable elution material such as acid like 0.1 M HCl or ligand. Elution with increasing concentrations of ligand could elute displayed binding molecules of increasing affinity.

The binders can be isolated and then re-amplified in suitable host cells by infecting the cells with the viral particles that are binders (and helper phage if necessary, e.g. when viral particle is a phagemid particle) and the host cells are cultured under conditions suitable for amplification of the particles that display the desired fusion polypeptide. The phage particles are then collected and the selection process is repeated one or more times until binders of the target antigen are enriched in a way. Any number of rounds of selection or sorting can be utilized. One of the selection or sorting procedures can involve isolating binders that bind to a generic affinity protein such as protein L or an antibody to a polypeptide tag present in a displayed polypeptide such as antibody to the gD protein or polyhistidine tag.

Another selection method is the "solution-binding method" which allows solution phase sorting with an improved efficiency over the conventional solution sorting method. The solution binding method has been used for finding original binders from a random library or finding improved binders from a library that was designated to improve affinity of a particular binding clone or group of clones. The method comprises contacting a plurality of polypeptides, such as those displayed on phage or phagemid particles (library), with a target antigen labeled or fused with a tag molecule. The tag could be biotin or other moieties for which specific binders are available. The stringency of the solution phase can be varied by using decreasing concentrations of labeled target antigen in the first solution binding phase.

To further increase the stringency, the first solution binding phase can be followed by a second solution phase having high concentration of unlabeled target antigen after the initial binding with the labeled target in the first solution phase. Usually, 100 to 1000 fold of unlabeled target over labeled target is used in the second phase (if included). The length of time of incubation of the first solution phase can vary from a few minutes to one to two hours or longer to reach equilibrium. Using a shorter time for binding in this first phase may bias or select for binders that have fast on-rate. The length of time and temperature of incubation in second phase can be varied to increase the stringency. This provides for a selection bias for binders that have slow rate of coming off the target (off-rate).

After contacting the plurality of polypeptides (displayed on the phage/phagemid particles) with a target antigen, the phage or phagemid particles that are bound to labeled targets are separated from phage that do not bind. The particle-target mixture from solution phase of binding is isolated by contacting it with the labeled target moiety and allowing for its binding to, a molecule that binds the labeled target moiety for a short period of time (e.g. 2-5 min). The initial concentration of the labeled target antigen can range from about 0.1 nM to about 1000 nM. The bound particles are eluted and can be propagated for next round of sorting. Multiple rounds of sorting are preferred using a lower concentration of labeled target antigen with each round of sorting.

For example, an initial sort or selection using about 100 to 250 nM labeled target antigen should be sufficient to capture a wide range of affinities, although this factor can be determined empirically and/or to suit the desire of the practitioner. In the second round of selection, about 25 to 100 nM of labeled target antigen may be used. In the third round of selection, about 0.1 to 25 nM of labeled target antigen may be used. For example, to improve the affinity of a 100 nM binder, it may be desirable to start with 20 nM and then progress to 5 and 1 nM labeled target, then, followed by even lower concentrations such as about 0.1 nM labeled target antigen.

As described herein, combinations of solid support and solution sorting methods can be advantageously used to isolate binders having desired characteristics. After selection/sorting on target antigen for a few rounds, screening of individual clones from the selected pool generally is performed to identify specific binders with the desired properties/characteristics. Preferably, the process of screening is carried out by automated systems to allow for high-throughput screening of library candidates.

Two major screening methods are described below. However, other methods may also be used. The first screening method comprises a phage ELISA assay with immobilized target antigen, which provides for identification of a specific binding clone from a non-binding clone. Specificity can be determined by simultaneous assay of the clone on target coated well and BSA or other non-target protein coated wells. This assay is automatable for high throughput screening.

One embodiment provides a method of selecting for an antibody variable domain that binds to a specific target antigen from a library of antibody variable domain by generating a library of replicable expression vectors comprising a plurality of polypeptides; contacting the library with a target antigen and at least one nontarget antigen under conditions suitable for binding; separating the polypeptide binders in the library from the nonbinders; identifying the binders that bind to the target antigen and do not bind to the nontarget antigen; eluting the binders from the target antigen; and amplifying the replicable expression vectors comprising the polypeptide binder that bind to a specific antigen.

The second screening assay is an invention embodied in this application which is an affinity screening assay that provides for screening for clones that have high affinity from clones that have low affinity in a high throughput manner. In the assay, each clone is assayed with and without first incubating with target antigen of certain concentration for a period of time (for e.g 30-60 min) before application to target coated wells briefly (e.g. 5-15 min). Then bound phage is measured by usual phage ELISA method, e.g. using anti-M13 HRP conjugates. The ratio of binding signal of the two wells, one well having been preincubated with target and the other well not preincubated with target antigen is an indication of affinity. The selection of the concentration of target for first incubation depends on the affinity range of interest. For example, if binders with affinity higher than 10 nM are desired, 1000 nM of target in the first incubation is often used. Once binders are found from a particular round of sorting (selection), these clones can be screened with affinity screening assay to identify binders with higher affinity.

Combinations of any of the sorting/selection methods described above may be combined with the screening methods. For example, in one embodiment, polypeptide binders are first selected for binding to immobilized target antigen.

Polypeptide binders that bind to the immobilized target antigen can then be amplified and screened for binding to the target antigen and for lack of binding to nontarget antigens. Polypeptide binders that bind specifically to the target antigen are amplified. These polypeptide binders can then selected for higher affinity by contact with a concentration of a labeled target antigen to form a complex, wherein the concentration ranges of labeled target antigen from about 0.1 nM to about 1000 nM, the complexes are isolated by contact with an agent that binds to the label on the target antigen. The polypeptide binders are then eluted from the labeled target antigen and optionally, the rounds of selection are repeated, each time a lower concentration of labeled target antigen is used. The high affinity polypeptide binders isolated using this selection method can then be screened for high affinity using for example, a solution phase ELISA assay or a spot competition ELISA assay.

After binders are identified by binding to the target antigen, the nucleic acid can be extracted. Extracted DNA can then be used directly to transform E. coli host cells or alternatively, the encoding sequences can be amplified, for example using PCR with suitable primers, and sequenced by typical sequencing method. Variable domain DNA of the binders can be restriction enzyme digested and then inserted into a vector for protein expression.

In some embodiments, libraries comprising polypeptides of the invention are subjected to a plurality of sorting rounds, wherein each sorting round comprises contacting the binders obtained from the previous round with a target antigen distinct from the target antigen(s) of the previous round(s).

In another aspect of the invention provides methods for selecting for high affinity binders to specific target antigens such as growth hormone, bovine growth hormone, insulin like growth factors, human growth hormone including n-methionyl human growth hormone, parathyroid hormone, thyroxine, insulin, proinsulin, amylin, relaxin, prorelaxin, glycoprotein hormones such as follicle stimulating hormone (FSH), leutinizing hormone (LH), hemapoietic growth factor, fibroblast growth factor, prolactin, placenta lactogen, tumor necrosis factors, mullerian inhibiting substance, mouse gonadotropin-associated polypeptide, inhibin, activin, vascular endothelial growth factors, integrin, nerve growth factors such as NGF-beta, insulin-like growth factor-I and II, erythropoietin, osteoinductive factors, interferons, colony stimulating factors, interleukins, bone morphogenetic proteins, LIF, SCF, FLT-3 ligand and kit-ligand.

The methods of the invention provide for libraries of polypeptides (e.g. antigen specific antigen binding molecules) with one or more diversified CDR regions. These libraries are sorted (selected) and/or screened to identify high affinity binders to a target antigen. In one aspect, polypeptide binders from the library are selected for binding to target antigens, and for affinity. The polypeptide binders selected using one or more of these selection strategies, then, may be screened for affinity and/or for specificity (binding only to target antigen and not to non-target antigens).

A method comprises generating a plurality of polypeptides with one or more diversified CDR regions, sorting the plurality of polypeptides for binders to a target antigen by contacting the plurality of polypeptides with a target antigen under conditions suitable for binding; separating the binders to the target antigen from those that do not bind; isolating the binders; and identifying the high affinity binders. The affinity of the binders that bind to the target antigen can be determined using competition ELISA such as described herein. Optionally, the polypeptides can be fused to a polypeptide tag such as gD, poly his or FLAG which can be used to sort binders in combination with sorting for the target antigen.

Another embodiment provides a method of selecting for an antigen specific antigen binding molecule that binds to a target antigen from a library of VNARs comprising: a) generating a library of replicable expression vectors comprising a plurality of polypeptides of the invention; b) isolating polypeptide binders to a target antigen from the library by contacting the library with an immobilized target antigen under conditions suitable for binding; c) separating the polypeptide binders in the library from the nonbinders and eluting the binders from the target antigen; d) amplifying the replicable expression vectors having the polypeptide binders; and e) optionally, repeating steps a-d at least twice.

The method may further comprise: f) incubating the amplified replicable expression vectors comprising polypeptide binders with a concentration of labeled target antigen in the range of 0.1 nM to 1000 nM under conditions suitable for binding to form a mixture; g) contacting the mixture with an immobilized agent that binds to the label on the target antigen; h) separating the polypeptide binders bound to labeled target antigen and eluting the polypeptide binders from the labeled target antigen; i) amplifying replicable expression vectors comprising the polypeptide binders; and j) optionally, repeating steps f) to i) at least twice, using a lower concentration of labeled target antigen each time. Optionally, the method may comprise adding an excess of unlabeled target antigen to the mixture and incubating for a period of time sufficient to elute low affinity binders from the labeled target antigen.

Another embodiment provides a method of isolating or selecting for high affinity binders to a target antigen from a library of replicable expression vectors comprising: a) generating a library of replicable expression vectors comprising a plurality of polypeptides of the invention; b) contacting the library with a target antigen in a concentration of at least about 0.1 nM to 1000 nM to isolate polypeptide binders to the target antigen; c) separating the polypeptide binders from the target antigen and amplifying the replicable expression vector comprising the polypeptide binders; d) optionally, repeating steps a-c at least twice, each time with a lower concentration of target antigen to isolate polypeptide binders that bind to lowest concentration of target antigen; e) selecting the polypeptide binder that binds to the lowest concentration of the target antigen for high affinity by incubating the polypeptide binders with several different dilutions of the target antigen and determining the IC50 of the polypeptide binder; and f) identifying a polypeptide binder that has an affinity for the target antigen of about 0.1 nM to 200 nM.

Another embodiment provides an assay for selecting polypeptide binders from a library of replicable expression vectors comprising a plurality of polypeptides of the invention comprising: a) contacting the library with a concentration of labeled target antigen in a concentration range of 0.1 nM to 1000 nM, under conditions suitable for binding to form a complex of a polypeptide binders and the labeled target antigen; b) isolating the complexes and separating the polypeptide binders from the labeled target antigen; c) amplifying the replicable expression vector comprising the polypeptide binders; d) optionally, repeating steps a-c at least twice, each time using a lower concentration of target antigen.

Optionally, the method may further comprise adding an excess of unlabeled target antigen to the complex of the polypeptide binder and target antigen. In a preferred embodiment, the steps of the method are repeated twice and the concentrations of target in the first round of selection is about 100 nM to 250 nM, and in the second round of selection is about 25 nM to 100 nM, and in the third round of selection is about 0.1 nM to 25 nM.

The invention also includes a method of screening a library of replicable expression vectors comprising a plurality of polypeptides of the invention comprising: a) incubating first a sample of the library with a concentration of a target antigen under conditions suitable for binding of the polypeptides to the target antigen; b) incubating a second sample of the library without a target antigen; c) contacting each of the first and second sample with immobilized target antigen under conditions suitable for binding of the polypeptide to the immobilized target antigen; d) detecting the amount of the bound polypeptides to immobilized target antigen for each sample; e) determining the affinity of the polypeptide for the target antigen by calculating the ratio of the amounts of bound polypeptide from the first sample over the amount of bound polypeptide from the second sample.

The libraries generated as described herein may also be screened for binding to a specific target and for lack of binding to nontarget antigens. In one aspect, another embodiment provides a method of screening for an antibody variable domain that binds to a specific target antigen from a library of VNARs comprising: a) generating a library of replicable expression vectors comprising a plurality of polypeptides of the invention; b) contacting the library with a target antigen and at least one nontarget antigen under conditions suitable for binding; c) separating the polypeptide binders in the library from the nonbinders; d) identifying the binders that bind to the target antigen and do not bind to the nontarget antigen; e) eluting the binders from the target antigen; and f) amplifying the replicable expression vectors comprising the polypeptide binder that bind to a specific antigen.

Combinations of any of the sorting/selection methods described above may be combined with the screening methods. For example, in one embodiment, polypeptide binders are first selected for binding to immobilized target antigen.

Polypeptide binders that bind to the immobilized target antigen can then be amplified and screened for binding to the target antigen and for lack of binding to nontarget antigens. Polypeptide binders that bind specifically to the target antigen are amplified. These polypeptide binders can then selected for higher affinity by contact with a concentration of a labeled target antigen to form a complex, wherein the concentration range of labeled target antigen is from about 0.1 nM to about 1000 nM, the complexes are isolated by contact with an agent that binds to the label on the target antigen. The polypeptide binders are then eluted from the labeled target antigen and optionally, the rounds of selection are repeated, each time a lower concentration of labeled target antigen is used. The high affinity polypeptide binders isolated using this selection method can then be screened for high affinity using for example, a solution phase ELISA assay or a spot competition ELISA assay.

Pharmaceutical Compositions and Uses

According to the invention, there is provided a pharmaceutical composition of antigen specific antigen binding molecule of the invention. Such compositions include fusion proteins comprising said antigen specific antigen binding molecules.

The pharmaceutical composition may also comprise an antigen specific antigen binding molecule of the present invention fused to a therapeutic protein, or a fragment thereof. The therapeutic protein may be a hormone, a growth factor (e.g. TGFβ, epidermal growth factor (EGF), platelet derived growth factor (PDGF), nerve growth factor (NGF), colony stimulating factor (CSF), hepatocyte growth factor, insulin-like growth factor, placenta growth factor); a differentiation factor; a blood clotting factor (for example, Factor Vila, Factor VIII, Factor IX, von Willebrand Factor or Protein C) or another protein from the blood coagulation cascade (for example, antithrombin); a cytokine e.g. an interleukin, (e.g. IL1, IL-2, IL-3, IL-4, IL-5, IL-6, IL-7, IL-8, IL-9, IL-10, IL-11, IL-12, IL-13, IL-14, IL-15, IL-16, IL-17, IL-18, IL-19, IL-20, IL-21, IL-22, IL-23, IL-24, IL-25, IL-26, IL-27, IL-28, IL-29, IL-30, IL-31, IL-32 or IL-33 or an interferon (e.g. IFN-α, IFN-β and IFN-γ), tumour necrosis factor (TNF), IFN-γ inducing factor (IGIF), a bone morphogenetic protein (BMP, e.g. BMP-1, BMP-2, BMP-3, BMP-4, BMP-4, BMP-5, BMP-6, BMP-7, BMP-8, BMP-9, BMP10, BMP-11, BMP-12, BMP-13); an interleukin receptor antagonist (e.g. IL-1ra, IL-1RII); a chemokine (e.g. MIPs (Macrophage Inflammatory Proteins) e.g. MIP1a and MIP1β; MCPs (Monocyte Chemotactic Proteins) e.g. MCP1, 2 or 3; RANTES (regulated upon activation normal T-cell expressed and secreted)); a trophic factor; a cytokine inhibitor; a cytokine receptor; an enzyme, for example a free-radical scavenging enzyme e.g. superoxide dismutase or catalase or a pro-drug converting enzyme (e.g. angiotensin converting enzyme, deaminases, dehydrogenases, reductases, kinases and phosphatases); a peptide mimetic; a protease inhibitor; a tissue inhibitor of metalloproteinases (TIMPs e.g. TIMP1, TIMP2, TIMP3 or TIMP4) or a serpin (inhibitors of serine proteases).

In other embodiments of the invention, the therapeutic protein in the fusion protein may be an antibody, or a engineered fragment thereof, including Fab, Fc, F(ab')$_2$ (including chemically linked F(ab')$_2$ chains), Fab', scFv (including multimer forms thereof, i.e. di-scFv, or tri-scFv), sdAb, or BITE (bi-specific T-cell engager). Antibody fragments also include variable domains and fragments thereof, as well as other VNAR type fragments (IgNAR molecules). The antigen specific binding molecules of the invention can be monomeric or dimeric or trimeric or multimeric and can be homologous or heterologous capable of binding the same or different targets and/or the same or different epitopes on the same target. In other words, the antigen specific binding molecules may be monospecific, bispecific, trispecific or multispecific. Reference to heterologous antigen specific binding molecules of the invention refers to binding to different epitopes on the same target. Engineered fragments also include Fc-fusions of an antigen specific binding molecule of the invention and an Fc fragment of an antibody.

The pharmaceutical composition may be composed of a number of antigen specific antigen binding molecules of the invention, for example dimers, trimers, or higher order multimers, i.e. 2, 3, 4, 5, 6, 7, or 8-mers, fused to the therapeutic protein.

The fusion of the antigen specific antigen binding molecules of the invention to the therapeutic protein may at any convenient site on the protein and may be N-, C- and/or N-/C-terminal fusion(s). In one embodiment of the invention, the fusion of the antigen specific antigen binding molecules of the invention is to both the N- and C-terminals of a therapeutic protein.

Pharmaceutical compositions of the invention may comprise any suitable and pharmaceutically acceptable carrier, diluent, adjuvant or buffer solution. The composition may comprise a further pharmaceutically active agent. Such carriers may include, but are not limited to, saline, buffered saline, dextrose, liposomes, water, glycerol, ethanol and combinations thereof.

Such compositions may comprise a further pharmaceutically active agent as indicated. The additional agents may be therapeutic compounds, e.g. anti-inflammatory drugs, cytotoxic agents, cytostatic agents or antibiotics. Such additional agents may be present in a form suitable for administration to patient in need thereof and such administration may be simultaneous, separate or sequential. The components may be prepared in the form of a kit which may comprise instructions as appropriate.

The pharmaceutical compositions may be administered in any effective, convenient manner effective for treating a patient's disease including, for instance, administration by oral, topical, intravenous, intramuscular, intranasal, or intradermal routes among others. In therapy or as a prophylactic, the active agent may be administered to an individual as an injectable composition, for example as a sterile aqueous dispersion, preferably isotonic.

For administration to mammals, and particularly humans, it is expected that the daily dosage of the active agent will be from 0.01 mg/kg body weight, typically around 1 mg/kg, 2 mg/kg or up to 4 mg/kg. The physician in any event will determine the actual dosage which will be most suitable for an individual which will be dependent on factors including the age, weight, sex and response of the individual. The above dosages are exemplary of the average case. There can, of course, be instances where higher or lower dosages are merited, and such are within the scope of this invention.

According to the invention, there is provided an antigen specific antigen binding molecule of the invention for use in medicine. This aspect of the invention therefore extends to the use of such of an antigen specific antigen binding molecule of the invention in the manufacture of a medicament for the treatment of a disease in a patient in need thereof. An antigen specific antigen binding molecule of the invention can also be used to prepare a fusion protein comprising such a specific binding molecule as defined above in relation to pharmaceutical compositions of the invention.

Such uses also embrace methods of treatment of diseases in patients in need of treatment comprising administration to the patient of a therapeutically effective dosage of a pharmaceutical composition as defined herein comprising an antigen specific antigen binding molecule of the invention.

As used herein, the term "treatment" includes any regime that can benefit a human or a non-human animal. The treatment of "non-human animals" in veterinary medicine extends to the treatment of domestic animals, including horses and companion animals (e.g. cats and dogs) and farm/agricultural animals including members of the ovine, caprine, porcine, bovine and equine families. The treatment may be a therapeutic treatment in respect of any existing condition or disorder, or may be prophylactic (preventive treatment). The treatment may be of an inherited or an acquired disease. The treatment may be of an acute or chronic condition. The treatment may be of a condition/disorder associated with inflammation and/or cancer. The antigen specific antigen binding molecules of the invention may be used in the treatment of a disorder, including, but not limited to osteoarthritis, scleroderma, renal disease, rheumatoid arthritis, inflammatory bowel disease, multiple sclerosis, atherosclerosis, or any inflammatory disease.

The antigen specific antigen binding molecules of the present invention may also be used to investigate the nature of a disease condition in a patient. The antigen specific antigen binding molecules may be used to prepare images of sites of disease in the body of a subject using imaging techniques such as X-ray, gamma-ray, or PET scanning, or similar. The invention may therefore extend to a method of imaging a site of disease in a subject, comprising administration of a suitably detectably labeled antigen specific antigen binding molecule to a subject and scanning the subject's body subsequently. Alternatively, administration of said molecules to a subject may provide for a test result by analysing a sample from the subject following administration of the molecule.

Alternatively, the antigen specific antigen binding molecules may be used to assay for the presence of target analytes in an in vitro sample or in a patient's body. The sample may any biological sample material from the body such as cells, tissue, blood, plasma, saliva, tears, semen, cerebrospinal fluid (CSF) and/or milk. Such methods may comprise the addition of a suitably labelled antigen specific antigen binding molecule to a sample of interest. The binding of the labelled antigen specific antigen binding molecule to the target analyte can then be detected by any suitable means such as fluorescence, radioactivity etc. according standard enzyme-linked immunosorbent assay (ELISA) and/or radio-immunoassay (RIA) assays.

Such embodiments may include a method of diagnosis of a disease or medical condition in a subject comprising administration to the subject of an antigen specific antigen binding molecule of the invention, or the addition of said antigen specific antigen binding molecule to a sample.

The antigen specific antigen binding molecule may find further use in the immunoaffinity purification of a molecule of interest. Suitably the antigen specific antigen binding molecule of the invention may be bound to a substrate over which a sample containing the molecule of interest is passed or introduced such that the molecule of interest binds in a releasable manner to the antigen specific antigen binding molecule. Such methods of immunoaffinity purification can find use in bioprocessing of substances from biological sources or chemical reactions which may be otherwise difficult to prepare in a sufficiently pure form, such as for example therapeutic substances.

The substrate to which the antigen specific antigen binding molecule can be bound may be a column comprising a polymer in the form of beads or powder, a plate (e.g. a multi-well plate), microfluidic system. Such substrates may be composed of any suitable inert material such as silicon, glass or a plastics material, optionally in the form of a chip. In some arrangements, it may be convenient to site multiple antigen specific antigen binding molecules of the same or different antigen specific on such substrates. After binding of the substance to the antigen specific antigen binding molecule, the substrate can be washed to remove unbound material and then the purified substance can be eluted by suitable means.

In the present application reference is made to a number of drawings in which:

FIG. 1 shows structure of rearranged IgNAR genes showing positions of canonical (○) and non-canonical (●)

cysteine residues, disulphide bonds (connecting lines), conserved tryptophan (W), and hyper-variable (CDR/HV) regions.

Figure 1:
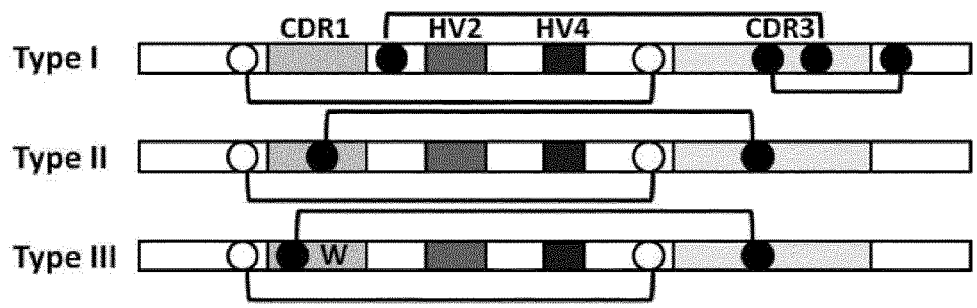
Figure 2:
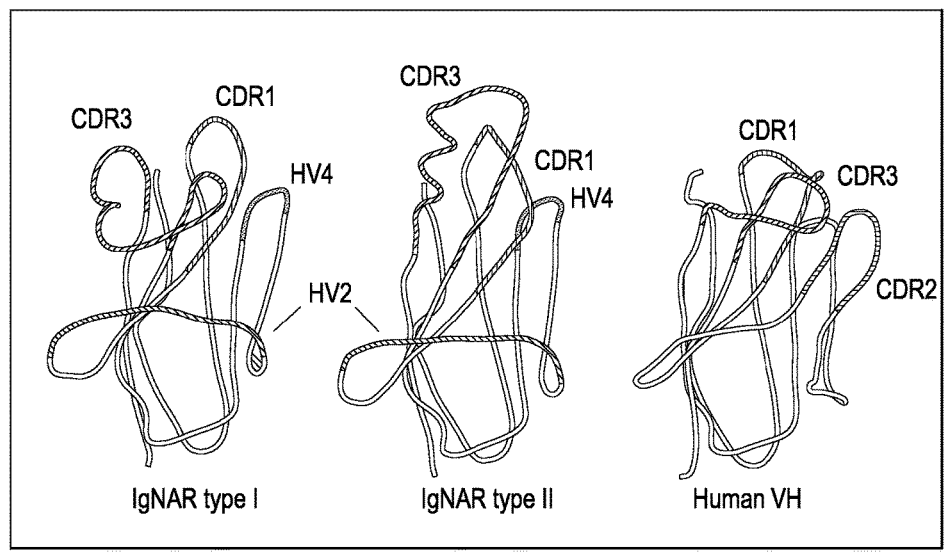
FIG. 2 shows Backbone structures of type I and type II anti-lysozyme IgNAR compared with a human VH domain.
Figure 3:
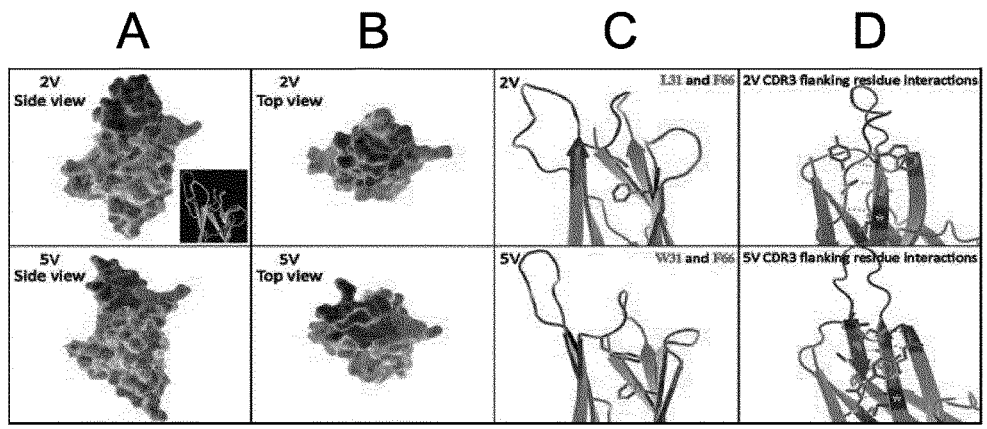
FIG. 3 shows the crystal structures of the template VNAR domains 2V and 5V derived from *Squalus acanthias*.
Figure 4:
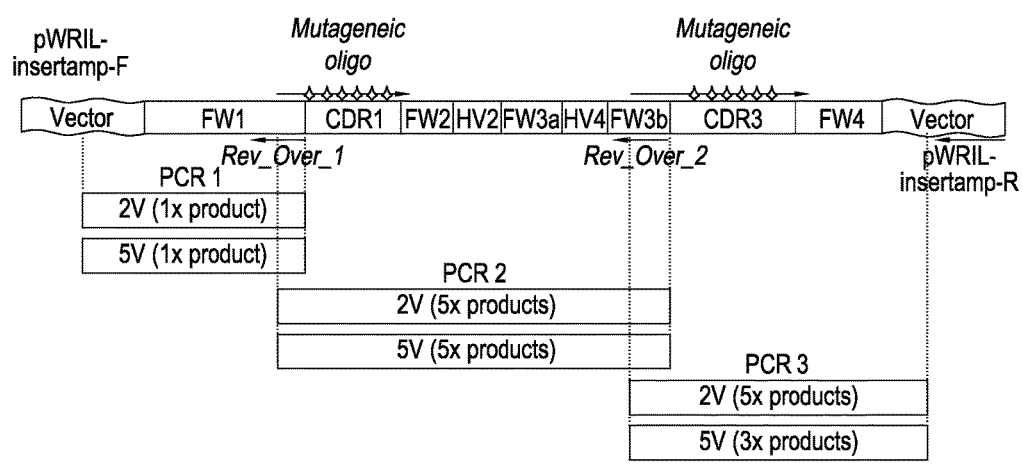

FIG. 4 shows the library design and framework diversity created from hybrid sequences using both 2V and 5V template frameworks. Design for 2V and 5V framework fusion based library using SOE PCR. Primer positions are shown as arrows.

FIG. 5 shows example affinities of hits against different targets. ELSS1 was screened against a range of different classes of target (hDLL4, HSA, hRAGE). Positive hits were purified, the concentration determined and were passed over CM5-chip immobilized target on a BIAcore T-2000 to calculate the kinetics of binding.

Figure 6A:
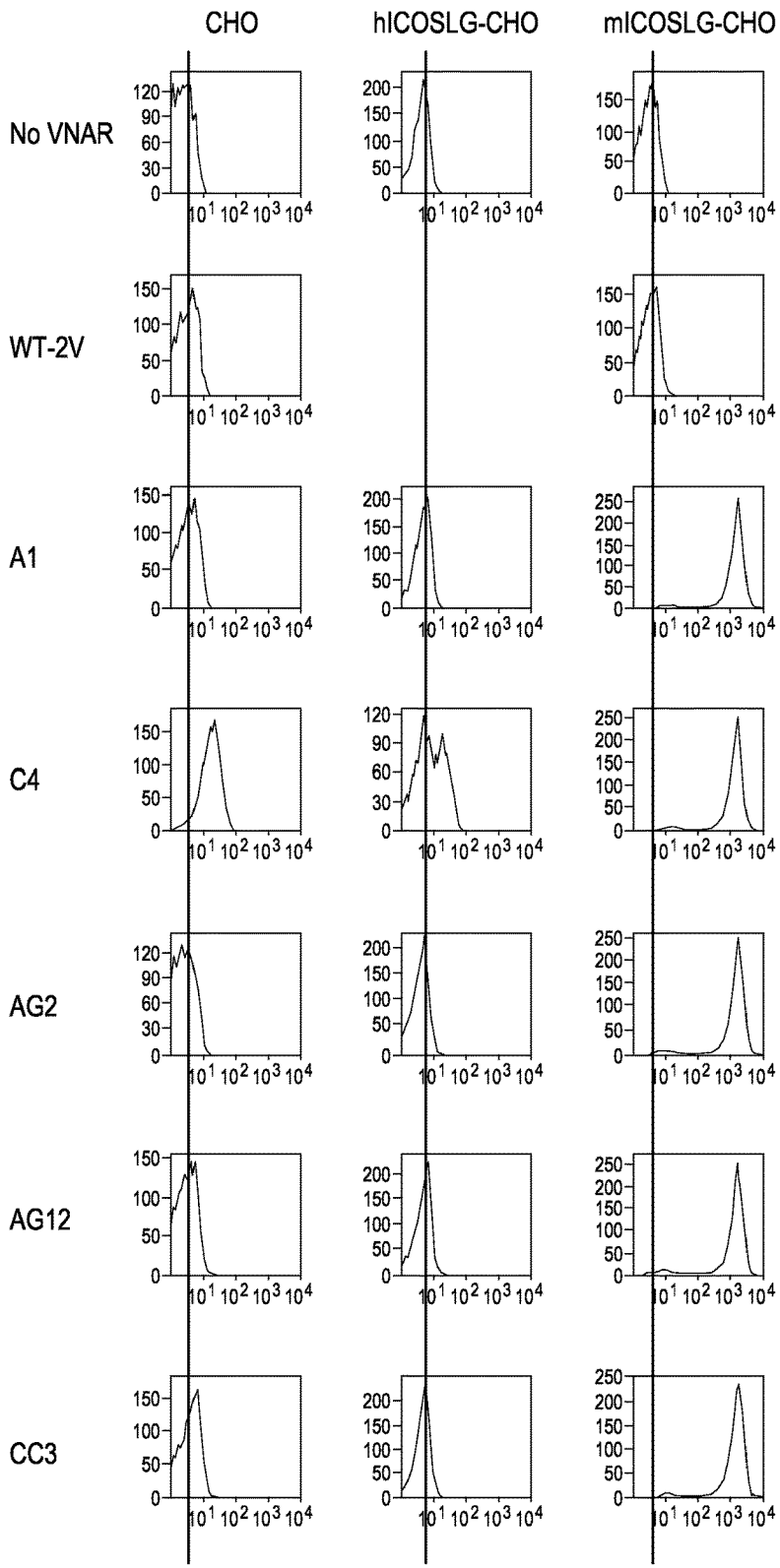

FIG. 6 shows data which exemplify selectivity of ELSS1 library hits. FIG. 6A shows the selectivity of hits isolated against mICOSL. ELSS1 was screened against mouse ICOSL and positive hits tested for binding to cell surface expressed target compared to parental using a FACS based assay. FIG. 6B shows the selectivity of hits isolated against DLL4. ELSS1 was screened against human and mouse DLL4 and positive hits assessed for selectivity of binding to cell surface target by a FACS based assay. The greater the number, the greater the binding to the cell type indicated in the tables.

Figure 7D:
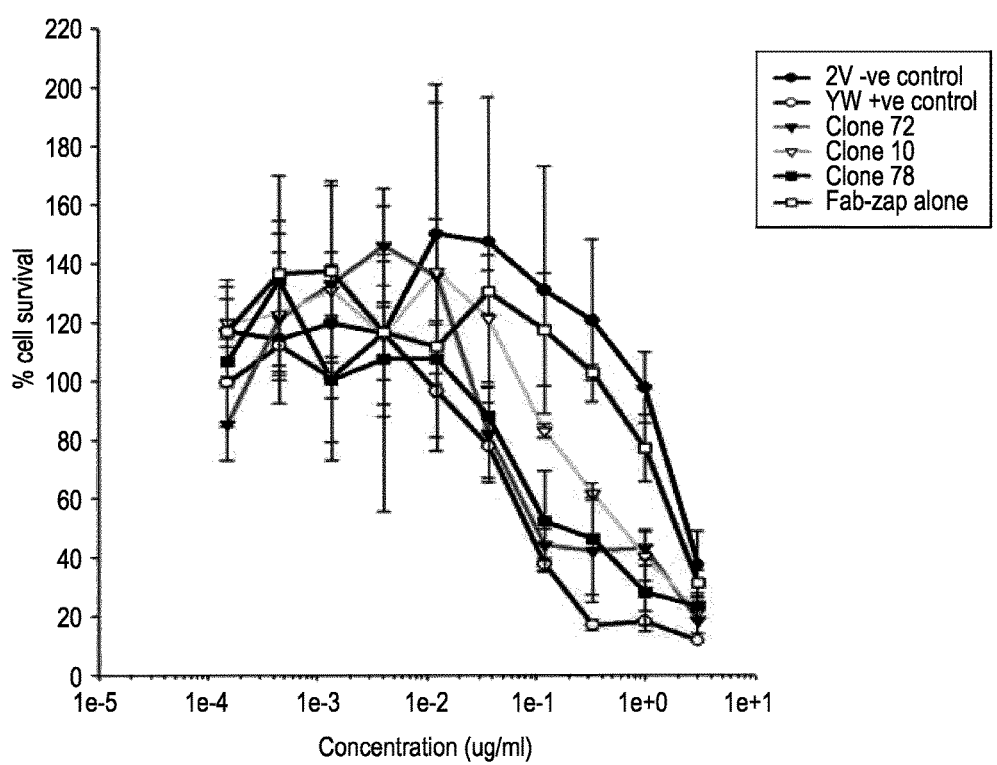

FIGS. 7A to 7D show data which exemplify in vitro efficacy of ELSS1 library hits against different targets. FIG. 7A shows the selectivity of hits isolated against mICOSL in a cell based neutralization assay. Positive VNAR hits from the ELSS1 library against mICOSL were assessed for their ability to inhibit ligand (ICOSL) from binding to cognate receptor (ICOS). VNAR hits, C4, CC3, A1, AG12 and AG2 were compared to negative VNAR control 2V. All clones were expressed and purified and titrated in the presence of labeled ligand to show efficacy of inhibiting ligand binding to receptor. All IC50 measured were single digit nanomolar. FIG. 7B shows the ability of the isolated and purified anti-mICOSL VNARs to inhibit the proliferation of T cells in a murine D10 assay (T-cell proliferation assay). FIG. 7C shows the ability of anti-hDLL4 VNAR domains isolated from ELSS1 to inhibit the binding of DLL4 to cell surface Notch1 receptor (neutralisation assay). The data is calculated as percentage neutralisation with the greater the value showing the greater the inhibition of ligand binding receptor. FIG. 7D shows the ability of anti-DLL4 VNARs to bind to and become internalised by cell surface expressed DLL4. The anti-DLL4 VNAR domains are fused to human Fc and internalisation is measured through cell survival, the lower the survival, the greater the efficiency of internalisation. Clones 72, 10 and 78 are VNAR hits. 2V is the negative VNAR control, YW is the mAb positive control.

FIG. 8 shows the in vivo efficacy of anti-mICOSL VNARs in a mouse model of human Rheumatoid Arthritis (RA). The left hand graph shows the ability of all 5 lead VNARs (A1, C4, CC3, AG2 and AG12) to reduce the overall clinical score or level of inflammation in a collagen induced mouse model of RA compared to the negative control 2V. Clones A1 and CC3 significantly reduced inflammation as compared to a lead mAb raised against mICOSL (right hand graph). All anti-mICOSL VNAR domains and the isotype control VNAR, 2V, are re-formatted as human Fc fusion proteins.

FIG. 9 shows amino acid and nucleotide sequences of clones 2V and 5V (SEQ ID NO:s 9, 10, 11 and 12).

FIG. 10(a) shows primer sequences uses in preparation of library (SEQ ID NO: 13-32).

FIG. 10(b) shows oligonucleotide derived diversity for CDR1.

FIG. 11 shows library framework combinations for 2V and 5V sequences (SEQ ID NO: 33-40). Framework: 67/89=75.3%. Maximum diversity (CDR1 and CDR3): 67/111=60%.

FIG. 12 shows amino acid sequences of anti-mICOSL antigen specific antigen binding molecules (VNAR) (SEQ ID NO: 41-67).

Figure 13:
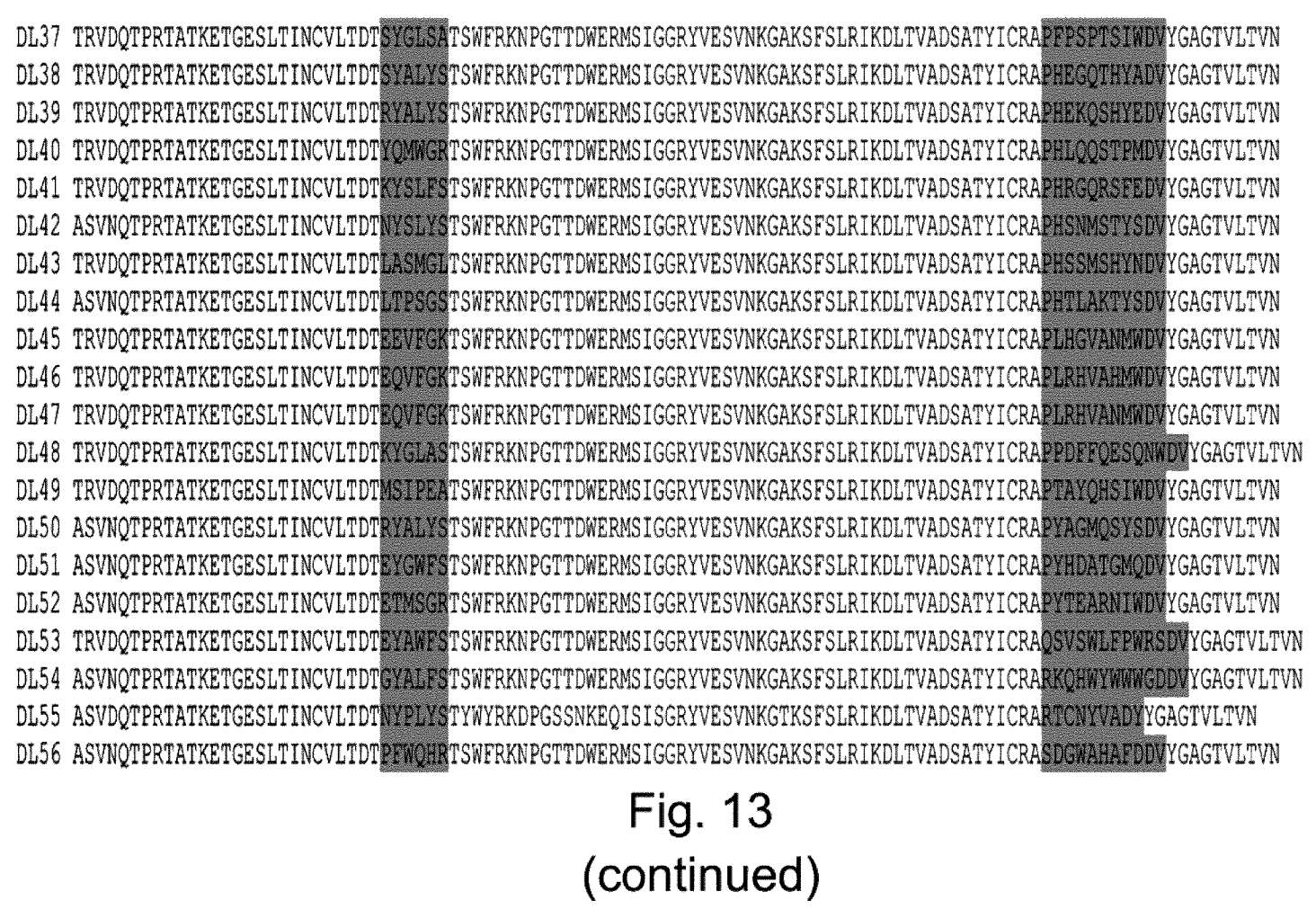

FIG. 13 shows amino acid sequences of anti-mDLL4 antigen specific antigen binding molecules (VNAR) (SEQ ID NO: 68-154).

FIG. 14 shows amino acid sequences of anti-HSA antigen specific antigen binding molecules (VNAR) (SEQ ID NO: 155-157).

FIG. 15 (a) shows amino acid sequences of anti-hRAGE antigen specific antigen binding molecules (VNAR) (SEQ ID NO: 158-163); (b) shows amino acid sequences of anti-TNF-alpha antigen specific binding molecules (VNAR) (SEQ ID NO: 164-169).

Figure 16:
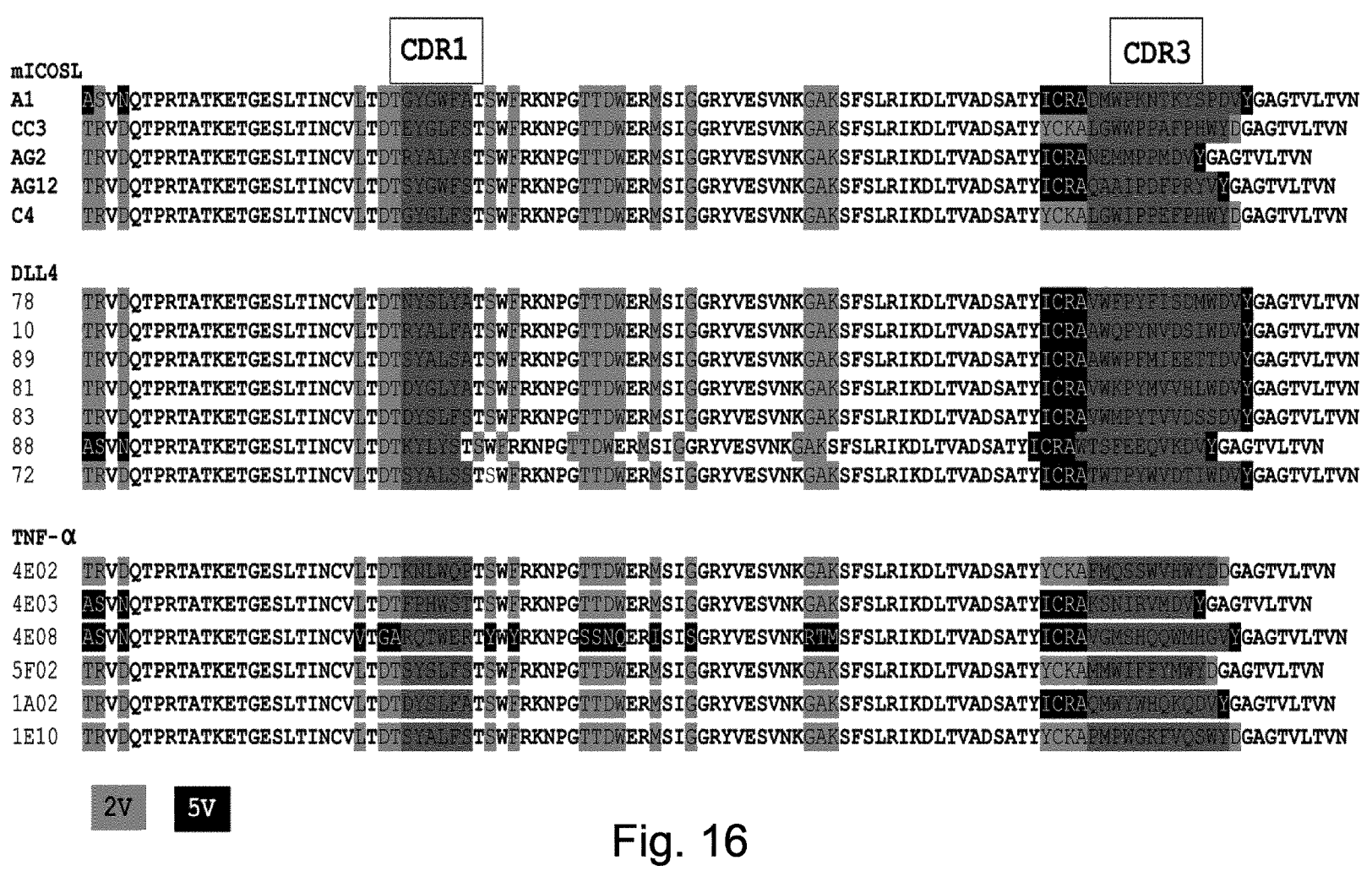

FIG. 16 shows an alignment of the lead clones against three targets that were used to screen ELSS1. Any unshaded amino acids are conserved between both frameworks so are standardised throughout the library. The regions highlighted are where there are differences introduced depending on whether the clone selected had contributions from 5V and/or 2V sequences (mICOSL—(SEQ ID NO: 41-45); DLL4—(SEQ ID NO: 143, 77, 154, 146, 148, 153, & 138, respectively); TNFalpha—(SEQ ID NO: 164-169)).

FIG. 17 shows amino acid sequences of CDR1 (SEQ ID NO: 170-297) and CDR3 (SEQ ID NO: 298-428) domains in antigen specific antigen binding molecules of the invention.

Figure 18:
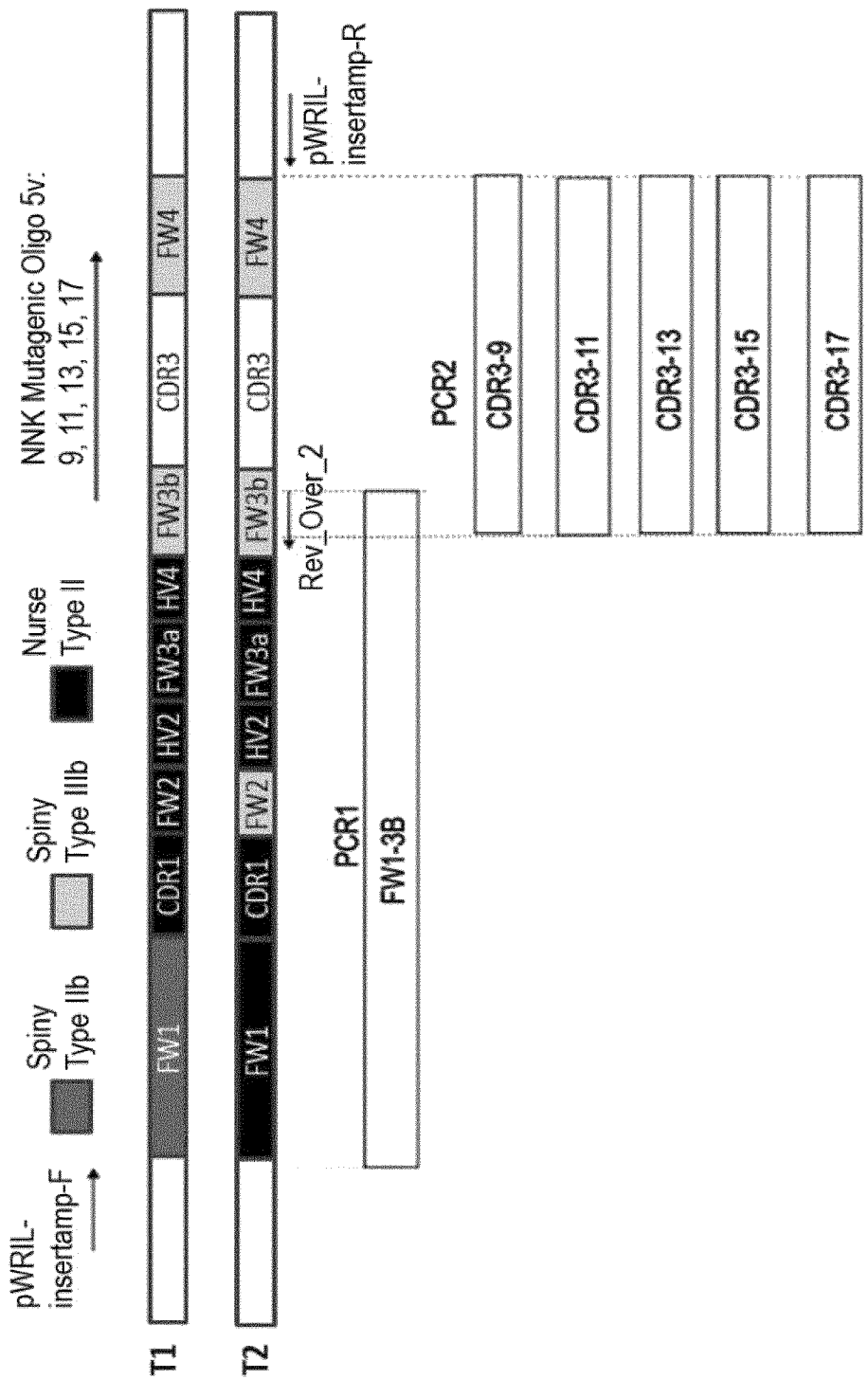

FIG. 18 shows the library design for ELSS2 using the spiny dogfish Type IIIb VNAR 5V, spiny dogfish Type IIb VNAR, 2V and the nurse shark Type II VNAR E9. 5V and 2V are the same VNAR domains used for ELSS1 and VNAR domain E9 was isolated from an immunized nurse shark library.

Figure 19:
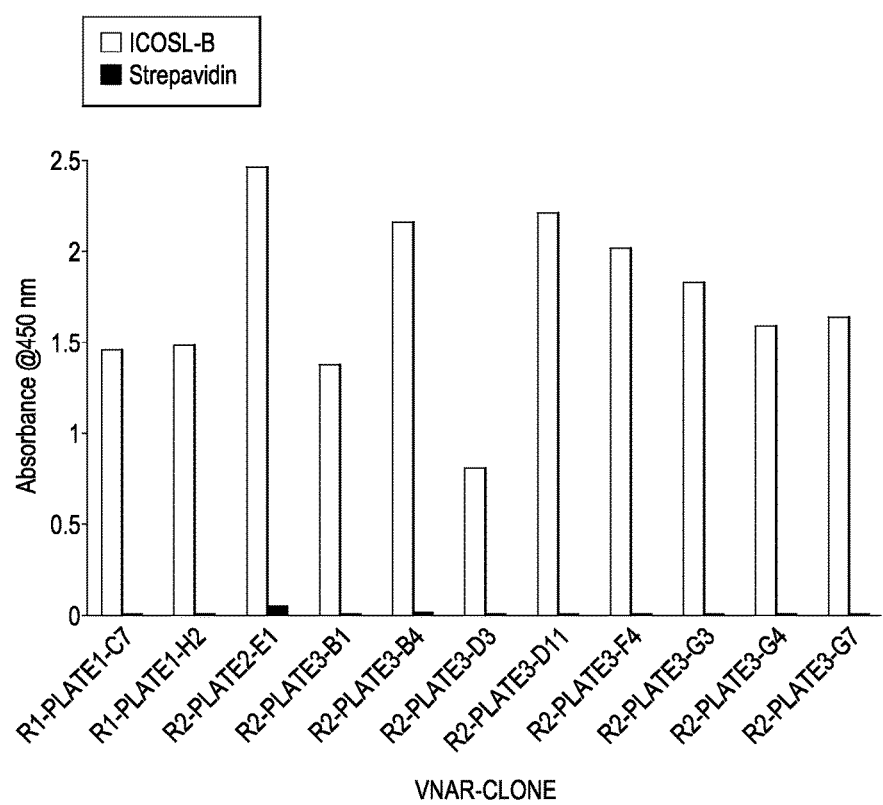

FIG. 19 shows the phage positive hits isolated from ELSS2 after selections against biotinylated ICOSL.

Figure 20:
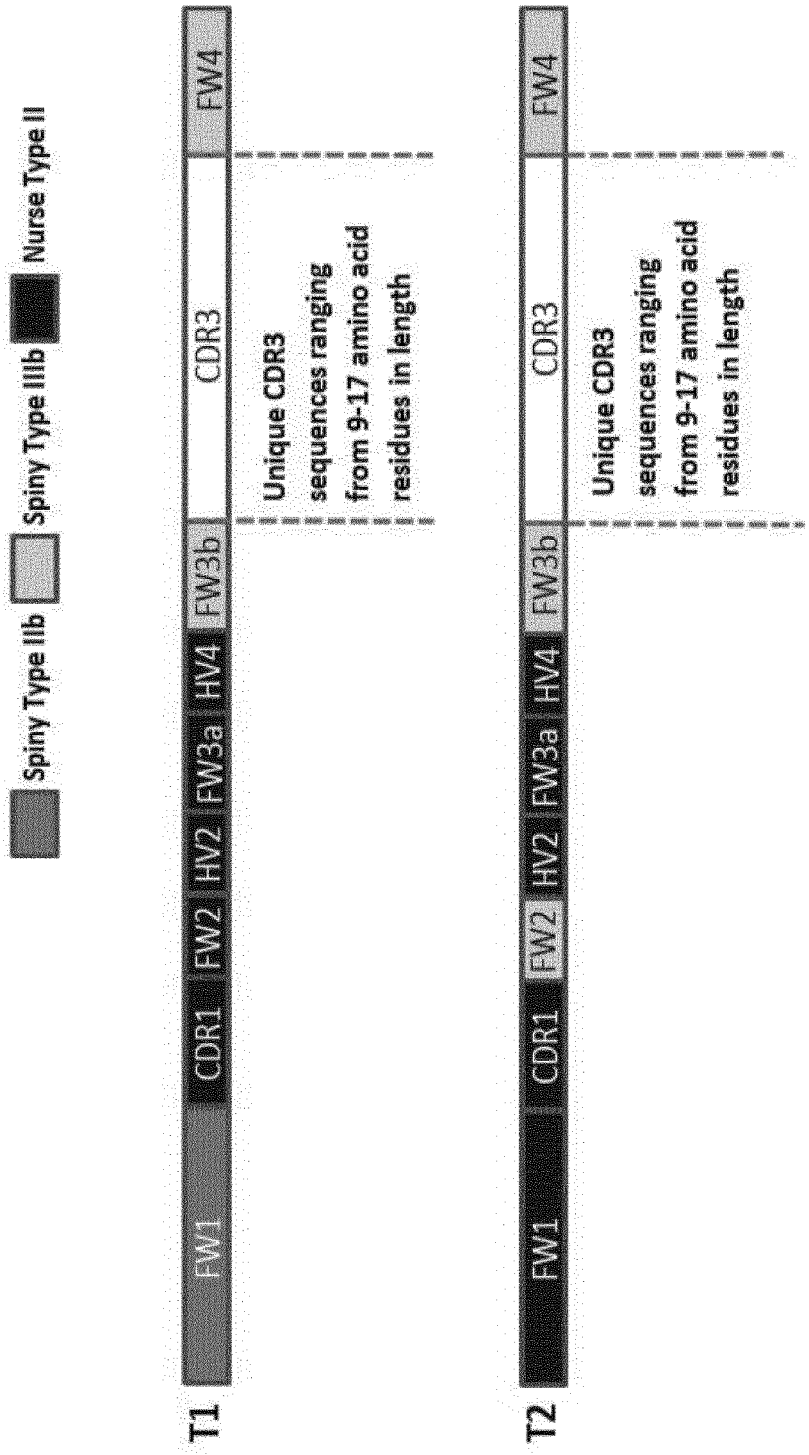

FIG. 20 shows the sequences of ICOSL positive VNAR clones isolated from ELSS2. Positive hits were all cross-species and cross-isotype framework fusions as illustrated.

The present invention will also be further described by way of reference to the following Examples which are present for the purposes of illustration only and are not to be construed as being limitations on the invention.

Abbreviations Used:

VNAR, Variable Novel Antigen Receptor; scFv, single chain antibody fragment; FW, framework; HV, Hypervariable loop; CDR, complementarity determining region; SOE-PCR, splice-by-overlap extension polymerase chain reaction.

EXAMPLE 1 SEQUENCE DATABASE CONSTRUCTION OF VNAR FROM *SQUALUS ACANTHIAS* (SPINY DOGFISH)

RNA was isolated from spiny dogfish tissues using multiple molecular biological techniques as detailed below.

RNA Isolation from Tissue:

Total RNA was isolated from shark tissue using Invitrogen's TRIzol reagent (Sigma Aldrich, Cat 15596). Approximately 50-100 mg of tissue was homogenized with a standard power homogenizer in 1 ml of TRIzol reagent. Homogenized samples were incubated at room temperature for 5 min to allow complete dissociation of nucleoprotein complexes after which 0.2 ml of chloroform was added per ml of TRIzol used. Tubes were vigorously shaken by hand for 15 seconds then centrifuged at 12000×g for 15 minutes at 4° C. Following the centrifugation, the aqueous phase containing RNA is transferred to a new tube and 1 ml of 75% ethanol or alternatively 0.5 ml isopropanol per ml of TRIzol in the initial step is added and samples incubated for 10 min at room temperature. The sample is then centrifuge again at 7500×g for 5 minutes at 4° C. Following removal of the supernatant the RNA pellet was washed once in 1 ml 70% (v/v) RNase-free ethanol, allowed to air dry and resuspended in an appropriate volume of RNase-free water (20-300 µl dependent upon the size of the resultant RNA pellet). RNA samples were quantified by spectrophotometry.

Alternatively, RNA was isolated from tissues as follows. Tissues were harvested and immediately suspended in RNAlater buffer (QIAGEN) according to the manufacturer's protocol. Total RNA was isolated using RNeasy Midi Kit (QIAGEN) for tissue according manufacturers manual, using the UltraTurax (Odds X1030D, Ing. Büro CAT, Zipperer GmBH), including DNaseI digestion on column).

RNA Isolation from Whole Blood:

RNA was isolated from whole blood samples (treated with sodium citrate (NaCitrate) to prevent coagulation and stored in RNAlater buffer) using the RiboPure-Blood Procedure from Ambion (Cat#AM1928) according to the manufacturer's protocol.

Degenerate PCR:

Prior to building a phage display library, it was essential to compile a comprehensive cDNA sequence database for the purposes of designing primers to amplify a repertoire representative of all the natural IgNAR transcripts. To achieve this, the database was created in a step-wise fashion beginning with degenerate PCR to gain a partial sequence from which to design 3' RACE primers. To isolate IgNAR encoding sequences degenerate PCR was carried out using primers based on nurse shark IgNAR sequences (for example, GenBank accession no: U18701) (SEQ ID NO: 435). From these, the constant domains were isolated and sequenced resulting in the design of 5' RACE primers to complete the full length IgNAR sequences from leader, through variable region to the constant domains.

Extracted RNA was reverse transcribed to generate cDNA using the SuperScript III Reverse Transcriptase (Invitrogen Cat 18080-044) or M-MLV Reverse Transcriptase (Promega M170B) and protocol. cDNA synthesis from spiny tissue was generated with the constant domain 1 primers:

```
C1-for1:
                                    (SEQ ID NO: 436)
5' ATA GTA TCC GCT GAT TAG ACA 3',
and Nar-C1-ForM1:
                                    (SEQ ID NO: 437)
5'GAGTGGAGGAGACTGACTATTG3'.
```

IgNAR sequences obtained by degenerate PCR techniques as described above were analyzed and multiple primers were designed for use in amplification of the 3' end of IgNAR transcripts (3'RACE) as follows. Total RNA was isolated as described in Example 2 and 3' RACE was performed using Invitrogen's GeneRacer Kit (Cat L1500-01) or Invitrogen's 5'RACE System (Cat 18374-058). First strand cDNA is synthesized from total RNA using Invitrogen's GeneRacer Oligo dT primer or Invitrogen's 5'RACE System 3' RACE Adapter Primer (#836: 5'-GGC CAC GCG TCG ACT AGT AC (T)17-3') (SEQ ID NO: 438) and SuperScript II or III according to the manufacturer's protocol but incubated at 42° C. instead of 50° C. The first strand cDNA is used for PCR amplification using Clontech's Advantage cDNA PCR polymerase Mix or BIOTAQ DNA Polymerase (Bioline cat BIO-21060) according to the recommended protocol and the primers listed below in Table 1. The PCR products were analyzed on a standard agarose gel, and the correct size band was gel purified and cloned into Promega's pGEM Teasy vector (Cat A1360) or TA cloned following the cloning kit's protocols. The clones containing PCR products were sequenced.

TABLE 1

Spiny dogfish 3' RACE primers
(SEQ ID NOS: 439-445)

| | |
|---|---|
| spiny_3R_Fm1_f34 | CGGCAACGAAAGAGACAGGAG |
| spiny_3R_Fm1_f47 | GACAGGAGAATCCCTGACCATCA |
| spiny_3R_Fm1_f54 | GAATCCCTGACCATCAATTGCGTCC |
| spiny_3R_Fm2_f113 | CTGGTACCGGAAAAATCCGGG |
| spiny_3R_Fm3_f202 | CATTTTCTCTGCGAATCAAGGACC |
| spiny_3R_Fm3_r226 | GGTCCTTGATTCGCAGAGAAAATG |
| spiny_3R_Fm3_r250 | TACGTGGCACTGTCTGCAACTG |

Isolation of NAR Encoding cDNAs Using Tm Specific Primers:

RNA was extracted from spiny dogfish tissues as described above and was reverse transcribed using the SMART RACE cDNA amplification kit (Clonetech) according to the manufacturer's protocol. First round PCRs were carried out again according to kit instructions with the generated 3' RACE cDNA, the supplied universal primer and the spiny IgNAR C3 specific primer C3_for1 (5'-GCC TCC TGC CTC CAT CGC CAG-3') (SEQ ID NO: 446). The resultant PCR products were cloned into pGEM-Teasy vector (Promega) and sequenced using the T7 and Sp6 priming sites in this vector. One clone out of 12 sequenced encoded the transmembrane tail, with the rest being the previously cloned secretory form. This clone enabled the design of another Tm-specific primer, NAR_Tm rev1 (5'-GAG AAT AAA CAG GAT CAC GAG AGC G-3') (SEQ ID NO: 447) which was used with the NAR V region specific primer NAR_Fr1 for1 (5' GGA GAA TCC CTG ACC ATC AAC TGC G-3') (SEQ ID NO: 448) to amplify full-length NAR V-C3-Tm and NAR V-C5-Tm versions from spleen cDNA.

Isolation of NAR Encoding cDNAs Using 5' RACE:

NAR cDNA clones encoding 5' untranslated region, splice leader, variable domain and partial constant domains were obtained as follows. Nucleotide sequences encoding the constant domains (isolated by 3'RACE as described above) for each species were analyzed to identify conserved regions. Primers were designed in these regions of high identity and used for 5'RACE amplification of NAR encoding sequences as follows:

Amplification of cDNA ends was achieved using Invitrogen's 5' RACE system (Invitrogen, Cat 18374-41; 18374-058) and standard protocol. Total RNA was extracted from tissue and first strand cDNA synthesised using a gene specific primer and SuperScript II/III and dC-tailed according to the recommended protocol. The dC-tailed cDNA is used for PCR amplification using Clontech's Advantage cDNA PCR polymerase Mix or BIOTAQ DNA Polymerase (Bioline cat BIO-21060) in combination with a gene specific primer (listed on Table 2). PCR amplification was carried out according to the appropriate manufacturer's protocol. Amplified products of the correct size, as judged by standard agarose gel electrophoresis, were gel purified and TA cloned following Invitrogen's TA cloning kit's protocol or alternatively cloned into Promega's pGEM Teasy vector (Promega A1360) using the manufacturer's standard protocol. The clones containing PCR products were sent for sequencing.

TABLE 2

Spiny dogfish 5'RACEprimers
(SEQ ID NOS: 449-463)

| | |
|---|---|
| shark_C1_f395 | CACCAATCATCAGTCTCCTCTAC |
| shark_C1_f411 | CTACTCTGCAACTGACGAACTG |
| shark_C1_r505 | CTCACTCCAATGCTTTCTGGCTGG |
| shark_C1_r549 | GTGGTAAAGCCAGACTGTATGG |
| shark_C1_r594 | GGTGGAGCTAAAGTCTCCGTTCG |
| shark_C1_r655 | CACTTGGCAGCTGTACATTGAAC |
| shark_C1_r697 | CTAATTTCTTTCCGTTGGTTACTG |
| spiny_c_r869 | CTTCCACGCTGCTGGTCAAG |
| spiny_c_r1011 | GAATCTCCTCTGGCGATGGAG |
| spiny_c_r1050 | CTCTTATCAAACAGGTGAGAGTAG |
| spiny_c_f1224 | CACATCCACCTTCACAATCCAC |
| spiny_c_r1246 | GTGGATTGTGAAGGTGGATGTG |
| spiny_c_r1560 | GGCAATGCACTGTCTTCTAC |
| spiny_c_r1745 | CAAAAGGGTGTCATTGGCCATCC |
| spiny_c_r1867 | CCCACTAAACAGGAGTAAGTGG |

Isolation of NAR Encoding cDNAs Using PCR:

NAR cDNA clones encoding the splice leader region, variable domain, and partial constant domain 1 were obtained by PCR amplification as follows: Sequences obtained by 5'RACE as described above were analyzed to identify the splice leader sequence. The nucleotide sequences were aligned and primers designed in regions of high nucleotide identity (designated forward primers). Similarly, sequences obtained by 3'RACE were analyzed to identify regions of high nucleotide identity in the constant domain to design primers (designated reverse primers). PCR amplification to obtain NAR cDNA clones was performed using these forward and reverse primers as follows.

RNA was extracted from multiple spiny dogfish tissues as previously described. First strand cDNA is synthesized from total RNA using Promega's or Invitrogen's oligo dT primer and SuperScript II/III following the manufacturer's protocol. Forward and Reverse primers (Table 3) were used to PCR amplify the NAR specific clones using from this cDNA. Amplified products of the correct size, as judged by standard agarose gel electrophoresis, were gel purified and TA cloned following Invitrogen's TA cloning kit's protocol or alternatively cloned into Promega's pGEM Teasy vector (Promega A1360) using the manufacturer's standard protocol and were sequenced.

TABLE 3

Spiny dogfish primers used for
Variable PCR (SEQ ID NOS: 464-469)

| | | |
|---|---|---|
| Forward | 997-spiny_utrPAGEETM_f113 | GCCTGCTGGTGAAGAAACAATGC |
| Forward | 994-spiny_sigMHIFWV_f132 | ATGCATATTTTCTGGGTTTCGGTC |
| Reverse | 879-shark_C1_r655 | CACTTGGCAGCTGTACATTGAAC |
| Forward | 1005-spiny_utrPAGEETM_f113a | CCCTGCTGGTGAAGAAACAATG |
| Forward | 1006-spiny_utrPAGEETM_f113b | CTTTGCTGGTGAAGAAACAATG |
| Reverse | 879-shark_C1_r655 | CACTTGGCAGCTGTACATTGAAC |

Spiny Dogfish IgNAR Primer Cluster Analyses:

Bioinformatic analyses were performed to identify and characterize spiny dogfish IgNAR sequences. Identification of the open reading frame, and nucleotide sequence analysis of cDNA clones isolated as described, enabled the design of NAR-specific primers for each species that could be used to construct large libraries of NAR encoding clones. The nurse shark IgNAR protein sequence (Genbank accession#U18721) (SEQ ID NO: 470) served as a template to first define the IgNAR sequences from spiny dogfish. Sequentially, several seed spiny IgNAR sequences were selected to generate a multiple sequence alignment using the CLUSTALW alignment program. This multiple alignment was used to construct a Hidden Markov Model (HMM) profile specific for spiny IgNAR using HMMERBUILD program. This HMM profile was then used to search the entire spiny cDNAs sequence database using the GENEWISEDB program. The open reading frame for each of the IgNAR cDNA sequences was identified and translated to the amino acid sequence. Next, all the IgNAR amino acid sequences were aligned using the CLUSTALW program and compared to the known nurse shark IgNAR gene structure to identify the IgNAR domains (FW1, CDR1, FW2, HV2, FW3a, HV4, FW3b, CDR3 and FW4).

EXAMPLE 2 SEQUENCE, EXPRESSION AND CRYSTALLISATION OF 2V AND 5V SPINY VNAR DOMAINS

Clones 2V and 5V (sequences shown in FIG. 9) were cloned into phagemid display vector pWRIL-1 (Finlay, W. J., et al., J Mol Biol, 2009. 388(3): p. 541-58) and showed high levels of bacterial expression. For crystallization trials, both proteins were expressed transiently in HEK293 cells and purified via Nickel capture followed by Superdex 200. Briefly, the conditioned media was adjusted to 50 mM Tris pH 8.5 prior to loading onto 15 ml bed Nickel resin followed by successive washes with Tris 20 mM NaCl, 20 mM Imidazole 0-20 mM. Protein was eluted by gradient in Tris 20 mM NaCl 20-150 mM Imidazole. The pooled protein was diluted with 25 mM MES, 25 Mm HEPES pH 6.8 and passed over a Superdex 200 16/20 300 ml bed column. After dialysis against Tris 20 mM, NaCl 20 mM pH 8.0 the protein solutions of 2V and 5V were concentrated to 10 mg/ml and 19 mg/ml, respectively. Hanging drop experiments using the vapor-diffusion method resulted in crystals from two different conditions: 20% PEG3350 and 200 mM MG SO$_4$ for 2V and 25% PEG4K, 0.1M HEPES pH 7.5 for 5V.

EXAMPLE 3 ELSS1 SYNTHETIC LIBRARY DESIGN

A comprehensive 'natural' spiny dogfish VNAR (AA) sequence database was prepared using PCR amplified cDNA as described above, the database comprised of full length unique cDNA VNAR clones from a range of different spiny dogfish animals and tissue types. The compiled translated VNAR domains were examined in terms of (AA) content, relative positional conservation and frequency across the analysed population in addition to CDR3 length distribution. This analysis was used to guide the synthetic library design. Beginning at the CDR1 and CDR3 loops, we looked at the content across these loops, the adjacent framework residues and the loop length range and distribution. Sequences within the database were binned as unique clones according to length (n 100) pools. Overall CDR3 loop lengths ranging from 11 to 16 amino acids were focused on as they corresponded to what we had defined as the average spiny dogfish CDR3 length of 13±2 amino acids. Detailed content analysis for each length binned pool highlighted conserved residues within framework 3 & 4 adjoining the CDR3. Specifically, we defined these as the final three FW3b and the first three FW4 residue positions after CDR3. In addition, we found an apparent conservation of certain amino acids at N- and C-terminal ends within CDR3 loops themselves. The FW3a positions-3, -2, & -1, immediately adjacent to the CDR 3 loop showed clear preferences for CKA, CRA & to a much lesser extent CNA sequence motifs. It should be noted that additional diversity was observed in some clones; however it was at considerably lower frequency. It is generally understood that such flanking residues can have significant influence on loop presentation in three-dimensional space and thus exert influence on paratope conformation. With this in mind we postulated these residues would be critical to functional loop presentation and thus maintained template domain motifs as we had. With our dual template design we modulated these particular regions and thus represented either CKA or CRA motifs in the synthetic library. In effect this approach allowed us to represent 76% of the 'natural' (AA) sequence diversity as found in the database. The first three FW4 residues immediately after the CDR3 in the sequence database showed higher occurrence of the DGA motif, and to a lesser extent YGA. Again the dual template domain method we used facilitated the incorporation of both these motifs into the final synthetic library clones and thus mimicked the 'natural' diversity in these positions.

Within the CDR3 loop itself we could clearly see existing bias for particular residues at C-terminal CDR3 end as eluded to earlier, especially the penultimate and ultimate residues. This bias may most probably be introduced by the usage of specific joining or J-gene segments, as yet to be elucidated. It may have been naturally evolved for biophysical or functional reasons. In addition, there appear to be changes in the particular preferred residues found in such positions as CDR3's extend in length. A specific example of this is when we examine the penultimate and ultimate C-terminal end CDR3 residues and starting from the shortest CDR3 analysed (11 AA) to the longest (16 AA). Here we found a clear reduction in combined conservation for the DV residue motif (D 46%→14% and V 45%→14%) with a reciprocal increased tendency to contain WY residues (W 42%→66% and Y 43%→83%). This may be suggestive of a potential covariance relationship between these particular terminal residues which thus far appears to correlate well with extending CDR3 length.

EXAMPLE 4 ELSS1 SYNTHETIC LIBRARY CONSTRUCTION

PCR of respective template regions off plasmid-borne 2V and 5V sequences using specific mutagenic oligonucleotides were performed using Phusion high fidelity (HF) polymerase master mix (Finnzymes), according to the manufacturer's recommendations. Briefly, equimolar amounts of each PCR product from three primary PCR product sets (fragments consisting FW1, CDR1-FW3, and CDR3-FW4, respectively) were mixed as master mixes. These fragments were subsequently joined by Splice-by-Overlap Extension (SOE) PCR. SOE-PCR products were digested with SfiI restriction endonuclease and ligated into similarly digested pWRIL-1 phagemid vector. Four template derived variant sub-libraries were constructed by SOE-PCR, pools were defined based on the origins of the CDR1-FW3 and CDR3-FW4 fragments used to construct them. For all pools equal amounts of the FW1 fragments derived from both templates were included with added oligonucleotide-directed synthetic diversity in both CDR1 and CDR3 loops. Electrocompetant E. coli TG1 cells (Lucigen) were transformed with ligated pWRIL-1 containing the appropriate inserts. In constructing the sub-libraries, we produced three sets of primary PCR products from each original template, essentially the templates were divided into three distinct regions mostly comprising the framework 1 (FW1), CDR1 and CDR3. Defined CDR1 and CDR3 loop regions were mutated using template-specific trinucleotide (TRM) oligomers (Genelink) (Virnekas, B., et al., Nucleic Acids Res, 1994. 22(25): p. 5600-7). TRM oligonucleotides were designed to incorporate any (AA) at a particular position at random with the exception of cysteine which was purposely omitted. In addition to the TRM oligos, we also used three additional template-specific CDR1-targeted oligos for incorporating mutations defined by a more rational design approach. The designed content was decided upon using analysis of 'natural' spiny VNAR domain sequences and was incorporated into the library using oligonucleotides with defined degenerate codons and direct homologue codons. The number of transformants for each of the pools was as follows: Pool A (2V-2V) $1.38 \times 10^{10}$, Pool B (5V-2V) $2.72 \times 10^{10}$, Pool C (2V-5V) $1.94 \times 10^{10}$ and Pool D (5V-5V) $3.24 \times 10^{10}$, thus the maximum final combined library pool size was $9.28 \times 10^{10}$.

EXAMPLE 5 QC ANALYSES OF UNSELECTED ELSS1 SYNTHETIC LIBRARY CLONES

Unselected ELSS1 library clones were picked at random, DNA isolated and their sequences analysed. The purpose of this analysis was to determine the extent to which all the intended design features were successfully incorporated in the final library. On the whole we found examples of all the incorporated shuffling and oligonucleotide-directed mutagenesis which was included in the design with no exceptions. In addition, several sample clones were chosen randomly and induced to express VNAR protein, periplasmic fractions were isolated and analyzed by Western blot in order to confirm protein was produced and localizing to the bacterial periplasmic extract. We also confirmed protein expression in hybrid clones derived from the two template design. In addition, we compared the content distribution of both the targeted loops, the CDR1 (n=285) and CDR3 (n=246) for a panel of unselected library clones with the original 'natural' database. On the whole, the analysis showed that the unselected ELSS1 synthetic clones gave similarly diverse (AA) content and it was similar to the 'natural' spiny dogfish database used to guide its synthesis. We compared the CDR3 loop length distributions of 'natural', unselected and selected ELSS1 library clones. Here we found that, for the most part, unselected synthetic library population was fairly evenly distributed over the 8-16 (AA) loop lengths with slight over representation of loops at 9 (AA) long.

EXAMPLE 6 FUNCTIONAL CONTENT VALIDATION BY BIOPANNING OF ELSS1 SYNTHETIC VNAR LIBRARY AGAINST MULTIPLE TARGETS

To validate the quality and functionality of the ELSS1 library, both solid state and pre-coated bead based methods were used against a variety of targets: human serum albumin (HSA), human RAGE, human DLL-4, hen egg lysozyme (HEL), and mouse ICOSL. Positive hits were obtained against each target (FIGS. 5-12). In brief, solid state selections were carried out as follows: an immunotube was coated with the target antigen at the desired concentration in 4 ml PBS. The tubes was then sealed and left to incubate O/N at 4° C. with rotation. After washing 3× with PBS, block the tube with 2% (w/v) M-PBS for 1 h. Block 0.5-1 ml input phage in M-PBS (2% (w/v) final concentration) with rotation for 1 h. Then add blocked phage to the tube, make up to 4 ml with 2% (w/v) M-PBS and incubate with rotation at 20 rpm for 1 h followed by static incubation for a further 1 h. Unbound phage is discarded and the tube is washed 5-10× with PBST followed by 5-10× washes with PBS. Phage was eluted by adding 1 ml of 100 mM triethylamine with rotation at 20 rpm for up to 10 min. The output phage solution is neutralized by the addition 0.5 ml 1M Tris-HCl pH 7.5. The eluted phage is added to 10 ml of mid-log ER2738 cells, mixed and incubated without agitation at 37° C. for 30 min followed by centrifugation at 2,500×g for 15 min. The pellet was re-suspended in 1 ml 2×TY-G and spread onto a Bio-Assay dish containing TYE-GA agar and incubated O/N at 30° C. O/N.

For the pre-coated bead assays, antigen was biotinylated as per manufacturer's instructions. Biotinylated material was incubated with 30 μl of Dynabeads M-280 Streptavidin (Invitrogen) for 30 min at R/T rotating at 20 rpm. Library selection with pre-decorated beads was carried out using essentially the same method described above where input phage and Dynabeads were pre-blocked with 4% (w/v) M-PBS for 1 h rotating at R/T. Phage were then de-selected by the addition of blocked beads for 1 h, rotating at R/T followed by the addition of antigen coated beads for 1 h at R/T at 20 rpm. After washing 5× with PBST, bound phage was eluted by rotating for 8 min in 400 μl 100 mM TEA and neutralised by the addition of 200 μl 1M Tris-HCl pH 7.5. E coli infection of eluted phage was carried out as described for the solid state selections.

Affinity measurements of hits (FIG. 5): All BIAcore analysis was performed using the T-100 biosensor, series S CM5 chips, an amine-coupling kit, 10 mM Sodium acetate immobilization buffers at pH 4, 4.5, 5.0, and 5.5, 10×HBS-P running buffer and 50 mM NaOH (GE Healthcare). Assay conditions were established to minimize the influence of mass transfer, avidity and rebinding events, detailed as below. An immobilization using hRAGE protein was carried out on a separate flow cell (Fc1) for reference subtraction and specificity analysis. The purified VNAR proteins were diluted in HBS-P running buffer to a range of final concentrations (2-fold dilutions starting from 600-37.5 nM for calculation of kinetic constants using global fit analysis). Each concentration was injected for 3 min at a fast flow rate of 30 ml/min and allowed to dissociate for 5 min, followed by a 5 sec regeneration pulse with 50 mM NaOH. Reference subtracted sensorgrams for each concentration were analyzed using BIAcore T100 evaluation software (1.1.1).

BIAcore Analysis of Purified Anti-HSA VNAR Proteins

This analysis was carried out as set out above with the following exceptions. A targeted immobilised surface density of 300 RU was tested in addition to 1000 RU surfaces for human and mouse serum albumen (HSA/MSA) on flow cells 3 & 4, respectively. In addition, the negative Fc 1 was coated with Dll4 protein. Having more protein from purification we tested a more concentrated range, 2-fold dilutions starting from 800-50 nM.

BIAcore Analysis of Purified Anti-RAGE VNAR Proteins

This analysis was carried out as set out above with the following exceptions. The targeted immobilised surface density of flow cells were as follows: Fc 1-1000 RU DLL4 negative control surface; Fc 2-1000 RU hRAGE (monomer); Fc 3-1000 RU hRAGE (dimer); Fc 4-1000 RU mRAGE (dimer).

BIAcore Analysis of Purified Anti-DLL4 VNAR Proteins

This analysis was carried out as set out above. Selectivity of hits were carried out by both ELISA based (data not shown) and FACS based methods (FIGS. 6A and B). ELISAs were carried out as follows: antigen was coated O/N at 4° C. 96-well plates were blocked for 1 h at 37° C. with 4% MPBS (Marvel PBS). Detection antibody (diluted to appropriate concentration in PBS) was incubated for 1 h at R/T. Followed by secondary HRP-conjugated antibody for 1 h at R/T. Signal generation was achieved by the adding TMB substrate.

Selected positive monomeric VNAR domains were PCR amplified with primers introducing restriction sites and flanking sequences compatible for cloning into a proprietary Fc mammalian expression vector which facilitated Protein A affinity purification of expressed proteins post PEI-mediated transient expression in HEK 293 suspension culture. Expression levels of VNAR Fc fusion proteins were generally in the region of 50-70 mg per liter using serum free media. Essentially, post expression cell debris was removed from conditioned media by centrifugation and 0.2 μm filtration, then following affinity chromatography as detailed above proteins were subjected to a final polishing step by passage over a Superdex 200 26/60 size-exclusion column equilibrated with PBS. Eluted peaks from SEC were concentrated using Amicon ultra filtration units and protein concentrations determined by UV spectroscopy.

FACS assays were carried out as follows: parental, mICOSL and hICOSL ligand expressing CHO cells were washed in PBS and removed from flasks by the addition of PBS and 5% EDTA at 37° C. for 10-15 min. Cells were monodispersed by pipetting up and down against the surface of the flask, spun down at 1200 rpm and re-suspended in DMEM plus 5% FCS. Cells are aliquoted at a density of 0.5-1×10$^6$ cells/well into a 96-well U-bottomed plate. Cells are incubated with 100 μl tissue culture supernatant containing HEK293 VNAR-hFc expressed proteins for 30 min at 16° C. followed by 3× washes with PBS plus 2% FCS. Cells were then incubated with 100 μl anti-hFc-biotin (eBioscience) at 1 μg/ml for 30 min at 16° C. After 3× washes with PBS plus 2% FCS, streptavidin-APC (eBioscience) was added at 1 µg/ml for 30 min at 16° C. After 1× wash with PBS plus 2% FCS, cells were resuspended in 400 µl PBS plus 2% FCS and transferred into FACS tubes for analyses on a FACS-Canto-2.

EXAMPLE 7 IN VITRO AND IN VIVO FUNCTIONAL VALIDATION OF HITS AGAINST MICOSL AND DLL4

In vitro efficacy of anti-mICOSL hits were measured by two cell based assays. The first was a ligand-receptor neutralization assay (FIG. 7A) where CHO cells expressing murine ICOS receptor were grown to confluency in DMEM/F12+5% FBS media in 96-well cell culture plates (Greiner, Bio-One). mICOSL-hFc (20 µl at 450 ng/ml) was pre-incubated for 1 h with 40 µl of anti-mICOSL-VNAR-hFC in DMEM/F12+2% FBS and then added to the cells. Following 1 h incubation at 16° C. cells were gently washed 3 times with DMEM/F12+2% FBS and incubated for another 40 min at 16° C. with goat anti-human Fc-HRP (SIGMA) diluted 1:10 000 in the same media. Afterwards the cells were washed again 3 times with DMEM/F12+2% FBS media and ones with PBS and developed with TMB substrate. The second assay was D10 proliferation assay (FIG. 7B) carried out briefly as follows: Tosyl activated magnetic Dynal beads were coated per product insert instructions with mICOSL, anti-mu CD3e and hIgG1 filler (1 µg ICOSL/0.5 µg anti-CD3/3.5 µg hIgG1 per 1×10$^7$ beads). Prior to assay set up, beads were titred to determine optimal concentration to give a reading of approximately 8000-40,000 CPM. 50 µl/well of the beads are added to a 96-well plate containing titred antibody diluted in 100 µl of RPMI, 10% FCS, 2 mM glutamine, pen strep, 10 mM Hepes, 1 mM NaPyruvate, 2 g/l glucose and 50 µM BME.

D10.G4.1 cells were washed 4× with assay media and resuspended in the above medium plus 10% Rat T stim factor with Con A (BD cat#354115), 2.5 ng/ml IL-2 and 10 pg/ml IL-1 alpha to 8×10$^5$ cells/ml and added at 50 µl/well=40,000 cells/well. All wells are brought up to a final volume of 200 µl and incubated for 48 hours. 1 µci/well $^3$H thymidine is added and incubated for 5-7 hours. Harvest and count CPM.

In vitro efficacy of anti-DLL4 hits were measured (FIGS. 7C and D) by cell based neutralization assays and cell death, internalization assays. Neutralization assays (FIG. 7C) were carried out as follows: HEK293/DLL4 and parental HEK293 cells were grown in MEM, 1× (Cellgro #10-010-CV), 10% FBS, 1% pen strep, 1% glutamine plus 500 µg/ml G418 sulphate until 60-75% confluent. U-2 OS/Notch1 (luciferase reporter strain) and U-2 OS parental cells were grown in McCoy's 5A (GIBCO, #12605), 10% FBS, 1% pen strep, 1% glutamine plus 250 µg/ml G418 sulphate, 300 µg/ml hygromycin, 1 µg/ml puromycin until 60-75% confluent. For the assay, both media were mixed 1:1. Approximately 10,000 Notch1 and DLL4 cells/well in a total volume of 100 µl were seeded into white opaque-bottom 96-well plates in triplicate. Test antibody samples were titrated across the plate and incubated for 24 h at 37° C., 5% CO$_2$. To each, 100 µl Dual-glo luciferase buffer (Promega, #E2980) was added followed by shaking for 20 min at R/T. The luminescence signal was measured @700 nm. Stop and Glo substrate buffer was diluted 1/100 and 100 µl added to each sample for 20 min at R/T followed by a second set of luminescence measurements at approximately 700 nm (background renilla luminescence). Ratios of both measurements were taken as the output.

DLL4 over expressing HEK293 cells were grown as described above and seeded in 120 µl/well in a 96-well plate at a cell density that ensured proliferation for four further days of incubation. Cells were incubated 4-6 h at 37° C., 5% CO$_2$ to allow for adherence. A 5× stock solution of test antibody and secondary saporin reagent (Advanced Targeting Systems #IT-51) at a molar ratio of 1:2 in medium was mixed and left for in excess of 5 min at R/T to allow complex formation. This mixture was then serially diluted and 30 ml added to each well of cells. Plates were incubated for four days followed by the addition of Cell Titer 96 Aqueous Non-radioactive Cell Proliferation Assay at a 1/5 dilution (MTS) (Promega #G5430). Plates were then incubated at 37° C. for 1.5-5 h depending on colour development and read at an absorbance of 490 nm and 650 nm (for background subtraction).

In vivo efficacy of anti-mICOSL hits were determined in a mouse model of Rheumatoid Arthritis (FIG. 8). The model was a collagen induced mouse model of RA (Iwai et al, Journal of Immunology, 2002:169) where groups of 10 female DBA1 mice were injected with bovine collagen in Freunds Complete adjuvant (Day 0) followed by a boost on day 20. Test anti-mICOSL VNAR-hFc domains, positive (HK5.3 mAb) and negative controls (2V-hFc) were dosed on days 20, 22, 24 and 26 at 15 mg/kg in PBS i.p. Clinical score and weight were measured twice weekly. Clinical scores were based on caliper measurements of footpad and digit inflammation: 1 pt/digit, 5 pts/swollen footpad, 5 pts/swollen ankle therefore giving 15 pts/foot and 60 pts/animal.

EXAMPLE 8 ALIGNMENT OF CLONES AGAINST TARGETS

FIG. 16 shows an alignment of the lead clones against three targets that were used to screen ELSS1. The alignment shows that combinations of 2V and 5V frameworks have contributed to these clones. Any unshaded amino acids are conserved between both frameworks so are standardised throughout the library. The regions highlighted are where there are differences introduced depending on whether the clone selected had contributions from 5V and/or 2V sequences. All these clones are lead clones showing efficacy in various in vitro assays and the mICOSL also show efficacy in the in vivo assays. Five of these clones have 2V across the sequences (CC3, C4, 1D12, 2D4, 1H02). All the others including all the DLL4 clones are 2V/5V framework fusions.

EXAMPLE 9 ELSS2 SYNTHETIC LIBRARY DESIGN

A second framework library was designed and constructed incorporating the frameworks of three different isotypes of VNAR domains from two different species of Elasmobranchii: *Squalus acanthias* and *Ginglymostoma cirratum*. Two template framework fusion constructs were designed based on sequence analysis between the three different VNAR domain isotypes; spiny dogfish 2V (isotype IIb) and 5V (isotype IIIb) VNAR domains in addition to the Type II istoype domain E9 which was isolated from an immunized nurse shark. FIG. 18 illustrates the two hybrid template framework sequences constructed (Life Technologies) as the basis of the ELSS2 library. Two template derived variant sub-libraries were constructed by SOE-PCR with added oligonucleotide-directed (NNK oligos) synthetic diversity in both the length (9, 11, 13, 15 and 17 amino acids) and sequence of the CDR3 loops.

EXAMPLE 10 ELSS2 LIBRARY CONSTRUCTION AND BIOPANNING

Two framework fusion templates were designed based on 2V, 5V and E9 VNAR domains. Plasmid constructs containing the fusion templates were synthesized (Life Technologies) and gene inserts were either digested with KpnI and Sac I restriction endonucleases or PCR amplified with Phusion high fidelity polymerase master mix (NEB) according to the manufacturer's recommendations. Random oligonucleotide synthetic diversity across the CDR3 loops on both framework templates was achieved by incorporating NNK oligos of fixed length (9, 11, 13, 15 or 17 amino acids). Full-length VNAR gene sequences were assembled by SOE-PCR using FW1-FW3 and CDR3-FW4 amplicons. PCR products were digested with SfiI restriction endonuclease, ligated into similarly digested phagemid vector and transformed into electrocompetant E. coli ER2738 cells (Lucigen) resulting in two sub-libraries with a combined size of approximately $2 \times 10^8$ clones.

To validate the quality and functionality of the ELSS2 library, pre-coated bead based biopanning methods were used against ICOSL using the same method as described in Example 6. Positive phage hits were obtained after pan 2 (FIG. 19). Eleven positive clones were sequenced with seven originating from the template 1 framework construct and the remaining four from the template 2 framework construct. All CDR3 sequences were unique (FIG. 20). Of these positive clones, a total of five (three from template one and two from templates two) had Cys residues in both CDR1 and CDR3 which correlates with a Type II configuration.

The invention claimed is:

1. A method for the production of a library of antigen specific antigen binding molecules having a peptide domain structure represented by the following formula (I):

FW1-CDR1-FW2-HV2-FW3a-HV4-FW3b-CDR3-FW4, comprising:
(1) isolating RNA from a member of a species in the Elasmobranchii subclass;
(2) amplifying DNA sequences from RNA obtained in (1) which encode antigen specific antigen binding molecules to create a database of DNA sequences encoding antigen specific binding molecules;
(3) selecting a DNA sequence from the database prepared in (2);
(4) amplifying DNA sequences encoding two or more contiguous peptide domains of FW1-CDR1-FW2-HV2-FW3a-HV4-FW3b-CDR3-FW4 wherein said two or more contiguous peptide domains when ligated encode an antigen specific antigen binding molecule of formula (I) and where said two or more contiguous peptide domains are from at least two heterologous DNA sequences selected in (3) in the presence of a plurality of heterologous oligomers complementary to CDR1 or CDR3 domains in sequences selected in (3) to form a plurality of amplified DNA sequences encoding an antigen specific antigen binding molecule of formula (I), wherein said two or more contiguous peptide domains are FW1, CDR1-FW2-HV2-FW3a-HV4-FW3b, and CDR3-FW4;
(5) ligating together said amplified DNA sequences encoding two or more contiguous peptide domains to form DNA sequences encoding an antigen specific binding molecule having the peptide domain structure of formula (I);
(6) cloning the amplified DNA obtained in (3) into a display vector; and
(7) transforming a host with said display vector to produce a library of said antigen specific antigen binding molecules.

2. A process for the production of an antigen specific antigen binding molecule, comprising
(1) selecting desired clones from the library prepared according to a method of claim 1;
(2) isolating and purifying the antigen specific antigen binding molecules from these clones;
(3) cloning the DNA sequences encoding the antigen specific antigen binding molecules into an expression vector; and
(4) transforming a host to allow expression of the expression vector.

3. A method for the production of an antigen specific antigen binding molecule having a peptide domain structure represented by the following formula (I):

FW1-CDR1-FW2-HV2-FW3a-HV4-FW3b-CDR3-FW4, comprising:
(1) isolating RNA from a member of a species in the Elasmobranchii subclass;
(2) amplifying DNA sequences from RNA obtained in (1) which encode antigen specific antigen binding molecules to create a database of DNA sequences encoding antigen specific binding molecules
(3) selecting a DNA sequence from the database prepared in (2):
(4) amplifying DNA sequences encoding two or more contiguous peptide domains of FW1-CDR1-FW2-HV2-FW3a-HV4-FW3b-CDR3-FW4 wherein said two or more contiguous peptide domains when ligated encode an antigen specific antigen binding molecule of formula (I) and where said two or more contiguous peptide domains are from at least two heterologous DNA sequences selected in (3) in the presence of a plurality of heterologous oligomers complementary to CDR1 or CDR3 domains in sequences selected in (3) to form a plurality of amplified DNA sequences encoding an antigen specific antigen binding molecule of formula (I), wherein said two or more contiguous peptide domains are FW1, CDR1-FW2-HV2-FW3a-HV4-FW3b, and CDR3-FW1;
(5) ligating together said amplified DNA sequences encoding two or more contiguous peptide domains to form DNA sequences encoding an antigen specific binding molecule having the peptide domain structure of formula (I);
(6) cloning the amplified DNA obtained in (5) into a display vector;

(7) transforming a host with said display vector to produce a library of said antigen specific antigen binding molecules;
(8) selecting a desired clone from the library;
(9) isolating and purifying the antigen specific antigen binding molecule from the done;
(10) cloning the DNA sequences encoding the antigen specific antigen binding molecule into an expression vector; and
(11) transforming a host to allow expression of the expression vector.

* * * * *

UNITED STATES PATENT AND TRADEMARK OFFICE
CERTIFICATE OF CORRECTION

PATENT NO. : 10,202,438 B2
APPLICATION NO. : 14/786074
DATED : February 12, 2019
INVENTOR(S) : Caroline Jane Barelle et al.

Page 1 of 1

It is certified that error appears in the above-identified patent and that said Letters Patent is hereby corrected as shown below:

In the Claims

At Column 295, Line 6 Claim 3, "binding molecule from the done;" should read --binding molecule from the clone;--

Signed and Sealed this
Thirtieth Day of July, 2019

Andrei Iancu
*Director of the United States Patent and Trademark Office*